United States Patent
Walter et al.

(10) Patent No.: US 10,933,132 B2
(45) Date of Patent: Mar. 2, 2021

(54) COMBINATION OF EPIGENETIC FACTORS AND BISPECIFIC COMPOUNDS TARGETING CD33 AND CD3 IN THE TREATMENT OF MYELOID LEUKEMIA

(71) Applicants: AMGEN RESEARCH (MUNICH) GMBH, Munich (DE); AMGEN INC., Thousand Oaks, CA (US)

(72) Inventors: Roland B. Walter, Seattle, WA (US); Marion Subklewe, Munich (DE); Christina Krupka, Munich (DE)

(73) Assignees: AMGEN RESEARCH (MUNICH) GMBH, Munich (DE); AMGEN INC., Thousand Oaks, CA (US)

( * ) Notice: Subject to any disclaimer, the term of this patent is extended or adjusted under 35 U.S.C. 154(b) by 504 days.

(21) Appl. No.: 14/916,201

(22) PCT Filed: Sep. 15, 2014

(86) PCT No.: PCT/EP2014/069575
§ 371 (c)(1),
(2) Date: Mar. 3, 2016

(87) PCT Pub. No.: WO2015/036583
PCT Pub. Date: Mar. 19, 2015

(65) Prior Publication Data
US 2016/0317657 A1    Nov. 3, 2016

Related U.S. Application Data

(60) Provisional application No. 61/877,714, filed on Sep. 13, 2013.

(51) Int. Cl.
| | |
|---|---|
| *C07K 16/00* | (2006.01) |
| *A61K 39/395* | (2006.01) |
| *A61K 31/4045* | (2006.01) |
| *C07K 16/28* | (2006.01) |
| *A61K 39/00* | (2006.01) |

(52) U.S. Cl.
CPC .... *A61K 39/39558* (2013.01); *A61K 31/4045* (2013.01); *C07K 16/2803* (2013.01); *C07K 16/2809* (2013.01); *A61K 2039/505* (2013.01); *C07K 2317/31* (2013.01); *C07K 2317/33* (2013.01); *C07K 2317/622* (2013.01)

(58) Field of Classification Search
None
See application file for complete search history.

(56) References Cited

U.S. PATENT DOCUMENTS

| | | |
|---|---|---|
| 3,691,016 A | 9/1972 | Patel et al. |
| 3,773,919 A | 11/1973 | Boswell et al. |
| 3,969,287 A | 7/1976 | Jaworek et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,301,144 A | 11/1981 | Iwashita et al. |
| 4,330,440 A | 5/1982 | Ayers et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,485,045 A | 11/1984 | Regen |

(Continued)

FOREIGN PATENT DOCUMENTS

| | | |
|---|---|---|
| EP | 0036676 A1 | 9/1981 |
| EP | 0058481 A1 | 8/1982 |

(Continued)

OTHER PUBLICATIONS

Aigner et al. (Leukemia, Apr. 2013, vol. 27, No. 5, pp. 1107-1115) (Year: 2013).*
Budman et al. (The Journal of New Anticancer Agents, vol. 29, No. 6, Jun. 2010, pp. 1224-1229) (Year: 2010).*
Aigner et al. (Leukemia, vol. 29, No. 6, 1107-1115, 2013) cited on IDS (Year: 2013).*
Altschul et al., Basic local alignment search tool. *J. Mol. Biol.* 215:403-10 (1990).
Altschul et al., Gapped BLAST and PSI-BLAST: a new generation of protein database search programs. *Nucl. Acids Res.* 25: 3389-402 (1993).
Altschul et al., Local alignment statistics. *Meth. Enzymol.* 266: 460-80 (1996).

(Continued)

*Primary Examiner* — Meera Natarajan
(74) *Attorney, Agent, or Firm* — Marshall, Gerstein & Borun LLP; Lynn L. Janulis

(57) ABSTRACT

The present invention provides a combination epigenetic factors and bispecific compounds targeting CD33 and CD3 in the treatment of myeloid leukemia, wherein the epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone demethylase inhibitors and ATRA (All Trans-retinoic acid). Accordingly, the invention provides a pharmaceutical composition comprising a CD33 targeting compound and at least one epigenetic factor and an epigenetic factor for use in the amelioration and/or treatment of a myeloid leukemia, wherein the epigenetic factor increases the responsiveness of a patient to a CD33 targeting compound. Moreover, the invention provides the use of at least one an epigenetic factor for increasing the responsiveness of a myeloid leukemia patient to a treatment with a CD33 targeting compound, a method for the treatment of a myeloid leukemia, the method comprising the administration of at least one epigenetic factor and a CD33 targeting compound to a patient in the need thereof and a kit comprising a pharmaceutical composition of the invention or an epigenetic factor of the invention and a bispecific CD33 targeting compound.

21 Claims, 5 Drawing Sheets
Specification includes a Sequence Listing.

(56) References Cited

U.S. PATENT DOCUMENTS

| | | |
|---|---|---|
| 4,486,194 A | 12/1984 | Ferrara |
| 4,487,603 A | 12/1984 | Harris |
| 4,496,689 A | 1/1985 | Mitra |
| 4,544,545 A | 10/1985 | Ryan et al. |
| 4,596,556 A | 6/1986 | Morrow et al. |
| 4,640,835 A | 2/1987 | Shimizu et al. |
| 4,670,417 A | 6/1987 | Iwasaki et al. |
| 4,751,180 A | 6/1988 | Cousens et al. |
| 4,790,824 A | 12/1988 | Morrow et al. |
| 4,791,192 A | 12/1988 | Nakagawa et al. |
| 4,816,567 A | 3/1989 | Cabilly et al. |
| 4,935,233 A | 6/1990 | Bell et al. |
| 4,941,880 A | 7/1990 | Burns |
| 4,946,778 A | 8/1990 | Ladner et al. |
| 5,013,556 A | 5/1991 | Woodle et al. |
| 5,064,413 A | 11/1991 | McKinnon et al. |
| 5,292,658 A | 3/1994 | Cormier et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,418,155 A | 5/1995 | Cormier et al. |
| 5,565,332 A | 10/1996 | Hoogenboom et al. |
| 5,648,260 A | 7/1997 | Winter et al. |
| 5,683,888 A | 11/1997 | Campbell |
| 5,741,668 A | 4/1998 | Ward et al. |
| 5,777,079 A | 7/1998 | Tsien et al. |
| 5,804,387 A | 9/1998 | Cormack et al. |
| 5,874,304 A | 2/1999 | Zolotukhin et al. |
| 5,876,995 A | 3/1999 | Bryan |
| 5,925,558 A | 7/1999 | Tsien et al. |
| 2011/0038856 A1* | 2/2011 | Drachman ......... A61K 39/3955 424/133.1 |

FOREIGN PATENT DOCUMENTS

| | | |
|---|---|---|
| EP | 0088046 A2 | 9/1983 |
| EP | 0133988 A2 | 3/1985 |
| EP | 0143949 A1 | 6/1985 |
| EP | 0183070 A2 | 6/1986 |
| EP | 0244234 A2 | 11/1987 |
| EP | 0402226 A1 | 12/1990 |
| WO | WO-1987/005330 A1 | 9/1987 |
| WO | WO-1988/009344 A1 | 12/1988 |
| WO | WO-1992/015673 A1 | 9/1992 |
| WO | WO-1993/015722 A1 | 8/1993 |
| WO | WO-1994/010308 A1 | 5/1994 |
| WO | WO-1995/007463 A1 | 3/1995 |
| WO | WO-1998/014605 A1 | 4/1998 |
| WO | WO-1998/026277 A2 | 6/1998 |
| WO | WO-1999/049019 A2 | 9/1999 |
| WO | WO-1999/054440 A1 | 10/1999 |
| WO | WO-2006/138181 A2 | 12/2006 |
| WO | WO-2007/042261 A2 | 4/2007 |
| WO | WO/2008/119567 * | 10/2008 |
| WO | WO-2008/119567 A2 | 10/2008 |
| WO | WO-2012/045752 A1 | 4/2012 |

OTHER PUBLICATIONS

Aplin et al., Preparation, properties, and applications of carbohydrate conjugates of proteins and lipids. *CRC Crit. Rev. Biochem.* 259-306 (1981).

Arakawa et al., Protein-solvent interactions in pharmaceutical formulations. *Pharm Res.* 8(3): 285-91 (1991).

Artsaenko et al., Expression of a single-chain Fv antibody against abscisic acid creates a wilty phenotype in transgenic tobacco. *Plant J.* 8: 745-50 (1995).

Baeuerle et al., BiTE: Teaching antibodies to engage T-cells for cancer therapy. *Curr. Opin. Mol. Ther.* 11: 22-30 (2009).

Brühl et al., Depletion of CCR5-expressing cells with bispecific antibodies and chemokine toxins: a new strategy in the treatment of chronic inflammatory diseases and HIV. *Immunol.* 166: 2420-6 (2001).

Carter et al., High level *Escherichia coli* expression and production of a bivalent humanized antibody fragment. *Biotechnology* 10: 163-7 (1992).

Chalfie et al., Green fluorescent protein as a marker for gene expression. *Science* 263: 802-5 (1994).

Cheadle et al., Cloning and expression of the variable regions of mouse myeloma protein MOPC315 in *E. coli*: recovery of active FV fragments. *Mol. Immunol.* 29: 21-30 (1992).

Cheson et al., Report of an international workshop to standardize response criteria for non-Hodgkin's lymphomas. NCI Sponsored International Working Group. *J. Clin. Oncol.* 17(4): 1244-53 (1999).

Chothia et al., Canonical structures for the hypervariable regions of immunoglobulins. *J. Mol. Biol.* 196: 901-17 (1987).

Chothia et al., Conformation of immunoglobulin hypervariable regions. *Nature* 342: 877-83 (1989).

Chothia et al., Structural repertoire of the human VH segments. *J. Mol. Biol.* 227: 799-817 (1987).

Clackson et al., Making antibody fragments using phage display libraries. *Lett. Nature* 352: 624-8 (1991).

Dall'Acqua et al., Contribution of domain interface residues to the stability of antibody CH3 domain homodimers. *Biochemistry* 37: 9266-73 (1998).

Devereux et al., A comprehensive set of sequence analysis programs for the VAX. *Nucl. Acid. Res.* 12:387-95 (1984).

Duskin et al., Relationship of the structure and biological activity of the natural homologues of tunicamycin. *J. Biol. Chem.* 257(6): 3105-9 (1982).

Edge et al., Deglycosylation of glycoproteins by trifluoromethanesulfonic acid. *Anal. Biochem.* 118: 131-7 (1981).

Eppstein et al., Biological activity of liposome-encapsulated murine interferon γ is mediated by a cell membrane receptor. *Proc. Natl. Acad. Sci. USA* 82: 3688-92 (1985).

Fanslow et al., Structural characteristics of CD40 ligand that determine biological function. *Semin. Immunol.* 6: 267-78 (1994).

Fecker et al., Expression of single-chain antibody fragments (scFv) specific for beet necrotic yellow vein virus coat protein or 25 kDa protein in *Escherichia coli* and *Nicotiana benthamiana*. *Plant Mol. Biol.* 32: 979-86 (1996).

Feng et al., Progressive sequence alignment as a prerequisite to correct phylogenetic trees. *J. Mol. Evol.*. 35: 351-60 (1987).

Gabizon et al., Pharmacokinetics and tissue distribution of doxorubicin encapsulated in stable liposomes with long circulation times. *J. Natl. Cancer Inst.* 8: 1484-8 (1989).

Graham et al., Characteristics of a human cell line transformed by DNA from human adenovirus type 5. *J. Gen Virol.* 36: 59-74 (1977).

Hakimuddin et al., A chemical method for the deglycosylation of proteins. *Arch. Biochem. Biophys.* 259: 52-7 (1987).

Hawkins et al., Selection of phage antibodies by binding affinity. *J. Mol. Biol.* 254: 889-96 (1992).

Heim et al., Engineering green fluorescent protein for improved brightness, longer wavelengths and fluorescence resonance energy transfer. *Curr. Biol.* 6: 178-82 (1996).

Hiatt et al., Production of antibodies in transgenic plants. *Nature*, 342: 76-8 (1989).

Higgins et al., Fast and sensitive multiple sequence alignments on a microcomputer. *CABIOS* 5: 151-3 (1989).

Hoppe et al., A parallel three stranded alpha-helical bundle at the nucleation site of collagen triple-helix formation. *FEBS Lett.* 344: 191-5 (1994).

Hosse et al., A new generation of protein display scaffolds for molecular recognition. *Protein Sci.* 15: 14-27 (2006).

Huston et al., Protein engineering of antibody binding sites: recovery of specific activity in an anti-digoxin single-chain Fv analogue produced in *Escherichia coli*. *Proc. Natl. Acad. Sci. USA* 85: 5879-83 (1988).

Hwang et al., Hepatic uptake and degradation of unilamellar sphingomyelin/cholesterol liposomes: A kinetic study. *Proc. Natl. Acad. Sci. USA* 77: 4030-4 (1980).

Ichiki et al., Regulation of the expression of human C epsilon germline transcript. Identification of a novel IL-4 responsive element. *J. Immunol.* 150: 5408-17 (1993).

(56) References Cited

OTHER PUBLICATIONS

Karlin et al., Applications and statistics for multiple high-scoring segments in molecular sequences. *Proc. Natl. Acad. Sci. USA* 90:5873-7 (1993).
Kendrick et al., "Physical stabilization of proteins in aqueous solution," in: Rational Design of Stable Protein Formulations: Theory and Practice, Carpenter and Manning, eds. *Pharmaceutical Biotechnology* 13: 61-84 (2002).
Kipriyanov et al., Bispecific tandem diabody for tumor therapy with improved antigen binding and pharmacokinetics. *J. Mol. Biol.* 293: 41-56 (1999).
Kohler et al., Continuous cultures of fused cells secreting antibody of predefined specificity. *Nature* 256:495-7 (1975).
Kozbor et al., The production of monoclonal antibodies from human lymphocytes. *Immunol. Today* 4(3): 72-9 (1983).
Kufer et al., Construction and biological activity of a recombinant bispecific single-chain antibody designed for therapy of minimal residual colorectal cancer. *Cancer Immunol. Immunother.* 45: 193-7 (1997).
Landschulz et al., The leucine zipper: A hypothetical structure common to a new class of DNA binding proteins. *Science* 240: 1759-64 (1988).
Langer et al., Biocompatibility of polymeric delivery systems for macromolecules. *J. Biomed. Mater. Res.* 15(2): 267-77 (1981).
Langer, Controlled release of macromolecules, *Chem. Tech.* 12: 98-105 (1982).
Lowman et al., Selecting high-affinity binding proteins by monovalent phage display. *Biochemistry* 30: 10832-7 (1991).
Löffler et al., A recombinant bispecific single-chain antibody, CD19 x CD3, induces rapid and high lymphoma-directed cytotoxicity by unstimulated T lymphocytes. *Blood* 95(6): 2098-103 (2000).
MacCallum et al., Antibody-antigen intractions: Contact analysis and binding site technology. *J. Mol. Biol.* 262: 732-45 (1996).
Mack et al., A small bispecific antibody construct expressed as a functional single-chain molecule with high tumor cell cytotoxicity. *Proc. Natl. Acad. Sci. USA* 92: 7021-5 (1995).
Mack et al., Biologic properties of a bispecific single-chain antibody directed against 17-1A (EpCAM) and CD3: tumor cell-dependent T cell stimulation and cytotoxic activity. *J. Immunol.* 158: 3965-70 (1997).
Malmborg et al., BIAcore as a tool in antibody engineering. *J. Immunol. Methods* 183: 7-13 (1995).
Marks et al., By-passing immunization: Human antibodies from V-gene libraries displayed on phage. *J. Mol. Biol.* 222:581-97 (1991).
Martin et al., Irreversible coupling of immunoglobulin fragments to preformed vesicles. *J. Biol. Chem.* 257: 286-8 (1982).
Martin et al., Structural families in loops of homologous proteins: automatic classification, modelling and application to antibodies. *J. Mol. Biol.* 263: 800-15 (1996).
Mather et al., Culture of testicular cells in hormone-supplemented serum-free medium. *Ann. N.Y. Acad. Sci.* 383: 44-68 (1982).
Mather, Establishment and characterization of two distinct mouse testicular epithelial cell lines. *Biol. Reprod.* 23: 243-51 (1980).
Needleman et al., A general method applicable to the search for similarities in the amino acid sequqnece of two proteins. *J. Mol. Biol.* 48:443-53 (1970).
Nicaise et al., Affinity transfer by CDR grafting on a nonimmunoglobulin scaffold. *Protein Sci.* 13 : 1882-91 (2004).
Nolan et al., Fluorescence-activated cell analysis and sorting of viable mammalian cells based on beta-D-galactosidase activity after transduction of Escherichia coli lacZ. *Proc. Natl. Acad. Sci. USA* 85: 2603-7 (1988).
Nygren et al., Scaffolds for engineering novel binding sites in proteins. *Curr. Opin. Struc. Biol.* 7: 463-9 (1997).
Owen et al., Synthesis of a functional anti-phytochrome single-chain Fv protein in transgenic tobacco. *Bio/Technology* 10: 790-4 (1992).
Pearson et al., Improved tools for biological sequence comparison. *Proc. Natl. Acad. Sci. USA* 85:2444-8 (1988).

Raag et al., Single-chain Fvs. *FASEB J.* 9(1): 73-80 (1995).
Randolph et al., Surfactant-protein interactions. *Pharm Biotechnol.* 13: 159-75 (2002).
Schier et al., Efficient in vitro affinity maturation of phage antibodies using BIAcore guided selections. *Hum. Antibodies Hybridomas* 7(3): 97-105 (1996).
Sidman et al., Controlled release of macromolecules and pharmaceuticals from synthetic polypeptides based on glutamic acid. *Biopolymers* 2: 547-56 (1983).
Skerra, Alternative non-antibody scaffolds for molecular recognition. *Curr. Opin. Biotechnol.* 18: 295-304 (2005).
Smith et al., Comparison of biosequences. *Adv. Appl. Math.* 2: 482-9 (1981).
Stauber et al., Development and applications of enhanced green fluorescent protein mutants. *Biotechniques* 24: 462-71 (1998).
Stumpp et al., DARPins: A true alternative to antibodies. *Curr. Opin. Drug Discov. Devel.* 10(2): 153-9 (2007).
Sutherland et al., 5-azacytidine enhances the anti-leukemic activity of lintuzumab (SGN-33) in preclinical models of acute myeloid leukemia. *mAbs* 2(4): 440-8 (2010).
Thotakura et al., Enzymatic deglycosylation of glycoproteins. *Meth. Enzymol.* 138: 350-9 (1987).
Tomlinson et al., The structural repertoire of the human V kappa domain. *EMBO J.* 14: 4628-38 (1995).
Urlaub et al., Isolation of Chinese hamster cell mutants deficient in dihydrofolate reductase activity. *Proc. Natl. Acad. Sci. USA* 77: 4216-20 (1980).
Walter et al., Influence of CD33 expression levels and ITIM-dependent internalization on gemtuzumab ozogamicin-induced cytotoxicity. *Blood* 105(3): 1295-302 (2005).
Walter et al., Multidrug resistance protein attenuates gemtuzumab ozogamicin-induced cytotoxicity in acute myeloid leukemia cells. *Blood* 102(4): 1466-73 (2003).
Walter et al., The peripheral benzodiazepine receptor ligand PK11195 overcomes different resistance mechanisms to sensitize AML cells to gemtuzumab ozogamicin. *Blood* 103(11): 4276-84 (2004).
Ward et al., Binding activities of a repertoire of single immunoglobulin variable domains secreted from Escherichia coli. *Nature* 341: 544-6 (1989).
Aigner et al., T lymphocytes can be effectively recruited for ex vivo and in vivo lysis of AML blasts by a novel CD33/CD3-bispecific BiTE antibody construct. *Leukemia* 27(5): 1107-15 (2012).
Bross et al., Approval summary: Gemtuzumab ozogamincin in relapsed acute myeloid leukemia. *Clin. Cancer Res.* 7(6): 1490-6 (2001).
Budman et al., The histone deacetylase inhibitor panobinostat demonstrates marked synergy with conventional chemotherapeutic agents in human ovarian cancer cell lines. *Invest. New Drugs* 29(6): 1224-9 (2010).
Jiang et al., Synergistic effect of panobinostat and bortezomib on chemoresistant acute myelogenous leukemia cells via AKT and NF-κB pathways. *Cancer Lett.* 326(2): 135-42 (2012).
Lapusan et al., Phase I studies of AVE9633, an anit-CD33 antibody-maytansinoid conjugate, in adult patients with relapsed/refractory acute myeloid leukemia. *Invest. New Drugs* 30(3): 1121-31 (2011).
Maiso et al., The histone deacetylase inhibitor LBH589 is a potent antimyeloma agent that overcomes drug resistance. *Cancer Res.* 66(11): 5781-9 (2006).
Maiso et al., The synergy of panobinostat plus doxorubicin in acute myeloid leukemia suggests a role for HDAC inhibitors in the control of DNA repair. *Leukemia* 23(12): 2265-74 (2009).
Nand et al., Hydroxyurea, azacitidine and gemtuzumab ozogamicin therapy in patients with previously untreated non-M3 acute myeloid leukemia and high-risk myelodysplastic syndromes in the elderly: Results from a pilot trial. *Leuk. Lymph.* 49(11): 2141-7 (2008).
Sanchez et al., The histone deacetylase inhibitor LBH589 enhances the anti-myeloma effects of chemotherapy in vitro and in vivo. *Leukemia Res.* 35(3): 373-9 (2010).
Sutherland et al., 5-azacytidine enhances the anti-leukemic activity of lintuzumab (SGN-33) in preclinical models of acute myeloid leukemia. *MABS Landes Biosci.* 24: 440-8 (2010).

(56) References Cited

OTHER PUBLICATIONS

Walter et al., Phase II of vorinostat and post-remission therapy in older adults with previously untreated acute myeloid leukemia. *Haematologica* 97(5): 739-42 (2012).

International Search Report and Written Opinion of the International Searching Authority issued in connection with International Application No. PCT/EP2014/069575, dated Apr. 16, 2015.

Kurimoto et al., Pretreatment of leukemic cells with low-dose decitabine markedly enhances the cytotoxicity of gemtuzumab ozogamicin, Leuk, 27(1):233-5 (2013).

* cited by examiner

SEQUENCE LISTING

<160> NUMBER OF SEQ ID NOS: 227

<210> SEQ ID NO 1
<211> LENGTH: 122
<212> TYPE: PRT
<213> ORGANISM: artificial
<220> FEATURE:
<223> OTHER INFORMATION: CD33 VH of AH3

<400> SEQUENCE: 1

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 2
<211> LENGTH: 5
<212> TYPE: PRT
<213> ORGANISM: artificial
<220> FEATURE:
<223> OTHER INFORMATION: CD33 HCDR1 of AH3

<400> SEQUENCE: 2

Asn Tyr Gly Met Asn

<210> SEQ ID NO 3
<211> LENGTH: 17
<212> TYPE: PRT
<213> ORGANISM: artificial
<220> FEATURE:
<223> OTHER INFORMATION: CD33 HCDR2 of AH3

<400> SEQUENCE: 3

Trp Ile Asn Thr Tyr Thr Gly Glu Pro Thr Tyr Ala Asp Asp Phe Lys
1               5                   10                  15

Gly

<210> SEQ ID NO 4
<211> LENGTH: 13
<212> TYPE: PRT
<213> ORGANISM: artificial
<220> FEATURE:
<223> OTHER INFORMATION: CD33 HCDR3 of AH3

<400> SEQUENCE: 4

Trp Ser Trp Ser Asp Gly Tyr Tyr Val Tyr Phe Asp Tyr
1               5                   10

<210> SEQ ID NO 5
<211> LENGTH: 366
<212> TYPE: DNA
<213> ORGANISM: artificial
<220> FEATURE:
<223> OTHER INFORMATION: CD33 VH of AH3

<400> SEQUENCE: 5
caggtgcagc tggtgcagtc tggagctgag gtgaaaaagc ctggagagtc agtcaaggtc      60
tcctgcaagg ctagcgggta taccttcaca aactatggaa tgaactgggt gaggcaggct     120
ccaggacagg gtttagagtg gatgggctgg ataaacacct acactggaga gccaacatat     180
gctgatgact tcaagggacg ggttaccatg tcttcggata cctctaccag cactgcctat     240
ttggaaatca cagcctcag aagtgatgac acggctatat attactgtgc gcgctggagt     300
tggagtgatg gttactacgt ttactttgac tactggggcc aaggcactac ggtcaccgtc     360
tcctca                                                                366

<210> SEQ ID NO 6
<211> LENGTH: 113
<212> TYPE: PRT
<213> ORGANISM: artificial
<220> FEATURE:
<223> OTHER INFORMATION: CD33 VL of AH3

<400> SEQUENCE: 6

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Lys Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
            85                  90                  95

Ser Ala His Phe Pro Ile Thr Phe Gly Gln Gly Thr Arg Leu Glu Ile
        100                 105                 110

Lys

<210> SEQ ID NO 7
<211> LENGTH: 17
<212> TYPE: PRT
<213> ORGANISM: artificial
<220> FEATURE:
<223> OTHER INFORMATION: CD33 LCDR1 of AH3

<400> SEQUENCE: 7

Lys Ser Ser Gln Ser Val Leu Asp Ser Ser Lys Asn Lys Asn Ser Leu
1               5                   10                  15

Ala

<210> SEQ ID NO 8
<211> LENGTH: 7
<212> TYPE: PRT
<213> ORGANISM: artificial
<220> FEATURE:
<223> OTHER INFORMATION: CD33 LCDR2 of AH3

<400> SEQUENCE: 8

Trp Ala Ser Thr Arg Glu Ser
1               5

<210> SEQ ID NO 9
<211> LENGTH: 9
<212> TYPE: PRT
<213> ORGANISM: artificial
<220> FEATURE:
<223> OTHER INFORMATION: CD33 LCDR3 of AH3

<400> SEQUENCE: 9

Gln Gln Ser Ala His Phe Pro Ile Thr
1               5

<210> SEQ ID NO 10
<211> LENGTH: 339
<212> TYPE: DNA
<213> ORGANISM: artificial
<220> FEATURE:
<223> OTHER INFORMATION: CD33 VL of AH3

<400> SEQUENCE: 10
gacatcgtga tgacacagtc tccagactcc ctgactgtgt ctctgggcga gaggaccacc      60
atcaactgca agtccagcca gagtgtttta gacagctcca agaataagaa ctccttagct     120
tggtaccagc agaaaccagg acagcctcct aaattactcc tttcctgggc atctacgcgg     180
gaatccggga tccctgaccg attcagtggc agcgggtctg ggacagattt cactctcact     240
attgacagcc tgcagcctga agattctgca acttactatt gtcaacagtc tgcccacttc     300
ccgatcacct ttggccaagg gacacgactg gagattaaa                            339

<210> SEQ ID NO 11
<211> LENGTH: 250
<212> TYPE: PRT
<213> ORGANISM: artificial
<220> FEATURE:
<223> OTHER INFORMATION: CD33 CD33 HL of AH3

<400> SEQUENCE: 11

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Val Met Thr Gln Ser
130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
            165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Leu Gln Pro Glu
        210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 12
<211> LENGTH: 750
<212> TYPE: DNA
<213> ORGANISM: artificial
<220> FEATURE:
<223> OTHER INFORMATION: CD33 HL of AH3

<400> SEQUENCE: 12

```
caggtgcagc tggtgcagtc tggagctgag gtgaaaaagc ctggagagtc agtcaaggtc    60
tcctgcaagg ctagcgggta ccttcaca aactatggaa tgaactgggt gaggcaggct   120
ccaggacagg gtttagagtg gatgggctgg ataaacacct acactggaga gccaacatat   180
gctgatgact tcaagggacg ggttaccatg tcttcggata cctctaccag cactgcctat   240
ttggaaatca acagcctcag aagtgatgac acggctatat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgactgtg tctctgggcg agaggaccac catcaactgc   480
aagtccagcc agagtgtttt agacagctcc aagaataaga actccttagc ttggtaccag   540
cagaaaccag acagcctcc taaattactc ctttcctggg catctacgcg ggaatccggg   600
```

```
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa                                     750
```

<210> SEQ ID NO 13
<211> LENGTH: 505
<212> TYPE: PRT
<213> ORGANISM: artificial
<220> FEATURE:
<223> OTHER INFORMATION: CD33 AH3 HL x H2C HL

<400> SEQUENCE: 13

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335
```

```
Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Tyr Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
                485                 490                 495

Gly Gly Gly Thr Lys Leu Thr Val Leu
            500                 505

<210> SEQ ID NO 14
<211> LENGTH: 1515
<212> TYPE: DNA
<213> ORGANISM: artificial
<220> FEATURE:
<223> OTHER INFORMATION: CD33 AH3 HL x H2C HL

<400> SEQUENCE: 14
caggtgcagc tggtgcagtc tggagctgag gtgaaaaagc ctggagagtc agtcaaggtc      60
tcctgcaagg ctagcgggta taccttcaca aactatggaa tgaactgggt gaggcaggct     120
ccaggacagg gtttagagtg gatgggctgg ataaacacct acactggaga gccaacatat     180
gctgatgact tcaagggacg ggttaccatg tcttcggata cctctaccag cactgcctat     240
ttggaaatca cagcctcag aagtgatgac acggctatat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc aagaataaga actccttagc ttggtaccag     540
cagaaaccag acagcctcc taaattactc ctttcctggg catctacgcg ggaatccggg      600
atccctgacc gattcagtgg cagcgggtct gggacagatt tcactctcac tattgacagc     660
ctgcagcctg aagattctgc aacttactat tgtcaacagt ctgcccactt cccgatcacc     720
tttggccaag ggacacgact ggagattaaa tccggaggtg gtggctccga ggtgcagctg     780
gtcgagtctg gaggaggatt ggtgcagcct ggagggtcat tgaaactctc atgtgcagcc     840
tctggattca ccttcaataa gtacgccatg aactgggtcc gccaggctcc aggaaagggt     900
ttggaatggg ttgctcgcat aagaagtaaa tataataatt atgcaacata ttatgccgat     960
tcagtgaaaa gcacaggttca catctccaga gatgattcaa aaaacactgc ctatctacaa    1020
atgaacaact tgaaaactga ggacactgcc gtgtactact gtgtgagaca tgggaacttc    1080
```

```
ggtaatagct acatatccta ctgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggctactac ccaaactggg tccaacaaaa accaggtcag    1320
gcaccccgtg gtctaatagg tgggactaag ttcctcgccc ccggtactcc tgccagattc    1380
tcaggctccc tgcttggagg caaggctgcc ctcaccctct caggggtaca gccagaggat    1440
gaggcagaat attactgtgc tctatggtac agcaaccgct gggtgttcgg tggaggaacc    1500
aaactgactg tccta                                                    1515
```

<210> SEQ ID NO 15
<211> LENGTH: 505
<212> TYPE: PRT
<213> ORGANISM: artificial
<220> FEATURE:
<223> OTHER INFORMATION: CD33 AH3 HL x F12Q HL

<400> SEQUENCE: 15

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Ser Tyr
```

```
                275                 280                 285
Ala Met Asn Trp Val Arg Gln Ala Pro Gly Lys Gly Leu Glu Trp Val
    290                 295                 300
Ala Arg Ile Arg Ser Lys Tyr Asn Asn Tyr Ala Thr Tyr Tyr Ala Asp
305                 310                 315                 320
Ser Val Lys Gly Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Val Ser Trp Trp
                355                 360                 365
Ala Tyr Trp Gly Gln Gly Thr Leu Val Thr Val Ser Ser Gly Gly Gly
        370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Asn Tyr Pro Asn
            420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
    450                 455                 460
Leu Gly Gly Lys Ala Ala Leu Thr Leu Ser Gly Val Gln Pro Glu Asp
465                 470                 475                 480
Glu Ala Glu Tyr Tyr Cys Val Leu Trp Tyr Ser Asn Arg Trp Val Phe
                485                 490                 495
Gly Gly Gly Thr Lys Leu Thr Val Leu
            500                 505

<210> SEQ ID NO 16
<211> LENGTH: 1515
<212> TYPE: DNA
<213> ORGANISM: artificial
<220> FEATURE:
<223> OTHER INFORMATION: CD33 AH3 HL x F12Q HL

<400> SEQUENCE: 16
caggtgcagc tggtgcagtc tggagctgag gtgaaaaagc ctggagagtc agtcaaggtc    60
tcctgcaagg ctagcgggta taccttcaca aactatggaa tgaactgggt gaggcaggct   120
ccaggacagg gtttagagtg gatgggctgg ataaacacct acactggaga gccaacatat   180
gctgatgact caagggacg ggttaccatg tcttcggata cctctaccag cactgcctat   240
ttggaaatca acagcctcag aagtgatgac acggctatat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgactgtg tctctgggcg agaggaccac catcaactgc   480
aagtccagcc agagtgtttt agacagctcc aagaataaga actccttagc ttggtaccag   540
cagaaaccag gacagcctcc taaattactc ctttcctggg catctacgcg ggaatccggg   600
atccctgacc gattcagtgg cagcgggtct gggacagatt tcactctcac tattgacagc   660
ctgcagcctg aagattctgc aacttactat tgtcaacagt ctgcccactt cccgatcacc   720
tttggccaag ggacacgact ggagattaaa tccggaggtg gtggctccga ggtgcagctg   780
```

```
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaacactgcc tatctacaa    1020 atgaacaact tgaaaactga ggacactgcc gtgtactact gtgtgagaca tgggaacttc    1080
ggtaatagct acgtttcctg gtgggcttac tggggcaagg gactctggtc accgtctcc    1140 tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320 gcacccgtg gtctaatagg tgggactaag ttcctcgccc ccggtactcc tgccagattc    1380
tcaggctccc tgcttggagg caaggctgcc ctcaccctct caggggtaca gccagaggat    1440
gaggcagaat attactgtgt tctatggtac agcaaccgct gggtgttcgg tggaggaacc    1500
aaactgactg tccta                                                    1515

<210> SEQ ID NO 17
<211> LENGTH: 505
<212> TYPE: PRT
<213> ORGANISM: artificial
<220> FEATURE:
<223> OTHER INFORMATION: CD33 AH3 HL x I2C HL

<400> SEQUENCE: 17

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Lys Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220
```

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
            245                 250                 255

Glu Val Gln Leu Val Glu Ser Gly Gly Gly Leu Val Gln Pro Gly Gly
        260                 265                 270

Ser Leu Lys Leu Ser Cys Ala Ala Ser Gly Phe Thr Phe Asn Lys Tyr
    275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 18
<211> LENGTH: 1515
<212> TYPE: DNA
<213> ORGANISM: artificial
<220> FEATURE:
<223> OTHER INFORMATION: CD33 AH3 HL x I2C HL

<400> SEQUENCE: 18
caggtgcagc tggtgcagtc tggagctgag gtgaaaaagc ctggagagtc agtcaaggtc    60
tcctgcaagg ctagcgggta taccttcaca aactatggaa tgaactgggt gaggcaggct   120
ccaggacagg gtttagagtg gatgggctgg ataaacacct acactggaga gccaacatat   180
gctgatgact caagggacg ggttaccatg tcttcggata cctctaccag cactgcctat   240
ttggaaatca acagcctcag aagtgatgac acggctatat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgactgtg tctctgggcg agaggaccac catcaactgc   480

```
aagtccagcc agagtgtttt agacagctcc aagaataaga actccttagc ttggtaccag    540
cagaaaccag acagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaacactgc  ctatctacaa   1020 atgaacaact tgaaaactga ggacactgcc gtgtactact gtgtgagaca tgggaacttc   1080
ggtaatagct acatatccta ctgggcttac tggggccaag ggactctggt caccgtctcc   1140
tcaggtggtg gtggttctgg cggcggcggc tccgtggtgg gtggttctca gactgttgtg   1200
actcaggaac cttcactcac cgtatcacct ggtggaacag tcacactcac ttgtggctcc   1260
tcgactgggg ctgttacatc tggcaactac ccaaactggg tccaacaaaa accaggtcag   1320
gcaccccgtg gtctaatagg tgggactaag ttcctcgccc ccggtactcc tgccagattc   1380
tcaggctccc tgcttggagg caaggctgcc ctcaccctct cagggggtaca gccagaggat   1440 gaggcagaat attactgtgt tctatggtac agcaaccgct gggtgttcgg tggaggaacc   1500
aaactgactg tccta                                                    1515
```

<210> SEQ ID NO 19
<211> LENGTH: 122
<212> TYPE: PRT
<213> ORGANISM: artificial
<220> FEATURE:
<223> OTHER INFORMATION: CD33 VH of AF5

<400> SEQUENCE: 19

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120
```

<210> SEQ ID NO 20
<211> LENGTH: 5
<212> TYPE: PRT
<213> ORGANISM: artificial
<220> FEATURE:
<223> OTHER INFORMATION: CD33 HCDR1 of AF5

-continued

```
<400> SEQUENCE: 20

Asn Tyr Gly Met Asn
1               5

<210> SEQ ID NO 21
<211> LENGTH: 17
<212> TYPE: PRT
<213> ORGANISM: artificial
<220> FEATURE:
<223> OTHER INFORMATION: CD33 HCDR2 of AF5

<400> SEQUENCE: 21

Trp Ile Asn Thr Tyr Thr Gly Glu Pro Thr Tyr Ala Asp Asp Phe Lys
1               5                   10                  15

Gly

<210> SEQ ID NO 22
<211> LENGTH: 13
<212> TYPE: PRT
<213> ORGANISM: artificial
<220> FEATURE:
<223> OTHER INFORMATION: CD33 HCDR3 of AF5

<400> SEQUENCE: 22

Trp Ser Trp Ser Asp Gly Tyr Tyr Val Tyr Phe Asp Tyr
1               5                   10

<210> SEQ ID NO 23
<211> LENGTH: 366
<212> TYPE: DNA
<213> ORGANISM: artificial
<220> FEATURE:
<223> OTHER INFORMATION: CD33 VH of AF5

<400> SEQUENCE: 23
caggtgcagc tggtgcagtc tggagctgag gtgaagaagc ctggagcgtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact caagggacg gttaccatg acttcgata cctctaccag cactgcctat         240
ttggaactcc acaacctcag aagtgatgac acggctgtat attactgtgc gcgctggagt     300
tggagtgatg gttactacgt ttactttgac tactggggcc aaggcactac ggtcaccgtc     360
tcctca                                                                366

<210> SEQ ID NO 24
<211> LENGTH: 113
<212> TYPE: PRT
<213> ORGANISM: artificial
<220> FEATURE:
<223> OTHER INFORMATION: CD33 VL of AF5

<400> SEQUENCE: 24

Asp Ile Val Met Thr Gln Ser Pro Asp Ser Leu Thr Val Ser Leu Gly
1               5                   10                  15

Glu Arg Thr Thr Ile Asn Cys Lys Ser Gln Ser Val Leu Asp Ser
            20                  25                  30

Ser Lys Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
    50                  55                  60
```

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 25
<211> LENGTH: 17
<212> TYPE: PRT
<213> ORGANISM: artificial
<220> FEATURE:
<223> OTHER INFORMATION: CD33 LCDR1 of AF5

<400> SEQUENCE: 25

Lys Ser Ser Gln Ser Val Leu Asp Ser Ser Lys Asn Lys Asn Ser Leu
1               5                   10                  15

Ala

<210> SEQ ID NO 26
<211> LENGTH: 7
<212> TYPE: PRT
<213> ORGANISM: artificial
<220> FEATURE:
<223> OTHER INFORMATION: CD33 LCDR2 of AF5

<400> SEQUENCE: 26

Trp Ala Ser Thr Arg Glu Ser
1               5

<210> SEQ ID NO 27
<211> LENGTH: 9
<212> TYPE: PRT
<213> ORGANISM: artificial
<220> FEATURE:
<223> OTHER INFORMATION: CD33 LCDR3 of AF5

<400> SEQUENCE: 27

Gln Gln Ser Ala His Phe Pro Ile Thr
1               5

<210> SEQ ID NO 28
<211> LENGTH: 339
<212> TYPE: DNA
<213> ORGANISM: artificial
<220> FEATURE:
<223> OTHER INFORMATION: CD33VL of AF5

<400> SEQUENCE: 28
gacatcgtga tgacacagtc tccagactcc ctgactgtgt ctctgggcga gaggaccacc      60
atcaactgca agtccagcca gagtgtttta gacagctcca agaataagaa ctccttagct     120
tggtaccagc agaaaccagg acagcctcct aaattactcc tttcctgggc atctacgcgg     180
gaatccggga tccctgaccg attcagtggc agcgggtctg ggacagattt cactctcact     240
attgacagcc tgcagcctga agattctgca acttactatt gtcaacagtc tgcccacttc     300
ccgatcacct ttggccaagg gacacgactg gagattaaa                            339

<210> SEQ ID NO 29
<211> LENGTH: 250
<212> TYPE: PRT
<213> ORGANISM: artificial

<220> FEATURE:
<223> OTHER INFORMATION: CD33HL of AF5

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Ser Thr Ala Tyr
65                  70                  75                  80

Leu Glu Leu His Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 30
<211> LENGTH: 750
<212> TYPE: DNA
<213> ORGANISM: artificial
<220> FEATURE:
<223> OTHER INFORMATION: CD33HL of AF5

<400> SEQUENCE: 30
caggtgcagc tggtgcagtc tggagctgag gtgaagaagc ctggagcgtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg acttcggata cctctaccag cactgcctat     240
ttggaactcc acaacctcag aagtgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480

| | |
|---|---:|
| aagtccagcc agagtgtttt agacagctcc aagaataaga actccttagc ttggtaccag | 540 |
| cagaaaccag dacagcctcc taaattactc ctttcctggg catctacgcg ggaatccggg | 600 |
| atccctgacc gattcagtgg cagcgggtct gggacagatt tcactctcac tattgacagc | 660 |
| ctgcagcctg aagattctgc aacttactat tgtcaacagt ctgcccactt cccgatcacc | 720 |
| tttggccaag ggacacgact ggagattaaa | 750 |

```
<210> SEQ ID NO 31
<211> LENGTH: 505
<212> TYPE: PRT
<213> ORGANISM: artificial
<220> FEATURE:
<223> OTHER INFORMATION: CD33 AF5 HL x H2C HL

<400> SEQUENCE: 31
```

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320
```

```
Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Tyr Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
                485                 490                 495

Gly Gly Gly Thr Lys Leu Thr Val Leu
            500                 505

<210> SEQ ID NO 32
<211> LENGTH: 1515
<212> TYPE: DNA
<213> ORGANISM: artificial
<220> FEATURE:
<223> OTHER INFORMATION: CD33 AF5 HL x H2C HL

<400> SEQUENCE: 32
caggtgcagc tggtgcagtc tggagctgag gtgaagaagc ctggagcgtc agtcaaggtc    60
tcctgcaagg ctagcgggta taccttcaca aactatggaa tgaactgggt gaagcaggct   120
ccaggacagg gtttaaagtg gatgggctgg ataaacacct acactggaga gccaacatat   180
gctgatgact caagggacg gggttaccatg acttcgata cctctaccag cactgcctat   240
```

```
tcagtgaaag acaggttcac catctccaga gatgattcaa aaaacactgc ctatctacaa    1020
atgaacaact tgaaaactga ggacactgcc gtgtactact gtgtgagaca tgggaacttc    1080
ggtaatagct acatatccta ctgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggctactac ccaaactggg tccaacaaaa accaggtcag    1320 gcacccegtg gtctaatagg tgggactaag ttcctcgccc ccggtactcc tgccagattc    1380
tcaggctccc tgcttggagg caaggctgcc ctcaccctct cagggtacag ccagaggat    1440 gaggcagaat attactgtgc tctatggtac agcaaccgct gggtgttcgg tggaggaacc    1500
aaactgactg tccta                                                    1515
```

<210> SEQ ID NO 33
<211> LENGTH: 505
<212> TYPE: PRT
<213> ORGANISM: artificial
<220> FEATURE:
<223> OTHER INFORMATION: CD33 AF5 HL x F12Q HL

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly

|     |     |     |     |     | 260 |     |     |     | 265 |     |     |     |     | 270 |
| --- | --- | --- | --- | --- | --- | --- | --- | --- | --- | --- | --- | --- | --- | --- |
| Ser | Leu | Lys | Leu | Ser | Cys | Ala | Ala | Ser | Gly | Phe | Thr | Phe | Asn | Ser | Tyr |
|     |     |     | 275 |     |     |     |     | 280 |     |     |     |     | 285 |     |     |
| Ala | Met | Asn | Trp | Val | Arg | Gln | Ala | Pro | Gly | Lys | Gly | Leu | Glu | Trp | Val |
|     | 290 |     |     |     |     |     | 295 |     |     |     |     | 300 |     |     |     |
| Ala | Arg | Ile | Arg | Ser | Lys | Tyr | Asn | Asn | Tyr | Ala | Thr | Tyr | Tyr | Ala | Asp |
| 305 |     |     |     |     | 310 |     |     |     |     | 315 |     |     |     |     | 320 |
| Ser | Val | Lys | Gly | Arg | Phe | Thr | Ile | Ser | Arg | Asp | Asp | Ser | Lys | Asn | Thr |
|     |     |     |     | 325 |     |     |     |     | 330 |     |     |     |     | 335 |     |
| Ala | Tyr | Leu | Gln | Met | Asn | Asn | Leu | Lys | Thr | Glu | Asp | Thr | Ala | Val | Tyr |
|     |     |     | 340 |     |     |     |     | 345 |     |     |     |     | 350 |     |     |
| Tyr | Cys | Val | Arg | His | Gly | Asn | Phe | Gly | Asn | Ser | Tyr | Val | Ser | Trp | Trp |
|     |     | 355 |     |     |     |     | 360 |     |     |     |     | 365 |     |     |     |
| Ala | Tyr | Trp | Gly | Gln | Gly | Thr | Leu | Val | Thr | Val | Ser | Ser | Gly | Gly | Gly |
|     | 370 |     |     |     |     | 375 |     |     |     |     | 380 |     |     |     |     |
| Gly | Ser | Gly | Gly | Gly | Gly | Ser | Gly | Gly | Gly | Ser | Gln | Thr | Val | Val |
| 385 |     |     |     |     | 390 |     |     |     |     | 395 |     |     |     |     | 400 |
| Thr | Gln | Glu | Pro | Ser | Leu | Thr | Val | Ser | Pro | Gly | Gly | Thr | Val | Thr | Leu |
|     |     |     |     | 405 |     |     |     |     | 410 |     |     |     |     | 415 |     |
| Thr | Cys | Gly | Ser | Ser | Thr | Gly | Ala | Val | Thr | Ser | Gly | Asn | Tyr | Pro | Asn |
|     |     |     | 420 |     |     |     |     | 425 |     |     |     |     | 430 |     |     |
| Trp | Val | Gln | Gln | Lys | Pro | Gly | Gln | Ala | Pro | Arg | Gly | Leu | Ile | Gly | Gly |
|     |     | 435 |     |     |     |     | 440 |     |     |     |     | 445 |     |     |     |
| Thr | Lys | Phe | Leu | Ala | Pro | Gly | Thr | Pro | Ala | Arg | Phe | Ser | Gly | Ser | Leu |
|     | 450 |     |     |     |     | 455 |     |     |     |     | 460 |     |     |     |     |
| Leu | Gly | Gly | Lys | Ala | Ala | Leu | Thr | Leu | Ser | Gly | Val | Gln | Pro | Glu | Asp |
| 465 |     |     |     |     | 470 |     |     |     |     | 475 |     |     |     |     | 480 |
| Glu | Ala | Glu | Tyr | Tyr | Cys | Val | Leu | Trp | Tyr | Ser | Asn | Arg | Trp | Val | Phe |
|     |     |     |     | 485 |     |     |     |     | 490 |     |     |     |     | 495 |     |
| Gly | Gly | Gly | Thr | Lys | Leu | Thr | Val | Leu |
|     |     |     | 500 |     |     |     |     | 505 |

<210> SEQ ID NO 34
<211> LENGTH: 1515
<212> TYPE: DNA
<213> ORGANISM: artificial
<220> FEATURE:
<223> OTHER INFORMATION: CD33 AF5 HL x F12Q HL

<400> SEQUENCE: 34

```
caggtgcagc tggtgcagtc tggagctgag gtgaagaagc ctggagcgtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg acttcggata cctctaccag cactgcctat     240
ttggaactcc acaacctcag aagtgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc aagaataaga actccttagc ttggtaccag     540
cagaaaccag gacagcctcc taaattactc ctttcctggg catctacgcg ggaatccggg     600
atccctgacc gattcagtgg cagcgggtct gggacagatt tcactctcac cattgacagc     660
```

```
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaacactgc ctatctacaa    1020
atgaacaact tgaaaactga ggacactgcc gtgtactact gtgtgagaca tgggaacttc    1080
ggtaatagct acgtttcctg gtgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcacccgtg gtctaatagg tgggactaag ttcctcgccc ccggtactcc tgccagattc    1380
tcaggctccc tgcttggagg caaggctgcc ctcaccctct caggggtaca gccagaggat    1440
gaggcagaat attactgtgt tctatggtac agcaaccgct gggtgttcgg tggaggaacc    1500
aaactgactg tccta                                                    1515

<210> SEQ ID NO 35
<211> LENGTH: 505
<212> TYPE: PRT
<213> ORGANISM: artificial
<220> FEATURE:
<223> OTHER INFORMATION: CD33 AF5 HL x I2C HL

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205
```

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 36
<211> LENGTH: 1515
<212> TYPE: DNA
<213> ORGANISM: artificial
<220> FEATURE:
<223> OTHER INFORMATION: CD33 AF5 HL x I2C HL

<400> SEQUENCE: 36
caggtgcagc tggtgcagtc tggagctgag gtgaagaagc ctggagcgtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg acttcggata cctctaccag cactgcctat     240
ttggaactcc acaacctcag aagtgatgac acggctgtat attactgtgc gcgctggagt     300
tggagtgatg gttactacgt ttactttgac tactgggggcc aaggcactac ggtcaccgtc     360

```
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aagaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaacactgc ctatctacaa    1020 atgaacaact tgaaaactga ggacactgcc gtgtactact gtgtgagaca tgggaacttc    1080
ggtaatagct acatatccta ctgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcaccccgtg gtctaatagg tgggactaag ttcctcgccc ccgtactcc tgccagattc    1380 tcaggctccc tgcttggagg caaggctgcc ctcaccctct caggggtaca gccagaggat    1440
gaggcagaat attactgtgt tctatggtac agcaaccgct gggtgttcgg tggaggaacc    1500
aaactgactg tccta                                                    1515
```

<210> SEQ ID NO 37
<211> LENGTH: 122
<212> TYPE: PRT
<213> ORGANISM: artificial
<220> FEATURE:
<223> OTHER INFORMATION: CD33 VH of AC8

<400> SEQUENCE: 37

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120
```

<210> SEQ ID NO 38
<211> LENGTH: 5
<212> TYPE: PRT
<213> ORGANISM: artificial

```
<220> FEATURE:
<223> OTHER INFORMATION: CD33 HCDR1 of AC8

<400> SEQUENCE: 38

Asn Tyr Gly Met Asn
1               5

<210> SEQ ID NO 39
<211> LENGTH: 17
<212> TYPE: PRT
<213> ORGANISM: artificial
<220> FEATURE:
<223> OTHER INFORMATION: CD33 HCDR2 of AC8

<400> SEQUENCE: 39

Trp Ile Asn Thr Tyr Thr Gly Glu Pro Thr Tyr Ala Asp Asp Phe Lys
1               5                   10                  15

Gly

<210> SEQ ID NO 40
<211> LENGTH: 13
<212> TYPE: PRT
<213> ORGANISM: artificial
<220> FEATURE:
<223> OTHER INFORMATION: CD33 HCDR3 of AC8

<400> SEQUENCE: 40

Trp Ser Trp Ser Asp Gly Tyr Tyr Val Tyr Phe Asp Tyr
1               5                   10

<210> SEQ ID NO 41
<211> LENGTH: 366
<212> TYPE: DNA
<213> ORGANISM: artificial
<220> FEATURE:
<223> OTHER INFORMATION: CD33 VH of AC8

<400> SEQUENCE: 41
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttaaagtg gatgggctgg ataaacacct acactggaga gccaacatat   180
gctgatgact caagggacg ggttaccatg actacggata cctctaccag cactgcctat   240
atggaaatcc gcaacctcag aaatgatgac acggctgtat attactgtgc gcgctggagt   300
tggagtgatg gttactacgt ttactttgac tactggggcc aaggcactac ggtcaccgtc   360
tcctca                                                              366

<210> SEQ ID NO 42
<211> LENGTH: 113
<212> TYPE: PRT
<213> ORGANISM: artificial
<220> FEATURE:
<223> OTHER INFORMATION: CD33 VL of AC8

<400> SEQUENCE: 42

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Lys Asn Lys Asn Ser Leu Ala Trp Tyr Gln Gln Lys Pro Gly Gln
        35                  40                  45
```

```
Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys
```

```
<210> SEQ ID NO 43
<211> LENGTH: 17
<212> TYPE: PRT
<213> ORGANISM: artificial
<220> FEATURE:
<223> OTHER INFORMATION: CD33 LCDR1 of AC8

<400> SEQUENCE: 43

Lys Ser Ser Gln Ser Val Leu Asp Ser Ser Lys Asn Lys Asn Ser Leu
1               5                   10                  15

Ala
```

```
<210> SEQ ID NO 44
<211> LENGTH: 7
<212> TYPE: PRT
<213> ORGANISM: artificial
<220> FEATURE:
<223> OTHER INFORMATION: CD33 LCDR2 of AC8

<400> SEQUENCE: 44

Trp Ala Ser Thr Arg Glu Ser
1               5
```

```
<210> SEQ ID NO 45
<211> LENGTH: 9
<212> TYPE: PRT
<213> ORGANISM: artificial
<220> FEATURE:
<223> OTHER INFORMATION: CD33 LCDR3 of AC8

<400> SEQUENCE: 45

Gln Gln Ser Ala His Phe Pro Ile Thr
1               5
```

```
<210> SEQ ID NO 46
<211> LENGTH: 339
<212> TYPE: DNA
<213> ORGANISM: artificial
<220> FEATURE:
<223> OTHER INFORMATION: CD33 VL of AC8

<400> SEQUENCE: 46
gacatcgtga tgacacagtc tccagactcc ctgactgtgt ctctgggcga gagggaccacc      60 atcaactgca agtccagcca gagtgtttta gacagctcca agaataagaa ctccttagct     120
tggtaccagc agaaaccagg acagcctcct aaattactcc tttcctgggc atctacgcgg     180
gaatccggga tccctgaccg attcagtggc agcgggtctg ggacagattt cactctcact     240
attgacagcc tgcagcctga agattctgca acttactatt gtcaacagtc tgcccacttc     300
ccgatcacct ttggccaagg gacacgactg gagattaaa                             339
```

```
<210> SEQ ID NO 47
```

```
<211> LENGTH: 250
<212> TYPE: PRT
<213> ORGANISM: artificial
<220> FEATURE:
<223> OTHER INFORMATION: CD33 HL of AC8

<400> SEQUENCE: 47
```

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

```
<210> SEQ ID NO 48
<211> LENGTH: 750
<212> TYPE: DNA
<213> ORGANISM: artificial
<220> FEATURE:
<223> OTHER INFORMATION: CD33 HL of AC8

<400> SEQUENCE: 48
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact caagggacg ggttaccatg actacggata cctctaccag cactgcctat      240
atggaaatcc gcaacctcag aaatgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
```

```
atgacacagt ctccagactc cctgactgtg tctctgggcg agaggaccac catcaactgc    480
aagtccagcc agagtgtttt agacagctcc aagaataaga actccttagc ttggtaccag    540
cagaaaccag acagcctcc taaattactc ctttcctggg catctacgcg ggaatccggg     600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa                                     750
```

<210> SEQ ID NO 49
<211> LENGTH: 505
<212> TYPE: PRT
<213> ORGANISM: artificial
<220> FEATURE:
<223> OTHER INFORMATION: CD33 AC8 HL x H2C HL

<400> SEQUENCE: 49

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

```
Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Tyr Tyr Pro Asn
            420                 425                 430

Trp Val Gln Gln Lys Pro Gly Gln Ala Pro Arg Gly Leu Ile Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
                485                 490                 495

Gly Gly Gly Thr Lys Leu Thr Val Leu
            500                 505

<210> SEQ ID NO 50
<211> LENGTH: 1515
<212> TYPE: DNA
<213> ORGANISM: artificial
<220> FEATURE:
<223> OTHER INFORMATION: CD33 AC8 HL x H2C HL

<400> SEQUENCE: 50
caggtgcagc tggtgcagtc tggagctgag gtgaagaagc ctggagagtc agtcaaggtc        60
tcctgcaagg ctagcgggta taccttcaca aactatggaa tgaactgggt gaagcaggct       120
ccaggacagg gtttaaagtg gatgggctgg ataaacacct acactggaga gccaacatat       180
gctgatgact caagggacg ggttaccatg actacggata cctctaccag cactgcctat        240
atggaaatcc gcaacctcag aaatgatgac acggctgtat attactgtgc gcgctggagt       300
tggagtgatg gttactacgt ttactttgac tactgggggcc aaggcactac ggtcaccgtc      360
tcctcaggtg gtggtggttc tggcggcggc ggctccggtg gtggttc tgacatcgtg         420 atgacacagt ctccagactc cctgactgtg tctctgggcg agaggaccac catcaactgc       480
aagtccagcc agagtgtttt agacagctcc aagaataaga ctccttagc ttggtaccag        540 cagaaaccag gacagcctcc taaattactc ctttcctggg catctacgcg ggaatccggg       600
atccctgacc gattcagtgg cagcgggtct gggacagatt tcactctcac tattgacagc       660
ctgcagcctg aagattctgc aacttactat tgtcaacagt ctgcccactt cccgatcacc       720
tttggccaag ggacacgact ggagattaaa tccggaggtg gtggctccga ggtgcagctg       780
gtcgagtctg gaggaggatt ggtgcagcct ggagggtcat tgaaactctc atgtgcagcc       840
tctggattca ccttcaataa gtacgccatg aactgggtcc gccaggctcc aggaaagggt       900
```

-continued

```
ttggaatggg ttgctcgcat aagaagtaaa tataataatt atgcaacata ttatgccgat    960
tcagtgaaag acaggttcac catctccaga gatgattcaa aaaacactgc ctatctacaa   1020
atgaacaact tgaaaactga ggacactgcc gtgtactact gtgtgagaca tgggaacttc   1080
ggtaatagct acatatccta ctgggcttac tggggccaag ggactctggt caccgtctcc   1140
tcaggtggtg gtggttctgg cggcggcggc tccggtggtg gtggttctca gactgttgtg   1200
actcaggaac cttcactcac cgtatcacct ggtggaacag tcacactcac ttgtggctcc   1260
tcgactgggg ctgttacatc tggctactac ccaaactggg tccaacaaaa accaggtcag   1320 gcacccgtg gtctaatagg tgggactaag ttcctcgccc ccggtactcc tgccagattc   1380
tcaggctccc tgcttggagg caaggctgcc ctcacccttct caggggtaca gccagaggat   1440
gaggcagaat attactgtgc tctatggtac agcaaccgct gggtgttcgg tggaggaacc   1500
aaactgactg tccta                                                    1515
```

<210> SEQ ID NO 51
<211> LENGTH: 505
<212> TYPE: PRT
<213> ORGANISM: artificial
<220> FEATURE:
<223> OTHER INFORMATION: CD33 AC8 HL x F12Q HL

<400> SEQUENCE: 51

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Lys Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
```

```
            245                 250                 255
Glu Val Gln Leu Val Glu Ser Gly Gly Gly Leu Val Gln Pro Gly Gly
        260                 265                 270

Ser Leu Lys Leu Ser Cys Ala Ala Ser Gly Phe Thr Phe Asn Ser Tyr
    275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Val Ser Trp Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 52
<211> LENGTH: 1515
<212> TYPE: DNA
<213> ORGANISM: artificial
<220> FEATURE:
<223> OTHER INFORMATION: CD33 AC8 HL x F12Q HL

<400> SEQUENCE: 52
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg actacgata cctctaccag cactgcctat     240
atggaaatcc gcaacctcag aaatgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc aagaataaga actccttagc ttggtaccag     540
cagaaaccag gacagcctcc taaattactc ctttcctggg catctacgcg ggaatccggg     600
```

```
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaaacactgc ctatctacaa   1020
atgaacaact tgaaaactga ggacactgcc gtgtactact gtgtgagaca tgggaacttc   1080
ggtaatagct acgtttcctg gtgggcttac tggggccaag ggactctggt caccgtctcc   1140
tcaggtggtg gtggttctgg cggcggcggc tccggtggtg gtggttctca gactgttgtg   1200
actcaggaac cttcactcac cgtatcacct ggtggaacag tcacactcac ttgtggctcc   1260
tcgactgggg ctgttacatc tggcaactac ccaaactggg tccaacaaaa accaggtcag   1320
gcaccccgtg gtctaatagg tgggactaag ttcctcgccc ccggtactcc tgccagattc   1380
tcaggctccc tgcttggagg caaggctgcc ctcaccctct caggggtaca gccagaggat   1440
gaggcagaat attactgtgt tctatggtac agcaaccgct gggtgttcgg tggaggaacc   1500
aaactgactg tccta                                                    1515

<210> SEQ ID NO 53
<211> LENGTH: 505
<212> TYPE: PRT
<213> ORGANISM: artificial
<220> FEATURE:
<223> OTHER INFORMATION: CD33 AC8 HL x I2C HL

<400> SEQUENCE: 53
```

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Leu Gln Pro Glu
210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 54
<211> LENGTH: 1515
<212> TYPE: DNA
<213> ORGANISM: artificial
<220> FEATURE:
<223> OTHER INFORMATION: CD33 AC8 HL x I2C HL

<400> SEQUENCE: 54
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact caagggacgg ggttaccatg actacggata cctctaccag cactgcctat     240
atggaaatcc gcaacctcag aaatgatgac acggctgtat attactgtgc gcgctggagt     300

```
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aagaataaga actccttagc ttggtaccag    540
cagaaaccag acagcctcc taaattactc ctttcctggg catctacgcg ggaatccggg     600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag gcacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaaacactgc ctatctacaa   1020
atgaacaact tgaaaactga ggacactgcc gtgtactact gtgtgagaca tgggaacttc   1080
ggtaatagct acatatccta ctgggcttac tggggccaag gactctggt caccgtctcc    1140 tcaggtggtg gtggttctgg cggcggcggc tccggtggtg gtggttctca gactgttgtg   1200
actcaggaac cttcactcac cgtatcacct ggtggaacag tcacactcac ttgtggctcc   1260
tcgactgggg ctgttacatc tggcaactac ccaaactggg tccaacaaaa accaggtcag   1320
gcaccccgtg gtctaatagg tgggactaag ttcctcgccc ccggtactcc tgccagattc   1380
tcaggctccc tgcttggagg caaggctgcc ctcacccctct caggggtaca gccagaggat   1440
gaggcagaat attactgtgt tctatggtac agcaaccgct gggtgttcgg tggaggaacc   1500
aaactgactg tccta                                                    1515
```

<210> SEQ ID NO 55
<211> LENGTH: 122
<212> TYPE: PRT
<213> ORGANISM: artificial
<220> FEATURE:
<223> OTHER INFORMATION: CD33 VH of AH11

<400> SEQUENCE: 55

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Met Glu Ile Ser Ser Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 56

```
<211> LENGTH: 5
<212> TYPE: PRT
<213> ORGANISM: artificial
<220> FEATURE:
<223> OTHER INFORMATION: CD33 HCDR1 of AH11

<400> SEQUENCE: 56

Asn Tyr Gly Met Asn
1               5

<210> SEQ ID NO 57
<211> LENGTH: 17
<212> TYPE: PRT
<213> ORGANISM: artificial
<220> FEATURE:
<223> OTHER INFORMATION: CD33 HCDR2 of AH11

<400> SEQUENCE: 57

Trp Ile Asn Thr Tyr Thr Gly Glu Pro Thr Tyr Ala Asp Asp Phe Lys
1               5                   10                  15
Gly

<210> SEQ ID NO 58
<211> LENGTH: 13
<212> TYPE: PRT
<213> ORGANISM: artificial
<220> FEATURE:
<223> OTHER INFORMATION: HCDR3

<400> SEQUENCE: 58

Trp Ser Trp Ser Asp Gly Tyr Tyr Val Tyr Phe Asp Tyr
1               5                   10

<210> SEQ ID NO 59
<211> LENGTH: 366
<212> TYPE: DNA
<213> ORGANISM: artificial
<220> FEATURE:
<223> OTHER INFORMATION: CD33 VH of AH11

<400> SEQUENCE: 59
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg acttcggata cctctaccag cactgcctat     240
atggaaatca gcagcctcag aagtgatgac acggctgtat attactgtgc gcgctggagt     300
tggagtgatg gttactacgt ttactttgac tactggggcc aaggcactac ggtcaccgtc     360
tcctca                                                                366

<210> SEQ ID NO 60
<211> LENGTH: 113
<212> TYPE: PRT
<213> ORGANISM: artificial
<220> FEATURE:
<223> OTHER INFORMATION: CD33 VL of AH11

<400> SEQUENCE: 60

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30
```

Ser Lys Asn Lys Asn Ser Leu Ala Trp Tyr Gln Gln Lys Pro Gly Gln
           35                  40                  45

Pro Pro Lys Leu Leu Leu Ser Trp Ala Ser Thr Arg Glu Ser Gly Ile
 50                  55                  60

Pro Asp Arg Phe Ser Gly Ser Gly Ser Gly Thr Asp Phe Thr Leu Thr
 65                  70                  75                  80

Ile Asp Ser Leu Gln Pro Glu Asp Ser Ala Thr Tyr Tyr Cys Gln Gln
                 85                  90                  95

Ser Ala His Phe Pro Ile Thr Phe Gly Gln Gly Thr Arg Leu Glu Ile
            100                 105                 110

Lys

<210> SEQ ID NO 61
<211> LENGTH: 17
<212> TYPE: PRT
<213> ORGANISM: artificial
<220> FEATURE:
<223> OTHER INFORMATION: CD33 LCDR1 of AH11

<400> SEQUENCE: 61

Lys Ser Ser Gln Ser Val Leu Asp Ser Ser Lys Asn Lys Asn Ser Leu
 1               5                  10                  15

Ala

<210> SEQ ID NO 62
<211> LENGTH: 7
<212> TYPE: PRT
<213> ORGANISM: artificial
<220> FEATURE:
<223> OTHER INFORMATION: CD33 LCDR2 of AH11

<400> SEQUENCE: 62

Trp Ala Ser Thr Arg Glu Ser
 1               5

<210> SEQ ID NO 63
<211> LENGTH: 9
<212> TYPE: PRT
<213> ORGANISM: artificial
<220> FEATURE:
<223> OTHER INFORMATION: CD33LCDR3 of AH11

<400> SEQUENCE: 63

Gln Gln Ser Ala His Phe Pro Ile Thr
 1               5

<210> SEQ ID NO 64
<211> LENGTH: 339
<212> TYPE: DNA
<213> ORGANISM: artificial
<220> FEATURE:
<223> OTHER INFORMATION: CD33 VL of AH11

<400> SEQUENCE: 64
gacatcgtga tgacacagtc tccagactcc ctgactgtgt ctctgggcga gaggaccacc      60
atcaactgca agtccagcca gagtgtttta gacagctcca agaataagaa ctccttagct     120
tggtaccagc agaaaccagg acagcctcct aaattactcc tttcctgggc atctacgcgg     180
gaatccggga tccctgaccg attcagtggc agcgggtctg ggacagattt cactctcact     240
attgacagcc tgcagcctga agattctgca acttactatt gtcaacagtc tgcccacttc     300
ccgatcacct ttggccaagg gacacgactg gagattaaa                            339

<210> SEQ ID NO 65
<211> LENGTH: 250
<212> TYPE: PRT
<213> ORGANISM: artificial
<220> FEATURE:
<223> OTHER INFORMATION: CD33 HL of AH11

<400> SEQUENCE: 65

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Met Glu Ile Ser Ser Leu Arg Ser Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Ser Gly
            115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 66
<211> LENGTH: 750
<212> TYPE: DNA
<213> ORGANISM: artificial
<220> FEATURE:
<223> OTHER INFORMATION: CD33 HL of AH11

<400> SEQUENCE: 66
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact caagggacg ggttaccatg acttcggata cctctaccag cactgcctat     240
atggaaatca gcagcctcag aagtgatgac acggctgtat attactgtgc gcgctggagt     300

```
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aagaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa                                    750
```

```
<210> SEQ ID NO 67
<211> LENGTH: 505
<212> TYPE: PRT
<213> ORGANISM: artificial
<220> FEATURE:
<223> OTHER INFORMATION: CD33 AH11 HL x H2C HL

<400> SEQUENCE: 67
```

| Gln | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Gly | Met | Asn | Trp | Val | Lys | Gln | Ala | Pro | Gly | Gln | Gly | Leu | Lys | Trp | Met |
| | | 35 | | | | | 40 | | | | | 45 | | | |
| Gly | Trp | Ile | Asn | Thr | Tyr | Thr | Gly | Glu | Pro | Thr | Tyr | Ala | Asp | Asp | Phe |
| | 50 | | | | | 55 | | | | | 60 | | | | |
| Lys | Gly | Arg | Val | Thr | Met | Thr | Ser | Asp | Thr | Ser | Thr | Ser | Thr | Ala | Tyr |
| 65 | | | | | 70 | | | | | 75 | | | | | 80 |
| Met | Glu | Ile | Ser | Ser | Leu | Arg | Ser | Asp | Asp | Thr | Ala | Val | Tyr | Tyr | Cys |
| | | | | 85 | | | | | 90 | | | | | 95 | |
| Ala | Arg | Trp | Ser | Trp | Ser | Asp | Gly | Tyr | Tyr | Val | Tyr | Phe | Asp | Tyr | Trp |
| | | | 100 | | | | | 105 | | | | | 110 | | |
| Gly | Gln | Gly | Thr | Thr | Val | Thr | Val | Ser | Ser | Gly | Gly | Gly | Gly | Ser | Gly |
| | | 115 | | | | | 120 | | | | | 125 | | | |
| Gly | Gly | Gly | Ser | Gly | Gly | Gly | Ser | Asp | Ile | Val | Met | Thr | Gln | Ser |
| | | 130 | | | | | 135 | | | | | 140 | | | |
| Pro | Asp | Ser | Leu | Thr | Val | Ser | Leu | Gly | Glu | Arg | Thr | Thr | Ile | Asn | Cys |
| 145 | | | | | 150 | | | | | 155 | | | | | 160 |
| Lys | Ser | Ser | Gln | Ser | Val | Leu | Asp | Ser | Ser | Lys | Asn | Lys | Asn | Ser | Leu |
| | | | | 165 | | | | | 170 | | | | | 175 | |
| Ala | Trp | Tyr | Gln | Gln | Lys | Pro | Gly | Gln | Pro | Pro | Lys | Leu | Leu | Leu | Ser |
| | | | 180 | | | | | 185 | | | | | 190 | | |
| Trp | Ala | Ser | Thr | Arg | Glu | Ser | Gly | Ile | Pro | Asp | Arg | Phe | Ser | Gly | Ser |
| | | 195 | | | | | 200 | | | | | 205 | | | |
| Gly | Ser | Gly | Thr | Asp | Phe | Thr | Leu | Thr | Ile | Asp | Ser | Leu | Gln | Pro | Glu |
| | | 210 | | | | | 215 | | | | | 220 | | | |
| Asp | Ser | Ala | Thr | Tyr | Tyr | Cys | Gln | Gln | Ser | Ala | His | Phe | Pro | Ile | Thr |
| 225 | | | | | 230 | | | | | 235 | | | | | 240 |
| Phe | Gly | Gln | Gly | Thr | Arg | Leu | Glu | Ile | Lys | Ser | Gly | Gly | Gly | Gly | Ser |
| | | | | 245 | | | | | 250 | | | | | 255 | |
| Glu | Val | Gln | Leu | Val | Glu | Ser | Gly | Gly | Gly | Leu | Val | Gln | Pro | Gly | Gly |
| | | | 260 | | | | | 265 | | | | | 270 | | |
| Ser | Leu | Lys | Leu | Ser | Cys | Ala | Ala | Ser | Gly | Phe | Thr | Phe | Asn | Lys | Tyr |
| | | 275 | | | | | 280 | | | | | 285 | | | |

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Tyr Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
                485                 490                 495

Gly Gly Gly Thr Lys Leu Thr Val Leu
            500                 505

<210> SEQ ID NO 68
<211> LENGTH: 1515
<212> TYPE: DNA
<213> ORGANISM: artificial
<220> FEATURE:
<223> OTHER INFORMATION: CD33 AH11 HL x H2C HL

<400> SEQUENCE: 68
caggtgcagc tggtgcagtc tggagctgag gtgaagaagc ctggagagtc agtcaaggtc     60
tcctgcaagg ctagcgggta taccttcaca aactatggaa tgaactgggt gaagcaggct    120
ccaggacagg gtttaaagtg gatgggctgg ataaacacct acactggaga gccaacatat    180
gctgatgact tcaagggacg ggttaccatg acttcggata cctctaccag cactgcctat    240
atggaaatca gcagcctcag aagtgatgac acggctgtat attactgtgc cgctggagtt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aagaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgccccact tccgatcacc    720
tttggccaag ggacacgact ggagattaaa tccggaggtg gtggctccga ggtgcagctg    780

```
gtcgagtctg aggaggatt ggtgcagcct ggagggtcat tgaaactctc atgtgcagcc      840
tctggattca ccttcaataa gtacgccatg aactgggtcc gccaggctcc aggaaagggt      900
ttggaatggg ttgctcgcat aagaagtaaa tataataatt atgcaacata ttatgccgat      960
tcagtgaaag acaggttcac catctccaga gatgattcaa aaacactgcc tatctacaa      1020
atgaacaact tgaaaactga ggacactgcc gtgtactact gtgtgagaca tgggaacttc      1080
ggtaatagct acatatccta ctgggcttac tggggccaag ggactctggt caccgtctcc      1140
tcaggtggtg gtggttctgg cggcggcggc tccggtggtg gtggttctca gactgttgtg      1200
actcaggaac cttcactcac cgtatcacct ggtggaacag tcacactcac ttgtggctcc      1260
tcgactgggg ctgttacatc tggctactac ccaaactggg tccaacaaaa accaggtcag      1320
gcacccgtg gtctaatagg tgggactaag ttcctcgccc ccggtactcc tgccagattc      1380
tcaggctccc tgcttggagg caaggctgcc ctcaccctct caggggtaca gccagaggat      1440
gaggcagaat attactgtgc tctatggtac agcaaccgct gggtgttcgg tggaggaacc      1500
aaactgactg tccta                                                    1515
```

<210> SEQ ID NO 69
<211> LENGTH: 505
<212> TYPE: PRT
<213> ORGANISM: artificial
<220> FEATURE:
<223> OTHER INFORMATION: CD33 AH11 HL x F12Q HL

<400> SEQUENCE: 69

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Gly | Met | Asn | Trp | Val | Lys | Gln | Ala | Pro | Gly | Gln | Gly | Leu | Lys | Trp | Met |
| | | 35 | | | | | 40 | | | | | 45 | | | |
| Gly | Trp | Ile | Asn | Thr | Tyr | Thr | Gly | Glu | Pro | Thr | Tyr | Ala | Asp | Asp | Phe |
| | 50 | | | | | 55 | | | | | 60 | | | | |
| Lys | Gly | Arg | Val | Thr | Met | Thr | Ser | Asp | Thr | Ser | Thr | Ser | Thr | Ala | Tyr |
| 65 | | | | | 70 | | | | | 75 | | | | | 80 |
| Met | Glu | Ile | Ser | Ser | Leu | Arg | Ser | Asp | Asp | Thr | Ala | Val | Tyr | Tyr | Cys |
| | | | | 85 | | | | | 90 | | | | | 95 | |
| Ala | Arg | Trp | Ser | Trp | Ser | Asp | Gly | Tyr | Tyr | Val | Tyr | Phe | Asp | Tyr | Trp |
| | | | 100 | | | | | 105 | | | | | 110 | | |
| Gly | Gln | Gly | Thr | Thr | Val | Thr | Val | Ser | Ser | Gly | Gly | Gly | Gly | Ser | Gly |
| | | 115 | | | | | 120 | | | | | 125 | | | |
| Gly | Gly | Gly | Ser | Gly | Gly | Gly | Gly | Ser | Asp | Ile | Val | Met | Thr | Gln | Ser |
| | 130 | | | | | 135 | | | | | 140 | | | | |
| Pro | Asp | Ser | Leu | Thr | Val | Ser | Leu | Gly | Glu | Arg | Thr | Thr | Ile | Asn | Cys |
| 145 | | | | | 150 | | | | | 155 | | | | | 160 |
| Lys | Ser | Ser | Gln | Ser | Val | Leu | Asp | Ser | Ser | Lys | Asn | Lys | Asn | Ser | Leu |
| | | | | 165 | | | | | 170 | | | | | 175 | |
| Ala | Trp | Tyr | Gln | Gln | Lys | Pro | Gly | Gln | Pro | Pro | Lys | Leu | Leu | Leu | Ser |
| | | | 180 | | | | | 185 | | | | | 190 | | |
| Trp | Ala | Ser | Thr | Arg | Glu | Ser | Gly | Ile | Pro | Asp | Arg | Phe | Ser | Gly | Ser |
| | | 195 | | | | | 200 | | | | | 205 | | | |
| Gly | Ser | Gly | Thr | Asp | Phe | Thr | Leu | Thr | Ile | Asp | Ser | Leu | Gln | Pro | Glu |
| | 210 | | | | | 215 | | | | | 220 | | | | |
| Asp | Ser | Ala | Thr | Tyr | Tyr | Cys | Gln | Gln | Ser | Ala | His | Phe | Pro | Ile | Thr |

```
                225                 230                 235                 240
    Phe Gly Gln Gly Thr Arg Leu Glu Ile Lys Ser Gly Gly Gly Ser
                    245                 250                 255
    Glu Val Gln Leu Val Glu Ser Gly Gly Leu Val Gln Pro Gly Gly
                    260                 265                 270
    Ser Leu Lys Leu Ser Cys Ala Ala Ser Gly Phe Thr Phe Asn Ser Tyr
                    275                 280                 285
    Ala Met Asn Trp Val Arg Gln Ala Pro Gly Lys Gly Leu Glu Trp Val
                290                 295                 300
    Ala Arg Ile Arg Ser Lys Tyr Asn Asn Tyr Ala Thr Tyr Tyr Ala Asp
    305                 310                 315                 320
    Ser Val Lys Gly Arg Phe Thr Ile Ser Arg Asp Asp Ser Lys Asn Thr
                    325                 330                 335
    Ala Tyr Leu Gln Met Asn Asn Leu Lys Thr Glu Asp Thr Ala Val Tyr
                    340                 345                 350
    Tyr Cys Val Arg His Gly Asn Phe Gly Asn Ser Tyr Val Ser Trp Trp
                    355                 360                 365
    Ala Tyr Trp Gly Gln Gly Thr Leu Val Thr Val Ser Ser Gly Gly Gly
                370                 375                 380
    Gly Ser Gly Gly Gly Gly Ser Gly Gly Gly Gly Ser Gln Thr Val Val
    385                 390                 395                 400
    Thr Gln Glu Pro Ser Leu Thr Val Ser Pro Gly Gly Thr Val Thr Leu
                    405                 410                 415
    Thr Cys Gly Ser Ser Thr Gly Ala Val Thr Ser Gly Asn Tyr Pro Asn
                    420                 425                 430
    Trp Val Gln Gln Lys Pro Gly Gln Ala Pro Arg Gly Leu Ile Gly Gly
                    435                 440                 445
    Thr Lys Phe Leu Ala Pro Gly Thr Pro Ala Arg Phe Ser Gly Ser Leu
                    450                 455                 460
    Leu Gly Gly Lys Ala Ala Leu Thr Leu Ser Gly Val Gln Pro Glu Asp
    465                 470                 475                 480
    Glu Ala Glu Tyr Tyr Cys Val Leu Trp Tyr Ser Asn Arg Trp Val Phe
                    485                 490                 495
    Gly Gly Gly Thr Lys Leu Thr Val Leu
                    500                 505

<210> SEQ ID NO 70
<211> LENGTH: 1515
<212> TYPE: DNA
<213> ORGANISM: artificial
<220> FEATURE:
<223> OTHER INFORMATION: CD33 AH11 HL x F12Q HL

<400> SEQUENCE: 70
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttaaagtg gatgggctgg ataaacacct acactggaga gccaacatat   180
gctgatgact caagggacg ggttaccatg acttcggata cctctaccag cactgcctat   240
atggaaatca gcagcctcag aagtgatgac acggctgtat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgactgtg tctctgggcg agaggaccac catcaactgc   480
```

```
aagtccagcc agagtgtttt agacagctcc aagaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaaacactgc ctatctacaa    1020
atgaacaact tgaaaactga ggacactgcc gtgtactact gtgtgagaca tgggaacttc    1080
ggtaatagct acgtttcctg gtgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcaccccgtg gtctaatagg tggactaag ttcctcgccc ccgtactcc tgccagattc    1380
tcaggctccc tgcttggagg caaggctgcc ctcaccctct cagggggtaca gccagaggat    1440
gaggcagaat attactgtgt tctatggtac agcaaccgct gggtgttcgg tggaggaacc    1500
aaactgactg tccta                                                    1515
```

<210> SEQ ID NO 71
<211> LENGTH: 505
<212> TYPE: PRT
<213> ORGANISM: artificial
<220> FEATURE:
<223> OTHER INFORMATION: CD33 AH11 HL x I2C HL

<400> SEQUENCE: 71

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Met Glu Ile Ser Ser Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175
```

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200             205

Gly Ser Gly Thr Asp Phe Thr Leu Thr Ile Asp Ser Leu Gln Pro Glu
        210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
            290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
        370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 72
<211> LENGTH: 1515
<212> TYPE: DNA
<213> ORGANISM: artificial
<220> FEATURE:
<223> OTHER INFORMATION: CD33 AH11 HL x I2C HL

<400> SEQUENCE: 72
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180

```
gctgatgact tcaagggacg ggttaccatg acttcggata cctctaccag cactgcctat      240
atggaaatca gcagcctcag aagtgatgac acggctgtat attactgtgc gcgctggagt      300
tggagtgatg gttactacgt ttactttgac tactggggcc aaggcactac ggtcaccgtc      360
tcctcaggtg gtggtggttc tggcggcggc ggctccggtg gtggtggttc tgacatcgtg      420
atgacacagt ctccagactc cctgactgtg tctctgggcg agaggaccac catcaactgc      480
aagtccagcc agagtgtttt agacagctcc aagaataaga actccttagc ttggtaccag      540
cagaaaccag gacagcctcc taaattactc ctttcctggg catctacgcg ggaatccggg      600
atccctgacc gattcagtgg cagcgggtct gggacagatt tcactctcac tattgacagc      660
ctgcagcctg aagattctgc aacttactat tgtcaacagt ctgcccactt cccgatcacc      720
tttggccaag ggacacgact ggagattaaa tccggaggtg gtggctccga ggtgcagctg      780
gtcgagtctg gaggaggatt ggtgcagcct ggagggtcat tgaaactctc atgtgcagcc      840
tctggattca ccttcaataa gtacgccatg aactgggtcc gccaggctcc aggaaagggt      900
ttggaatggg ttgctcgcat aagaagtaaa tataataatt atgcaacata ttatgccgat      960
tcagtgaaag acaggttcac catctccaga gatgattcaa aaacactgcc tatctacaa      1020 atgaacaact gaaaactga ggacactgcc gtgtactact gtgtgagaca tgggaacttc      1080
ggtaatagct acatatccta ctgggcttac tggggccaag ggactctggt caccgtctcc      1140
tcaggtggtg gtggttctgg cggcggcggc tccggtggtg gtggttctca gactgttgtg      1200
actcaggaac cttcactcac cgtatcacct ggtggaacag tcacactcac ttgtggctcc      1260
tcgactgggg ctgttacatc tggcaactac ccaaactggg tccaacaaaa accaggtcag      1320 gcacccgtg gtctaatagg tgggactaag ttcctcgccc ccggtactcc tgccagattc      1380
tcaggctccc tgcttggagg caaggctgcc ctcaccctct caggggtaca gccagaggat      1440
gaggcagaat attactgtgt tctatggtac agcaaccgct gggtgttcgg tggaggaacc      1500
aaactgactg tccta                                                      1515
```

<210> SEQ ID NO 73
<211> LENGTH: 122
<212> TYPE: PRT
<213> ORGANISM: artificial
<220> FEATURE:
<223> OTHER INFORMATION: CD33 VH of B3

<400> SEQUENCE: 73

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120
```

<210> SEQ ID NO 74
<211> LENGTH: 5
<212> TYPE: PRT
<213> ORGANISM: artificial
<220> FEATURE:
<223> OTHER INFORMATION: CD33 HCDR1 of B3

<400> SEQUENCE: 74

Asn Tyr Gly Met Asn
1               5

<210> SEQ ID NO 75
<211> LENGTH: 17
<212> TYPE: PRT
<213> ORGANISM: artificial
<220> FEATURE:
<223> OTHER INFORMATION: CD33 HCDR2 of B3

<400> SEQUENCE: 75

Trp Ile Asn Thr Tyr Thr Gly Glu Thr Asn Tyr Ala Asp Lys Phe Gln
1               5                   10                  15

Gly

<210> SEQ ID NO 76
<211> LENGTH: 13
<212> TYPE: PRT
<213> ORGANISM: artificial
<220> FEATURE:
<223> OTHER INFORMATION: CD33 HCDR3 of B3

<400> SEQUENCE: 76

Trp Ser Trp Ser Asp Gly Tyr Tyr Val Tyr Phe Asp Tyr
1               5                   10

<210> SEQ ID NO 77
<211> LENGTH: 366
<212> TYPE: DNA
<213> ORGANISM: artificial
<220> FEATURE:
<223> OTHER INFORMATION: CD33 VH of B3

<400> SEQUENCE: 77
caggtgcagc tggtgcagtc tggagctgag gtgaagaagc ctggagagtc agtcaaggtc     60
tcctgcaagg ctagcgggta taccttcaca aactatggaa tgaactgggt gaagcaggct    120
ccaggacagg gtttagagtg gatgggctgg ataaacacct acactggaga gacaaactat    180
gctgataagt tccagggacg cgttaccttc acttcggata cctctaccag cactgcctat    240
atggaactcc gcaacctcaa aagtgatgac acggctgtat attactgtgc gcgctggagt    300
tggagtgatg gttactacgt ttactttgac tactggggcc aaggcactac ggtcaccgtc    360
tcctca                                                              366

<210> SEQ ID NO 78
<211> LENGTH: 113
<212> TYPE: PRT
<213> ORGANISM: artificial
<220> FEATURE:
<223> OTHER INFORMATION: CD33 VL of B3

<400> SEQUENCE: 78

Asp Ile Val Met Thr Gln Ser Pro Asp Ser Met Thr Val Ser Leu Gly
1               5                   10                  15

```
Glu Arg Thr Thr Ile Asn Cys Lys Ser Ser Gln Ser Val Leu Asp Ser
                20                  25                  30

Ser Thr Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Asp Ile
            100                 105                 110

Lys

<210> SEQ ID NO 79
<211> LENGTH: 17
<212> TYPE: PRT
<213> ORGANISM: artificial
<220> FEATURE:
<223> OTHER INFORMATION: CD33 LCDR1 of B3

<400> SEQUENCE: 79

Lys Ser Ser Gln Ser Val Leu Asp Ser Ser Thr Asn Lys Asn Ser Leu
1               5                   10                  15

Ala

<210> SEQ ID NO 80
<211> LENGTH: 6
<212> TYPE: PRT
<213> ORGANISM: artificial
<220> FEATURE:
<223> OTHER INFORMATION: CD33 LCDR2 of B3

<400> SEQUENCE: 80

Trp Ala Ser Thr Arg Glu
1               5

<210> SEQ ID NO 81
<211> LENGTH: 9
<212> TYPE: PRT
<213> ORGANISM: artificial
<220> FEATURE:
<223> OTHER INFORMATION: CD33LCDR3 of B3

<400> SEQUENCE: 81

Gln Gln Ser Ala His Phe Pro Ile Thr
1               5

<210> SEQ ID NO 82
<211> LENGTH: 339
<212> TYPE: DNA
<213> ORGANISM: artificial
<220> FEATURE:
<223> OTHER INFORMATION: CD33 VL of B3

<400> SEQUENCE: 82
gacatcgtga tgacacagtc tccagactcc atgactgtgt ctctgggcga gaggaccacc    60
atcaactgca agtccagcca gagtgtttta gacagctcca cgaataagaa ctccttagct   120
tggtaccagc agaaaccagg acagcctcct aaattactcc tttcctgggc atctacgcgg   180
gaatccggga tccctgaccg attcagtggc agcgggtctg ggacagattt cactctcact   240
```

```
attgacagcc tgcagcctga agattctgca acttactatt gtcaacagtc tgcccacttc    300
ccgatcacct ttggccaagg gacacgactg gacattaaa                           339
```

<210> SEQ ID NO 83
<211> LENGTH: 250
<212> TYPE: PRT
<213> ORGANISM: artificial
<220> FEATURE:
<223> OTHER INFORMATION: CD33 HL of B3

<400> SEQUENCE: 83

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Met Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Asp Ile Lys
                245                 250
```

<210> SEQ ID NO 84
<211> LENGTH: 750
<212> TYPE: DNA
<213> ORGANISM: artificial
<220> FEATURE:
<223> OTHER INFORMATION: CD33 HL of B3

<400> SEQUENCE: 84

```
caggtgcagc tggtgcagtc tggagctgag gtgaagaagc ctggagagtc agtcaaggtc    60
tcctgcaagg ctagcgggta ccttcaca aactatggaa tgaactgggt gaagcaggct     120
ccaggacagg gtttagagtg gatgggctgg ataaacacct acactggaga gacaaactat    180
gctgataagt tccagggacg cgttaccttc acttcggata cctctaccag cactgcctat    240
```

```
atggaactcc gcaacctcaa aagtgatgac acggctgtat attactgtgc gcgctggagt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc catgactgtg tctctgggcg agaggaccac catcaactgc    480
aagtccagcc agagtgtttt agacagctcc acgaataaga actccttagc ttggtaccag    540
cagaaaccag gacagcctcc taaattactc ctttcctggg catctacgcg ggaatccggg    600
gtccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggacattaaa                                      750
```

<210> SEQ ID NO 85
<211> LENGTH: 505
<212> TYPE: PRT
<213> ORGANISM: artificial
<220> FEATURE:
<223> OTHER INFORMATION: CD33 B3 HL x H2C HL

<400> SEQUENCE: 85

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Met Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Asp Ile Lys Ser Gly Gly Gly Gly Ser
                245                 250                 255

Glu Val Gln Leu Val Glu Ser Gly Gly Gly Leu Val Gln Pro Gly Gly
            260                 265                 270
```

```
Ser Leu Lys Leu Ser Cys Ala Ala Ser Gly Phe Thr Phe Asn Lys Tyr
        275                 280                 285
Ala Met Asn Trp Val Arg Gln Ala Pro Gly Lys Gly Leu Glu Trp Val
    290                 295                 300
Ala Arg Ile Arg Ser Lys Tyr Asn Asn Tyr Ala Thr Tyr Tyr Ala Asp
305                 310                 315                 320
Ser Val Lys Asp Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Ile Ser Tyr Trp
        355                 360                 365
Ala Tyr Trp Gly Gln Gly Thr Leu Val Thr Val Ser Ser Gly Gly Gly
    370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Tyr Tyr Pro Asn
            420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
    450                 455                 460
Leu Gly Gly Lys Ala Ala Leu Thr Leu Ser Gly Val Gln Pro Glu Asp
465                 470                 475                 480
Glu Ala Glu Tyr Tyr Cys Ala Leu Trp Tyr Ser Asn Arg Trp Val Phe
                485                 490                 495
Gly Gly Gly Thr Lys Leu Thr Val Leu
            500                 505

<210> SEQ ID NO 86
<211> LENGTH: 1515
<212> TYPE: DNA
<213> ORGANISM: artificial
<220> FEATURE:
<223> OTHER INFORMATION: CD33 B3 HL x H2C HL

<400> SEQUENCE: 86
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
ccaggacagg gtttagagtg gatgggctgg ataaacacct acactggaga gacaaactat     180
gctgataagt tccagggacg cgttaccttc acttcggata cctctaccag cactgcctat     240
atggaactcc gcaacctcaa aagtgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc catgactgtg tctctgggcg agagccac catcaactgc     480 aagtccagcc agagtgtttt agacagctcc acgaataaga actccttagc ttggtaccag     540
cagaaaccag gacagcctcc taaattactc ctttcctggg catctacgcg ggaatccggg     600
atccctgacc gattcagtgg cagcgggtct gggacagatt tcactctcac tattgacagc     660
ctgcagcctg aagattctgc aacttactat tgtcaacagt ctgcccactt cccgatcacc     720
```

-continued

```
tttggccaag ggacacgact ggacattaaa tccggaggtg gtggctccga ggtgcagctg      780
gtcgagtctg gaggaggatt ggtgcagcct ggagggtcat tgaaactctc atgtgcagcc      840
tctggattca ccttcaataa gtacgccatg aactgggtcc gccaggctcc aggaaagggt      900
ttggaatggg ttgctcgcat aagaagtaaa tataataatt atgcaacata ttatgccgat      960
tcagtgaaag acaggttcac catctccaga gatgattcaa aaacactgcc tatctacaa     1020 atgaacaact tgaaaactga ggacactgcc gtgtactact gtgtgagaca tgggaacttc     1080
ggtaatagct acatatccta ctgggcttac tggggccaag ggactctggt caccgtctcc     1140
tcaggtggtg gtggttctgg cggcggcggc tccggtggtg gtggttctca gactgttgtg     1200
actcaggaac cttcactcac cgtatcacct ggtggaacag tcacactcac ttgtggctcc     1260
tcgactgggg ctgttacatc tggctactac ccaaactggg tccaacaaaa accaggtcag     1320 gcacccccgtg gtctaatagg tgggactaag ttcctcgccc ccggtactcc tgccagattc     1380
tcaggctccc tgcttggagg caaggctgcc ctcaccctct cagggtaca gccagaggat     1440 gaggcagaat attactgtgc tctatggtac agcaaccgct gggtgttcgg tggaggaacc     1500
aaactgactg tccta                                                     1515
```

```
<210> SEQ ID NO 87
<211> LENGTH: 505
<212> TYPE: PRT
<213> ORGANISM: artificial
<220> FEATURE:
<223> OTHER INFORMATION: CD33 B3 HL x F12Q HL

<400> SEQUENCE: 87
```

```
Gln Val Gln Leu Val Gln Ser Gly Ala Glu Val Lys Lys Pro Gly Glu
 1               5                  10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Met Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
```

```
                210                 215                 220
Asp Ser Ala Thr Tyr Tyr Cys Gln Gln Ser Ala His Phe Pro Ile Thr
225                 230                 235                 240

Phe Gly Gln Gly Thr Arg Leu Asp Ile Lys Ser Gly Gly Gly Gly Ser
            245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Ser Tyr
            275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Val Ser Trp Trp
            355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
            405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
            485                 490                 495

Gly Gly Gly Thr Lys Leu Thr Val Leu
            500                 505

<210> SEQ ID NO 88
<211> LENGTH: 1515
<212> TYPE: DNA
<213> ORGANISM: artificial
<220> FEATURE:
<223> OTHER INFORMATION: CD33 B3 HL x F12Q HL

<400> SEQUENCE: 88
caggtgcagc tggtgcagtc tggagctgag gtgaagaagc tggagagtca gtcaaggtc        60 tcctgcaagg ctagcgggta taccttcaca aactatggaa tgaactgggt gaagcaggct     120
ccaggacagg gtttagagtg gatgggctgg ataaacacct acactggaga gacaaaactat    180 gctgataagt tccagggacg cgttaccttc acttcggata cctctaccag cactgcctat     240
atggaactcc gcaacctcaa aagtgatgac acggctgtat attactgtgc gcgctggagt    300
tggagtgatg gttactacgt ttactttgac tactggggcc aaggcactac ggtcaccgtc     360
tcctcaggtg gtggtggttc tggcggcggc ggctccggtg gtggtggttc tgacatcgtg    420
```

```
atgacacagt ctccagactc catgactgtg tctctgggcg agaggaccac catcaactgc    480
aagtccagcc agagtgtttt agacagctcc acgaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggacattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaaacactgc ctatctacaa    1020
atgaacaact tgaaaactga ggacactgcc gtgtactact gtgtgagaca tgggaacttc    1080
ggtaatagct acgtttcctg gtgggcttac tggggccaag gactctggt caccgtctcc    1140 tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320 gcacccgtg gtctaatagg tgggactaag ttcctcgccc ccgtactcc tgccagattc    1380 tcaggctccc tgcttggagg caaggctgcc ctcacctct caggggtaca gccagaggat    1440
gaggcagaat attactgtgt tctatggtac agcaaccgct gggtgttcgg tggaggaacc    1500
aaactgactg tccta                                                    1515
```

<210> SEQ ID NO 89
<211> LENGTH: 505
<212> TYPE: PRT
<213> ORGANISM: artificial
<220> FEATURE:
<223> OTHER INFORMATION: CD33 B3 HL x I2C HL

<400> SEQUENCE: 89

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Met Thr Val Ser Leu Gly Glu Arg Thr Thr Ile Asn Cys
145                 150                 155                 160
```

```
Lys Ser Ser Gln Ser Val Leu Asp Ser Ser Thr Asn Lys Asn Ser Leu
                165                 170                 175
Ala Trp Tyr Gln Gln Lys Pro Gly Gln Pro Pro Lys Leu Leu Leu Ser
            180                 185                 190
Trp Ala Ser Thr Arg Glu Ser Gly Ile Pro Asp Arg Phe Ser Gly Ser
        195                 200                 205
Gly Ser Gly Thr Asp Phe Thr Leu Thr Ile Asp Ser Leu Gln Pro Glu
    210                 215                 220
Asp Ser Ala Thr Tyr Tyr Cys Gln Gln Ser His Phe Pro Ile Thr
225                 230                 235                 240
Phe Gly Gln Gly Thr Arg Leu Asp Ile Lys Ser Gly Gly Gly Gly Ser
                245                 250                 255
Glu Val Gln Leu Val Glu Ser Gly Gly Gly Leu Val Gln Pro Gly Gly
            260                 265                 270
Ser Leu Lys Leu Ser Cys Ala Ala Ser Gly Phe Thr Phe Asn Lys Tyr
        275                 280                 285
Ala Met Asn Trp Val Arg Gln Ala Pro Gly Lys Gly Leu Glu Trp Val
    290                 295                 300
Ala Arg Ile Arg Ser Lys Tyr Asn Asn Tyr Ala Thr Tyr Tyr Ala Asp
305                 310                 315                 320
Ser Val Lys Asp Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Ile Ser Tyr Trp
        355                 360                 365
Ala Tyr Trp Gly Gln Gly Thr Leu Val Thr Val Ser Ser Gly Gly Gly
    370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Asn Tyr Pro Asn
            420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
    450                 455                 460
Leu Gly Gly Lys Ala Ala Leu Thr Leu Ser Gly Val Gln Pro Glu Asp
465                 470                 475                 480
Glu Ala Glu Tyr Tyr Cys Val Leu Trp Tyr Ser Asn Arg Trp Val Phe
                485                 490                 495
Gly Gly Gly Thr Lys Leu Thr Val Leu
                500                 505

<210> SEQ ID NO 90
<211> LENGTH: 1515
<212> TYPE: DNA
<213> ORGANISM: artificial
<220> FEATURE:
<223> OTHER INFORMATION: CD33 B3 HL x I2C HL

<400> SEQUENCE: 90
caggtgcagc tggtgcagtc tggagctgag gtgaagaagc ctggagagtc agtcaaggtc      60
tcctgcaagg ctagcgggta taccttcaca aactatggaa tgaactgggt gaagcaggct     120
```

```
ccaggacagg gtttagagtg gatgggctgg ataaacacct acactggaga gacaaactat    180
gctgataagt tccagggacg cgttaccttc acttcggata cctctaccag cactgcctat    240
atggaactcc gcaacctcaa aagtgatgac acggctgtat attactgtgc gcgctggagt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc catgactgtg tctctgggcg agaggaccac catcaactgc    480
aagtccagcc agagtgtttt agacagctcc acgaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggacattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaaacactgc ctatctacaa    1020
atgaacaact tgaaaactga ggacactgcc gtgtactact gtgtgagaca tgggaacttc    1080
ggtaatagct acatatccta ctgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcaccccgtg gtctaatagg tgggactaag ttcctcgccc ccggtactcc tgccagattc    1380
tcaggctccc tgcttggagg caaggctgcc ctcaccctct caggggtaca gccagaggat    1440
gaggcagaat attactgtgt ctatggtac agcaaccgct gggtgttcgg tggaggaacc    1500
aaactgactg tccta    1515
```

<210> SEQ ID NO 91
<211> LENGTH: 122
<212> TYPE: PRT
<213> ORGANISM: artificial
<220> FEATURE:
<223> OTHER INFORMATION: CD33 VH of F2

<400> SEQUENCE: 91

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 92
<211> LENGTH: 5
<212> TYPE: PRT
<213> ORGANISM: artificial
<220> FEATURE:
<223> OTHER INFORMATION: CD33 HCDR1 of F2

<400> SEQUENCE: 92

Asn Tyr Gly Met Asn
1               5

<210> SEQ ID NO 93
<211> LENGTH: 17
<212> TYPE: PRT
<213> ORGANISM: artificial
<220> FEATURE:
<223> OTHER INFORMATION: CD33 HCDR2 of F2

<400> SEQUENCE: 93

Trp Ile Asn Thr Tyr Thr Gly Glu Thr Asn Tyr Ala Asp Lys Phe Gln
1               5                   10                  15

Gly

<210> SEQ ID NO 94
<211> LENGTH: 13
<212> TYPE: PRT
<213> ORGANISM: artificial
<220> FEATURE:
<223> OTHER INFORMATION: CD33 HCDR3 of F2

<400> SEQUENCE: 94

Trp Ser Trp Ser Asp Gly Tyr Tyr Val Tyr Phe Asp Tyr
1               5                   10

<210> SEQ ID NO 95
<211> LENGTH: 366
<212> TYPE: DNA
<213> ORGANISM: artificial
<220> FEATURE:
<223> OTHER INFORMATION: CD33 VH of F2

<400> SEQUENCE: 95
caggtgcagc tggtgcagtc tggagctgag gtgaagaagc ctggagagtc agtcaaggtc      60
tcctgcaagg ctagcgggta taccttcaca actatggaa tgaactgggt gaagcaggct      120
ccaggacagg gtttagagtg gatgggctgg ataaacacct acactggaga gacaaactat     180
gctgataagt tccagggacg cgttaccttc acttcggata cctctaccag cactgcctat     240
atggaactcc gcaacctcaa aagtgatgac acggctgtat attactgtgc gcgctggagt     300
tggagtgatg gttactacgt ttactttgac tactggggcc aaggcactac ggtcaccgtc     360
tcctca                                                                366

<210> SEQ ID NO 96
<211> LENGTH: 113
<212> TYPE: PRT
<213> ORGANISM: artificial
<220> FEATURE:
<223> OTHER INFORMATION: CD33 VL of F2

<400> SEQUENCE: 96

Asp Ile Val Met Thr Gln Ser Pro Asp Ser Leu Ser Val Ser Leu Gly
1               5                   10                  15

Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 97
<211> LENGTH: 17
<212> TYPE: PRT
<213> ORGANISM: artificial
<220> FEATURE:
<223> OTHER INFORMATION: CD33 LCDR1 of F2

<400> SEQUENCE: 97

Lys Ser Ser Gln Ser Val Leu Asp Ser Ser Thr Asn Lys Asn Ser Leu
1               5                   10                  15

Ala

<210> SEQ ID NO 98
<211> LENGTH: 7
<212> TYPE: PRT
<213> ORGANISM: artificial
<220> FEATURE:
<223> OTHER INFORMATION: CD33 LCDR2 of F2

<400> SEQUENCE: 98

Trp Ala Ser Thr Arg Glu Ser
1               5

<210> SEQ ID NO 99
<211> LENGTH: 9
<212> TYPE: PRT
<213> ORGANISM: artificial
<220> FEATURE:
<223> OTHER INFORMATION: CD33 LCDR3 of F2

<400> SEQUENCE: 99

Gln Gln Ser Ala His Phe Pro Ile Thr
1               5

<210> SEQ ID NO 100
<211> LENGTH: 339
<212> TYPE: DNA
<213> ORGANISM: artificial
<220> FEATURE:
<223> OTHER INFORMATION: CD33 VL of F2

<400> SEQUENCE: 100
gacatcgtga tgacacagtc tccagactcc ctgtctgtgt ctctgggcga gaggaccacc        60
atcaactgca agtccagcca gagtgtttta gacagctcca cgaataagaa ctccttagct       120
tggtaccagc agaaaccagg acagcctcct aaattactcc tttcctgggc atctacgcgg       180

```
gaatccggga tccctgaccg attcagtggc agcgggtctg ggacagattt cactctcact    240
attgacagcc tgcagcctga agattctgca acttactatt gtcaacagtc tgcccacttc    300
ccgatcacct ttggccaagg gacacgactg gagattaaa                           339
```

<210> SEQ ID NO 101
<211> LENGTH: 250
<212> TYPE: PRT
<213> ORGANISM: artificial
<220> FEATURE:
<223> OTHER INFORMATION: CD33 HL of F2

<400> SEQUENCE: 101

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Ser Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250
```

<210> SEQ ID NO 102
<211> LENGTH: 750
<212> TYPE: DNA
<213> ORGANISM: artificial
<220> FEATURE:
<223> OTHER INFORMATION: CD33 HL of F2

<400> SEQUENCE: 102

```
caggtgcagc tggtgcagtc tggagctgag gtgaagaagc ctggagagtc agtcaaggtc     60
tcctgcaagg ctagcgggta taccttcaca aactatggaa tgaactgggt gaagcaggct    120
```

```
ccaggacagg gtttagagtg gatgggctgg ataaacacct acactggaga gacaaactat    180
gctgataagt tccagggacg cgttaccttc acttcggata cctctaccag cactgcctat    240
atggaactcc gcaacctcaa aagtgatgac acggctgtat attactgtgc gcgctggagt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgtctgtg tctctgggcg agaggaccac catcaactgc    480
aagtccagcc agagtgtttt agacagctcc acgaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa                                      750
```

<210> SEQ ID NO 103
<211> LENGTH: 505
<212> TYPE: PRT
<213> ORGANISM: artificial
<220> FEATURE:
<223> OTHER INFORMATION: CD33 F2 HL x H2C HL

<400> SEQUENCE: 103

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Ser Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255
```

```
Glu Val Gln Leu Val Glu Ser Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
        340                 345                 350

Tyr Cys Val Arg His Gly Asn Phe Gly Asn Ser Tyr Ile Ser Tyr Trp
    355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
            405                 410                 415

Thr Cys Gly Ser Ser Thr Gly Ala Val Thr Ser Gly Tyr Tyr Pro Asn
        420                 425                 430

Trp Val Gln Gln Lys Pro Gly Gln Ala Pro Arg Gly Leu Ile Gly Gly
    435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
            470                 475                 480
465

Glu Ala Glu Tyr Tyr Cys Ala Leu Trp Tyr Ser Asn Arg Trp Val Phe
        485                 490                 495

Gly Gly Gly Thr Lys Leu Thr Val Leu
                500                 505

<210> SEQ ID NO 104
<211> LENGTH: 1515
<212> TYPE: DNA
<213> ORGANISM: artificial
<220> FEATURE:
<223> OTHER INFORMATION: CD33 F2 HL x H2C HL

<400> SEQUENCE: 104
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gacaaactat   180
gctgataagt tccagggacg cgttaccttc acttcggata cctctaccag cactgcctat   240
atggaactcc gcaacctcaa aagtgatgac acggctgtat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgtctgtg tctctgggcg agaggaccac catcaactgc   480
aagtccagcc agagtgtttt agacagctcc acgaataaga actccttagc ttggtaccag   540
cagaaaccag gacagcctcc taaattactc ctttcctggg catctacgcg ggaatccggg   600
```

```
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaaacactgc ctatctacaa   1020
atgaacaact tgaaaactga ggacactgcc gtgtactact gtgtgagaca tgggaacttc   1080
ggtaatagct acatatccta ctgggcttac tggggccaag ggactctggt caccgtctcc   1140
tcaggtggtg gtggttctgg cggcggcggc tccggtggtg gtggttctca gactgttgtg   1200
actcaggaac cttcactcac cgtatcacct ggtggaacag tcacactcac ttgtggctcc   1260
tcgactgggg ctgttacatc tggctactac ccaaactggg tccaacaaaa accaggtcag   1320
gcaccccgtg gtctaatagg tggactaag ttcctcgccc ccgtactcc tgccagattc     1380 tcaggctccc tgcttggagg caaggctgcc ctcaccctct caggggtaca gccagaggat   1440
gaggcagaat attactgtgc tctatggtac agcaaccgct gggtgttcgg tggaggaacc   1500
aaactgactg tccta                                                    1515
```

<210> SEQ ID NO 105
<211> LENGTH: 505
<212> TYPE: PRT
<213> ORGANISM: artificial
<220> FEATURE:
<223> OTHER INFORMATION: CD33 F2 HL x F12Q HL

<400> SEQUENCE: 105

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Ser Val Ser Leu Gly Glu Arg Thr Thr Ile Asn Cys
145                 150                 155                 160

Lys Ser Ser Gln Ser Val Leu Asp Ser Thr Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser 195                 200                 205
Gly Ser Gly Thr Asp Phe Thr Leu Thr Ile Asp Ser Leu Gln Pro Glu
        210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Leu Val Gln Pro Gly Gly
        260                 265                 270

Ser Leu Lys Leu Ser Cys Ala Ala Ser Gly Phe Thr Phe Asn Ser Tyr
        275                 280                 285

Ala Met Asn Trp Val Arg Gln Ala Pro Gly Lys Gly Leu Glu Trp Val
        290                 295                 300

Ala Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
        340                 345                 350

Tyr Cys Val Arg His Gly Asn Phe Gly Asn Ser Tyr Val Ser Trp Trp
        355                 360                 365

Ala Tyr Trp Gly Gln Gly Thr Leu Val Thr Val Ser Ser Gly Gly Gly
        370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
        420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
                500                 505

<210> SEQ ID NO 106
<211> LENGTH: 1515
<212> TYPE: DNA
<213> ORGANISM: artificial
<220> FEATURE:
<223> OTHER INFORMATION: CD33 F2 HL x F12Q HL

<400> SEQUENCE: 106
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gacaaactat   180
gctgataagt tccagggacg cgttaccttc acttcggata cctctaccag cactgcctat   240
atggaactcc gcaacctcaa aagtgatgac acggctgtat attactgtgc gcgctggagt   300

```
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgtctgtg tctctgggcg agaggaccac catcaactgc    480
aagtccagcc agagtgtttt agacagctcc acgaataaga actccttagc ttggtaccag    540
cagaaaccag acagcctcc taaattactc ctttcctggg catctacgcg ggaatccggg    600
atccctgacc gattcagtgg cagcgggtct gggacagatt tcactctcac tattgacagc    660
ctgcagcctg aagattctgc aacttactat tgtcaacagt ctgcccactt cccgatcacc    720
tttggccaag gacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaacactgc ctatctacaa   1020
atgaacaact gaaaactga ggacactgcc gtgtactact gtgtgagaca tgggaacttc   1080
ggtaatagct acgtttcctg gtgggcttac tggggccaag gactctggt caccgtctcc   1140
tcaggtggtg gtggttctgg cggcggcggc tccggtggtg gtggttctca gactgttgtg   1200
actcaggaac cttcactcac cgtatcacct ggtggaacag tcacactcac ttgtggctcc   1260
tcgactgggc tgttacatc tggcaactac ccaaactggg tccaacaaaa accaggtcag   1320
gcacccgtg gtctaatagg tgggactaag ttcctcgcc ccggtactcc tgccagattc   1380
tcaggctccc tgcttggagg caaggctgcc ctcaccctct caggggtaca gccagaggat   1440
gaggcagaat attactgtgt tctatggtac agcaaccgct gggtgttcgg tggaggaacc   1500
aaactgactg tccta                                                    1515
```

<210> SEQ ID NO 107
<211> LENGTH: 505
<212> TYPE: PRT
<213> ORGANISM: artificial
<220> FEATURE:
<223> OTHER INFORMATION: CD33 F2 HL x I2C HL

<400> SEQUENCE: 107

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140
```

```
Pro Asp Ser Leu Ser Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
            165                 170                 175

Ala Trp Tyr Gln Gln Lys Pro Gly Gln Pro Pro Lys Leu Leu Leu Ser
        180                 185                 190

Trp Ala Ser Thr Arg Glu Ser Gly Ile Pro Asp Arg Phe Ser Gly Ser
    195                 200                 205

Gly Ser Gly Thr Asp Phe Thr Leu Thr Ile Asp Ser Leu Gln Pro Glu
210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Leu Val Gln Pro Gly Gly
                260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
        290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
                500                 505

<210> SEQ ID NO 108
<211> LENGTH: 1515
<212> TYPE: DNA
<213> ORGANISM: artificial
<220> FEATURE:
<223> OTHER INFORMATION: CD33 F2 HL x I2C HL

<400> SEQUENCE: 108
```

```
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gacaaactat   180
gctgataagt tccagggacg cgttaccttc acttcggata cctctaccag cactgcctat   240
atggaactcc gcaacctcaa aagtgatgac acggctgtat attactgtgc gcgctggagt   300
tggagtgatg gttactacgt ttactttgac tactggggcc aaggcactac ggtcaccgtc   360
tcctcaggtg gtggtggttc tggcggcggc ggctccggtg gtggtggttc tgacatcgtg   420
atgacacagt ctccagactc cctgtctgtg tctctgggcg agaggaccac catcaactgc   480
aagtccagcc agagtgtttt agacagctcc acgaataaga actccttagc ttggtaccag   540
cagaaaccag gacagcctcc taaattactc ctttcctggg catctacgcg ggaatccggg   600
atccctgacc gattcagtgg cagcgggtct gggacagatt tcactctcac tattgacagc   660
ctgcagcctg aagattctgc aacttactat tgtcaacagt ctgcccactt cccgatcacc   720
tttggccaag ggacacgact ggagattaaa tccggaggtg gtggctccga ggtgcagctg   780
gtcgagtctg gaggaggatt ggtgcagcct ggagggtcat tgaaactctc atgtgcagcc   840
tctggattca ccttcaataa gtacgccatg aactgggtcc gccaggctcc aggaaagggt   900
ttggaatggg ttgctcgcat aagaagtaaa tataataatt atgcaacata ttatgccgat   960
tcagtgaaag acaggttcac catctccaga gatgattcaa aaaacactgc ctatctacaa  1020
atgaacaact tgaaaactga ggacactgcc gtgtactact gtgtgagaca tgggaacttc  1080
ggtaatagct acatatccta ctgggcttac tggggccaag ggactctggt caccgtctcc  1140
tcaggtggtg gtggttctgg cggcggcggc tccggtggtg gtggttctca gactgttgtg  1200
actcaggaac cttcactcac cgtatcacct ggtggaacag tcacactcac ttgtggctcc  1260
tcgactgggg ctgttacatc tggcaactac ccaaactggg tccaacaaaa accaggtcag  1320
gcacccctgg gtctaatagg tgggactaag ttcctcgccc ccggtactcc tgccagattc  1380
tcaggctccc tgcttggagg caaggctgcc ctcacccctct caggggtaca gccagaggat  1440
gaggcagaat attactgtgt tctatggtac agcaaccgct gggtgttcgg tggaggaacc  1500
aaactgactg tccta                                                   1515
```

<210> SEQ ID NO 109
<211> LENGTH: 122
<212> TYPE: PRT
<213> ORGANISM: artificial
<220> FEATURE:
<223> OTHER INFORMATION: CD33 VH of B10

<400> SEQUENCE: 109

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 110
<211> LENGTH: 5
<212> TYPE: PRT
<213> ORGANISM: artificial
<220> FEATURE:
<223> OTHER INFORMATION: CD33 HCDR1 of B10

<400> SEQUENCE: 110

Asn Tyr Gly Met Asn
1               5

<210> SEQ ID NO 111
<211> LENGTH: 17
<212> TYPE: PRT
<213> ORGANISM: artificial
<220> FEATURE:
<223> OTHER INFORMATION: CD33HCDR2 of B10

<400> SEQUENCE: 111

Trp Ile Asn Thr Tyr Thr Gly Glu Pro Thr Tyr Ala Asp Lys Phe Gln
1               5                   10                  15

Gly

<210> SEQ ID NO 112
<211> LENGTH: 13
<212> TYPE: PRT
<213> ORGANISM: artificial
<220> FEATURE:
<223> OTHER INFORMATION: CD33 HCDR3 of B10

<400> SEQUENCE: 112

Trp Ser Trp Ser Asp Gly Tyr Tyr Val Tyr Phe Asp Tyr
1               5                   10

<210> SEQ ID NO 113
<211> LENGTH: 366
<212> TYPE: DNA
<213> ORGANISM: artificial
<220> FEATURE:
<223> OTHER INFORMATION: CD33 VH of B10

<400> SEQUENCE: 113
caggtgcagc tggtgcagtc tggagctgag gtgaagaagc ctggtgagtc agtcaaggtc      60
tcctgcaagg ctagcgggta taccttcaca aactatggaa tgaactgggt gaagcaggct     120
ccaggacagg gtttagagtg gatgggctgg ataaacacct acactggaga gccaacctat     180
gctgataagt tccagggacg cgttaccatg actacggata cctctaccag cactgcctat     240
atggaaatcc gcaacctcag aagtgatgac acggctgtat attactgtgc gcgctggagt     300
tggagtgatg gttactacgt ttactttgac tactggggcc aaggcactac ggtcaccgtc     360
tcctca                                                                366

<210> SEQ ID NO 114
<211> LENGTH: 113
<212> TYPE: PRT
<213> ORGANISM: artificial
<220> FEATURE:
<223> OTHER INFORMATION: CD33 VL of B10

<400> SEQUENCE: 114

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Asn Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Gly Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 115
<211> LENGTH: 17
<212> TYPE: PRT
<213> ORGANISM: artificial
<220> FEATURE:
<223> OTHER INFORMATION: CD33 LCDR1 of B10

<400> SEQUENCE: 115

Lys Ser Ser Gln Ser Val Leu Asp Ser Ser Asn Asn Lys Asn Ser Leu
1               5                   10                  15

Ala

<210> SEQ ID NO 116
<211> LENGTH: 7
<212> TYPE: PRT
<213> ORGANISM: artificial
<220> FEATURE:
<223> OTHER INFORMATION: CD33 LCDR2 of B10

<400> SEQUENCE: 116

Trp Ala Ser Thr Arg Glu Ser
1               5

<210> SEQ ID NO 117
<211> LENGTH: 9
<212> TYPE: PRT
<213> ORGANISM: artificial
<220> FEATURE:
<223> OTHER INFORMATION: CD33 LCDR3 of B10

<400> SEQUENCE: 117

Gln Gln Ser Ala His Phe Pro Ile Thr
1               5

<210> SEQ ID NO 118
<211> LENGTH: 339
<212> TYPE: DNA
<213> ORGANISM: artificial
<220> FEATURE:
<223> OTHER INFORMATION: CD33 VL of B10

<400> SEQUENCE: 118
gacatcgtga tgacacagtc tccagactcc ctgactgtgt ctctgggcga gaggaccacc    60

| | |
|---|---|
| atcaactgca agtccagcca gagtgtttta gacagctcca acaataagaa ctccttagct | 120 |
| tggtaccagc agaaaccagg acagcctcct aaattactcc tttcctgggc atctacgcgg | 180 |
| gaatccggga tccctgaccg attcagtggc agcggttctg ggacagattt cactctcact | 240 |
| attgacggcc tgcagcctga agattctgca acttactatt gtcaacagtc tgcccacttc | 300 |
| ccgatcacct ttggccaagg gacacgactg gagattaaa | 339 |

<210> SEQ ID NO 119
<211> LENGTH: 250
<212> TYPE: PRT
<213> ORGANISM: artificial
<220> FEATURE:
<223> OTHER INFORMATION: CD33 HL of B10

<400> SEQUENCE: 119

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Asn Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Gly Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 120
<211> LENGTH: 750
<212> TYPE: DNA
<213> ORGANISM: artificial
<220> FEATURE:
<223> OTHER INFORMATION: CD33 HL of B10

<400> SEQUENCE: 120

| | |
|---|---|
| caggtgcagc tggtgcagtc tggagctgag gtgaagaagc ctggtgagtc agtcaaggtc | 60 |

```
tcctgcaagg ctagcgggta taccttcaca aactatggaa tgaactgggt gaagcaggct    120
ccaggacagg gtttagagtg gatgggctgg ataaacacct acactggaga gccaacctat    180
gctgataagt tccagggacg cgttaccatg actacggata cctctaccag cactgcctat    240
atggaaatcc gcaacctcag aagtgatgac acggctgtat attactgtgc gcgctggagt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aacaataaga actccttagc ttggtaccag    540
cagaaaccag gacagcctcc taaattactc ctttcctggg catctacgcg ggaatccggg    600
atccctgacc gattcagtgg cagcggttct gggacagatt tcactctcac tattgacggc    660
ctgcagcctg aagattctgc aacttactat tgtcaacagt ctgcccactt cccgatcacc    720
tttggccaag ggacacgact ggagattaaa                                     750
```

```
<210> SEQ ID NO 121
<211> LENGTH: 505
<212> TYPE: PRT
<213> ORGANISM: artificial
<220> FEATURE:
<223> OTHER INFORMATION: CD33 B10 HL x H2C HL

<400> SEQUENCE: 121
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Glu|
|1| | | |5| | | | |10| | | | |15|

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Asn Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Gly Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Ser
              245                 250                 255

Glu Val Gln Leu Val Glu Ser Gly Gly Gly Leu Val Gln Pro Gly Gly
              260                 265                 270

Ser Leu Lys Leu Ser Cys Ala Ala Ser Gly Phe Thr Phe Asn Lys Tyr
              275                 280                 285

Ala Met Asn Trp Val Arg Gln Ala Pro Gly Lys Gly Leu Glu Trp Val
              290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
              325                 330                 335

Ala Tyr Leu Gln Met Asn Asn Leu Lys Thr Glu Asp Thr Ala Val Tyr
              340                 345                 350

Tyr Cys Val Arg His Gly Asn Phe Gly Asn Ser Tyr Ile Ser Tyr Trp
              355                 360                 365

Ala Tyr Trp Gly Gln Gly Thr Leu Val Thr Val Ser Ser Gly Gly Gly
              370                 375                 380

Gly Ser Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
              405                 410                 415

Thr Cys Gly Ser Ser Thr Gly Ala Val Thr Ser Gly Tyr Tyr Pro Asn
              420                 425                 430

Trp Val Gln Gln Lys Pro Gly Gln Ala Pro Arg Gly Leu Ile Gly Gly
              435                 440                 445

Thr Lys Phe Leu Ala Pro Gly Thr Pro Ala Arg Phe Ser Gly Ser Leu
              450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
              485                 490                 495

Gly Gly Gly Thr Lys Leu Thr Val Leu
              500                 505

<210> SEQ ID NO 122
<211> LENGTH: 1515
<212> TYPE: DNA
<213> ORGANISM: artificial
<220> FEATURE:
<223> OTHER INFORMATION: CD33 B10 HL x H2C HL

<400> SEQUENCE: 122
caggtgcagc tggtgcagtc tggagctgag gtgaagaagc ctggtgagtc agtcaaggtc     60
tcctgcaagg ctagcgggta taccttcaca aactatggaa tgaactgggt gaagcaggct    120
ccaggacagg gtttagagtg gatgggctgg ataaacacct acactggaga gccaacctat    180
gctgataagt tccagggacg cgttaccatg actacggata cctctaccag cactgcctat    240
atggaaatcc gcaaccctca gaagtgatga cacggctgta tattactgtg cgcgctggag    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aacaataaga actccttagc ttggtaccag    540

```
cagaaaccag gacagcctcc taaattactc ctttcctggg catctacgcg ggaatccggg      600
atccctgacc gattcagtgg cagcggttct gggacagatt tcactctcac tattgacggc      660
ctgcagcctg aagattctgc aacttactat tgtcaacagt ctgcccactt cccgatcacc      720
tttggccaag gcacacgact ggagattaaa tccggaggtg gtggctccga ggtgcagctg      780
gtcgagtctg gaggaggatt ggtgcagcct ggagggtcat tgaaactctc atgtgcagcc      840
tctggattca ccttcaataa gtacgccatg aactgggtcc gccaggctcc aggaaagggt      900
ttggaatggg ttgctcgcat aagaagtaaa tataataatt atgcaacata ttatgccgat      960
tcagtgaaag acaggttcac catctccaga tgattcaa aaaacactgc ctatctacaa       1020
atgaacaact tgaaaactga ggacactgcc gtgtactact gtgtgagaca tgggaacttc      1080
ggtaatagct acatatccta ctgggcttac tggggccaag ggactctggt caccgtctcc      1140
tcaggtggtg gtggttctgg cggcggcggc tccggtggtg gtggttctca gactgttgtg      1200
actcaggaac cttcactcac cgtatcacct ggtggaacag tcacactcac ttgtggctcc      1260
tcgactgggg ctgttacatc tggctactac ccaaactggg tccaacaaaa accaggtcag      1320
gcacccegtg gtctaatagg tgggactaag ttcctcgccc ccggtactcc tgccagattc      1380
tcaggctccc tgcttggagg caaggctgcc ctcaccctct caggggtaca gccagaggat      1440
gaggcagaat attactgtgc tctatggtac agcaaccgct gggtgttcgg tggaggaacc      1500
aaactgactg tccta                                                      1515

<210> SEQ ID NO 123
<211> LENGTH: 505
<212> TYPE: PRT
<213> ORGANISM: artificial
<220> FEATURE:
<223> OTHER INFORMATION: CD33 B10 HL x F12Q HL

<400> SEQUENCE: 123

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Asn Asn Lys Asn Ser Leu
                165                 170                 175

Ala Trp Tyr Gln Gln Lys Pro Gly Gln Pro Pro Lys Leu Leu Leu Ser
```

```
                  180                 185                 190
Trp Ala Ser Thr Arg Glu Ser Gly Ile Pro Asp Arg Phe Ser Gly Ser
            195                 200                 205
Gly Ser Gly Thr Asp Phe Thr Leu Thr Ile Asp Gly Leu Gln Pro Glu
        210                 215                 220
Asp Ser Ala Thr Tyr Tyr Cys Gln Gln Ser Ala His Phe Pro Ile Thr
225                 230                 235                 240
Phe Gly Gln Gly Thr Arg Leu Glu Ile Lys Ser Gly Gly Gly Gly Ser
                245                 250                 255
Glu Val Gln Leu Val Glu Ser Gly Gly Gly Leu Val Gln Pro Gly Gly
            260                 265                 270
Ser Leu Lys Leu Ser Cys Ala Ala Ser Gly Phe Thr Phe Asn Ser Tyr
        275                 280                 285
Ala Met Asn Trp Val Arg Gln Ala Pro Gly Lys Gly Leu Glu Trp Val
    290                 295                 300
Ala Arg Ile Arg Ser Lys Tyr Asn Asn Tyr Ala Thr Tyr Tyr Ala Asp
305                 310                 315                 320
Ser Val Lys Gly Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Val Ser Trp Trp
        355                 360                 365
Ala Tyr Trp Gly Gln Gly Thr Leu Val Thr Val Ser Ser Gly Gly Gly
    370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Asn Tyr Pro Asn
            420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
    450                 455                 460
Leu Gly Gly Lys Ala Ala Leu Thr Leu Ser Gly Val Gln Pro Glu Asp
465                 470                 475                 480
Glu Ala Glu Tyr Tyr Cys Val Leu Trp Tyr Ser Asn Arg Trp Val Phe
                485                 490                 495
Gly Gly Gly Thr Lys Leu Thr Val Leu
            500                 505

<210> SEQ ID NO 124
<211> LENGTH: 1515
<212> TYPE: DNA
<213> ORGANISM: artificial
<220> FEATURE:
<223> OTHER INFORMATION: CD33 B10 HL x F12Q HL

<400> SEQUENCE: 124
caggtgcagc tggtgcagtc tggagctgag gtgaagaagc ctggtgagtc agtcaaggtc    60
tcctgcaagg ctagcgggta ccttcaca aactatggaa tgaactgggt gaagcaggct   120
ccaggacagg gtttagagtg gatgggctgg ataaacacct acactggaga gccaacctat   180
gctgataagt tccagggacg cgttaccatg actacggata cctctaccag cactgcctat   240
```

```
atggaaatcc gcaacctcag aagtgatgac acggctgtat attactgtgc gcgctggagt    300
tggagtgatg gttactacgt ttactttgac tactggggcc aaggcactac ggtcaccgtc    360
tcctcaggtg gtggtggttc tggcggcggc ggctccggtg gtggtggttc tgacatcgtg    420
atgacacagt ctccagactc cctgactgtg tctctgggcg agaggaccac catcaactgc    480
aagtccagcc agagtgtttt agacagctcc aacaataaga actccttagc ttggtaccag    540
cagaaaccag gacagcctcc taaattactc ctttcctggg catctacgcg ggaatccggg    600
atccctgacc gattcagtgg cagcggttct gggacagatt tcactctcac tattgacggc    660
ctgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaatag ctacgccatg aactgggtcc gccaggctcc aggaaagggt    900
ttggaatggg ttgctcgcat aagaagtaaa tataataatt atgcaacata ttatgccgat    960
tcagtgaaag gcaggttcac catctccaga gatgattcaa aaacactgc ctatctacaa    1020 atgaacaact tgaaaactga ggacactgcc gtgtactact gtgtgagaca tgggaacttc    1080
ggtaatagct acgtttcctg gtgggcttac tggggccaag gactctggt caccgtctcc    1140 tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320 gcacccctgtg gtctaatagg tgggactaag ttcctcgccc ccggtactcc tgccagattc    1380
tcaggctccc tgcttggagg caaggctgcc ctcaccctct cagggtaca gccagaggat    1440 gaggcagaat attactgtgt ctatggtac agcaaccgct gggtgttcgg tggaggaacc    1500
aaactgactg tccta                                                    1515
```

<210> SEQ ID NO 125
<211> LENGTH: 505
<212> TYPE: PRT
<213> ORGANISM: artificial
<220> FEATURE:
<223> OTHER INFORMATION: CD33 B10 HL x I2C HL

<400> SEQUENCE: 125

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125
```

```
Gly Gly Gly Ser Gly Gly Gly Ser Asp Ile Val Met Thr Gln Ser
    130             135             140
Pro Asp Ser Leu Thr Val Ser Leu Gly Glu Arg Thr Thr Ile Asn Cys
145             150             155                 160
Lys Ser Ser Gln Ser Val Leu Asp Ser Ser Asn Asn Lys Asn Ser Leu
                165             170                 175
Ala Trp Tyr Gln Gln Lys Pro Gly Gln Pro Pro Lys Leu Leu Leu Ser
            180             185             190
Trp Ala Ser Thr Arg Glu Ser Gly Ile Pro Asp Arg Phe Ser Gly Ser
            195             200             205
Gly Ser Gly Thr Asp Phe Thr Leu Thr Ile Asp Gly Leu Gln Pro Glu
    210             215             220
Asp Ser Ala Thr Tyr Tyr Cys Gln Gln Ser Ala His Phe Pro Ile Thr
225             230             235                 240
Phe Gly Gln Gly Thr Arg Leu Glu Ile Lys Ser Gly Gly Gly Gly Ser
                245             250                 255
Glu Val Gln Leu Val Glu Ser Gly Gly Gly Leu Val Gln Pro Gly Gly
            260             265             270
Ser Leu Lys Leu Ser Cys Ala Ala Ser Gly Phe Thr Phe Asn Lys Tyr
    275             280             285
Ala Met Asn Trp Val Arg Gln Ala Pro Gly Lys Gly Leu Glu Trp Val
290             295             300
Ala Arg Ile Arg Ser Lys Tyr Asn Asn Tyr Ala Thr Tyr Tyr Ala Asp
305             310             315                 320
Ser Val Lys Asp Arg Phe Thr Ile Ser Arg Asp Asp Ser Lys Asn Thr
                325             330                 335
Ala Tyr Leu Gln Met Asn Asn Leu Lys Thr Glu Asp Thr Ala Val Tyr
            340             345             350
Tyr Cys Val Arg His Gly Asn Phe Gly Asn Ser Tyr Ile Ser Tyr Trp
    355             360             365
Ala Tyr Trp Gly Gln Gly Thr Leu Val Thr Val Ser Ser Gly Gly Gly
    370             375             380
Gly Ser Gly Gly Gly Gly Ser Gly Gly Gly Gly Ser Gln Thr Val Val
385             390             395             400
Thr Gln Glu Pro Ser Leu Thr Val Ser Pro Gly Gly Thr Val Thr Leu
                405             410                 415
Thr Cys Gly Ser Ser Thr Gly Ala Val Thr Ser Gly Asn Tyr Pro Asn
            420             425             430
Trp Val Gln Gln Lys Pro Gly Gln Ala Pro Arg Gly Leu Ile Gly Gly
            435             440             445
Thr Lys Phe Leu Ala Pro Gly Thr Pro Ala Arg Phe Ser Gly Ser Leu
450             455             460
Leu Gly Gly Lys Ala Ala Leu Thr Leu Ser Gly Val Gln Pro Glu Asp
465             470             475                 480
Glu Ala Glu Tyr Tyr Cys Val Leu Trp Tyr Ser Asn Arg Trp Val Phe
                485             490                 495
Gly Gly Gly Thr Lys Leu Thr Val Leu
            500             505

<210> SEQ ID NO 126
<211> LENGTH: 1515
<212> TYPE: DNA
<213> ORGANISM: artificial
<220> FEATURE:
<223> OTHER INFORMATION: CD33 B10 HL x I2C HL
```

<400> SEQUENCE: 126

```
caggtgcagc tggtgcagtc tggagctgag gtgaagaagc ctggtgagtc agtcaaggtc      60
tcctgcaagg ctagcgggta taccttcaca aactatggaa tgaactgggt gaagcaggct     120
ccaggacagg gtttagagtg gatgggctgg ataaacacct acactggaga gccaacctat     180
gctgataagt tccagggacg cgttaccatg actacggata cctctaccag cactgcctat     240
atggaaatcc gcaacctcag aagtgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc aacaataaga actccttagc ttggtaccag     540
cagaaaccag gacagcctcc taaattactc ctttcctggg catctacgcg ggaatccggg     600
atccctgacc gattcagtgg cagcggttct gggacagatt tcactctcac tattgacggc     660
ctgcagcctg aagattctgc aacttactat tgtcaacagt ctgcccactt cccgatcacc     720
tttggccaag ggacacgact ggagattaaa tccggaggtg gtggctccga ggtgcagctg     780
gtcgagtctg gaggaggatt ggtgcagcct ggagggtcat tgaaactctc atgtgcagcc     840
tctggattca ccttcaataa gtacgccatg aactgggtcc gccaggctcc aggaaagggt     900
ttggaatggg ttgctcgcat aagaagtaaa tataataatt atgcaacata ttatgccgat     960
tcagtgaaag acaggttcac catctccaga gatgattcaa aaaacactgc ctatctacaa    1020
atgaacaact tgaaaactga ggacactgcc gtgtactact gtgtgagaca tgggaacttc    1080
ggtaatagct acatatccta ctgggcttac tggggccaag gactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcacccgtg gtctaatagg tgggactaag ttcctcgccc ccggtactcc tgccagattc    1380
tcaggctccc tgcttggagg caaggctgcc ctcacctct caggggtaca gccagaggat    1440
gaggcagaat attactgtgt tctatggtac agcaaccgct gggtgttcgg tggaggaacc    1500
aaactgactg tccta                                                    1515
```

<210> SEQ ID NO 127
<211> LENGTH: 122
<212> TYPE: PRT
<213> ORGANISM: artificial
<220> FEATURE:
<223> OTHER INFORMATION: CD33 VH of E11

<400> SEQUENCE: 127

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Tyr Ala Asp Lys Phe
    50                  55                  60

Gln Gly Arg Val Thr Met Thr Thr Asp Thr Ser Thr Ser Thr Ala Tyr
65                  70                  75                  80
```

```
Met Glu Ile Arg Asn Leu Gly Gly Asp Asp Thr Ala Val Tyr Tyr Cys
                 85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120
```

<210> SEQ ID NO 128
<211> LENGTH: 5
<212> TYPE: PRT
<213> ORGANISM: artificial
<220> FEATURE:
<223> OTHER INFORMATION: CD33 HCDR1 of E11

<400> SEQUENCE: 128

```
Asn Tyr Gly Met Asn
1               5
```

<210> SEQ ID NO 129
<211> LENGTH: 17
<212> TYPE: PRT
<213> ORGANISM: artificial
<220> FEATURE:
<223> OTHER INFORMATION: CD33 HCDR2 of E11

<400> SEQUENCE: 129

```
Trp Ile Asn Thr Tyr Thr Gly Glu Pro Thr Tyr Ala Asp Lys Phe Gln
1               5                   10                  15

Gly
```

<210> SEQ ID NO 130
<211> LENGTH: 13
<212> TYPE: PRT
<213> ORGANISM: artificial
<220> FEATURE:
<223> OTHER INFORMATION: CD33 HCDR3 of E11

<400> SEQUENCE: 130

```
Trp Ser Trp Ser Asp Gly Tyr Tyr Val Tyr Phe Asp Tyr
1               5                   10
```

<210> SEQ ID NO 131
<211> LENGTH: 366
<212> TYPE: DNA
<213> ORGANISM: artificial
<220> FEATURE:
<223> OTHER INFORMATION: CD33 VH of E11

<400> SEQUENCE: 131

```
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gccaacctat   180
gctgataagt tccagggacg cgttaccatg actacggata cctctaccag cactgcctat   240
atggaaatcc gcaacctcgg aggtgatgac acggctgtat attactgtgc gcgctggagt   300
tggagtgatg gttactacgt ttactttgac tactggggcc aaggcacttc ggtcaccgtc   360
tcctca                                                             366
```

<210> SEQ ID NO 132
<211> LENGTH: 113
<212> TYPE: PRT

```
<213> ORGANISM: artificial
<220> FEATURE:
<223> OTHER INFORMATION: CD33 VL of E11

<400> SEQUENCE: 132

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Lys Pro Gly Gln
        35                  40                  45

Pro Pro Lys Leu Leu Leu Ser Trp Ala Ser Thr Arg Glu Ser Gly Ile
50                  55                  60

Pro Asp Arg Phe Ser Gly Ser Gly Ser Gly Thr Asp Phe Thr Leu Thr
65                  70                  75                  80

Ile Asp Ser Pro Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 133
<211> LENGTH: 17
<212> TYPE: PRT
<213> ORGANISM: artificial
<220> FEATURE:
<223> OTHER INFORMATION: CD33 LCDR1 of E11

<400> SEQUENCE: 133

Lys Ser Ser Gln Ser Val Leu Asp Ser Ser Thr Asn Lys Asn Ser Leu
1               5                   10                  15

Ala

<210> SEQ ID NO 134
<211> LENGTH: 7
<212> TYPE: PRT
<213> ORGANISM: artificial
<220> FEATURE:
<223> OTHER INFORMATION: CD33 LCDR2 of E11

<400> SEQUENCE: 134

Trp Ala Ser Thr Arg Glu Ser
1               5

<210> SEQ ID NO 135
<211> LENGTH: 9
<212> TYPE: PRT
<213> ORGANISM: artificial
<220> FEATURE:
<223> OTHER INFORMATION: CD33 LCDR3 of E11

<400> SEQUENCE: 135

Gln Gln Ser Ala His Phe Pro Ile Thr
1               5

<210> SEQ ID NO 136
<211> LENGTH: 339
<212> TYPE: DNA
<213> ORGANISM: artificial
<220> FEATURE:
<223> OTHER INFORMATION: CD33 VL of E11

<400> SEQUENCE: 136
```

```
gacatcgtga tgacacagtc tccagactcc ctgactgtgt ctctgggcga gaggaccacc    60
atcaactgca agtccagcca gagtgtttta gacagctcca cgaataagaa ctccttagct   120
tggtaccagc agaaaccagg acagcctcct aaattactcc tttcctgggc atctacgcgg   180
gaatccggga tccctgaccg attcagtggc agcgggtctg ggacagattt cactctcact   240
attgacagcc gcagcctga gattctgca acttactatt gtcaacagtc tgcccacttc    300
ccgatcacct ttggccaagg gacacgactg gagattaaa                         339
```

<210> SEQ ID NO 137
<211> LENGTH: 250
<212> TYPE: PRT
<213> ORGANISM: artificial
<220> FEATURE:
<223> OTHER INFORMATION: CD33 HL of E11

<400> SEQUENCE: 137

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250
```

<210> SEQ ID NO 138
<211> LENGTH: 750
<212> TYPE: DNA
<213> ORGANISM: artificial
<220> FEATURE:
<223> OTHER INFORMATION: CD33 HL of E11

<400> SEQUENCE: 138

```
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gccaacctat   180
gctgataagt tccagggacg cgttaccatg actacggata cctctaccag cactgcctat   240
atggaaatcc gcaacctcgg aggtgatgac acggctgtat attactgtgc gcgctggagt   300
tggagtgatg gttactacgt ttactttgac tactggggcc aaggcacttc ggtcaccgtc   360
tcctcaggtg gtggtggttc tggcggcggc ggctccggtg gtggtggttc tgacatcgtg   420
atgacacagt ctccagactc cctgactgtg tctctgggcg agaggaccac catcaactgc   480
aagtccagcc agagtgtttt agacagctcc acgaataaga actccttagc ttggtaccag   540
cagaaaccag gacagcctcc taaattactc ctttcctggg catctacgcg ggaatccggg   600
atccctgacc gattcagtgg cagcgggtct gggacagatt tcactctcac tattgacagc   660
ccgcagcctg aagattctgc aacttactat tgtcaacagt ctgcccactt cccgatcacc   720
tttggccaag ggacacgact ggagattaaa                                     750
```

<210> SEQ ID NO 139
<211> LENGTH: 505
<212> TYPE: PRT
<213> ORGANISM: artificial
<220> FEATURE:
<223> OTHER INFORMATION: CD33 E11 HL x H2C HL

<400> SEQUENCE: 139

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220
```

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
            245                 250                 255

Glu Val Gln Leu Val Glu Ser Gly Gly Gly Leu Val Gln Pro Gly Gly
        260                 265                 270

Ser Leu Lys Leu Ser Cys Ala Ala Ser Gly Phe Thr Phe Asn Lys Tyr
    275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
        340                 345                 350

Tyr Cys Val Arg His Gly Asn Phe Gly Asn Ser Tyr Ile Ser Tyr Trp
    355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
            405                 410                 415

Thr Cys Gly Ser Ser Thr Gly Ala Val Thr Ser Gly Tyr Tyr Pro Asn
        420                 425                 430

Trp Val Gln Gln Lys Pro Gly Gln Ala Pro Arg Gly Leu Ile Gly Gly
    435                 440                 445

Thr Lys Phe Leu Ala Pro Gly Thr Pro Ala Arg Phe Ser Gly Ser Leu
450                 455                 460

Leu Gly Gly Lys Ala Ala Leu Thr Leu Ser Gly Val Gln Pro Glu Asp
465                 470                 475                 480

Glu Ala Glu Tyr Tyr Cys Ala Leu Trp Tyr Ser Asn Arg Trp Val Phe
            485                 490                 495

Gly Gly Gly Thr Lys Leu Thr Val Leu
        500                 505

<210> SEQ ID NO 140
<211> LENGTH: 1515
<212> TYPE: DNA
<213> ORGANISM: artificial
<220> FEATURE:
<223> OTHER INFORMATION: CD33 E11 HL x H2C HL

<400> SEQUENCE: 140
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120
ccaggacagg gtttagagtg gatgggctgg ataaacacct acactggaga gccaacctat   180
gctgataagt tccagggacg cgttaccatg actacggata cctctaccag cactgcctat   240
atggaaatcc gcaacctcgg aggtgatgac acggctgtat attactgtgc gcgctggagt   300
tggagtgatg gttactacgt ttactttgac tactggggcc aaggcacttc ggtcaccgtc   360
tcctcaggtg gtggtggttc tggcggcggc ggctccggtg gtggtggttc tgacatcgtg   420

```
atgacacagt ctccagactc cctgactgtg tctctgggcg agaggaccac catcaactgc    480
aagtccagcc agagtgtttt agacagctcc acgaataaga actccttagc ttggtaccag    540
cagaaaccag gacagcctcc taaattactc ctttcctggg catctacgcg ggaatccggg    600
atccctgacc gattcagtgg cagcgggtct gggacagatt tcactctcac tattgacagc    660
ccgcagcctg aagattctgc aacttactat tgtcaacagt ctgcccactt cccgatcacc    720
tttggccaag ggacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga gatgattcaa aaacactgcc tatctacaa    1020
atgaacaact tgaaaactga ggacactgcc gtgtactact gtgtgagaca tgggaacttc    1080
ggtaatagct acatatccta ctgggcttac tggggccaag gactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggctactac ccaaactggg tccaacaaaa accaggtcag    1320
gcacccccgtg gtctaatagg tgggactaag ttcctcgccc ccggtactcc tgccagattc    1380
tcaggctccc tgcttggagg caaggctgcc ctcaccctct caggggtaca gccagaggat    1440
gaggcagaat attactgtgc tctatggtac agcaaccgct gggtgttcgg tggaggaacc    1500
aaactgactg tccta                                                     1515

<210> SEQ ID NO 141
<211> LENGTH: 505
<212> TYPE: PRT
<213> ORGANISM: artificial
<220> FEATURE:
<223> OTHER INFORMATION: CD33 E11 HL x F12Q HL

<400> SEQUENCE: 141

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
```

165                 170                 175
Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
        210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Leu Val Gln Pro Gly Gly
            260                 265                 270

Ser Leu Lys Leu Ser Cys Ala Ala Ser Gly Phe Thr Phe Asn Ser Tyr
            275                 280                 285

Ala Met Asn Trp Val Arg Gln Ala Pro Gly Lys Gly Leu Glu Trp Val
            290                 295                 300

Ala Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Val Ser Trp Trp
            355                 360                 365

Ala Tyr Trp Gly Gln Gly Thr Leu Val Thr Val Ser Ser Gly Gly Gly
        370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
        450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 142
<211> LENGTH: 1515
<212> TYPE: DNA
<213> ORGANISM: artificial
<220> FEATURE:
<223> OTHER INFORMATION: CD33 E11 HL x F12Q HL

<400> SEQUENCE: 142
caggtgcagc tggtgcagtc tggagctgag gtgaagaagc ctggagagtc agtcaaggtc    60
tcctgcaagg ctagcgggta taccttcaca aactatggaa tgaactgggt gaagcaggct   120

| | |
|---|---|
| ccaggacagg gtttagagtg gatgggctgg ataaacacct acactggaga gccaacctat | 180 |
| gctgataagt tccagggacg cgttaccatg actacggata cctctaccag cactgcctat | 240 |
| atggaaatcc gcaacctcgg aggtgatgac acggctgtat attactgtgc gcgctggagt | 300 |
| tggagtgatg gttactacgt ttactttgac tactgggggcc aaggcacttc ggtcaccgtc | 360 |
| tcctcaggtg gtggtggttc tggcggcggc ggctccggtg gtggtggttc tgacatcgtg | 420 |
| atgacacagt ctccagactc cctgactgtg tctctgggcg agaggaccac catcaactgc | 480 |
| aagtccagcc agagtgtttt agacagctcc acgaataaga actccttagc ttggtaccag | 540 |
| cagaaaccag gacagcctcc taaattactc ctttcctggg catctacgcg ggaatccggg | 600 |
| atccctgacc gattcagtgg cagcgggtct gggacagatt tcactctcac tattgacagc | 660 |
| ccgcagcctg aagattctgc aacttactat tgtcaacagt ctgcccactt cccgatcacc | 720 |
| tttggccaag ggacacgact ggagattaaa tccggaggtg gtggctccga ggtgcagctg | 780 |
| gtcgagtctg gaggaggatt ggtgcagcct ggagggtcat tgaaactctc atgtgcagcc | 840 |
| tctggattca ccttcaatag ctacgccatg aactgggtcc gccaggctcc aggaaagggt | 900 |
| ttggaatggg ttgctcgcat aagaagtaaa tataataatt atgcaacata ttatgccgat | 960 |
| tcagtgaaag gcaggttcac catctccaga gatgattcaa aaaacactgc ctatctacaa | 1020 |
| atgaacaact tgaaaactga ggacactgcc gtgtactact gtgtgagaca tgggaacttc | 1080 |
| ggtaatagct acgtttcctg gtgggcttac tggggccaag gactctggt caccgtctcc | 1140 |
| tcaggtggtg gtggttctgg cggcggcggc tccggtggtg gtggttctca gactgttgtg | 1200 |
| actcaggaac cttcactcac cgtatcacct ggtggaacag tcacactcac ttgtggctcc | 1260 |
| tcgactgggg ctgttacatc tggcaactac ccaaactggg tccaacaaaa accaggtcag | 1320 |
| gcaccccgtg gtctaatagg tgggactaag ttcctcgccc ccgtactcc tgccagattc | 1380 |
| tcaggctccc tgcttggagg caaggctgcc ctcacccctct caggggtaca gccagaggat | 1440 |
| gaggcagaat attactgtgt tctatggtac agcaaccgct gggtgttcgg tggaggaacc | 1500 |
| aaactgactg tccta | 1515 |

<210> SEQ ID NO 143
<211> LENGTH: 505
<212> TYPE: PRT
<213> ORGANISM: artificial
<220> FEATURE:
<223> OTHER INFORMATION: CD33 E11 HL x I2C HL

<400> SEQUENCE: 143

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Lys Phe
        50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Ser Gly
            115                 120                 125
Gly Gly Gly Ser Gly Gly Gly Ser Asp Ile Val Met Thr Gln Ser
        130                 135                 140
Pro Asp Ser Leu Thr Val Ser Leu Gly Glu Arg Thr Thr Ile Asn Cys
145                 150                 155                 160
Lys Ser Ser Gln Ser Val Leu Asp Ser Ser Thr Asn Lys Asn Ser Leu
                165                 170                 175
Ala Trp Tyr Gln Gln Lys Pro Gly Gln Pro Pro Lys Leu Leu Leu Ser
            180                 185                 190
Trp Ala Ser Thr Arg Glu Ser Gly Ile Pro Asp Arg Phe Ser Gly Ser
        195                 200                 205
Gly Ser Gly Thr Asp Phe Thr Leu Thr Ile Asp Ser Pro Gln Pro Glu
    210                 215                 220
Asp Ser Ala Thr Tyr Tyr Cys Gln Gln Ser Ala His Phe Pro Ile Thr
225                 230                 235                 240
Phe Gly Gln Gly Thr Arg Leu Glu Ile Lys Ser Gly Gly Gly Gly Ser
                245                 250                 255
Glu Val Gln Leu Val Glu Ser Gly Gly Gly Leu Val Gln Pro Gly Gly
            260                 265                 270
Ser Leu Lys Leu Ser Cys Ala Ala Ser Gly Phe Thr Phe Asn Lys Tyr
        275                 280                 285
Ala Met Asn Trp Val Arg Gln Ala Pro Gly Lys Gly Leu Glu Trp Val
    290                 295                 300
Ala Arg Ile Arg Ser Lys Tyr Asn Asn Tyr Ala Thr Tyr Tyr Ala Asp
305                 310                 315                 320
Ser Val Lys Asp Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Ile Ser Tyr Trp
        355                 360                 365
Ala Tyr Trp Gly Gln Gly Thr Leu Val Thr Val Ser Ser Gly Gly Gly
    370                 375                 380
Gly Ser Gly Gly Gly Gly Ser Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Asn Tyr Pro Asn
            420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
    450                 455                 460
Leu Gly Gly Lys Ala Ala Leu Thr Leu Ser Gly Val Gln Pro Glu Asp
465                 470                 475                 480
Glu Ala Glu Tyr Tyr Cys Val Leu Trp Tyr Ser Asn Arg Trp Val Phe
                485                 490                 495
Gly Gly Gly Thr Lys Leu Thr Val Leu
            500                 505

<210> SEQ ID NO 144
<211> LENGTH: 1515
<212> TYPE: DNA

<213> ORGANISM: artificial
<220> FEATURE:
<223> OTHER INFORMATION: CD33 E11 HL x I2C HL

<400> SEQUENCE: 144

| | | | | | |
|---|---|---|---|---|---|
| caggtgcagc | tggtgcagtc | tggagctgag | gtgaagaagc | ctggagagtc | agtcaaggtc | 60 |
| tcctgcaagg | ctagcgggta | taccttcaca | aactatggaa | tgaactgggt | gaagcaggct | 120 |
| ccaggacagg | gtttagagtg | gatgggctgg | ataaacacct | acactggaga | gccaacctat | 180 |
| gctgataagt | tccagggacg | cgttaccatg | actacggata | cctctaccag | cactgcctat | 240 |
| atggaaatcc | gcaacctcgg | aggtgatgac | acggctgtat | attactgtgc | gcgctggagt | 300 |
| tggagtgatg | gttactacgt | ttactttgac | tactggggcc | aaggcacttc | ggtcaccgtc | 360 |
| tcctcaggtg | gtggtggttc | tggcggcggc | ggctccggtg | gtggtggttc | tgacatcgtg | 420 |
| atgacacagt | ctccagactc | cctgactgtg | tctctgggcg | agaggaccac | catcaactgc | 480 |
| aagtccagcc | agagtgtttt | agacagctcc | acgaataaga | actccttagc | ttggtaccag | 540 |
| cagaaaccag | gacagcctcc | taaattactc | ctttcctggg | catctacgcg | ggaatccggg | 600 |
| atccctgacc | gattcagtgg | cagcgggtct | gggacagatt | tcactctcac | tattgacagc | 660 |
| ccgcagcctg | aagattctgc | aacttactat | tgtcaacagt | ctgcccactt | cccgatcacc | 720 |
| tttggccaag | ggacacgact | ggagattaaa | tccggaggtg | gtggctccga | ggtgcagctg | 780 |
| gtcgagtctg | gaggaggatt | ggtgcagcct | ggagggtcat | tgaaactctc | atgtgcagcc | 840 |
| tctggattca | ccttcaataa | gtacgccatg | aactgggtcc | gccaggctcc | aggaaagggt | 900 |
| ttggaatggg | ttgctcgcat | aagaagtaaa | tataataatt | atgcaacata | ttatgccgat | 960 |
| tcagtgaaag | acaggttcac | catctccaga | gatgattcaa | aaaacactgc | ctatctacaa | 1020 |
| atgaacaact | tgaaaactga | ggacactgcc | gtgtactact | gtgtgagaca | tgggaacttc | 1080 |
| ggtaatagct | acatatccta | ctgggcttac | tggggccaag | ggactctggt | caccgtctcc | 1140 |
| tcaggtggtg | gtggttctgg | cggcggcggc | tccggtggtg | gtggttctca | gactgttgtg | 1200 |
| actcaggaac | cttcactcac | cgtatcacct | ggtggaacag | tcacactcac | ttgtggctcc | 1260 |
| tcgactgggg | ctgttacatc | tggcaactac | ccaaactggg | tccaacaaaa | accaggtcag | 1320 |
| gcaccccgtg | gtctaatagg | tgggactaag | ttcctcgccc | ccggtactcc | tgccagattc | 1380 |
| tcaggctccc | tgcttggagg | caaggctgcc | ctcaccctct | caggggtaca | gccagaggat | 1440 |
| gaggcagaat | attactgtgt | tctatggtac | agcaaccgct | gggtgttcgg | tggaggaacc | 1500 |
| aaactgactg | tccta | | | | | 1515 |

<210> SEQ ID NO 145
<211> LENGTH: 1125
<212> TYPE: DNA
<213> ORGANISM: human

<400> SEQUENCE: 145

| | | | | | |
|---|---|---|---|---|---|
| atgggatgga | gctgtatcat | cctcttcttg | gtagcaacag | ctacaggtgt | acactccgat | 60 |
| ccaaatttct | ggctgcaagt | gcaggagtca | gtgacggtac | aggagggttt | gtgcgtcctc | 120 |
| gtgccctgca | ctttcttcca | tcccataccc | tactacgaca | agaactcccc | agttcatggt | 180 |
| tactggttcc | gggaaggagc | cattatatcc | ggggactctc | cagtggccac | aaacaagcta | 240 |
| gatcaagaag | tacaggagga | gactcagggc | agattccgcc | tccttgggga | tcccagtagg | 300 |
| aacaactgct | ccctgagcat | cgtagacgcc | aggaggagga | taatggttc | atacttcttt | 360 |
| cggatggaga | gaggaagtac | caaatacagt | tacaaatctc | cccagctctc | tgtgcatgtg | 420 |

```
acagacttga cccacaggcc caaaatcctc atccctggca ctctagaacc cggccactcc    480
aaaaacctga cctgctctgt gtcctgggcc tgtgagcagg gaacacccc  gatcttctcc    540 tggttgtcag ctgccccac  ctccctgggc cccaggacta ctcactcctc ggtgctcata    600
atcaccccac ggcccagga  ccacggcacc aacctgacct gtcaggtgaa gttcgctgga    660
gctggtgtga ctacggagag aaccatccag ctcaacgtca cctatgttcc acagaaccca    720
acaactggta tctttccagg agatggctca gggaaacaag agaccagagc aggagtggtt    780 catgggcca  ttggaggagc tggtgttaca gccctgctcg ctctttgtct ctgcctcatc    840
ttcttcatag tgaagaccca caggaggaaa gcagccagga cagcagtggg caggaatgac    900
acccacccta ccacagggtc agcctccccg aaacaccaga agaagtccaa gttacatggc    960
cccactgaaa cctcaagctg ttcaggtgcc gcccctactg tggagatgga tgaggagctg   1020
cattatgctt ccctcaactt tcatgggatg aatccttcca aggacacctc caccgaatac   1080
tcagaggtca ggacccagtc cgggcatcat caccatcatc attga                   1125
```

<210> SEQ ID NO 146
<211> LENGTH: 374
<212> TYPE: PRT
<213> ORGANISM: human

<400> SEQUENCE: 146

```
Met Gly Trp Ser Cys Ile Ile Leu Phe Leu Val Ala Thr Ala Thr Gly
1               5                   10                  15

Val His Ser Asp Pro Asn Phe Trp Leu Gln Val Gln Glu Ser Val Thr
            20                  25                  30

Val Gln Glu Gly Leu Cys Val Leu Val Pro Cys Thr Phe Phe His Pro
        35                  40                  45

Ile Pro Tyr Tyr Asp Lys Asn Ser Pro Val His Gly Tyr Trp Phe Arg
    50                  55                  60

Glu Gly Ala Ile Ile Ser Gly Asp Ser Pro Val Ala Thr Asn Lys Leu
65                  70                  75                  80

Asp Gln Glu Val Gln Glu Glu Thr Gln Gly Arg Phe Arg Leu Leu Gly
                85                  90                  95

Asp Pro Ser Arg Asn Asn Cys Ser Leu Ser Ile Val Asp Ala Arg Arg
            100                 105                 110

Arg Asp Asn Gly Ser Tyr Phe Phe Arg Met Glu Arg Gly Ser Thr Lys
        115                 120                 125

Tyr Ser Tyr Lys Ser Pro Gln Leu Ser Val His Val Thr Asp Leu Thr
    130                 135                 140

His Arg Pro Lys Ile Leu Ile Pro Gly Thr Leu Glu Pro Gly His Ser
145                 150                 155                 160

Lys Asn Leu Thr Cys Ser Val Ser Trp Ala Cys Glu Gln Gly Thr Pro
                165                 170                 175

Pro Ile Phe Ser Trp Leu Ser Ala Ala Pro Thr Ser Leu Gly Pro Arg
            180                 185                 190

Thr Thr His Ser Ser Val Leu Ile Ile Thr Pro Arg Pro Gln Asp His
        195                 200                 205

Gly Thr Asn Leu Thr Cys Gln Val Lys Phe Ala Gly Ala Gly Val Thr
    210                 215                 220

Thr Glu Arg Thr Ile Gln Leu Asn Val Thr Tyr Val Pro Gln Asn Pro
225                 230                 235                 240

Thr Thr Gly Ile Phe Pro Gly Asp Gly Ser Gly Lys Gln Glu Thr Arg
```

```
                245                 250                 255
Ala Gly Val Val His Gly Ala Ile Gly Gly Ala Gly Val Thr Ala Leu
            260                 265                 270
Leu Ala Leu Cys Leu Cys Leu Ile Phe Phe Ile Val Lys Thr His Arg
        275                 280                 285
Arg Lys Ala Ala Arg Thr Ala Val Gly Arg Asn Asp Thr His Pro Thr
    290                 295                 300
Thr Gly Ser Ala Ser Pro Lys His Gln Lys Lys Ser Lys Leu His Gly
305                 310                 315                 320
Pro Thr Glu Thr Ser Ser Cys Ser Gly Ala Ala Pro Thr Val Glu Met
                325                 330                 335
Asp Glu Glu Leu His Tyr Ala Ser Leu Asn Phe His Gly Met Asn Pro
            340                 345                 350
Ser Lys Asp Thr Ser Thr Glu Tyr Ser Glu Val Arg Thr Gln Ser Gly
        355                 360                 365
His His His His His His
    370

<210> SEQ ID NO 147
<211> LENGTH: 1083
<212> TYPE: DNA
<213> ORGANISM: macaque

<400> SEQUENCE: 147
atgccgctgc tgctactgct gccctgctg tgggcagggg ccctggctat ggatccaaga      60
gtcaggctgg aagtgcagga gtcagtgaca gtacaggagg gtttgtgcgt ccttgtgccc    120
tgcactttct ccatcccgt accctaccac accaggaatt ccccagttca tggttactgg    180
ttccgggaag gagccattgt atccttggac tctccagtgg ccacaaacaa gctagatcaa    240
gaagtacagg aggagaccca gggccgattc cgcctccttg gggatcccag taggaacaac    300
tgctccctga gcatcgtaga tgccaggagg agggataacg gttcatactt ctttcggatg    360
gagaaaggaa gtaccaaata cagttacaaa tctacccagc tctctgtgca gtgtgacagac    420
ttgacccaca gccccaaat cctcatccct ggagccctag accctgacca ctccaaaaac    480
ctgacctgct ctgtgccctg ggcctgtgag cagggaacac ctccaatctt ctcctggatg    540
tcagctgccc ccacctccct gggcctcagg accactcact cctcggtgct cataatcacc    600
ccacggcccc aggaccacgg caccaacctc acctgtcagg tgaagttccc tggagctggc    660
gtgaccacgg agagaaccat ccagctcaat gtctcctatg cttcacagaa cccaagaact    720
gatatctttc taggagacgg ctcagggaaa caaggagtgg ttcagggagc catcggggga    780
gctggtgtca gtcctgctg cgctctttgt ctctgcctca tcttcttcac agtgaagact    840
cacaggagga agcagccag acagcagtg ggcaggatcg acacccaccc cgccacaggg    900
ccaacatcct cgaaacacca gaagaagtcc aagttacatg gcgccactga acctcaggc    960
tgttcaggta ccaccttac tgtggagatg gatgaggagc tgcactacgc ttccctcaac   1020
tttcatggga tgaatccttc tgaggacacc tccaccgaat actcagaggt caggacccag   1080
tga                                                                  1083

<210> SEQ ID NO 148
<211> LENGTH: 505
<212> TYPE: PRT
<213> ORGANISM: artificial
<220> FEATURE:
<223> OTHER INFORMATION: CD33 UD H2C HL x AF5 HL
```

<400> SEQUENCE: 148

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
            165                 170                 175

Trp Val Gln Gln Lys Pro Gly Gln Ala Pro Arg Gly Leu Ile Gly Gly
        180                 185                 190

Thr Lys Phe Leu Ala Pro Gly Thr Pro Ala Arg Phe Ser Gly Ser Leu
    195                 200                 205

Leu Gly Gly Lys Ala Ala Leu Thr Leu Ser Gly Val Gln Pro Glu Asp
210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu Ser Gly Gly Gly Gly Ser Gln
            245                 250                 255

Val Gln Leu Val Gln Ser Gly Ala Glu Val Lys Lys Pro Gly Ala Ser
        260                 265                 270

Val Lys Val Ser Cys Lys Ala Ser Gly Tyr Thr Phe Thr Asn Tyr Gly
    275                 280                 285

Met Asn Trp Val Lys Gln Ala Pro Gly Gln Gly Leu Lys Trp Met Gly
290                 295                 300

Trp Ile Asn Thr Tyr Thr Gly Glu Pro Thr Tyr Ala Asp Asp Phe Lys
305                 310                 315                 320

Gly Arg Val Thr Met Thr Ser Asp Thr Ser Thr Ser Thr Ala Tyr Leu
            325                 330                 335

Glu Leu His Asn Leu Arg Ser Asp Asp Thr Ala Val Tyr Tyr Cys Ala
        340                 345                 350

Arg Trp Ser Trp Ser Asp Gly Tyr Tyr Val Tyr Phe Asp Tyr Trp Gly
    355                 360                 365

Gln Gly Thr Thr Val Thr Val Ser Ser Gly Gly Gly Gly Ser Gly Gly
370                 375                 380

Gly Gly Ser Gly Gly Gly Gly Ser Asp Ile Val Met Thr Gln Ser Pro
385                 390                 395                 400

Asp Ser Leu Thr Val Ser Leu Gly Glu Arg Thr Thr Ile Asn Cys Lys
```

405                 410                 415
Ser Ser Gln Ser Val Leu Asp Ser Ser Lys Asn Lys Asn Ser Leu Ala
            420                 425                 430

Trp Tyr Gln Gln Lys Pro Gly Gln Pro Pro Lys Leu Leu Leu Ser Trp
            435                 440                 445

Ala Ser Thr Arg Glu Ser Gly Ile Pro Asp Arg Phe Ser Gly Ser Gly
            450                 455                 460

Ser Gly Thr Asp Phe Thr Leu Thr Ile Asp Ser Leu Gln Pro Glu Asp
465                 470                 475                 480

Ser Ala Thr Tyr Tyr Cys Gln Gln Ser Ala His Phe Pro Ile Thr Phe
            485                 490                 495

Gly Gln Gly Thr Arg Leu Glu Ile Lys
            500                 505

<210> SEQ ID NO 149
<211> LENGTH: 1515
<212> TYPE: DNA
<213> ORGANISM: artificial
<220> FEATURE:
<223> OTHER INFORMATION: CD33 UD H2C HL x AF5 HL

<400> SEQUENCE: 149
gaggtgcagc tggtcgagtc tggaggagga ttggtgcagc ctggagggtc attgaaactc        60
tcatgtgcag cctctggatt cacctttcaat aagtacgcca tgaactgggt ccgccaggct      120
ccaggaaagg gtttggaatg ggttgctcgc ataagaagta aatataataa ttatgcaaca      180
tattatgccg attcagtgaa agacaggttc accatctcca gagatgattc aaaaaacact      240
gcctatctac aaatgaacaa cttgaaaact gaggacactg ccgtgtacta ctgtgtgaga      300
catgggaact tcggtaatag ctacatatcc tactgggctt actggggcca agggactctg      360
gtcaccgtct cctcaggtgg tggtggttct ggcggcggcg gctccggtgg tggtggttct      420
cagactgttg tgactcagga accttcactc accgtatcac ctggtggaac agtcacactc      480
acttgtggct cctcgactgg ggctgttaca tctggctact acccaaactg ggtccaacaa      540
aaaccaggtc aggcaccccg tggtctaata ggtgggacta gttcctcgc cccggtact      600
cctgccagat tctcaggctc cctgcttgga ggcaaggctg ccctcaccct ctcagggta      660
cagccagagg atgaggcaga atattactgt gctctatggt acagcaaccg ctgggtgttc      720
ggtggaggaa ccaaactgac tgtcctatcc ggaggtggtg gctcccaggt gcagctggtc      780
cagtctggag ctgaggtgaa gaagcctgga gcgtcagtca aggtctcctg caaggctagc      840
gggtatacct tcacaaacta tggaatgaac tgggtgaagc aggctccagg acagggttta      900
aagtggatgg gctggataaa cacctacact ggagagccaa catatgctga tgacttcaag      960
ggacgggtta ccatgacttc ggatacctct accagcactg cctatttgga actccacaac     1020
ctcagaagtg atgacacggc tgtatattac tgtgcgcgct ggagttggag tgatggttac     1080
tacgttttact ttgactactg gggccaaggc actacggtca ccgtctcctc aggtggtggt     1140
ggttctggcg gcggcggctc cggtggtggt ggttctgaca tcgtgatgac acagtctcca     1200
gactccctga ctgtgtctct gggcgagagg accaccatca actgcaagtc cagccagagt     1260
gttttagaca gctccaagaa taagaactcc ttagcttggt accagcagaa accaggacag     1320
cctcctaaat tactcctttc ctgggcatct acgcgggaat ccgggatccc tgaccgattc     1380
agtggcagcg gtctgggac agatttcact ctcactattg acagcctgca gcctgaagat     1440
tctgcaactt actattgtca acagtctgcc cacttcccga tcacctttgg ccaagggaca     1500
cgactggaga ttaaa                                                        1515

<210> SEQ ID NO 150
<211> LENGTH: 505
<212> TYPE: PRT
<213> ORGANISM: artificial
<220> FEATURE:
<223> OTHER INFORMATION: CD33 UD F12Q HL x AF5 HL

<400> SEQUENCE: 150

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Ser Gly Gly Gly Gly Ser Gln
                245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Asn Tyr Gly
        275                 280                 285

Met Asn Trp Val Lys Gln Ala Pro Gly Gln Gly Leu Lys Trp Met Gly
    290                 295                 300

Trp Ile Asn Thr Tyr Thr Gly Glu Pro Thr Tyr Ala Asp Asp Phe Lys
305                 310                 315                 320

Gly Arg Val Thr Met Thr Ser Asp Thr Ser Thr Ser Thr Ala Tyr Leu
                325                 330                 335

Glu Leu His Ser Asn Leu Arg Ser Asp Asp Thr Ala Val Tyr Tyr Cys Ala
            340                 345                 350

```
Arg Trp Ser Trp Ser Asp Gly Tyr Tyr Val Tyr Phe Asp Tyr Trp Gly
            355                 360                 365
Gln Gly Thr Thr Val Thr Val Ser Ser Gly Gly Gly Ser Gly Gly
        370                 375                 380
Gly Gly Ser Gly Gly Gly Ser Asp Ile Val Met Thr Gln Ser Pro
385                 390                 395                 400
Asp Ser Leu Thr Val Ser Leu Gly Glu Arg Thr Thr Ile Asn Cys Lys
                405                 410                 415
Ser Ser Gln Ser Val Leu Asp Ser Ser Lys Asn Lys Asn Ser Leu Ala
            420                 425                 430
Trp Tyr Gln Gln Lys Pro Gly Gln Pro Pro Lys Leu Leu Leu Ser Trp
            435                 440                 445
Ala Ser Thr Arg Glu Ser Gly Ile Pro Asp Arg Phe Ser Gly Ser Gly
        450                 455                 460
Ser Gly Thr Asp Phe Thr Leu Thr Ile Asp Ser Leu Gln Pro Glu Asp
465                 470                 475                 480
Ser Ala Thr Tyr Tyr Cys Gln Gln Ser Ala His Phe Pro Ile Thr Phe
                485                 490                 495
Gly Gln Gly Thr Arg Leu Glu Ile Lys
            500                 505
```

<210> SEQ ID NO 151
<211> LENGTH: 1515
<212> TYPE: DNA
<213> ORGANISM: artificial
<220> FEATURE:
<223> OTHER INFORMATION: CD33 UD F12Q HL x AF5 HL

<400> SEQUENCE: 151

| | | | | | |
|---|---|---|---|---|---|
| gaggtgcagc | tggtcgagtc | tggaggagga | ttggtgcagc | ctggagggtc | attgaaactc | 60 |
| tcatgtgcag | cctctggatt | caccttcaat | agctacgcca | tgaactgggt | ccgccaggct | 120 |
| ccaggaaagg | gtttggaatg | ggttgctcgc | ataagaagta | aatataataa | ttatgcaaca | 180 |
| tattatgccg | attcagtgaa | aggcaggttc | accatctcca | gagatgattc | aaaaaacact | 240 |
| gcctatctac | aaatgaacaa | cttgaaaact | gaggacactg | ccgtgtacta | ctgtgtgaga | 300 |
| catgggaact | tcggtaatag | ctacgttttcc | tggtgggctt | actggggcca | agggactctg | 360 |
| gtcaccgtct | cctcaggtgg | tggtggttct | ggcggcggcg | gctccggtgg | tggtggttct | 420 |
| cagactgttg | tgactcagga | accttcactc | accgtatcac | ctggtggaac | agtcacactc | 480 |
| acttgtggct | cctcgactgg | ggctgttaca | tctggcaact | acccaaactg | ggtccaacaa | 540 |
| aaaccaggtc | aggcaccccg | tggtctaata | ggtgggacta | agttcctcgc | cccggtact | 600 |
| cctgccagat | tctcaggctc | cctgcttgga | ggcaaggctg | ccctcaccct | ctcagggta | 660 |
| cagccagagg | atgaggcaga | atattactgt | gttctatggt | acagcaaccg | ctgggtgttc | 720 |
| ggtggaggaa | ccaaactgac | tgtcctatcc | ggaggtggtg | gctcccaggt | gcagctggtc | 780 |
| cagtctggag | ctgaggtgaa | gaagcctgga | gcgtcagtca | aggtctcctg | caaggctagc | 840 |
| gggtatacct | tcacaaacta | tggaatgaac | tgggtgaagc | aggctccagg | acagggttta | 900 |
| aagtggatgg | gctggataaa | cacctacact | ggagagccaa | catatgctga | tgacttcaag | 960 |
| ggacgggtta | ccatgacttc | ggatacctct | accagcactg | cctatttgga | actccacaac | 1020 |
| ctcagaagtg | atgacacggc | tgtatattac | tgtgcgcgct | ggagttggag | tgatggttac | 1080 |
| tacgtttact | ttgactactg | gggccaaggc | actacggtca | ccgtctcctc | aggtggtggt | 1140 |
| ggttctggcg | gcggcggctc | cggtggtggt | ggttctgaca | tcgtgatgac | acagtctcca | 1200 |

```
gactccctga ctgtgtctct gggcgagagg accaccatca actgcaagtc cagccagagt    1260
gttttagaca gctccaagaa taagaactcc ttagcttggt accagcagaa accaggacag    1320
cctcctaaat tactcctttc ctgggcatct acgcgggaat ccgggatccc tgaccgattc    1380
agtggcagcg gtctgggac  agatttcact ctcactattg acagcctgca gcctgaagat    1440
tctgcaactt actattgtca acagtctgcc cacttcccga tcacctttgg ccaagggaca    1500
cgactggaga ttaaa                                                     1515
```

<210> SEQ ID NO 152
<211> LENGTH: 505
<212> TYPE: PRT
<213> ORGANISM: artificial
<220> FEATURE:
<223> OTHER INFORMATION: CD33 UD I2C HL x AF5 HL

<400> SEQUENCE: 152

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Ser Gly Gly Gly Gly Ser Gln
                245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Asn Tyr Gly
        275                 280                 285

Met Asn Trp Val Lys Gln Ala Pro Gly Gln Gly Leu Lys Trp Met Gly
    290                 295                 300
```

```
Trp Ile Asn Thr Tyr Thr Gly Glu Pro Thr Tyr Ala Asp Asp Phe Lys
305                 310                 315                 320

Gly Arg Val Thr Met Thr Ser Asp Thr Ser Thr Ser Thr Ala Tyr Leu
            325                 330                 335

Glu Leu His Asn Leu Arg Ser Asp Asp Thr Ala Val Tyr Tyr Cys Ala
        340                 345                 350

Arg Trp Ser Trp Ser Asp Gly Tyr Tyr Val Tyr Phe Asp Tyr Trp Gly
    355                 360                 365

Gln Gly Thr Thr Val Thr Val Ser Ser Gly Gly Gly Gly Ser Gly Gly
370                 375                 380

Gly Gly Ser Gly Gly Gly Gly Ser Asp Ile Val Met Thr Gln Ser Pro
385                 390                 395                 400

Asp Ser Leu Thr Val Ser Leu Gly Glu Arg Thr Thr Ile Asn Cys Lys
            405                 410                 415

Ser Ser Gln Ser Val Leu Asp Ser Ser Lys Asn Lys Asn Ser Leu Ala
        420                 425                 430

Trp Tyr Gln Gln Lys Pro Gly Gln Pro Pro Lys Leu Leu Leu Ser Trp
    435                 440                 445

Ala Ser Thr Arg Glu Ser Gly Ile Pro Asp Arg Phe Ser Gly Ser Gly
450                 455                 460

Ser Gly Thr Asp Phe Thr Leu Thr Ile Asp Ser Leu Gln Pro Glu Asp
465                 470                 475                 480

Ser Ala Thr Tyr Tyr Cys Gln Gln Ser Ala His Phe Pro Ile Thr Phe
            485                 490                 495

Gly Gln Gly Thr Arg Leu Glu Ile Lys
            500                 505
```

<210> SEQ ID NO 153
<211> LENGTH: 1515
<212> TYPE: DNA
<213> ORGANISM: artificial
<220> FEATURE:
<223> OTHER INFORMATION: CD33 UD I2C HL x AF5 HL

<400> SEQUENCE: 153

| | | | | | |
|---|---|---|---|---|---|
| gaggtgcagc | tggtcgagtc | tggaggagga | ttggtgcagc | ctggagggtc | attgaaactc | 60 |
| tcatgtgcag | cctctggatt | caccttcaat | aagtacgcca | tgaactgggt | ccgccaggct | 120 |
| ccaggaaagg | gtttggaatg | ggttgctcgc | ataagaagta | aatataataa | ttatgcaaca | 180 |
| tattatgccg | attcagtgaa | agacaggttc | accatctcca | gagatgattc | aaaaaacact | 240 |
| gcctatctac | aaatgaacaa | cttgaaaact | gaggacactg | ccgtgtacta | ctgtgtgaga | 300 |
| catgggaact | tcggtaatag | ctacatatcc | tactgggctt | actggggcca | agggactctg | 360 |
| gtcaccgtct | cctcaggtgg | tggtggttct | ggcggcggcg | gctccggtgg | tggtggttct | 420 |
| cagactgttg | tgactcagga | accttcactc | accgtatcac | ctggtggaac | agtcacactc | 480 |
| acttgtggct | cctcgactgg | ggctgttaca | tctgcaact | acccaaactg | gtccaacaa | 540 |
| aaaccaggtc | aggcaccccg | tggtctaata | ggtgggacta | agttcctcgc | ccccggtact | 600 |
| cctgccagat | ctctcaggctc | cctgcttgga | ggcaaggctg | ccctcaccct | ctcagggta | 660 |
| cagccagagg | atgaggcaga | atattactgt | gttctatggt | acagcaaccg | ctgggtgttc | 720 |
| ggtggaggaa | ccaaactgac | tgtcctatcc | ggaggtggtg | ctcccaggt | gcagctggtc | 780 |
| cagtctggag | ctgaggtgaa | gaagcctgga | gcgtcagtca | aggtctcctg | caaggctagc | 840 |
| gggtatacct | tcacaaacta | tggaatgaac | tgggtgaagc | aggctccagg | acagggttta | 900 |

```
aagtggatgg gctggataaa cacctacact ggagagccaa catatgctga tgacttcaag    960
ggacgggtta ccatgacttc ggatacctct accagcactg cctatttgga actccacaac   1020
ctcagaagtg atgacacggc tgtatattac tgtgcgcgct ggagttggag tgatggttac   1080
tacgtttact ttgactactg gggccaaggc actacggtca ccgtctcctc aggtggtggt   1140
ggttctggcg gcggcggctc cggtggtggt ggttctgaca tcgtgatgac acagtctcca   1200
gactccctga ctgtgtctct gggcgagagg accaccatca actgcaagtc cagccagagt   1260
gttttagaca gctccaagaa taagaactcc ttagcttggt accagcagaa accaggacag   1320
cctcctaaat tactcctttc ctgggcatct acgcgggaat ccgggatccc tgaccgattc   1380
agtggcagcg ggtctgggac agatttcact ctcactattg acagcctgca gcctgaagat   1440
tctgcaactt actattgtca acagtctgcc cacttcccga tcacctttgg ccaagggaca   1500
cgactggaga ttaaa                                                   1515
```

<210> SEQ ID NO 154
<211> LENGTH: 109
<212> TYPE: PRT
<213> ORGANISM: artificial
<220> FEATURE:
<223> OTHER INFORMATION: VL of F6A

<400> SEQUENCE: 154

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 155
<211> LENGTH: 125
<212> TYPE: PRT
<213> ORGANISM: artificial
<220> FEATURE:
<223> OTHER INFORMATION: VH of F6A

<400> SEQUENCE: 155

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80
```

Ala Tyr Leu Gln Met Asn Asn Leu Lys Thr Glu Asp Thr Ala Val Tyr
            85                  90                  95

Tyr Cys Val Arg His Gly Asn Phe Gly Asn Ser Tyr Val Ser Phe Phe
        100                 105                 110

Ala Tyr Trp Gly Gln Gly Thr Leu Val Thr Val Ser Ser
        115                 120             125

<210> SEQ ID NO 156
<211> LENGTH: 249
<212> TYPE: PRT
<213> ORGANISM: artificial
<220> FEATURE:
<223> OTHER INFORMATION: VH-VL of F6A

<400> SEQUENCE: 156

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
            85                  90                  95

Tyr Cys Val Arg His Gly Asn Phe Gly Asn Ser Tyr Val Ser Phe Phe
        100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 157
<211> LENGTH: 109
<212> TYPE: PRT
<213> ORGANISM: artificial
<220> FEATURE:
<223> OTHER INFORMATION: VL-P of F6A

<400> SEQUENCE: 157

Glu Leu Val Val Thr Gln Glu Pro Ser Leu Thr Val Ser Pro Gly Gly
1               5                   10                  15

```
Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 158
<211> LENGTH: 125
<212> TYPE: PRT
<213> ORGANISM: artificial
<220> FEATURE:
<223> OTHER INFORMATION: VH-P of F6A

<400> SEQUENCE: 158

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser
            115                 120                 125
```

<210> SEQ ID NO 159
<211> LENGTH: 249
<212> TYPE: PRT
<213> ORGANISM: artificial
<220> FEATURE:
<223> OTHER INFORMATION: VH-VL-P of F6A

<400> SEQUENCE: 159

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
```

```
                        85                  90                  95

Tyr Cys Val Arg His Gly Asn Phe Gly Asn Ser Tyr Val Ser Phe Phe
                100                 105                 110

Ala Tyr Trp Gly Gln Gly Thr Leu Val Thr Val Ser Ser Gly Gly Gly
            115                 120                 125

Gly Ser Gly Gly Gly Ser Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 160
<211> LENGTH: 109
<212> TYPE: PRT
<213> ORGANISM: artificial
<220> FEATURE:
<223> OTHER INFORMATION: VL of H2C

<400> SEQUENCE: 160

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
                100                 105

<210> SEQ ID NO 161
<211> LENGTH: 125
<212> TYPE: PRT
<213> ORGANISM: artificial
<220> FEATURE:
<223> OTHER INFORMATION: VH of H2C

<400> SEQUENCE: 161

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30
```

```
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
            115                 120                 125

<210> SEQ ID NO 162
<211> LENGTH: 249
<212> TYPE: PRT
<213> ORGANISM: artificial
<220> FEATURE:
<223> OTHER INFORMATION: VH-VL of H2C

<400> SEQUENCE: 162

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 163
<211> LENGTH: 109
```

<212> TYPE: PRT
<213> ORGANISM: artificial
<220> FEATURE:
<223> OTHER INFORMATION: VL-P of H2C

<400> SEQUENCE: 163

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 164
<211> LENGTH: 125
<212> TYPE: PRT
<213> ORGANISM: artificial
<220> FEATURE:
<223> OTHER INFORMATION: VH-P of H2C

<400> SEQUENCE: 164

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 165
<211> LENGTH: 249
<212> TYPE: PRT
<213> ORGANISM: artificial
<220> FEATURE:
<223> OTHER INFORMATION: VH-VL-P of H2C

<400> SEQUENCE: 165

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val

```
                  35                  40                  45
Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Ser Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly
                180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 166
<211> LENGTH: 109
<212> TYPE: PRT
<213> ORGANISM: artificial
<220> FEATURE:
<223> OTHER INFORMATION: VL of H1E

<400> SEQUENCE: 166

Gln Thr Val Val Thr Gln Glu Pro Ser Leu Thr Val Ser Pro Gly Gly
  1               5                  10                  15

Thr Val Thr Leu Thr Cys Gly Ser Ser Thr Gly Ala Val Thr Ser Gly
                 20                  25                  30

Tyr Tyr Pro Asn Trp Val Gln Gln Lys Pro Gly Gln Ala Pro Arg Gly
             35                  40                  45

Leu Ile Gly Gly Thr Lys Phe Leu Ala Pro Gly Thr Pro Ala Arg Phe
     50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Arg Trp Val Phe Gly Gly Gly Thr Lys Leu Thr Val Leu
            100                 105

<210> SEQ ID NO 167
<211> LENGTH: 125
<212> TYPE: PRT
<213> ORGANISM: artificial
<220> FEATURE:
<223> OTHER INFORMATION: VH of H1E
```

<400> SEQUENCE: 167

Glu Val Gln Leu Val Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser
            115                 120                 125

<210> SEQ ID NO 168
<211> LENGTH: 249
<212> TYPE: PRT
<213> ORGANISM: artificial
<220> FEATURE:
<223> OTHER INFORMATION: VH-VL of H1E

<400> SEQUENCE: 168

Glu Val Gln Leu Val Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser Gly Gly Gly
            115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245

<210> SEQ ID NO 169
<211> LENGTH: 109
<212> TYPE: PRT
<213> ORGANISM: artificial
<220> FEATURE:
<223> OTHER INFORMATION: VL-P of H1E

<400> SEQUENCE: 169

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 170
<211> LENGTH: 125
<212> TYPE: PRT
<213> ORGANISM: artificial
<220> FEATURE:
<223> OTHER INFORMATION: VH-P of H1E

<400> SEQUENCE: 170

Glu Val Gln Leu Leu Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser
        115                 120                 125

<210> SEQ ID NO 171
<211> LENGTH: 249
<212> TYPE: PRT
<213> ORGANISM: artificial
<220> FEATURE:
<223> OTHER INFORMATION: VH-VL-P of H1E

<400> SEQUENCE: 171

```
Glu Val Gln Leu Leu Glu Ser Gly Gly Gly Leu Glu Gln Pro Gly Gly
1               5                   10                  15
Ser Leu Lys Leu Ser Cys Ala Ala Ser Gly Phe Thr Phe Asn Ser Tyr
            20                  25                  30
Ala Met Asn Trp Val Arg Gln Ala Pro Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Leu Ser Phe Trp
            100                 105                 110
Ala Tyr Trp Gly Gln Gly Thr Leu Val Thr Val Ser Ser Gly Gly Gly
        115                 120                 125
Gly Ser Gly Gly Gly Gly Ser Gly Gly Gly Gly Ser Glu Leu Val Val
    130                 135                 140
Thr Gln Glu Pro Ser Leu Thr Val Ser Pro Gly Gly Thr Val Thr Leu
145                 150                 155                 160
Thr Cys Gly Ser Ser Thr Gly Ala Val Thr Ser Gly Tyr Tyr Pro Asn
                165                 170                 175
Trp Val Gln Gln Lys Pro Gly Gln Ala Pro Arg Gly Leu Ile Gly Gly
            180                 185                 190
Thr Lys Phe Leu Ala Pro Gly Thr Pro Ala Arg Phe Ser Gly Ser Leu
        195                 200                 205
Leu Gly Gly Lys Ala Ala Leu Thr Leu Ser Gly Val Gln Pro Glu Asp
    210                 215                 220
Glu Ala Glu Tyr Tyr Cys Ala Leu Trp Tyr Ser Asn Arg Trp Val Phe
225                 230                 235                 240
Gly Gly Gly Thr Lys Leu Thr Val Leu
                245
```

<210> SEQ ID NO 172
<211> LENGTH: 125
<212> TYPE: PRT
<213> ORGANISM: artificial
<220> FEATURE:
<223> OTHER INFORMATION: VL of G4H

<400> SEQUENCE: 172

```
Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Asn Arg Tyr
            20                  25                  30
Ala Met Asn Trp Val Arg Gln Ala Pro Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Leu Ser Tyr Phe
```

```
                         100                 105                 110
Ala Tyr Trp Gly Gln Gly Thr Leu Val Thr Val Ser Ser
            115                 120                 125

<210> SEQ ID NO 173
<211> LENGTH: 125
<212> TYPE: PRT
<213> ORGANISM: artificial
<220> FEATURE:
<223> OTHER INFORMATION: VH of G4H

<400> SEQUENCE: 173

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser
            115                 120                 125

<210> SEQ ID NO 174
<211> LENGTH: 249
<212> TYPE: PRT
<213> ORGANISM: artificial
<220> FEATURE:
<223> OTHER INFORMATION: VH-VL of G4H

<400> SEQUENCE: 174

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160
```

```
Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

<210> SEQ ID NO 175
<211> LENGTH: 109
<212> TYPE: PRT
<213> ORGANISM: artificial
<220> FEATURE:
<223> OTHER INFORMATION: VL-P of G4H

<400> SEQUENCE: 175

```
Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 176
<211> LENGTH: 125
<212> TYPE: PRT
<213> ORGANISM: artificial
<220> FEATURE:
<223> OTHER INFORMATION: VH-P of G4H

<400> SEQUENCE: 176

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110
```

Ala Tyr Trp Gly Gln Gly Thr Leu Val Thr Val Ser Ser
            115                 120                 125

<210> SEQ ID NO 177
<211> LENGTH: 249
<212> TYPE: PRT
<213> ORGANISM: artificial
<220> FEATURE:
<223> OTHER INFORMATION: VH-VL-P of G4H

<400> SEQUENCE: 177

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 178
<211> LENGTH: 109
<212> TYPE: PRT
<213> ORGANISM: artificial
<220> FEATURE:
<223> OTHER INFORMATION: VL of A2J

<400> SEQUENCE: 178

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly

```
                35                  40                  45
Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 179
<211> LENGTH: 125
<212> TYPE: PRT
<213> ORGANISM: artificial
<220> FEATURE:
<223> OTHER INFORMATION: VH of A2J

<400> SEQUENCE: 179

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Trp Trp
            100                 105                 110

Ala Tyr Trp Gly Gln Gly Thr Leu Val Thr Val Ser Ser
        115                 120                 125

<210> SEQ ID NO 180
<211> LENGTH: 249
<212> TYPE: PRT
<213> ORGANISM: artificial
<220> FEATURE:
<223> OTHER INFORMATION: VH-VL of A2J

<400> SEQUENCE: 180

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Trp Trp
            100                 105                 110
```

```
Ala Tyr Trp Gly Gln Gly Thr Leu Val Thr Val Ser Ser Gly Gly
        115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Ala
                180                 185                 190

Thr Asp Met Arg Pro Ser Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245

<210> SEQ ID NO 181
<211> LENGTH: 109
<212> TYPE: PRT
<213> ORGANISM: artificial
<220> FEATURE:
<223> OTHER INFORMATION: VL-P of A2J

<400> SEQUENCE: 181

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
                100                 105

<210> SEQ ID NO 182
<211> LENGTH: 125
<212> TYPE: PRT
<213> ORGANISM: artificial
<220> FEATURE:
<223> OTHER INFORMATION: VH-P of A2J

<400> SEQUENCE: 182

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

```
Ser Val Lys Lys Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Leu Ser Trp Trp
            100                 105                 110

Ala Tyr Trp Gly Gln Gly Thr Leu Val Thr Val Ser Ser
            115                 120                 125
```

<210> SEQ ID NO 183
<211> LENGTH: 249
<212> TYPE: PRT
<213> ORGANISM: artificial
<220> FEATURE:
<223> OTHER INFORMATION: VH-VL-P of A2J

<400> SEQUENCE: 183

```
Glu Val Gln Leu Leu Glu Ser Gly Gly Gly Leu Val Gln Pro Gly Gly
 1               5                  10                  15

Ser Leu Lys Leu Ser Cys Ala Ala Ser Gly Phe Thr Phe Asn Val Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
         50                  55                  60

Ser Val Lys Lys Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Leu Ser Trp Trp
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Glu Leu Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Ala
            180                 185                 190

Thr Asp Met Arg Pro Ser Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

<210> SEQ ID NO 184
<211> LENGTH: 109
<212> TYPE: PRT
<213> ORGANISM: artificial
<220> FEATURE:
<223> OTHER INFORMATION: VL of E1L -continued

<400> SEQUENCE: 184

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Lys Pro Gly Gln Ala Pro Arg Gly
        35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 185
<211> LENGTH: 125
<212> TYPE: PRT
<213> ORGANISM: artificial
<220> FEATURE:
<223> OTHER INFORMATION: VH of E1L

<400> SEQUENCE: 185

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser
        115                 120                 125

<210> SEQ ID NO 186
<211> LENGTH: 249
<212> TYPE: PRT
<213> ORGANISM: artificial
<220> FEATURE:
<223> OTHER INFORMATION: VH-VL of E1L

<400> SEQUENCE: 186

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

```
Ser Val Lys Ser Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 187
<211> LENGTH: 109
<212> TYPE: PRT
<213> ORGANISM: artificial
<220> FEATURE:
<223> OTHER INFORMATION: VL-P of E1L

<400> SEQUENCE: 187

Glu Leu Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                 20                  25                  30

Tyr Tyr Pro Asn Trp Val Gln Gln Lys Pro Gly Gln Ala Pro Arg Gly
             35                  40                  45

Leu Ile Gly Gly Thr Lys Phe Leu Ala Pro Gly Thr Pro Ala Arg Phe
         50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Arg Trp Val Phe Gly Gly Gly Thr Lys Leu Thr Val Leu
            100                 105

<210> SEQ ID NO 188
<211> LENGTH: 125
<212> TYPE: PRT
<213> ORGANISM: artificial
<220> FEATURE:
<223> OTHER INFORMATION: VH-P of E1L

<400> SEQUENCE: 188

Glu Val Gln Leu Leu Glu Ser Gly Gly Gly Leu Val Gln Pro Gly Gly
 1               5                  10                  15
```

```
Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser
            115                 120                 125
```

<210> SEQ ID NO 189
<211> LENGTH: 249
<212> TYPE: PRT
<213> ORGANISM: artificial
<220> FEATURE:
<223> OTHER INFORMATION: VH-VL-P of E1L

<400> SEQUENCE: 189

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Glu Leu Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

```
<210> SEQ ID NO 190
<211> LENGTH: 109
<212> TYPE: PRT
<213> ORGANISM: artificial
<220> FEATURE:
<223> OTHER INFORMATION: VL of E2M

<400> SEQUENCE: 190

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 191
<211> LENGTH: 125
<212> TYPE: PRT
<213> ORGANISM: artificial
<220> FEATURE:
<223> OTHER INFORMATION: VH of E2M

<400> SEQUENCE: 191

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Glu Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
            100                 105                 110

Ala Tyr Trp Gly Gln Gly Thr Leu Val Thr Val Ser Ser
        115                 120                 125

<210> SEQ ID NO 192
<211> LENGTH: 249
<212> TYPE: PRT
<213> ORGANISM: artificial
<220> FEATURE:
<223> OTHER INFORMATION: VH-VL of E2M

<400> SEQUENCE: 192

Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Glu Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
            165                 170                 175

Trp Val Gln Gln Lys Pro Gly Gln Ala Pro Arg Gly Leu Ile Gly Ala
        180                 185                 190

Thr Asp Met Arg Pro Ser Gly Thr Pro Ala Arg Phe Ser Gly Ser Leu
    195                 200                 205

Leu Gly Gly Lys Ala Ala Leu Thr Leu Ser Gly Val Gln Pro Glu Asp
210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245

<210> SEQ ID NO 193
<211> LENGTH: 109
<212> TYPE: PRT
<213> ORGANISM: artificial
<220> FEATURE:
<223> OTHER INFORMATION: VL-P of E2M

<400> SEQUENCE: 193

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 194
<211> LENGTH: 125
```

<212> TYPE: PRT
<213> ORGANISM: artificial
<220> FEATURE:
<223> OTHER INFORMATION: VH-P of E2M

<400> SEQUENCE: 194

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Glu Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
            100                 105                 110

Ala Tyr Trp Gly Gln Gly Thr Leu Val Thr Val Ser Ser
        115                 120                 125

<210> SEQ ID NO 195
<211> LENGTH: 249
<212> TYPE: PRT
<213> ORGANISM: artificial
<220> FEATURE:
<223> OTHER INFORMATION: VH-VL-P of E2M

<400> SEQUENCE: 195

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Glu Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
            165                 170                 175

Trp Val Gln Gln Lys Pro Gly Gln Ala Pro Arg Gly Leu Ile Gly Ala
        180                 185                 190

Thr Asp Met Arg Pro Ser Gly Thr Pro Ala Arg Phe Ser Gly Ser Leu
    195                 200                 205

```
<210> SEQ ID NO 196
<211> LENGTH: 109
<212> TYPE: PRT
<213> ORGANISM: artificial
<220> FEATURE:
<223> OTHER INFORMATION: VL of F70

<400> SEQUENCE: 196

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 197
<211> LENGTH: 125
<212> TYPE: PRT
<213> ORGANISM: artificial
<220> FEATURE:
<223> OTHER INFORMATION: VH of F70

<400> SEQUENCE: 197

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
        115                 120                 125

<210> SEQ ID NO 198
<211> LENGTH: 249
<212> TYPE: PRT
```

The preceding (continued) sequence begins:

```
Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245
```

<213> ORGANISM: artificial
<220> FEATURE:
<223> OTHER INFORMATION: VH-VL of F70

<400> SEQUENCE: 198

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 199
<211> LENGTH: 109
<212> TYPE: PRT
<213> ORGANISM: artificial
<220> FEATURE:
<223> OTHER INFORMATION: VL-P of F70

<400> SEQUENCE: 199

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 200
<211> LENGTH: 125
<212> TYPE: PRT
<213> ORGANISM: artificial
<220> FEATURE:
<223> OTHER INFORMATION: VH-P of F70

<400> SEQUENCE: 200

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
        115                 120                 125

<210> SEQ ID NO 201
<211> LENGTH: 249
<212> TYPE: PRT
<213> ORGANISM: artificial
<220> FEATURE:
<223> OTHER INFORMATION: VH-VL-P of F70

<400> SEQUENCE: 201

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

```
Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

<210> SEQ ID NO 202
<211> LENGTH: 109
<212> TYPE: PRT
<213> ORGANISM: artificial
<220> FEATURE:
<223> OTHER INFORMATION: VL of F12Q

<400> SEQUENCE: 202

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
                100                 105
```

<210> SEQ ID NO 203
<211> LENGTH: 125
<212> TYPE: PRT
<213> ORGANISM: artificial
<220> FEATURE:
<223> OTHER INFORMATION: VH of F12Q

<400> SEQUENCE: 203

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
```

```
            100                 105                 110
Ala Tyr Trp Gly Gln Gly Thr Leu Val Thr Val Ser Ser
        115                 120                 125
```

<210> SEQ ID NO 204
<211> LENGTH: 249
<212> TYPE: PRT
<213> ORGANISM: artificial
<220> FEATURE:
<223> OTHER INFORMATION: VH-VL of F12Q

<400> SEQUENCE: 204

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 205
<211> LENGTH: 109
<212> TYPE: PRT
<213> ORGANISM: artificial
<220> FEATURE:
<223> OTHER INFORMATION: VL-P of F12Q

<400> SEQUENCE: 205

```
Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30
```

-continued

Asn Tyr Pro Asn Trp Val Gln Gln Lys Pro Gly Gln Ala Pro Arg Gly
                35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
                100                 105

<210> SEQ ID NO 206
<211> LENGTH: 125
<212> TYPE: PRT
<213> ORGANISM: artificial
<220> FEATURE:
<223> OTHER INFORMATION: VH-P of F12Q

<400> SEQUENCE: 206

Glu Val Gln Leu Leu Glu Ser Gly Gly Gly Leu Val Gln Pro Gly Gly
 1               5                   10                  15

Ser Leu Lys Leu Ser Cys Ala Ala Ser Gly Phe Thr Phe Asn Ser Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
         50                  55                  60

Ser Val Lys Gly Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
                100                 105                 110

Ala Tyr Trp Gly Gln Gly Thr Leu Val Thr Val Ser Ser
            115                 120                 125

<210> SEQ ID NO 207
<211> LENGTH: 249
<212> TYPE: PRT
<213> ORGANISM: artificial
<220> FEATURE:
<223> OTHER INFORMATION: VH-VL-P of F12Q

<400> SEQUENCE: 207

Glu Val Gln Leu Leu Glu Ser Gly Gly Gly Leu Val Gln Pro Gly Gly
 1               5                   10                  15

Ser Leu Lys Leu Ser Cys Ala Ala Ser Gly Phe Thr Phe Asn Ser Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
         50                  55                  60

Ser Val Lys Gly Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
                100                 105                 110

Ala Tyr Trp Gly Gln Gly Thr Leu Val Thr Val Ser Ser Gly Gly
            115                 120                 125

Gly Ser Gly Gly Gly Ser Gly Gly Gly Ser Glu Leu Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 208
<211> LENGTH: 109
<212> TYPE: PRT
<213> ORGANISM: artificial
<220> FEATURE:
<223> OTHER INFORMATION: VL of I2C

<400> SEQUENCE: 208

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 209
<211> LENGTH: 125
<212> TYPE: PRT
<213> ORGANISM: artificial
<220> FEATURE:
<223> OTHER INFORMATION: VH of I2C

<400> SEQUENCE: 209

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp

```
                    50                  55                  60
Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser
            115                 120                 125

<210> SEQ ID NO 210
<211> LENGTH: 249
<212> TYPE: PRT
<213> ORGANISM: artificial
<220> FEATURE:
<223> OTHER INFORMATION: VH-VL of I2C

<400> SEQUENCE: 210

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Asn Lys Tyr
                 20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
         50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 211
<211> LENGTH: 109
<212> TYPE: PRT
<213> ORGANISM: artificial
<220> FEATURE:
<223> OTHER INFORMATION: VL-P of I2C
```

<400> SEQUENCE: 211

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 212
<211> LENGTH: 125
<212> TYPE: PRT
<213> ORGANISM: artificial
<220> FEATURE:
<223> OTHER INFORMATION: VH-P of I2C

<400> SEQUENCE: 212

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 213
<211> LENGTH: 249
<212> TYPE: PRT
<213> ORGANISM: artificial
<220> FEATURE:
<223> OTHER INFORMATION: VH-VL-P of I2C

<400> SEQUENCE: 213

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
            85                  90                  95

Tyr Cys Val Arg His Gly Asn Phe Gly Asn Ser Tyr Ile Ser Tyr Trp
        100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Leu Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 214
<211> LENGTH: 1587
<212> TYPE: DNA
<213> ORGANISM: artificial
<220> FEATURE:
<223> OTHER INFORMATION: SA21-CD33 E11 HL x I2C HL (His Tag)

<400> SEQUENCE: 214
cgcctgattg aagatatttg cctgccgcgc tggggctgcc tgtgggaaga tgatcaggtg      60
cagctggtgc agtctggagc tgaggtgaag aagcctggag agtcagtcaa ggtctcctgc     120
aaggctagcg gtataccctt cacaaactat ggaatgaact gggtgaagca ggctccagga     180
cagggtttag agtggatggg ctggataaac acctacactg agagccaacc tatgctgat     240 aagttccagg gacgcgttac catgactacg gataccctca ccagcactgc ctatatggaa     300
atccgcaacc tcgaggtga tgacacggct gtatattact gtgcgcgctg gagttggagt     360
gatggttact acgtttactt tgactactgg ggccaaggca cttcggtcac cgtctcctca     420
ggtggtggtg gttctggcgg cggcggctcc ggtggtggtg gttctgacat cgtgatgaca     480
cagtctccag actccctgac tgtgtctctg ggcgagagga ccaccatcaa ctgcaagtcc     540
agccagagtg ttttagacag ctccacgaat aagaactcct tagcttggta ccagcagaaa     600
ccaggacagc ctcctaaatt actcctttcc tgggcatcta cgcgggaatc cggatccct     660 gaccgattca gtggcagcgg gtctgggaca gatttcactc tcactattga cagcccgcag     720
cctgaagatt ctgcaactta ctattgtcaa cagtctgccc acttcccgat cacctttggc     780
caagggacac gactggagat taaatccgga ggtggtggct ccgaggtgca gctggtcgag     840
tctggaggag gattggtgca gcctggaggg tcattgaaac tctcatgtgc agcctctgga     900
ttcaccttca ataagtacgc catgaactgg gtccgccagg ctccaggaaa gggtttggaa     960

```
tgggttgctc gcataagaag taaatataat aattatgcaa catattatgc cgattcagtg   1020
aaagacaggt tcaccatctc cagagatgat tcaaaaaaca ctgcctatct acaaatgaac   1080
aacttgaaaa ctgaggacac tgccgtgtac tactgtgtga catgggaa cttcggtaat     1140 agctacatat cctactgggc ttactggggc caagggactc tggtcaccgt ctcctcaggt   1200
ggtggtggtt ctggcggcgg cggctccggt ggtggtggtt ctcagactgt tgtgactcag   1260
gaaccttcac tcaccgtatc acctggtgga acagtcacac tcacttgtgg ctcctcgact   1320
ggggctgtta catctggcaa ctacccaaac tgggtccaac aaaaaccagg tcaggcaccc   1380
cgtggtctaa taggtgggac taagttcctc gcccccggta ctcctgccag attctcaggc   1440
tccctgcttg gaggcaaggc tgccctcacc ctctcagggg tacagccaga ggatgaggca   1500
gaatattact gtgttctatg gtacagcaac cgctgggtgt cggtggagg aaccaaactg    1560 actgtcctac atcaccatca ccatcac                                      1587
```

<210> SEQ ID NO 215
<211> LENGTH: 529
<212> TYPE: PRT
<213> ORGANISM: artificial
<220> FEATURE:
<223> OTHER INFORMATION: SA21-CD33 E11 HL x I2C HL H6

<400> SEQUENCE: 215

```
Arg Leu Ile Glu Asp Ile Cys Leu Pro Arg Trp Gly Cys Leu Trp Glu
1               5                   10                  15

Asp Asp Gln Val Gln Leu Val Gln Ser Gly Ala Glu Val Lys Lys Pro
            20                  25                  30

Gly Glu Ser Val Lys Val Ser Cys Lys Ala Ser Gly Tyr Thr Phe Thr
        35                  40                  45

Asn Tyr Gly Met Asn Trp Val Lys Gln Ala Pro Gly Gln Gly Leu Glu
    50                  55                  60

Trp Met Gly Trp Ile Asn Thr Tyr Thr Gly Glu Pro Thr Tyr Ala Asp
65                  70                  75                  80

Lys Phe Gln Gly Arg Val Thr Met Thr Thr Asp Thr Ser Thr Ser Thr
                85                  90                  95

Ala Tyr Met Glu Ile Arg Asn Leu Gly Gly Asp Thr Ala Val Tyr
            100                 105                 110

Tyr Cys Ala Arg Trp Ser Trp Ser Asp Gly Tyr Tyr Val Tyr Phe Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Asp Ile Val Met Thr
145                 150                 155                 160

Gln Ser Pro Asp Ser Leu Thr Val Ser Leu Gly Glu Arg Thr Thr Ile
                165                 170                 175

Asn Cys Lys Ser Ser Gln Ser Val Leu Asp Ser Ser Thr Asn Lys Asn
            180                 185                 190

Ser Leu Ala Trp Tyr Gln Gln Lys Pro Gly Gln Pro Pro Lys Leu Leu
        195                 200                 205

Leu Ser Trp Ala Ser Thr Arg Glu Ser Gly Ile Pro Asp Arg Phe Ser
    210                 215                 220

Gly Ser Gly Ser Gly Thr Asp Phe Thr Leu Thr Ile Asp Ser Pro Gln
225                 230                 235                 240

Pro Glu Asp Ser Ala Thr Tyr Tyr Cys Gln Gln Ser Ala His Phe Pro
                245                 250                 255
```

Ile Thr Phe Gly Gln Gly Thr Arg Leu Glu Ile Lys Ser Gly Gly Gly
            260                 265                 270

Gly Ser Glu Val Gln Leu Val Glu Ser Gly Gly Gly Leu Val Gln Pro
        275                 280                 285

Gly Gly Ser Leu Lys Leu Ser Cys Ala Ala Ser Gly Phe Thr Phe Asn
    290                 295                 300

Lys Tyr Ala Met Asn Trp Val Arg Gln Ala Pro Gly Lys Gly Leu Glu
305                 310                 315                 320

Trp Val Ala Arg Ile Arg Ser Lys Tyr Asn Asn Tyr Ala Thr Tyr Tyr
                325                 330                 335

Ala Asp Ser Val Lys Asp Arg Phe Thr Ile Ser Arg Asp Asp Ser Lys
            340                 345                 350

Asn Thr Ala Tyr Leu Gln Met Asn Asn Leu Lys Thr Glu Asp Thr Ala
        355                 360                 365

Val Tyr Tyr Cys Val Arg His Gly Asn Phe Gly Asn Ser Tyr Ile Ser
    370                 375                 380

Tyr Trp Ala Tyr Trp Gly Gln Gly Thr Leu Val Thr Val Ser Ser Gly
385                 390                 395                 400

Gly Gly Gly Ser Gly Gly Gly Ser Gly Gly Gly Ser Gln Thr
                405                 410                 415

Val Val Thr Gln Glu Pro Ser Leu Thr Val Ser Pro Gly Gly Thr Val
            420                 425                 430

Thr Leu Thr Cys Gly Ser Ser Thr Gly Ala Val Thr Ser Gly Asn Tyr
        435                 440                 445

Pro Asn Trp Val Gln Gln Lys Pro Gly Gln Ala Pro Arg Gly Leu Ile
    450                 455                 460

Gly Gly Thr Lys Phe Leu Ala Pro Gly Thr Pro Ala Arg Phe Ser Gly
465                 470                 475                 480

Ser Leu Leu Gly Gly Lys Ala Ala Leu Thr Leu Ser Gly Val Gln Pro
                485                 490                 495

Glu Asp Glu Ala Glu Tyr Tyr Cys Val Leu Trp Tyr Ser Asn Arg Trp
            500                 505                 510

Val Phe Gly Gly Gly Thr Lys Leu Thr Val Leu His His His His
        515                 520                 525

His

<210> SEQ ID NO 216
<211> LENGTH: 1575
<212> TYPE: DNA
<213> ORGANISM: artificial
<220> FEATURE:
<223> OTHER INFORMATION: SA25-CD33 E11 HL x I2C HL with His tag

<400> SEQUENCE: 216
gaggacatct gcctgcccag atggggctgc ctgtgggagg accaggtgca gctggtgcag      60
tctggagctg aggtgaagaa gcctggagag tcagtcaagg tctcctgcaa ggctagcggg     120
tataccttca caaactatgg aatgaactgg gtgaagcagg ctccaggaca gggtttagag     180
tggatgggct ggataaacac ctacactgga gagccaacct atgctgataa gttccaggga     240
cgcgttacca tgactacgga tacctctacc agcactgcct atatggaaat ccgcaacctc     300
ggaggtgatg acacggctgt atattactgt gcgcgctgga gttggagtga tggttactac     360
gtttactttg actactgggg ccaaggcact tcggtcaccg tctcctcagg tggtggtggt     420
tctggcggcg gcggctccgg tggtggtggt tctgacatcg tgatgacaca gtctccagac     480

```
tccctgactg tgtctctggg cgagaggacc accatcaact gcaagtccag ccagagtgtt      540
ttagacagct ccacgaataa gaactcctta gcttggtacc agcagaaacc aggacagcct      600
cctaaattac tcctttcctg ggcatctacg cgggaatccg ggatccctga ccgattcagt      660
ggcagcgggt ctgggacaga tttcactctc actattgaca gcccgcagcc tgaagattct      720
gcaacttact attgtcaaca gtctgcccac ttcccgatca cctttggcca agggacacga      780
ctggagatta atccggaggt ggtggctcc gaggtgcagc tggtcgagtc tggaggagga      840
ttggtgcagc ctggagggtc attgaaactc tcatgtgcag cctctggatt caccttcaat      900
aagtacgcca tgaactgggt ccgccaggct ccaggaaagg gtttggaatg ggttgctcgc      960
ataagaagta aatataataa ttatgcaaca tattatgccg attcagtgaa agacaggttc     1020
accatctcca gagatgattc aaaaaacact gcctatctac aaatgaacaa cttgaaaact     1080
gaggacactg ccgtgtacta ctgtgtgaga catgggaact tcggtaatag ctacatatcc     1140
tactgggctt actggggcca agggactctg gtcaccgtct cctcaggtgg tggtggttct     1200
ggcggcggcg gctccggtgg tggtggttct cagactgttg tgactcagga accttcactc     1260
accgtatcac ctggtggaac agtcacactc acttgtggct cctcgactgg ggctgttaca     1320
tctggcaact acccaaactg ggtccaacaa aaaccaggtc aggcaccccg tggtctaata     1380
ggtgggacta gttcctcgc cccggtact cctgccagat tctcaggctc cctgcttgga     1440
ggcaaggctg ccctcaccct ctcaggggta cagccagagg atgaggcaga atattactgt     1500
gttctatggt acagcaaccg ctgggtgttc ggtggaggaa ccaaactgac tgtcctacat     1560
caccatcacc atcac                                                      1575
```

<210> SEQ ID NO 217
<211> LENGTH: 525
<212> TYPE: PRT
<213> ORGANISM: artificial
<220> FEATURE:
<223> OTHER INFORMATION: SA25-CD33 E11 HL x I2C HL H6

<400> SEQUENCE: 217

```
Glu Asp Ile Cys Leu Pro Arg Trp Gly Cys Leu Trp Glu Asp Gln Val
1               5                   10                  15

Gln Leu Val Gln Ser Gly Ala Glu Val Lys Lys Pro Gly Glu Ser Val
            20                  25                  30

Lys Val Ser Cys Lys Ala Ser Gly Tyr Thr Phe Thr Asn Tyr Gly Met
        35                  40                  45

Asn Trp Val Lys Gln Ala Pro Gly Gln Gly Leu Glu Trp Met Gly Trp
    50                  55                  60

Ile Asn Thr Tyr Thr Gly Glu Pro Thr Tyr Ala Asp Lys Phe Gln Gly
65                  70                  75                  80

Arg Val Thr Met Thr Thr Asp Thr Ser Thr Ser Thr Ala Tyr Met Glu
                85                  90                  95

Ile Arg Asn Leu Gly Gly Asp Asp Thr Ala Val Tyr Tyr Cys Ala Arg
            100                 105                 110

Trp Ser Trp Ser Asp Gly Tyr Tyr Val Tyr Phe Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Asp Ile Val Met Thr Gln Ser Pro Asp
145                 150                 155                 160
```

Ser Leu Thr Val Ser Leu Gly Glu Arg Thr Thr Ile Asn Cys Lys Ser
        165                 170                 175

Ser Gln Ser Val Leu Asp Ser Ser Thr Asn Lys Asn Ser Leu Ala Trp
            180                 185                 190

Tyr Gln Gln Lys Pro Gly Gln Pro Pro Lys Leu Leu Leu Ser Trp Ala
            195                 200                 205

Ser Thr Arg Glu Ser Gly Ile Pro Asp Arg Phe Ser Gly Ser Gly Ser
        210                 215                 220

Gly Thr Asp Phe Thr Leu Thr Ile Asp Ser Pro Gln Pro Glu Asp Ser
225                 230                 235                 240

Ala Thr Tyr Tyr Cys Gln Gln Ser Ala His Phe Pro Ile Thr Phe Gly
            245                 250                 255

Gln Gly Thr Arg Leu Glu Ile Lys Ser Gly Gly Gly Gly Ser Glu Val
            260                 265                 270

Gln Leu Val Glu Ser Gly Gly Gly Leu Val Gln Pro Gly Gly Ser Leu
        275                 280                 285

Lys Leu Ser Cys Ala Ala Ser Gly Phe Thr Phe Asn Lys Tyr Ala Met
290                 295                 300

Asn Trp Val Arg Gln Ala Pro Gly Lys Gly Leu Glu Trp Val Ala Arg
305                 310                 315                 320

Ile Arg Ser Lys Tyr Asn Asn Tyr Ala Thr Tyr Tyr Ala Asp Ser Val
            325                 330                 335

Lys Asp Arg Phe Thr Ile Ser Arg Asp Asp Ser Lys Asn Thr Ala Tyr
            340                 345                 350

Leu Gln Met Asn Asn Leu Lys Thr Glu Asp Thr Ala Val Tyr Tyr Cys
        355                 360                 365

Val Arg His Gly Asn Phe Gly Asn Ser Tyr Ile Ser Tyr Trp Ala Tyr
370                 375                 380

Trp Gly Gln Gly Thr Leu Val Thr Val Ser Ser Gly Gly Gly Gly Ser
385                 390                 395                 400

Gly Gly Gly Gly Ser Gly Gly Gly Ser Gln Thr Val Val Thr Gln
            405                 410                 415

Glu Pro Ser Leu Thr Val Ser Pro Gly Gly Thr Val Thr Leu Thr Cys
            420                 425                 430

Gly Ser Ser Thr Gly Ala Val Thr Ser Gly Asn Tyr Pro Asn Trp Val
        435                 440                 445

Gln Gln Lys Pro Gly Gln Ala Pro Arg Gly Leu Ile Gly Gly Thr Lys
        450                 455                 460

Phe Leu Ala Pro Gly Thr Pro Ala Arg Phe Ser Gly Ser Leu Leu Gly
465                 470                 475                 480

Gly Lys Ala Ala Leu Thr Leu Ser Gly Val Gln Pro Glu Asp Glu Ala
            485                 490                 495

Glu Tyr Tyr Cys Val Leu Trp Tyr Ser Asn Arg Trp Val Phe Gly Gly
        500                 505                 510

Gly Thr Lys Leu Thr Val Leu His His His His His
            515                 520                 525

<210> SEQ ID NO 218
<211> LENGTH: 1596
<212> TYPE: DNA
<213> ORGANISM: artificial
<220> FEATURE:
<223> OTHER INFORMATION: SA08-CD33 E11 HL x I2C HL with His tag

<400> SEQUENCE: 218

| | | |
|---|---|---|
| cagggcctga tcggcgacat ctgcctgccc agatggggct gcctgtgggg cgactccgtg | 60 | |
| aaacaggtgc agctggtgca gtctggagct gaggtgaaga agcctggaga gtcagtcaag | 120 | |
| gtctcctgca aggctagcgg gtataccttc acaaactatg gaatgaactg ggtgaagcag | 180 | |
| gctccaggac agggtttaga gtggatgggc tggataaaca cctacactgg agagccaacc | 240 | |
| tatgctgata agttccaggg acgcgttacc atgactacgg atacctctac cagcactgcc | 300 | |
| tatatggaaa tccgcaacct cggaggtgat gacacggctg tatattactg tgcgcgctgg | 360 | |
| agttggagtg atggttacta cgtttacttt gactactggg gccaaggcac ttcggtcacc | 420 | |
| gtctcctcag gtggtggtgg ttctggcggc ggcggctccg gtggtggtgg ttctgacatc | 480 | |
| gtgatgacac agtctccaga ctccctgact gtgtctctgg gcgagaggac caccatcaac | 540 | |
| tgcaagtcca gccagagtgt tttagacagc tccacgaata agaactcctt agcttggtac | 600 | |
| cagcagaaac caggacagcc tcctaaatta ctcctttcct gggcatctac gcgggaatcc | 660 | |
| gggatccctg accgattcag tggcagcggg tctgggacag atttcactct cactattgac | 720 | |
| agcccgcagc ctgaagattc tgcaacttac tattgtcaac agtctgccca cttcccgatc | 780 | |
| acctttggcc aagggacacg actggagatt aaatccggag gtggtggctc cgaggtgcag | 840 | |
| ctggtcgagt ctggaggagg attggtgcag cctggagggt cattgaaact ctcatgtgca | 900 | |
| gcctctggat tcaccttcaa taagtacgcc atgaactggg tccgccaggc tccaggaaag | 960 | |
| ggtttggaat gggttgctcg cataagaagt aaatataata attatgcaac atattatgcc | 1020 | |
| gattcagtga aagacaggtt caccatctcc agagatgatt caaaaaacac tgcctatcta | 1080 | |
| caaatgaaca acttgaaaac tgaggacact gccgtgtact actgtgtgag acatgggaac | 1140 | |
| ttcggtaata gctacatatc ctactgggct tactggggcc aagggactct ggtcaccgtc | 1200 | |
| tcctcaggtg gtggtggttc tggcggcggc ggctccggtg gtggtggttc tcagactgtt | 1260 | |
| gtgactcagg aaccttcact caccgtatca cctggtggaa cagtcacact cacttgtggc | 1320 | |
| tcctcgactg gggctgttac atctggcaac tacccaaaac tgggtccaac aaaaaccaggt | 1380 | |
| caggcacccc gtggtctaat aggtgggact aagttcctcg cccccggtac tcctgccaga | 1440 | |
| ttctcaggct ccctgcttgg aggcaaggct gccctcaccc tctcaggggt acagccagag | 1500 | |
| gatgaggcag aatattactg tgttctatgg tacagcaacc gctgggtgtt cggtggagga | 1560 | |
| accaaactga ctgtcctaca tcaccatcac catcac | 1596 | |

<210> SEQ ID NO 219
<211> LENGTH: 532
<212> TYPE: PRT
<213> ORGANISM: artificial
<220> FEATURE:
<223> OTHER INFORMATION: SA08-CD33 E11 HL x I2C HL H6

<400> SEQUENCE: 219

```
Gln Gly Leu Ile Gly Asp Ile Cys Leu Pro Arg Trp Gly Cys Leu Trp
1               5                   10                  15

Gly Asp Ser Val Lys Gln Val Gln Leu Val Gln Ser Gly Ala Glu Val
            20                  25                  30

Lys Lys Pro Gly Glu Ser Val Lys Val Ser Cys Lys Ala Ser Gly Tyr
        35                  40                  45

Thr Phe Thr Asn Tyr Gly Met Asn Trp Val Lys Gln Ala Pro Gly Gln
    50                  55                  60

Gly Leu Glu Trp Met Gly Trp Ile Asn Thr Tyr Thr Gly Glu Pro Thr
65                  70                  75                  80
```

```
Tyr Ala Asp Lys Phe Gln Gly Arg Val Thr Met Thr Thr Asp Thr Ser
            85                  90                  95
Thr Ser Thr Ala Tyr Met Glu Ile Arg Asn Leu Gly Gly Asp Asp Thr
            100                 105                 110
Ala Val Tyr Tyr Cys Ala Arg Trp Ser Trp Ser Asp Gly Tyr Tyr Val
            115                 120                 125
Tyr Phe Asp Tyr Trp Gly Gln Gly Thr Ser Val Thr Val Ser Ser Gly
        130                 135                 140
Gly Gly Gly Ser Gly Gly Gly Ser Gly Gly Gly Ser Asp Ile
145                 150                 155                 160
Val Met Thr Gln Ser Pro Asp Ser Leu Thr Val Ser Leu Gly Glu Arg
            165                 170                 175
Thr Thr Ile Asn Cys Lys Ser Ser Gln Ser Val Leu Asp Ser Ser Thr
            180                 185                 190
Asn Lys Asn Ser Leu Ala Trp Tyr Gln Gln Lys Pro Gly Gln Pro Pro
            195                 200                 205
Lys Leu Leu Leu Ser Trp Ala Ser Thr Arg Glu Ser Gly Ile Pro Asp
    210                 215                 220
Arg Phe Ser Gly Ser Gly Ser Gly Thr Asp Phe Thr Leu Thr Ile Asp
225                 230                 235                 240
Ser Pro Gln Pro Glu Asp Ser Ala Thr Tyr Tyr Cys Gln Gln Ser Ala
            245                 250                 255
His Phe Pro Ile Thr Phe Gly Gln Gly Thr Arg Leu Glu Ile Lys Ser
            260                 265                 270
Gly Gly Gly Gly Ser Glu Val Gln Leu Val Glu Ser Gly Gly Gly Leu
        275                 280                 285
Val Gln Pro Gly Gly Ser Leu Lys Leu Ser Cys Ala Ala Ser Gly Phe
    290                 295                 300
Thr Phe Asn Lys Tyr Ala Met Asn Trp Val Arg Gln Ala Pro Gly Lys
305                 310                 315                 320
Gly Leu Glu Trp Val Ala Arg Ile Arg Ser Lys Tyr Asn Asn Tyr Ala
            325                 330                 335
Thr Tyr Tyr Ala Asp Ser Val Lys Asp Arg Phe Thr Ile Ser Arg Asp
        340                 345                 350
Asp Ser Lys Asn Thr Ala Tyr Leu Gln Met Asn Asn Leu Lys Thr Glu
            355                 360                 365
Asp Thr Ala Val Tyr Tyr Cys Val Arg His Gly Asn Phe Gly Asn Ser
        370                 375                 380
Tyr Ile Ser Tyr Trp Ala Tyr Trp Gly Gln Gly Thr Leu Val Thr Val
385                 390                 395                 400
Ser Ser Gly Gly Gly Gly Ser Gly Gly Gly Gly Ser Gly Gly Gly Gly
            405                 410                 415
Ser Gln Thr Val Val Thr Gln Glu Pro Ser Leu Thr Val Ser Pro Gly
            420                 425                 430
Gly Thr Val Thr Leu Thr Cys Gly Ser Ser Thr Gly Ala Val Thr Ser
            435                 440                 445
Gly Asn Tyr Pro Asn Trp Val Gln Gln Lys Pro Gly Gln Ala Pro Arg
    450                 455                 460
Gly Leu Ile Gly Gly Thr Lys Phe Leu Ala Pro Gly Thr Pro Ala Arg
465                 470                 475                 480
Phe Ser Gly Ser Leu Leu Gly Gly Lys Ala Ala Leu Thr Leu Ser Gly
            485                 490                 495
Val Gln Pro Glu Asp Glu Ala Glu Tyr Tyr Cys Val Leu Trp Tyr Ser
```

```
                  500             505             510
Asn Arg Trp Val Phe Gly Gly Gly Thr Lys Leu Thr Val Leu His His
        515             520             525
His His His His
    530
```

<210> SEQ ID NO 220
<211> LENGTH: 1569
<212> TYPE: DNA
<213> ORGANISM: artificial
<220> FEATURE:
<223> OTHER INFORMATION: SA21-CD33 E11 HL x I2C HL

<400> SEQUENCE: 220

```
cgcctgattg aagatatttg cctgccgcgc tggggctgcc tgtgggaaga tgatcaggtg      60
cagctggtgc agtctggagc tgaggtgaag aagcctggag agtcagtcaa ggtctcctgc     120
aaggctagcg gtataccttt cacaaactat ggaatgaact gggtgaagca ggctccagga     180
cagggtttag agtggatggg ctggataaac acctacactg gagagccaac ctatgctgat     240
aagttccagg gacgcgttac catgactacg gatacctcta ccagcactgc ctatatggaa     300
atccgcaacc tcgaggtga tgacacggct gtatattact gtgcgcgctg gagttggagt     360
gatggttact acgtttactt tgactactgg ggccaaggca cttcggtcac cgtctcctca     420
ggtggtggtg gttctggcgg cggcggctcc ggtggtggtg gttctgacat cgtgatgaca     480
cagtctccag actccctgac tgtgtctctg ggcgagagga ccaccatcaa ctgcaagtcc     540
agccagagtg ttttagacag ctccacgaat aagaactcct tagcttggta ccagcagaaa     600
ccaggacagc ctcctaaatt actcctttcc tgggcatcta cgcgggaatc cgggatccct     660
gaccgattca gtggcagcgg gtctgggaca gatttcactc tcactattga cagcccgcag     720
cctgaagatt ctgcaactta ctattgtcaa cagtctgccc acttcccgat caccttggc     780
caagggacac gactggagat taatccgga ggtggtggct ccgaggtgca gctggtcgag     840
tctggaggag gattggtgca gcctggaggg tcattgaaac tctcatgtgc agcctctgga     900
ttcaccttca ataagtacgc catgaactgg gtccgccagg ctccaggaaa gggtttggaa     960
tgggttgctc gcataagaag taaatataat aattatgcaa catattatgc cgattcagtg    1020
aaagacaggt tcaccatctc cagagatgat tcaaaaaaca ctgcctatct acaaatgaac    1080
aacttgaaaa ctgaggacac tgccgtgtac tactgtgtga catgggaa cttcggtaat    1140
agctacatat cctactgggc ttactggggc caagggactc tggtcaccgt ctcctcaggt    1200
ggtggtggtt ctggcggcgg cggctccggt ggtggtggtt ctcagactgt tgtgactcag    1260
gaaccttcac tcaccgtatc acctggtgga acagtcacac tcacttgtgg ctcctcgact    1320
ggggctgtta catctggcaa ctacccaaac tgggtccaac aaaaaccagg tcaggcaccc    1380
cgtggtctaa taggtgggac taagttcctc gccccggta ctcctgccag attctcaggc    1440
tccctgcttg gaggcaaggc tgccctcacc ctctcagggg tacagccaga ggatgaggca    1500
gaatattact gtgttctatg gtacagcaac cgctgggtgt cggtggagg aaccaaactg    1560
actgtccta                                                            1569
```

<210> SEQ ID NO 221
<211> LENGTH: 523
<212> TYPE: PRT
<213> ORGANISM: artificial
<220> FEATURE:
<223> OTHER INFORMATION: SA21-CD33 E11 HL x I2C HL

<400> SEQUENCE: 221

Arg Leu Ile Glu Asp Ile Cys Leu Pro Arg Trp Gly Cys Leu Trp Glu
1               5                   10                  15

Asp Asp Gln Val Gln Leu Val Gln Ser Gly Ala Glu Val Lys Lys Pro
            20                  25                  30

Gly Glu Ser Val Lys Val Ser Cys Lys Ala Ser Gly Tyr Thr Phe Thr
        35                  40                  45

Asn Tyr Gly Met Asn Trp Val Lys Gln Ala Pro Gly Gln Gly Leu Glu
50                  55                  60

Trp Met Gly Trp Ile Asn Thr Tyr Thr Gly Glu Pro Thr Tyr Ala Asp
65                  70                  75                  80

Lys Phe Gln Gly Arg Val Thr Met Thr Thr Asp Thr Ser Thr Ser Thr
                85                  90                  95

Ala Tyr Met Glu Ile Arg Asn Leu Gly Gly Asp Thr Ala Val Tyr Tyr
            100                 105                 110

Tyr Cys Ala Arg Trp Ser Trp Ser Asp Gly Tyr Tyr Val Tyr Phe Asp
        115                 120                 125

Tyr Trp Gly Gln Gly Thr Ser Val Thr Val Ser Ser Gly Gly Gly Gly
130                 135                 140

Ser Gly Gly Gly Gly Ser Gly Gly Gly Ser Asp Ile Val Met Thr
145                 150                 155                 160

Gln Ser Pro Asp Ser Leu Thr Val Ser Leu Gly Glu Arg Thr Thr Ile
                165                 170                 175

Asn Cys Lys Ser Ser Gln Ser Val Leu Asp Ser Ser Thr Asn Lys Asn
            180                 185                 190

Ser Leu Ala Trp Tyr Gln Gln Lys Pro Gly Gln Pro Pro Lys Leu Leu
        195                 200                 205

Leu Ser Trp Ala Ser Thr Arg Glu Ser Gly Ile Pro Asp Arg Phe Ser
210                 215                 220

Gly Ser Gly Ser Gly Thr Asp Phe Thr Leu Thr Ile Asp Ser Pro Gln
225                 230                 235                 240

Pro Glu Asp Ser Ala Thr Tyr Tyr Cys Gln Gln Ser Ala His Phe Pro
                245                 250                 255

Ile Thr Phe Gly Gln Gly Thr Arg Leu Glu Ile Lys Ser Gly Gly Gly
            260                 265                 270

Gly Ser Glu Val Gln Leu Val Glu Ser Gly Gly Gly Leu Val Gln Pro
        275                 280                 285

Gly Gly Ser Leu Lys Leu Ser Cys Ala Ala Ser Gly Phe Thr Phe Asn
290                 295                 300

Lys Tyr Ala Met Asn Trp Val Arg Gln Ala Pro Gly Lys Gly Leu Glu
305                 310                 315                 320

Trp Val Ala Arg Ile Arg Ser Lys Tyr Asn Asn Tyr Ala Thr Tyr Tyr
                325                 330                 335

Ala Asp Ser Val Lys Asp Arg Phe Thr Ile Ser Arg Asp Asp Ser Lys
            340                 345                 350

Asn Thr Ala Tyr Leu Gln Met Asn Asn Leu Lys Thr Glu Asp Thr Ala
        355                 360                 365

Val Tyr Tyr Cys Val Arg His Gly Asn Phe Gly Asn Ser Tyr Ile Ser
370                 375                 380

Tyr Trp Ala Tyr Trp Gly Gln Gly Thr Leu Val Thr Val Ser Ser Gly
385                 390                 395                 400

Gly Gly Gly Ser Gly Gly Gly Gly Ser Gly Gly Gly Gly Ser Gln Thr

```
            405                 410                 415
Val Val Thr Gln Glu Pro Ser Leu Thr Val Ser Pro Gly Gly Thr Val
            420                 425                 430

Thr Leu Thr Cys Gly Ser Ser Thr Gly Ala Val Thr Ser Gly Asn Tyr
            435                 440                 445

Pro Asn Trp Val Gln Gln Lys Pro Gly Gln Ala Pro Arg Gly Leu Ile
            450                 455                 460

Gly Gly Thr Lys Phe Leu Ala Pro Gly Thr Pro Ala Arg Phe Ser Gly
465                 470                 475                 480

Ser Leu Leu Gly Gly Lys Ala Ala Leu Thr Leu Ser Gly Val Gln Pro
                485                 490                 495

Glu Asp Glu Ala Glu Tyr Tyr Cys Val Leu Trp Tyr Ser Asn Arg Trp
            500                 505                 510

Val Phe Gly Gly Gly Thr Lys Leu Thr Val Leu
            515                 520

<210> SEQ ID NO 222
<211> LENGTH: 1557
<212> TYPE: DNA
<213> ORGANISM: artificial
<220> FEATURE:
<223> OTHER INFORMATION: SA25-CD33 E11 HL x I2C HL

<400> SEQUENCE: 222
gaggacatct gcctgcccag atggggctgc ctgtgggagg accaggtgca gctggtgcag      60
tctggagctg aggtgaagaa gcctggagag tcagtcaagg tctcctgcaa ggctagcggg     120
tataccttca caaactatgg aatgaactgg gtgaagcagg ctccaggaca gggtttagag     180
tggatgggct ggataaacac ctacactgga gagccaacct atgctgataa gttccaggga     240
cgcgttacca tgactacgga tacctctacc agcactgcct atatggaaat ccgcaacctc     300
ggaggtgatg acacggctgt atattactgt gcgcgctgga gttggagtga tggttactac     360
gtttactttg actactgggg ccaaggcact tcggtcaccg tctcctcagg tggtggtggt     420
tctggcggcg cggctccggt ggtggtggt tctgacatcg tgatgacaca gtctccagac     480
tccctgactg tgtctctggg cgagaggacc accatcaact gcaagtccag ccagagtgtt     540
ttagacagct ccacgaataa gaactcctta gcttggtacc agcagaaacc aggacagcct     600
cctaaattac tcctttcctg ggcatctacg cgggaatccg ggatccctga ccgattcagt     660
ggcagcgggt ctgggacaga tttcactctc actattgaca gcccgcagcc tgaagattct     720
gcaacttact attgtcaaca gtctgcccac ttcccgatca cctttggcca agggacacga     780
ctggagatta atccggaggt ggtggctcc gaggtgcagc tggtcgagtc tggaggagga     840
ttggtgcagc ctgagggtc attgaaactc tcatgtgcag cctctggatt cacccttcaat     900 aagtacgcca tgaactgggt ccgccaggct ccaggaaagg gtttggaatg ggttgctcgc     960
ataagaagta aatataataa ttatgcaaca tattatgccg attcagtgaa agacaggttc    1020
accatctcca gagatgattc aaaaaacact gcctatctac aaatgaacaa cttgaaaact    1080
gaggacactg ccgtgtacta ctgtgtgaga catgggaact tcggtaatag ctacatatcc    1140
tactgggctt actgggccca agggactctg gtcaccgtct cctcaggtgg tggtggttct    1200
ggcggcggcg gctccggtgg tggtggttct cagactgttg tgactcagga accttcactc    1260
accgtatcac ctggtggaac agtcacactc acttgtggct cctcgactgg ggctgttaca    1320
tctggcaact acccaaactg ggtccaacaa aaaccaggtc aggcaccccg tggtctaata    1380
```

```
ggtgggacta agttcctcgc ccccggtact cctgccagat tctcaggctc cctgcttgga   1440
ggcaaggctg ccctcaccct ctcaggggta cagccagagg atgaggcaga atattactgt   1500
gttctatggt acagcaaccg ctgggtgttc ggtggaggaa ccaaactgac tgtccta      1557
```

<210> SEQ ID NO 223
<211> LENGTH: 519
<212> TYPE: PRT
<213> ORGANISM: artificial
<220> FEATURE:
<223> OTHER INFORMATION: SA25-CD33 E11 HL x I2C HL

<400> SEQUENCE: 223

```
Glu Asp Ile Cys Leu Pro Arg Trp Gly Cys Leu Trp Glu Asp Gln Val
1               5                   10                  15

Gln Leu Val Gln Ser Gly Ala Glu Val Lys Lys Pro Gly Glu Ser Val
            20                  25                  30

Lys Val Ser Cys Lys Ala Ser Gly Tyr Thr Phe Thr Asn Tyr Gly Met
        35                  40                  45

Asn Trp Val Lys Gln Ala Pro Gly Gln Gly Leu Glu Trp Met Gly Trp
    50                  55                  60

Ile Asn Thr Tyr Thr Gly Glu Pro Thr Tyr Ala Asp Lys Phe Gln Gly
65                  70                  75                  80

Arg Val Thr Met Thr Thr Asp Thr Ser Thr Ser Thr Ala Tyr Met Glu
                85                  90                  95

Ile Arg Asn Leu Gly Gly Asp Asp Thr Ala Val Tyr Tyr Cys Ala Arg
            100                 105                 110

Trp Ser Trp Ser Asp Gly Tyr Tyr Val Tyr Phe Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Asp Ile Val Met Thr Gln Ser Pro Asp
145                 150                 155                 160

Ser Leu Thr Val Ser Leu Gly Glu Arg Thr Thr Ile Asn Cys Lys Ser
                165                 170                 175

Ser Gln Ser Val Leu Asp Ser Ser Thr Asn Lys Asn Ser Leu Ala Trp
            180                 185                 190

Tyr Gln Gln Lys Pro Gly Gln Pro Pro Lys Leu Leu Leu Ser Trp Ala
        195                 200                 205

Ser Thr Arg Glu Ser Gly Ile Pro Asp Arg Phe Ser Gly Ser Gly Ser
    210                 215                 220

Gly Thr Asp Phe Thr Leu Thr Ile Asp Ser Pro Gln Pro Glu Asp Ser
225                 230                 235                 240

Ala Thr Tyr Tyr Cys Gln Gln Ser Ala His Phe Pro Ile Thr Phe Gly
                245                 250                 255

Gln Gly Thr Arg Leu Glu Ile Lys Ser Gly Gly Gly Gly Ser Glu Val
            260                 265                 270

Gln Leu Val Glu Ser Gly Gly Gly Leu Val Gln Pro Gly Gly Ser Leu
        275                 280                 285

Lys Leu Ser Cys Ala Ala Ser Gly Phe Thr Phe Asn Lys Tyr Ala Met
    290                 295                 300

Asn Trp Val Arg Gln Ala Pro Gly Lys Gly Leu Glu Trp Val Ala Arg
305                 310                 315                 320

Ile Arg Ser Lys Tyr Asn Asn Tyr Ala Thr Tyr Tyr Ala Asp Ser Val
                325                 330                 335
```

```
Lys Asp Arg Phe Thr Ile Ser Arg Asp Asp Ser Lys Asn Thr Ala Tyr
            340                 345                 350

Leu Gln Met Asn Asn Leu Lys Thr Glu Asp Thr Ala Val Tyr Tyr Cys
        355                 360                 365

Val Arg His Gly Asn Phe Gly Asn Ser Tyr Ile Ser Tyr Trp Ala Tyr
    370                 375                 380

Trp Gly Gln Gly Thr Leu Val Thr Val Ser Ser Gly Gly Gly Gly Ser
385                 390                 395                 400

Gly Gly Gly Gly Ser Gly Gly Gly Ser Gln Thr Val Val Thr Gln
                405                 410                 415

Glu Pro Ser Leu Thr Val Ser Pro Gly Gly Thr Val Thr Leu Thr Cys
            420                 425                 430

Gly Ser Ser Thr Gly Ala Val Thr Ser Gly Asn Tyr Pro Asn Trp Val
        435                 440                 445

Gln Gln Lys Pro Gly Gln Ala Pro Arg Gly Leu Ile Gly Gly Thr Lys
    450                 455                 460

Phe Leu Ala Pro Gly Thr Pro Ala Arg Phe Ser Gly Ser Leu Leu Gly
465                 470                 475                 480

Gly Lys Ala Ala Leu Thr Leu Ser Gly Val Gln Pro Glu Asp Glu Ala
                485                 490                 495

Glu Tyr Tyr Cys Val Leu Trp Tyr Ser Asn Arg Trp Val Phe Gly Gly
            500                 505                 510

Gly Thr Lys Leu Thr Val Leu
            515
```

<210> SEQ ID NO 224
<211> LENGTH: 1578
<212> TYPE: DNA
<213> ORGANISM: artificial
<220> FEATURE:
<223> OTHER INFORMATION: SA08-CD33 E11 HL x I2C HL

<400> SEQUENCE: 224

```
cagggcctga tcggcgacat ctgcctgccc agatggggct gcctgtgggg cgactccgtg      60
aaacaggtgc agctggtgca gtctggagct gaggtgaaga agcctggaga gtcagtcaag     120
gtctcctgca aggctagcgg gtataccttc acaaactatg gaatgaactg ggtgaagcag     180
gctccaggac agggtttaga gtggatgggc tggataaaca cctacactgg agagccaacc     240
tatgctgata gttccaggg acgcgttacc atgactacgg atacctctac cagcactgcc      300
tatatggaaa tccgcaacct cggaggtgat gacacggctg tatattactg tgcgcgctgg     360
agttggagtg atggttacta cgtttacttt gactactggg gccaaggcac ttcggtcacc     420
gtctcctcag gtggtggtgg ttctggcggc ggcggctccg gtggtggtgg ttctgacatc     480
gtgatgacac agtctccaga ctccctgact gtgtctctgg gcgagaggac caccatcaac     540
tgcaagtcca gccagagtgt tttagacagc tccacgaata agaactcctt agcttggtac     600
cagcagaaac aggacagcc tcctaaatta ctcctttcct gggcatctac gcgggaatcc     660
gggatccctg accgattcag tggcagcggg tctgggacag atttcactct cactattgac     720
agcccgcagc tgaagattc tgcaacttac tattgtcaac agtctgccca cttcccgatc     780
accttggcc aagggacacg actggagatt aaatccggag gtggtggctc cgaggtgcag     840
ctggtcgagt ctggaggagg attggtgcag cctggagggt cattgaaact ctcatgtgca     900
gcctctggat tcacctttca taagtacgcc atgaactggg tccgccaggc tccaggaaag     960
ggtttggaat gggttgctcg cataagaagt aaatataata attatgcaac atattatgcc    1020
```

-continued

```
gattcagtga aagacaggtt caccatctcc agagatgatt caaaaaacac tgcctatcta    1080
caaatgaaca acttgaaaac tgaggacact gccgtgtact actgtgtgag acatgggaac    1140
ttcggtaata gctacatatc ctactgggct tactggggcc aagggactct ggtcaccgtc    1200
tcctcaggtg gtggtggttc tggcggcggc ggctccggtg gtggtggttc tcagactgtt    1260
gtgactcagg aaccttcact caccgtatca cctggtggaa cagtcacact cacttgtggc    1320
tcctcgactg gggctgttac atctggcaac tacccaaact gggtccaaca aaaaccaggt    1380
caggcacccc gtggtctaat aggtgggact aagttcctcg cccccggtac tcctgccaga    1440
ttctcaggct ccctgcttgg aggcaaggct gccctcaccc tctcagggt acagccagag     1500 gatgaggcag aatattactg tgttctatgg tacagcaacc gctgggtgtt cggtggagga    1560
accaaactga ctgtccta                                                  1578
```

<210> SEQ ID NO 225
<211> LENGTH: 526
<212> TYPE: PRT
<213> ORGANISM: artificial
<220> FEATURE:
<223> OTHER INFORMATION: SA08-CD33 E11 HL x I2C HL

<400> SEQUENCE: 225

```
Gln Gly Leu Ile Gly Asp Ile Cys Leu Pro Arg Trp Gly Cys Leu Trp
1               5                   10                  15

Gly Asp Ser Val Lys Gln Val Gln Leu Val Gln Ser Gly Ala Glu Val
                20                  25                  30

Lys Lys Pro Gly Glu Ser Val Lys Val Ser Cys Lys Ala Ser Gly Tyr
            35                  40                  45

Thr Phe Thr Asn Tyr Gly Met Asn Trp Val Lys Gln Ala Pro Gly Gln
        50                  55                  60

Gly Leu Glu Trp Met Gly Trp Ile Asn Thr Tyr Thr Gly Glu Pro Thr
65                  70                  75                  80

Tyr Ala Asp Lys Phe Gln Gly Arg Val Thr Met Thr Thr Asp Thr Ser
                85                  90                  95

Thr Ser Thr Ala Tyr Met Glu Ile Arg Asn Leu Gly Gly Asp Asp Thr
            100                 105                 110

Ala Val Tyr Tyr Cys Ala Arg Trp Ser Trp Ser Asp Gly Tyr Tyr Val
        115                 120                 125

Tyr Phe Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser Pro Asp Ser Leu Thr Val Ser Leu Gly Glu Arg
                165                 170                 175

Thr Thr Ile Asn Cys Lys Ser Ser Gln Ser Val Leu Asp Ser Ser Thr
            180                 185                 190

Asn Lys Asn Ser Leu Ala Trp Tyr Gln Gln Lys Pro Gly Gln Pro Pro
        195                 200                 205

Lys Leu Leu Leu Ser Trp Ala Ser Thr Arg Glu Ser Gly Ile Pro Asp
    210                 215                 220

Arg Phe Ser Gly Ser Gly Ser Gly Thr Asp Phe Thr Leu Thr Ile Asp
225                 230                 235                 240

Ser Pro Gln Pro Glu Asp Ser Ala Thr Tyr Tyr Cys Gln Gln Ser Ala
                245                 250                 255
```

His Phe Pro Ile Thr Phe Gly Gln Gly Thr Arg Leu Glu Ile Lys Ser
            260                 265                 270

Gly Gly Gly Gly Ser Glu Val Gln Leu Val Glu Ser Gly Gly Gly Leu
        275                 280                 285

Val Gln Pro Gly Gly Ser Leu Lys Leu Ser Cys Ala Ala Ser Gly Phe
    290                 295                 300

Thr Phe Asn Lys Tyr Ala Met Asn Trp Val Arg Gln Ala Pro Gly Lys
305                 310                 315                 320

Gly Leu Glu Trp Val Ala Arg Ile Arg Ser Lys Tyr Asn Asn Tyr Ala
            325                 330                 335

Thr Tyr Tyr Ala Asp Ser Val Lys Asp Arg Phe Thr Ile Ser Arg Asp
        340                 345                 350

Asp Ser Lys Asn Thr Ala Tyr Leu Gln Met Asn Asn Leu Lys Thr Glu
    355                 360                 365

Asp Thr Ala Val Tyr Tyr Cys Val Arg His Gly Asn Phe Gly Asn Ser
370                 375                 380

Tyr Ile Ser Tyr Trp Ala Tyr Trp Gly Gln Gly Thr Leu Val Thr Val
385                 390                 395                 400

Ser Ser Gly Gly Gly Gly Ser Gly Gly Gly Gly Ser Gly Gly Gly Gly
            405                 410                 415

Ser Gln Thr Val Val Thr Gln Glu Pro Ser Leu Thr Val Ser Pro Gly
        420                 425                 430

Gly Thr Val Thr Leu Thr Cys Gly Ser Ser Thr Gly Ala Val Thr Ser
    435                 440                 445

Gly Asn Tyr Pro Asn Trp Val Gln Gln Lys Pro Gly Gln Ala Pro Arg
450                 455                 460

Gly Leu Ile Gly Gly Thr Lys Phe Leu Ala Pro Gly Thr Pro Ala Arg
465                 470                 475                 480

Phe Ser Gly Ser Leu Leu Gly Gly Lys Ala Ala Leu Thr Leu Ser Gly
            485                 490                 495

Val Gln Pro Glu Asp Glu Ala Glu Tyr Tyr Cys Val Leu Trp Tyr Ser
        500                 505                 510

Asn Arg Trp Val Phe Gly Gly Gly Thr Lys Leu Thr Val Leu
    515                 520                 525

<210> SEQ ID NO 226
<211> LENGTH: 1533
<212> TYPE: DNA
<213> ORGANISM: artificial
<220> FEATURE:
<223> OTHER INFORMATION: CD33 E11 HL x I2C HL (His Tag)

<400> SEQUENCE: 226
caggtgcagc tggtgcagtc tgagctgag gtgaagaagc tggagagtc agtcaaggtc      60 tcctgcaagg ctagcgggta taccttcaca aactatggaa tgaactgggt gaagcaggct     120
ccaggacagg gtttagagtg gatgggctgg ataaacacct acactggaga gccaacctat     180
gctgataagt tccagggacg cgttaccatg actacggata cctctaccag cactgcctat     240
atggaaatcc gcaacctcgg aggtgatgac acggctgtat attactgtgc gcgctggagt     300
tggagtgatg gttactacgt ttactttgac tactggggcc aaggcacttc ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc acgaataaga actccttagc ttggtaccag     540

```
cagaaaccag gacagcctcc taaattactc ctttcctggg catctacgcg ggaatccggg    600
atccctgacc gattcagtgg cagcgggtct gggacagatt tcactctcac tattgacagc    660
ccgcagcctg aagattctgc aacttactat tgtcaacagt ctgcccactt cccgatcacc    720
tttggccaag gacacgact ggagattaaa tccggaggtg gtggctccga ggtgcagctg    780
gtcgagtctg gaggaggatt ggtgcagcct ggagggtcat tgaaactctc atgtgcagcc    840
tctggattca ccttcaataa gtacgccatg aactgggtcc gccaggctcc aggaaagggt    900
ttggaatggg ttgctcgcat aagaagtaaa tataataatt atgcaacata ttatgccgat    960
tcagtgaaag acaggttcac catctccaga tgattcaa aaacactgc ctatctacaa      1020 atgaacaact tgaaaactga ggacactgcc gtgtactact gtgtgagaca tgggaacttc    1080
ggtaatagct acatatccta ctgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcaccccgtg gtctaatagg tgggactaag ttcctcgccc ccggtactcc tgccagattc    1380
tcaggctccc tgcttggagg caaggctgcc ctcaccctct cagggtaca gccagaggat    1440 gaggcagaat attactgtgt tctatggtac agcaaccgct gggtgttcgg tggaggaacc    1500
aaactgactg tcctacatca ccatcaccat cac                                1533

<210> SEQ ID NO 227
<211> LENGTH: 511
<212> TYPE: PRT
<213> ORGANISM: artificial
<220> FEATURE:
<223> OTHER INFORMATION: CD33 E11 HL x I2C HL H6

<400> SEQUENCE: 227

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190
```

-continued

```
Trp Ala Ser Thr Arg Glu Ser Gly Ile Pro Asp Arg Phe Ser Gly Ser
        195                 200                 205
Gly Ser Gly Thr Asp Phe Thr Leu Thr Ile Asp Ser Pro Gln Pro Glu
        210                 215                 220
Asp Ser Ala Thr Tyr Tyr Cys Gln Gln Ser Ala His Phe Pro Ile Thr
225                 230                 235                 240
Phe Gly Gln Gly Thr Arg Leu Glu Ile Lys Ser Gly Gly Gly Gly Ser
                245                 250                 255
Glu Val Gln Leu Val Glu Ser Gly Gly Gly Leu Val Gln Pro Gly Gly
                260                 265                 270
Ser Leu Lys Leu Ser Cys Ala Ala Ser Gly Phe Thr Phe Asn Lys Tyr
        275                 280                 285
Ala Met Asn Trp Val Arg Gln Ala Pro Gly Lys Gly Leu Glu Trp Val
        290                 295                 300
Ala Arg Ile Arg Ser Lys Tyr Asn Asn Tyr Ala Thr Tyr Tyr Ala Asp
305                 310                 315                 320
Ser Val Lys Asp Arg Phe Thr Ile Ser Arg Asp Asp Ser Lys Asn Thr
                325                 330                 335
Ala Tyr Leu Gln Met Asn Asn Leu Lys Thr Glu Asp Thr Ala Val Tyr
                340                 345                 350
Tyr Cys Val Arg His Gly Asn Phe Gly Asn Ser Tyr Ile Ser Tyr Trp
        355                 360                 365
Ala Tyr Trp Gly Gln Gly Thr Leu Val Thr Val Ser Ser Gly Gly Gly
        370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                405                 410                 415
Thr Cys Gly Ser Ser Thr Gly Ala Val Thr Ser Gly Asn Tyr Pro Asn
        420                 425                 430
Trp Val Gln Gln Lys Pro Gly Gln Ala Pro Arg Gly Leu Ile Gly Gly
        435                 440                 445
Thr Lys Phe Leu Ala Pro Gly Thr Pro Ala Arg Phe Ser Gly Ser Leu
        450                 455                 460
Leu Gly Gly Lys Ala Ala Leu Thr Leu Ser Gly Val Gln Pro Glu Asp
465                 470                 475                 480
Glu Ala Glu Tyr Tyr Cys Val Leu Trp Tyr Ser Asn Arg Trp Val Phe
                485                 490                 495
Gly Gly Gly Thr Lys Leu Thr Val Leu His His His His His
                500                 505                 510
```

COMBINATION OF EPIGENETIC FACTORS AND BISPECIFIC COMPOUNDS TARGETING CD33 AND CD3 IN THE TREATMENT OF MYELOID LEUKEMIA

FIELD OF THE INVENTION

The present invention provides a combination epigenetic factors and bispecific compounds targeting CD33 and CD3 in the treatment of myeloid leukemia, wherein the epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone demethylase inhibitors and ATRA (All Trans-retinoic acid). Accordingly, the invention provides a pharmaceutical composition comprising a CD33 targeting compound and at least one epigenetic factor and an epigenetic factor for use in the amelioration, and/or treatment of a myeloid leukemia, wherein the epigenetic factor increases the responsiveness of a patient to a CD33 targeting compound. Moreover, the invention provides the use of at least one an epigenetic factor for increasing the responsiveness of a myeloid leukemia patient to a treatment with a CD33 targeting compound, a method for the treatment of a myeloid leukemia, the method comprising the administration of at least one epigenetic factor and a CD33 targeting compound to a patient in the need thereof and a kit comprising a pharmaceutical composition of the invention or an epigenetic factor of the invention and a bispecific CD33 targeting compound.

Incorporation by Reference of the Sequence Listing

This application includes a sequence listing submitted electronically as text file 50381_Subseqlisting.TXT; created Aug. 11, 2020; file size: 391,512 bytes and is incorporated herein by reference.

BACKGROUND OF THE INVENTION

Despite some gradual improvements over the last decades with the use of intensive therapies—including multiagent conventional chemotherapy and allogeneic stem cell transplantation (SCT)—the survival of patients with acute myeloid leukemia (AML) remains poor, and patient are at high risk of experiencing treatment-related morbidity and mortality. For example, although SCT has proven to provide a potent anti-leukemic effect that can lead to elimination of chemoresistant leukemic cells, a large number of patients will develop significant graft versus host (GvH) disease that will eventually be fatal in many. For many patients, in particular those who are not suitable for such intensive therapeutic strategies, novel therapeutic options including immunotherapeutic approaches are urgently sought after. A promising immunotherapeutic strategy devoid of GvH reactions is to recruit in-vivo the patient's own T-cells and retarget them directly at leukemic cells.

This approach became feasible by a novel class of bispecific single-chain antibodies, which direct cytotoxic T-lymphocytes at predefined surface antigens on tumor cells (Baeuerle et al. Curr Opin Mol Ther. 2009; 11:22-30). Clinical proof of concept was provided by blinatumomab, a bispecific antibody directed at both the CD19 B-cell surface antigen and the CD3c component of the T-cell receptor complex. Its therapeutic efficacy was shown for patients with B-cell lymphomas and B precursor acute lymphoblastic leukemia (ALL).

Acute myeloid leukemia (AML) has served as paradigm for the therapeutic use of monoclonal antibodies because of well-defined cell surface antigens and easy tumor accessibility. The most investigated target so far is CD33, a sialic-acid-dependent cytoadhesion molecule known as a myeloid differentiation antigen found on AML blasts in most patients and, perhaps, leukemic stem cells in some. While the intact humanized CD33 antibody lintuzumab induced complete remission in individual patients in a single-agent phase I and II trial, no survival benefit was found in a phase III trial when it was combined with a triple chemotherapy regimen.

SUMMARY OF THE INVENTION

The present invention provides a pharmaceutical composition comprising a CD33 targeting compound and at least one epigenetic factor, wherein
(a) the CD33 targeting compound is a bispecific construct comprising a first binding domain specifically binding to CD33 and a second binding domain specifically binding to CD3; and
(b) the at least one epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone methyltransferase (HMT) inhibitors and ATRA (All Trans-retinoic acid).

In one embodiment the pharmaceutical composition of the invention is characterized in a way that the at least one epigenetic factor is selected from the group comprising:
(a) a histone deacetylase (HDAC) inhibitor selected from the group consisting of panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid;
(b) a DNA methyltransferase (DNMT) I inhibitor selected from the group consisting of 5-azacitidine, decitabine, hydralazine, zebularine, procainamide, (−)-epigallocatechin-3-gallate, MG98, RG108, and SGI-110; and
(c) a histone methyltransferase (HMT) inhibitor selected from the group consisting of LSD1 (KDM1A) demethylase inhibitor, and chaetocin.

The invention also provides a pharmaceutical composition, wherein
(a) the epigenetic factor is administered prior to the administration of the CD33 targeting compound;
(b) the epigenetic factor is administered subsequent to the administration of the CD33 targeting compound; or
(c) the epigenetic factor and the CD33 targeting compound are administered simultaneously.

The invention further provides a pharmaceutical composition, wherein a first dose of the epigenetic factor is administered prior to the start of the administration of the CD33 targeting compound.

Moreover, the invention further provides a pharmaceutical composition, wherein the administration of the epigenetic factor is continued during the administration of the CD33 targeting compound.

In one embodiment the pharmaceutical composition of the invention is characterized in a way that the bispecific construct is a bispecific antibody construct.

In preferred embodiment of the pharmaceutical composition of the invention the bispecific antibody construct is a bispecific single chain antibody construct.

It is also preferred for the pharmaceutical composition of the invention that the bispecific antibody construct binds to human and cynomolgous CD3 and human and cynomolgous CD33.

In one embodiment of the pharmaceutical composition of invention the bispecific antibody construct comprises
  a first binding domain specifically binding to CD33 and comprising a VL chain having an amino acid sequence as depicted in SEQ ID NO: 6, 24, 42, 60, 78, 96, 114 and 132 and a VH chain having an amino acid sequence as depicted in SEQ ID NO:1, 19, 37, 55, 73, 91, 109 and 127; and
  a second binding domain specifically binding to CD3 and comprising a VL chain having an amino acid sequence as depicted in SEQ ID NO: 154, 157, 160, 163, 166, 169 and 172 and a VH chain having an amino acid sequence as depicted in SEQ ID NO:155, 158, 161, 164, 167, 170 and 173.

In preferred embodiment of the pharmaceutical composition the bispecific antibody construct comprises an amino acid sequence as depicted in any of SEQ ID NOs: 13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 and 227.

The pharmaceutical composition of the invention is envisaged for the treatment of CD33 expressing myeloid leukemia. Preferably, the myeloid leukemia is selected from the group consisting of acute myeloblastic leukemia, chronic neutrophilic leukemia, myeloid dendritic cell leukemia, accelerated phase chronic myelogenous leukemia, acute myelomonocytic leukemia, juvenile myelomonocytic leukemia, chronic myelomonocytic leukemia, acute basophilic leukemia, acute eosinophilic leukemia, chronic eosinophilic leukemia, Acute megakaryoblastic leukemia, essential thrombocytosis, acute erythroid leukemia, polycythemia vera, myelodysplastic syndrome, acute panmyelosis, myeloid sarcoma, and acute biphenotypic leukaemia.

In an alternative embodiment the invention provides an epigenetic factor for use in the amelioration and/or treatment of a myeloid leukemia, wherein the epigenetic factor increases the responsiveness of a patient to a CD33 targeting compound, wherein
(a) the CD33 targeting compound is a bispecific construct comprising a first binding domain specifically binding to CD33 and a second binding domain specifically binding to CD3; and
(b) the at least one epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone methyltransferase (HMT) inhibitors and ATRA (All Trans-retinoic acid).

In one embodiment of the epigenetic factor of the invention the epigenetic factor is selected from the group comprising
(a) a histone deacetylase (HDAC) inhibitor selected from the group consisting of panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid;
(b) a DNA methyltransferase (DNMT) I inhibitor selected from the group consisting of 5-azacitidine, decitabine, hydralazine, zebularine, procainamide, (−)-epigallocatechin-3-gallate, MG98, RG108, and SGI-110; and
(c) a histone methyltransferase (HMT) inhibitor selected from the group consisting of LSD1 (KDM1A) demethylase inhibitor, and chaetocin.

Moreover, in one embodiment of the epigenetic factor of the invention
(a) the epigenetic factor is administered prior to the administration of the CD33 targeting compound;
(b) the epigenetic factor is administered subsequent to the administration of the CD33 targeting compound; or
(c) the epigenetic factor and the CD33 targeting compound are administered simultaneously.

It is preferred for the epigenetic factor of the invention that a first dose of the epigenetic factor is administered prior to the start of the administration of the CD33 targeting compound.

Preferably, the administration of the epigenetic factor of the invention is continued during the administration of the CD33 targeting compound.

It is also preferred for the epigenetic factor the invention that the bispecific construct is a bispecific antibody construct.

In one embodiment of the epigenetic factor of the invention the bispecific antibody construct is a bispecific single chain antibody construct.

It is preferred for the epigenetic factor of the invention that the bispecific antibody construct binds to human and cynomolgous CD3 and CD33.

Also preferred for the epigenetic factor of the invention is that the bispecific antibody construct comprises
  a first binding domain specifically binding to CD33 and comprising a VL chain having an amino acid sequence as depicted in SEQ ID NO: 6, 24, 42, 60, 78, 96, 114 and 132 and a VH chain having an amino acid sequence as depicted in SEQ ID NO:1, 19, 37, 55, 73, 91, 109 and 127; and
  a second binding domain specifically binding to CD3 and comprising a VL chain having an amino acid sequence as depicted in SEQ ID NO: 154, 157, 160, 163, 166, 169 and 172 and a VH chain having an amino acid sequence as depicted in SEQ ID NO:155, 158, 161, 164, 167, 170 and 173.

In one embodiment of the epigenetic factor of the invention the bispecific antibody construct comprises an amino acid sequence as depicted in any of SEQ ID NOs: 13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 and 227.

In one embodiment of the epigenetic factor of the invention the myeloid leukemia is selected from the group consisting of acute myeloblastic leukemia, chronic neutrophilic leukemia, myeloid dendritic cell leukemia, accelerated phase chronic myelogenous leukemia, acute myelomonocytic leukemia, juvenile myelomonocytic leukemia, chronic myelomonocytic leukemia, acute basophilic leukemia, acute eosinophilic leukemia, chronic eosinophilic leukemia, Acute megakaryoblastic leukemia, essential thrombocytosis, acute erythroid leukemia, polycythemia vera, myelodysplastic syndrome, acute panmyelosis, myeloid sarcoma, and acute biphenotypic leukaemia.

An alternative embodiment of the invention provides a use of at least one an epigenetic factor for increasing the responsiveness of a myeloid leukemia patient to a treatment with a CD33 targeting compound, wherein
(a) the CD33 targeting compound is a bispecific construct comprising a first binding domain specifically binding to CD33 and a second binding domain specifically binding to CD3; and
(b) the at least one epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone demethylase inhibitors and ATRA (All Trans-retinoic acid).

In one embodiment of the use of the invention the at least one epigenetic factor is selected from the group comprising
(a) a histone deacetylase (HDAC) inhibitor selected from the group consisting of panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid;
(b) a DNA methyltransferase (DNMT) I inhibitor selected from the group consisting of 5-azacitidine, decitabine, hydralazine, zebularine, procainamide, (–)-epigallocatechin-3-gallate, MG98, RG108, and SGI-110; and
(c) a histone methyltransferase (HMT) inhibitor selected from the group consisting of LSD1 (KDM1A) demethylase inhibitor, and chaetocin.

Also in an embodiment of the use of the invention
(a) the epigenetic factor is administered prior to the administration of the CD33 targeting compound;
(b) the epigenetic factor is administered subsequent to the administration of the CD33 targeting compound; or
(c) the epigenetic factor and the CD33 targeting compound are administered simultaneously.

In a preferred use of any of the invention a first dose of the epigenetic factor is administered prior to the start of the administration of the CD33 targeting compound.

Moreover, in one embodiment of the use of the invention the administration of the epigenetic factor is continued during the administration of the CD33 targeting compound.

In one embodiment of the use of the invention the bispecific construct is a bispecific antibody construct.

In a preferred embodiment of the use of the invention the bispecific antibody construct is a bispecific single chain antibody construct.

In one embodiment of the use of the invention the bispecific antibody construct binds to human and cynomolgous CD3 and CD33.

According to one embodiment of the use of the invention the bispecific antibody construct comprises
    a first binding domain specifically binding to CD33 and comprising a VL chain having an amino acid sequence as depicted in SEQ ID NO: 6, 24, 42, 60, 78, 96, 114 and 132 and a VH chain having an amino acid sequence as depicted in SEQ ID NO:1, 19, 37, 55, 73, 91, 109 and 127; and
    a second binding domain specifically binding to CD3 and comprising a VL chain having an amino acid sequence as depicted in SEQ ID NO: 154, 157, 160, 163, 166, 169 and 172 and a VH chain having an amino acid sequence as depicted in SEQ ID NO:155, 158, 161, 164, 167, 170 and 173.

In a preferred embodiment of the use of the invention the bispecific antibody construct comprises an amino acid sequence as depicted in any of SEQ ID NOs: 13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 and 227.

Furthermore, in an embodiment of the use of the invention the myeloid leukemia is selected from the group consisting of acute myeloblastic leukemia, chronic neutrophilic leukemia, myeloid dendritic cell leukemia, accelerated phase chronic myelogenous leukemia, acute myelomonocytic leukemia, juvenile myelomonocytic leukemia, chronic myelomonocytic leukemia, acute basophilic leukemia, acute eosinophilic leukemia, chronic eosinophilic leukemia, Acute megakaryoblastic leukemia, essential thrombocytosis, acute erythroid leukemia, polycythemia vera, myelodysplastic syndrome, acute panmyelosis, myeloid sarcoma, and acute biphenotypic leukaemia.

In a further alternative embodiment the invention provides a method for the treatment of a myeloid leukemia, the method comprising the administration of at least one epigenetic factor and a CD33 targeting compound to a patient in the need thereof, wherein
(a) the CD33 targeting compound is a bispecific construct comprising a first binding domain specifically binding to CD33 and a second binding domain specifically binding to CD3; and
(b) the at least one epigenetic factor is selected from the group consisting of histone deacetylase (HDAC) inhibitors, DNA methyltransferase (DNMT) I inhibitors, hydroxyurea, Granulocyte-Colony Stimulating Factor (G-CSF), histone methyltransferase (HMT) inhibitors and ATRA (All Trans-retinoic acid).

In an embodiment of the method of the invention the at least one epigenetic factor is selected from the group comprising
(a) a histone deacetylase (HDAC) inhibitor selected from the group consisting of panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid;
(b) a DNA methyltransferase (DNMT) I inhibitor selected from the group consisting of 5-azacitidine, decitabine, hydralazine, zebularine, procainamide, (–)-epigallocatechin-3-gallate, MG98, RG108, and SGI-110; and
(c) a histone methyltransferase (HMT) inhibitor selected from the group consisting of LSD1 (KDM1A) demethylase inhibitor, and chaetocin.

Also in an embodiment of the method of the invention
(a) the epigenetic factor is administered prior to the administration of the CD33 targeting compound;
(b) the epigenetic factor is administered subsequent to the administration of the CD33 targeting compound; or
(c) the epigenetic factor and the CD33 targeting compound are administered simultaneously.

In a preferred embodiment of the method of the invention a first dose of the epigenetic factor is administered prior to the start of the administration of the CD33 targeting compound.

It is also preferred for the method of the invention that the administration of the epigenetic factor is continued during the administration of the CD33 targeting compound.

In one embodiment of the method of the invention the bispecific construct is a bispecific antibody construct.

It is preferred for the method of the invention that the bispecific antibody construct is a bispecific single chain antibody construct.

It is more preferred for the method of the invention that the bispecific antibody construct binds to human and cynomolgous CD3 and CD33.

In one embodiment of the method of the invention the bispecific antibody construct comprises
    a first binding domain specifically binding to CD33 and comprising a VL chain having an amino acid sequence as depicted in SEQ ID NO: 6, 24, 42, 60, 78, 96, 114 and 132 and a VH chain having an amino acid sequence as depicted in SEQ ID NO:1, 19, 37, 55, 73, 91, 109 and 127; and
    a second binding domain specifically binding to CD3 and comprising a VL chain having an amino acid sequence as depicted in SEQ ID NO: 154, 157, 160, 163, 166, 169 and 172 and a VH chain having an amino acid sequence as depicted in SEQ ID NO:155, 158, 161, 164, 167, 170 and 173.

Also in on one embodiment of the method of the invention the bispecific antibody construct comprises an amino acid sequence as depicted in any of SEQ ID NOs: 13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 and 227.

Furthermore, in one embodiment of the method of the invention the myeloid leukemia is selected from the group consisting of acute myeloblastic leukemia, chronic neutrophilic leukemia, myeloid dendritic cell leukemia, accelerated phase chronic myelogenous leukemia, acute myelomonocytic leukemia, juvenile myelomonocytic leukemia, chronic myelomonocytic leukemia, acute basophilic leukemia, acute eosinophilic leukemia, chronic eosinophilic leukemia, Acute megakaryoblastic leukemia, essential thrombocytosis, acute erythroid leukemia, polycythemia vera, myelodysplastic syndrome, acute panmyelosis, myeloid sarcoma, and acute biphenotypic leukaemia.

A further alternative embodiment of the invention provides a kit comprising a pharmaceutical composition of the invention or an epigenetic factor of the invention and a bispecific CD33 targeting compound comprising a first binding domain specifically binding to CD33 and a second binding domain specifically binding to CD3, to be employed in the amelioration and/or treatment of a myeloid leukemia.

DETAILED DESCRIPTION OF THE INVENTION

Definitions

Figure 1:
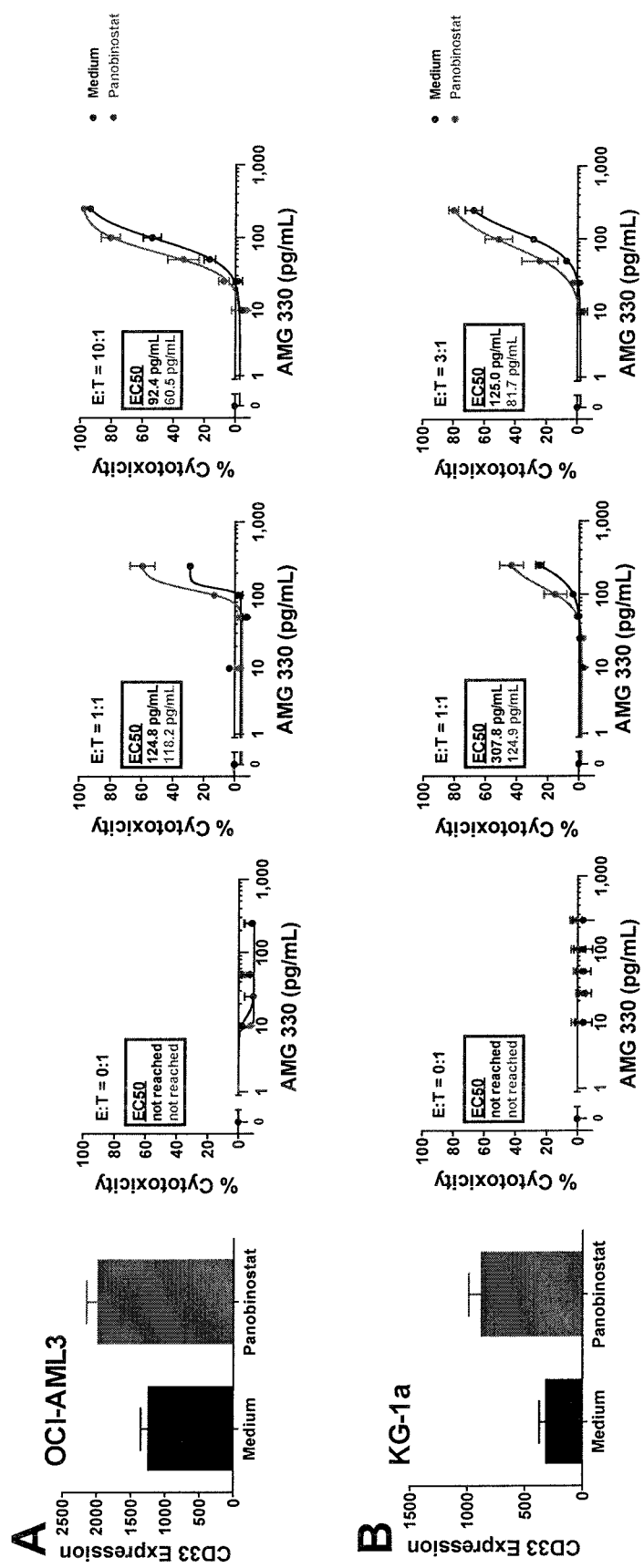
FIG. 1: Effect of panobinostat pretreatment on CD33 expression and AMG 330-induced cytotoxicity. Parental OCI-AML3 and KG-1a cells were either left untreated or pretreated with panobinostat for 72 hours. Subsequently, CD33 expression was quantified, and cells treated with/without AMG 330 (0-250 pg/mL) and various effector:target (E:T) cell ratios using healthy donor T-cells. 48 hours later, cell counts were determined and cytotoxicity was assessed with DAPI staining to quantify drug-specific cytotoxicity. Results are shown as mean±SEM from 3 independent experiments performed in duplicate wells using a single healthy donor as source for exogenous T-cells.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The term "CD33 targeting compound" defines in the context of the present invention a binding molecule capable of specifically binding to the extracellular domain of the cell surface molecule CD33. As mentioned above CD33, a sialic-acid-dependent cytoadhesion molecule, is known as a myeloid differentiation antigen found on AML blasts in most patients. As apparent from the description of the embodiments of the invention, the CD33 targeting compound in the sense of the invention is a bispecific compound comprising at least a binding domain for the extracellular domain of the cell surface molecule CD33 and the extracellular domain of the molecule CD3 expressed on T cells. It is emphasized that the CD33 targeting compound comprises in the sense of the invention at least the binding domain for CD33 and CD3 and may also comprise one or more additional binding domains for other target structures, which result in a tri- or multi-specific compound. In other words, the term "CD33 targeting compound" in the sense of the present disclosure indicates any molecule capable of (specifically) binding to, interacting with or recognizing the target molecule CD33 on the surface of a target cell and CD3 on the surface of a T cell. Such molecules or constructs may include proteinaceous parts and non-proteinaceous parts (e.g. chemical linkers or chemical cross-linking agents such as glutaraldehyde).

The term "binding molecule" in the sense of the present disclosure indicates any molecule capable of (specifically) binding to, interacting with or recognizing the target molecule.

A binding molecule, so to say, provides the scaffold for said one or more binding domains so that said binding domains can bind/interact with the surface molecule on a target cell and CD3 receptor complex on a T cell. For example, such a scaffold could be provided by protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain (Stumpp et al., Curr Opin Drug Discov Devel. 10(2), 153-159 (2007)) or thioredoxin (Skerra, Curr. Opin. Biotechnol. 18, 295-304 (2005); Hosse et al., Protein Sci. 15, 14-27 (2006); Nicaise et al., Protein Sci. 13, 1882-1891 (2004); Nygren and Uhlen, Curr. Opin. Struc. Biol. 7, 463-469 (1997)). A preferred binding molecule is an antibody, more preferably a bispecific antibody.

The term "single chain binding molecule" defines in connection with the present invention that the disclosed binding molecules in its simplest form are monomers. The molecules or constructs may include proteinaceous parts and non-proteinaceous parts (e.g. chemical linkers or chemical cross-linking agents such as glutaraldehyde). Thus, the single chain binding molecule may comprising accordance with the invention non-peptide linkers preferably to link at least two of the binding domains. Also in line with this invention are herein defined peptide linkers.

The definition of the term "antibody" includes embodiments such as monoclonal, chimeric, single chain, humanized and human antibodies, as well as antibody fragments, like, inter alia, Fab fragments. Antibody fragments or derivatives further comprise F(ab')$_2$, Fv, scFv fragments or single domain antibodies such as domain antibodies or nanobodies, single variable domain antibodies or immunoglobulin single variable domain comprising merely one variable domain, which might be VHH, VH or VL, that specifically bind an antigen or epitope independently of other V regions or domains; see, for example, Harlow and Lane (1988) and (1999), loc. cit.; Kontermann and Dübel, Antibody Engineering, Springer, 2nd ed. 2010 and Little, Recombinant Antibodies for Immunotherapy, Cambridge University Press 2009. Such immunoglobulin single variable domain encompasses not only an isolated antibody single variable domain polypeptide, but also larger polypeptides that comprise one or more monomers of an antibody single variable domain polypeptide sequence.

Monovalent antibody fragments in line with the above definition describe an embodiment of a binding domain in connection with this invention. Such monovalent antibody fragments bind to a specific antigen and can be also designated "antigen-binding domain", "antigen-binding fragment" or "antibody binding region".

In line with this definition all above described embodiments of the term antibody can be subsumed under the term "antibody construct". Said term also includes diabodies or Dual-Affinity Re-Targeting (DART) antibodies. Further envisaged are (bispecific) single chain diabodies, tandem diabodies (Tandab's), "minibodies" exemplified by a structure which is as follows: (VH-VL-CH3)$_2$, (scFv-CH3)$_2$ or (scFv-CH3-scFv)$_2$, "Fc DART" antibodies and "IgG DART" antibodies, and multibodies such as triabodies.

Immunoglobulin single variable domains encompass not only an isolated antibody single variable domain polypeptide, but also larger polypeptides that comprise one or more monomers of an antibody single variable domain polypeptide sequence.

Various procedures are known in the art and may be used for the production of such antibody constructs (antibodies and/or fragments). Thus, (antibody) derivatives can be produced by peptidomimetics. Further, techniques described for the production of single chain antibodies (see, inter alia, U.S. Pat. No. 4,946,778, Kontermann and Dübel (2010), loc. cit. and Little (2009), loc. cit.) can be adapted to produce single chain antibodies specific for elected polypeptide(s). Also, transgenic animals may be used to express humanized antibodies specific for polypeptides and fusion proteins of this invention. For the preparation of monoclonal antibodies, any technique, providing antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of a target polypeptide, such as CD3 epsilon (Schier, Human Antibodies Hybridomas 7 (1996), 97-105; Malmborg, J. Immunol. Methods 183 (1995), 7-13). It is also envisaged in the context of this invention that the term "antibody" comprises antibody constructs, which may be expressed in a host as described herein below, e.g. antibody constructs which may be transfected and/or transduced via, inter alia, viruses or plasmid vectors.

Furthermore, the term "antibody" as employed herein also relates to derivatives or variants of the antibodies described herein which display the same specificity as the described antibodies. Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

The terms "antigen-binding domain", "antigen-binding fragment" and "antibody binding region" when used herein refer to a part of an antibody molecule that comprises amino acids responsible for the specific binding between antibody and antigen. The part of the antigen that is specifically recognized and bound by the antibody is referred to as the "epitope" as described herein above. As mentioned above, an antigen-binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) a Fd fragment having the two VH and CH1 domains; (4) a Fv fragment having the VL and VH domains of a single arm of an antibody, (5) a dAb fragment (Ward et al., (1989) Nature 341:544-546), which has a VH domain;

(6) an isolated complementarity determining region (CDR), and (7) a single chain Fv (scFv). Although the two domains of the Fv fragment, VL and VH are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al. (1988) Proc. Natl. Acad. Sci USA 85:5879-5883). These antibody fragments are obtained using conventional techniques known to those with skill in the art, and the fragments are evaluated for function in the same manner as are intact antibodies.

In the event that a (synthetic) linker is used, this linker is preferably of a length and sequence sufficient to ensure that each of the first and second domains can, independently from one another, retain their differential binding specificities. Most preferably and as documented in the appended examples, the antibody construct of the invention is a "bispecific single chain antibody construct", more preferably a bispecific single chain Fv (scFv). Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56. One example of a CD33 targeting compound in connection with the present invention, which is a bispecific single chain molecule is AMG330, which has also been used in the appended examples.

The said variable domains comprised in the herein described antibody constructs may be connected by additional linker sequences. The term "peptide linker" defines in accordance with the present invention an amino acid sequence by which the amino acid sequences of the first domain and the second domain of the antibody construct of the invention are linked with each other. An essential technical feature of such peptide linker is that said peptide linker does not comprise any polymerization activity. Preferred amino acid residues for a peptide linker include Gly, Ser and Thr are characterized by a length between 5 and 25 amino acid residues. Among the suitable peptide linkers are those described in U.S. Pat. Nos. 4,751,180 and 4,935,233 or WO 88/09344. A preferred embodiment of the peptide linker is characterized by the amino acid sequence Gly-Gly-Gly-Gly-Ser, i.e. Gly$_4$Ser, or polymers thereof, i.e. (Gly$_4$Ser)x, where x is an integer 1 or greater. The characteristics of said peptide linker, which comprise the absence of the promotion of secondary structures are known in the art and described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which also do not promote any secondary structures are preferred. The linkage of said domains to each other can be provided by, e.g. genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

For peptide linkers, which connect the at least two binding domains in the antibody construct of the invention peptide linkers are preferred which comprise only a few number of amino acid residues, e.g. 12 amino acid residues or less. Thus, peptide linker of 12, 11, 10, 9, 8, 7, 6 or 5 amino acid residues are preferred. An envisaged peptide linker with less than 5 amino acids comprises 4, 3, 2 or one amino acid(s) wherein Gly-rich linkers are preferred. A particularly preferred "single" amino acid in context of said "peptide linker" is Gly. Accordingly, said peptide linker may consist of the single amino acid Gly.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The term "human antibody" includes antibodies having variable and constant regions corresponding substantially to human germline immunoglobulin sequences known in the art, including, for example, those described by Kabat et al. (See Kabat et al. (1991) loc. cit.). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence. It is emphasized that the definition of human antibodies as used herein also contemplates fully human antibodies, which include only non-artificially and/or genetically altered human sequences of antibodies as those can be derived by using technologies using systems such as the Xenomice.

Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function (s) (see, e.g., U.S. Pat. No. 5,648,260, Kontermann and Dübel (2010), loc. cit. and Little (2009), loc. cit.).

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term thus preferably excludes sequences generated by genomic rearrangement in an immune cell.

The pairing of a VH and VL together forms a single antigen-binding site. The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR 1, CDR2, and CDR3. Accordingly, CDR constituents on the heavy chain are referred to as H1, H2, and H3, while CDR constituents on the light chain are referred to as L1, L2, and L3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit.). The constant domains are not directly involved in antigen binding, but exhibit various effector functions, such as, for example, antibody-dependent, cell-mediated cytotoxicity and complement activation.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum (Kabat et al., loc. cit.; Chothia et al., J. Mol. Biol, 1987, 196: 901; and MacCallum et al., J. Mol. Biol, 1996, 262: 732). However, the numbering in accordance with the so-called Kabat system is preferred. The CDR3 of the light chain and, particularly, CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen.

"Consisting essentially of" means that the amino acid sequence can vary by about 1, 2, 3, 4, 5, 6, 7, 8, 9, 10, 11, 12, 13, 14, or 15% relative to the recited SEQ ID NO: sequence and still retain biological activity, as described herein.

In some embodiments, the binding molecules described herein are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as binding to an elected a cell surface molecule on a target cell.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I); leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr). The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i. e., Kabat et al., loc. cit.); and (2) An approach based on crystallographic studies of antigen-antibody complexes (Chothia, C. et al., J. Mol. Biol. 196: 901-917 (1987)). However, to the extent that two residue identification techniques define regions of overlapping, but not identical regions, they can be combined to define a hybrid CDR. However, in general, the CDR residues are preferably identified in accordance with the so-called Kabat (numbering) system.

The term "framework region" refers to the art-recognized portions of an antibody variable region that exist between the more divergent (i.e., hypervariable) CDRs. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800, each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues. The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1987; J. Mol. Biol. 227:799-817); and Tomlinson et al. (1995) EMBO J. 14: 4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, Calif., 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

It is also envisaged that the CD33 targeting compound described herein has, apart from its function to bind to the cell surface molecule CD33 on a target cell and CD3 on the cell surface of a T cell, may have an additional function. In this format, the compound is a multifunctional compound by targeting cells through binding to CD33 on the cell surface of a target cell, mediating cytotoxic T cell activity through CD3 binding and providing a further function such as a fully functional Fc constant domain mediating antibody-dependent cellular cytotoxicity through recruitment of effector cells like NK cells, a half life extending domain such as an albumin binding domain or a modified Fc constant domain lacking antibody-dependent cellular cytotoxicity but extending the molecular weight of the compound, mediation of a label (fluorescent etc.), a therapeutic agent such as, e.g. a toxin or radionuclide, and/or means to enhance serum half-life, etc.

The term "epitope" refers to a site on an antigen to which a binding domain, such as an antibody or immunoglobulin or derivative or fragment of an antibody or of an immunoglobulin, specifically binds. An "epitope" is antigenic and thus the term epitope is sometimes also referred to herein as "antigenic structure" or "antigenic determinant". Thus, the binding domain is an "antigen-interaction-site". Said binding/interaction is also understood to define a "specific recognition". In one example, said binding domain which (specifically) binds to/interacts with a given target epitope of CD33 on a cell surface molecule on a target cell or CD3 is an antibody or immunoglobulin, and said binding domain is a VH and/or VL region of an antibody or of an immunoglobulin.

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof (in the context of the present invention, the antigen for one of the binding domains is comprised within a cell surface molecule on a target cell). For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy. Moreover, the provided examples describe a further method to characterize a given binding domain by way of binning, which includes a test whether the given binding domain binds to one or more epitope cluster(s) of a given protein, in particular a cell surface molecule on a target cell.

As used herein, the term "epitope cluster" denotes the entirety of epitopes lying in a defined contiguous stretch of an antigen. An epitope cluster can comprise one, two or more epitopes. The concept of epitope cluster is also used in the characterization of the features of the binding molecules of the invention.

The terms "(capable of) binding to", "specifically recognizing", "directed to" and "reacting with" mean in accordance with this invention that a binding domain is capable of specifically interacting with one or more, preferably at least two, more preferably at least three and most preferably at least four amino acids of an epitope.

As used herein, the terms "specifically interacting", "specifically binding" or "specifically bind(s)" mean that a binding domain exhibits appreciable affinity for a particular protein or antigen and, generally, does not exhibit significant reactivity with proteins or antigens other than CD33 or CD3. "Appreciable affinity" includes binding with an affinity of about $10^{-6}$M (KD) or stronger. Preferably, binding is considered specific when binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Whether a binding domain specifically reacts with or binds to a target can be tested readily by, inter alia, comparing the reaction of said binding domain with a target protein or antigen with the reaction of said binding domain with proteins or antigens other than CD33 or CD3. Preferably, a binding domain of the invention does not essentially bind or is not capable of binding to proteins or antigens other than CD33 or CD3 (i.e. the first binding domain is not capable of binding to proteins other than CD33 and the second binding domain is not capable of binding to proteins other than CD3).

The term "does not essentially bind", or "is not capable of binding" means that a binding domain of the present invention does not bind another protein or antigen other than CD33 or CD3, i.e., does not show reactivity of more than 30%, preferably not more than 20%, more preferably not more than 10%, particularly preferably not more than 9%, 8%, 7%, 6% or 5% with proteins or antigens other than CD33 or CD3, whereby binding to CD33 or CD3, respectively, is set to be 100%.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-site with its specific antigen may result in a simple binding of said site to the antigen. Moreover, the specific interaction of the antigen-interaction-site with its specific antigen may alternatively or additionally result in the initiation of a signal, e.g. due to the induction of a change of the conformation of the antigen, an oligomerization of the antigen, etc.

Proteins (including fragments thereof, preferably biologically active fragments, and peptides, usually having less than 30 amino acids) comprise one or more amino acids coupled to each other via a covalent peptide bond (resulting in a chain of amino acids). The term "polypeptide" as used herein describes a group of molecules, which consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. A "polypeptide" when referred to herein may also be chemically modified such as pegylated. Such modifications are well known in the art.

"Isolated" when used to describe the CD33 targeting compound disclosed herein, means a compound that has been identified, separated and/or recovered from a component of its production environment. Preferably, the isolated compound is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the compound will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated compound will be prepared by at least one purification step.

Amino acid sequence modifications of the CD33 targeting compound described herein are contemplated. For example, it may be desirable to improve the binding affinity and/or other biological properties of the compound. Amino acid sequence variants of the CD33 targeting compounds are prepared by introducing appropriate nucleotide changes into the compounds nucleic acid, or by peptide synthesis.

Such modifications include, for example, deletions from, and/or insertions into, and/or substitutions of, residues within the amino acid sequences of the compound. Any combination of deletion, insertion, and substitution is made to arrive at the final construct, provided that the final construct possesses the desired characteristics. The amino acid changes also may alter post-translational processes of the compound, such as changing the number or position of glycosylation sites. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs). The substitutions are preferably conservative substitutions as described herein. Additionally or alternatively, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs.

A useful method for identification of certain residues or regions of the CD33 targeting compounds that are preferred locations for mutagenesis is called "alanine scanning mutagenesis" as described by Cunningham and Wells in Science, 244: 1081-1085 (1989). Here, a residue or group of target residues within the compound is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se needs not to be predetermined. For example, to analyze the performance of a mutation at a given site, ala scanning or random mutagenesis is conducted at a target codon or region and the expressed compound variants are screened for the desired activity.

Preferably, amino acid sequence insertions include amino- and/or carboxyl-terminal fusions ranging in length from 1, 2, 3, 4, 5, 6, 7, 8, 9 or 10 residues to polypeptides containing a hundred or more residues, as well as intrasequence insertions of single or multiple amino acid residues. An insertional variant of the CD33 targeting compound includes the fusion to the N- or C-terminus of the antibody to an enzyme or a fusion to a polypeptide which increases the serum half-life of the antibody.

Another type of variant is an amino acid substitution variant. These variants have preferably at least 1, 2, 3, 4, 5, 6, 7, 8, 9 or 10 amino acid residues in the compound replaced by a different residue. The sites of greatest interest for substitutional mutagenesis include the CDRs of the heavy and/or light chain, in particular the hypervariable regions, but FR alterations in the heavy and/or light chain are also contemplated.

For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs of the heavy and/or light chain, it is preferred that the then-obtained "substituted" sequence is at least 60%, more preferably 65%, even more preferably 70%, particularly preferably 75%, more particularly preferably 80% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the CD33 targeting compound may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions" listed in Table 1, below) is envisaged as long as the CD33 targeting compound retains its capability to bind to CD33 via the first binding domain and to CD3 epsilon via the second binding domain and/or its CDRs have an identity to the then substituted sequence (at least 60%, more preferably 65%, even more preferably 70%, particularly preferably 75%, more particularly preferably 80% identical to the "original" CDR sequence).

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE 1

Amino Acid Substitutions

| Original | Exemplary Substitutions | Preferred Substitutions |
|---|---|---|
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | ala | ala |
| His (H) | asn, gln, lys, arg | arg |
| Ile (I) | leu, val, met, ala, phe | leu |
| Leu (L) | norleucine, ile, val, met, ala | ile |

TABLE 1-continued

Amino Acid Substitutions

| Original | Exemplary Substitutions | Preferred Substitutions |
|---|---|---|
| Lys (K) | arg, gln, asn | arg |
| Met (M) | leu, phe, ile | leu |
| Phe (F) | leu, val, ile, ala, tyr | tyr |
| Pro (P) | ala | ala |
| Ser (S) | thr | thr |
| Thr (T) | ser | ser |
| Trp (W) | tyr, phe | tyr |
| Tyr (Y) | trp, phe, thr, ser | phe |
| Val (V) | ile, leu, met, phe, ala | leu |

Substantial modifications in the biological properties of the CD33 targeting compound described herein are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the CD33 targeting compound may be substituted, generally with serine, to improve the oxidative stability of the molecule and prevent aberrant crosslinking. Conversely, cysteine bond(s) may be added to the compound in case the compound is an antibody to improve its stability (particularly where the antibody is an antibody fragment such as an Fv fragment).

A particularly preferred type of substitutional variant involves substituting one or more hypervariable region residues of a parent antibody (e. g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e. g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e. g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., human CD33 or CD3. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

Other modifications of the CD33 targeting compound are contemplated herein. For example, the CD33 targeting compound may be linked to one of a variety of non-proteinaceous polymers, e.g., polyethylene glycol, polypropylene glycol, polyoxyalkylenes, or copolymers of polyethylene glycol and polypropylene glycol. The CD33 targeting compound may also be entrapped in microcapsules prepared, for example, by coacervation techniques or by interfacial polymerization (for example, hydroxymethylcellulose or gelatine-microcapsules and poly (methylmethacrylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

The CD33 targeting compound disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the compound are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

When using recombinant techniques, the CD33 targeting compound can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*.

The CD33 targeting compounds prepared from the cells can be purified using, for example, hydroxylapatite chromatography, gel electrophoresis, dialysis, and affinity chromatography, with affinity chromatography being the preferred purification technique.

The CD33 targeting compounds described herein may be provided in form of a fusion protein comprising at least two binding domains, with or without peptide linkers (spacer peptides). Among the suitable peptide linkers are those described in U.S. Pat. Nos. 4,751,180 and 4,935,233 or WO 88/09344.

Another method for preparing CD33 targeting compounds described herein in form of oligomeric antibody construct derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, *Semin. Immunol.* 6:267-78. In one approach, recombinant fusion proteins comprising a CD33 and a CD3 antibody fragment or derivative fused to a leucine zipper peptide are expressed in suitable host cells, and the soluble oligomeric CD33 and CD3 antibody fragments or derivatives that form are recovered from the culture supernatant.

Covalent modifications of antigen binding proteins are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antigen binding protein comprises linking the antigen binding protein to various non-proteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins described herein comprises the addition of one or more labels.

The term "labelling group" means any detectable label. Examples of suitable labelling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antigen binding protein via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

A CD33 targeting compound described herein may also comprise additional domains, which e.g. are helpful in the isolation of the molecule or relate to an adapted pharmacokinetic profile of the molecule.

Domains helpful for the isolation of an antibody construct may be elected from peptide motives or secondarily introduced moieties, which can be captured in an isolation method, e.g. an isolation column. A non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All herein disclosed antibody constructs characterized by the identified CDRs are preferred to comprise a His-tag domain, which is generally known as a repeat of consecutive His residues in the amino acid sequence of a molecule, preferably of six His residues.

The term "epigenetic factor" in connection with the present invention defines a compound which is capable of changing the gene expression or cellular phenotype of a cell population upon administration. It is understood that such change refers to one or more functional relevant modifications to the genome without involving a change in the nucleic acid sequence. Examples of such modifications are DNA methylation and histone modification, which are both important for the regulation of gene expression without altering the underlying DNA sequence. Particular examples for eipigentic factors suitable in the combination therapy approach according to the invention are selected from the group consisting of histone deacetylase (HDAC) inhibitors, DNA methyltransferase (DNMT) I inhibitors, hydroxyurea, Granulocyte-Colony Stimulating Factor (G-CSF), histone demethylase inhibitors and ATRA (All Trans-retinoic acid).

Histone deacetylases (HDACs) are a class of enzymes, that remove acetyl groups from ε-N-acetyl lysine amino acid on a histone. The deacetylated histone is suitable to wrap the DNA more thightly which negatively effects the expression genes in the region of the wraped DNA. Accordingly, HDAC inhibitors inhibit the enzymatic deacetylation of histone and allow for the expression or enhancement of expression of those genes located in the region of the acetylated histone. Non-limiting examples for HDAC inhibitors in connection with this invention comprise panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid.

DNA methyltransferase (DNMT) I is an enzyme, which catalyze the transfer of a methyl group to DNA. The degree of DNA methylisation is also decisive for the expression of genes. Non-limiting examples for DNMT I inhibitors in connection with this invention comprise 5-azacitidine, decitabine, hydralazine, zebularine, procainamide, (−)-epigallocatechin-3-gallate, MG98, RG108, and SGI-110.

Histone methyltransferases (HMT) are histone-modifying enzymeshat catalyze the transfer of one, two, or three methyl groups to lysine and arginine residues of histone proteins. Methylation of histones is important biologically because it is the principal epigenetic modification of chromatin that determines gene expression, genomic stability, stem cell maturation, cell lineage development, genetic imprinting, DNA methylation, and cell mitosis. Non-limiting examples for HMT inhibitors in connection with this invention comprise LSD1 (KDM1A) demethylase inhibitor, and chaetocin.

ATRA (All Trans-retinoic acid) is the carboxylic acid form of vitamin A and is also known as Tretinoin.

Hydroxyurea is also known as Hydroxycarbamide and is used as an antineoplastic drug. The compound is described to decreases the production of deoxyribonucleotides via inhibition of the enzyme ribonucleotide reductase.

Granulocyte-colony stimulating factor (G-CSF or GCSF), also known as colony-stimulating factor 3 (CSF 3), is a glycoprotein that stimulates the bone marrow to produce granulocytes and stem cells and release them into the bloodstream. Functionally, it is a cytokine and hormone, a type of colony-stimulating factor, and is produced by a number of different tissues. The pharmaceutical analogs of naturally occurring G-CSF are called filgrastim and lenograstim.

The term "nucleic acid" is well known to the skilled person and encompasses DNA (such as cDNA) and RNA (such as mRNA). The nucleic acid can be double stranded and single stranded, linear and circular. Said nucleic acid molecule is preferably comprised in a vector which is preferably comprised in a host cell. Said host cell is, e.g. after transformation or transfection with the nucleic acid sequence described herein, capable of expressing the CD33 targeting compound. For that purpose the nucleic acid molecule is operatively linked with control sequences.

A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences such as a promoter sequence that drives expression of the transgene. Insertion of a vector into the target cell is usually called "transformation" for bacteria, "transfection" for eukaryotic cells, although insertion of a viral vector is also called "transduction".

As used herein, the term "host cell" is intended to refer to a cell into which a nucleic acid encoding the CD33 targeting compound described herein is introduced by way of transformation, transfection and the like. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "expression" includes any step involved in the production of a CD33 targeting compound described herein including, but not limited to, transcription, post-transcriptional modification, translation, post-translational modification, and secretion.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "host cell," "target cell" or "recipient cell" are intended to include any individual cell or cell culture that can be or has/have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacteria, yeast cells, animal cells, and mammalian cells, e.g., murine, rat, macaque or human.

Suitable eukaryotic host cells include yeasts, fungi, insect cells and mammalian cells.

The CD33 targeting compound described herein can be produced in bacteria. After expression, the CD33 targeting compound, preferably the antibody construct is isolated from the *E. coli* cell paste in a soluble fraction and can be purified through, e.g., affinity chromatography and/or size exclusion. Final purification can be carried out similar to the process for purifying antibody expressed e. g, in CHO cells.

In addition to prokaryotes, eukaryotic microbes such as filamentous fungi or yeast are suitable cloning or expression hosts for the CD33 targeting compound described herein. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as, e.g., *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans,* and *K. marxianus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger.*

Suitable host cells for the expression of glycosylated CD33 targeting compounds described herein, preferably antibody derived antibody constructs are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e. g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TRI cells (Mather et al., Annals N.Y Acad. Sci. 383: 44-68 (1982)); MRC 5 cells; FS4 cells; and a human hepatoma line (Hep G2).

When using recombinant techniques, the CD33 targeting compound described herein can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The CD33 targeting compound described herein prepared from the host cells can be purified using, for example, hydroxylapatite chromatography, gel electrophoresis, dialysis, and affinity chromatography, with affinity chromatography being the preferred purification technique.

The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose. Where the CD33 targeting compound described herein comprises a CH3 domain, the Bakerbond ABXMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromato-focusing, SDS-PAGE, and ammonium sulfate precipitation are also available depending on the antibody to be recovered.

The term "culturing" refers to the in vitro maintenance, differentiation, growth, proliferation and/or propagation of cells under suitable conditions in a medium.

As used herein, the term "pharmaceutical composition" relates to a composition for administration to a patient, preferably a human patient. The particular preferred pharmaceutical composition of this invention comprises a CD33 targeting compound and at least one epigenetic factor, either in one single formulation or in separate formulations. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. In particular, the present invention provides for an uninterrupted administration of the suitable composition. As a non-limiting example, uninterrupted, i.e. continuous administration may be realized by a small pump system worn by the patient for metering the influx of therapeutic agent into the body of the patient. The pharmaceutical composition comprising the CD33 targeting compound or the CD33 targeting compound and at least one epigenetic factor can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the CD33 targeting compound described herein or the CD33 targeting compound and at least one epigenetic factor described herein may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

The inventive compositions may further comprise a pharmaceutically acceptable carrier. Examples of suitable pharmaceutical carriers are well known in the art and include solutions, e.g. phosphate buffered saline solutions, water, emulsions, such as oil/water emulsions, various types of wetting agents, sterile solutions, liposomes, etc. Compositions comprising such carriers can be formulated by well known conventional methods. Formulations can comprise carbohydrates, buffer solutions, amino acids and/or surfactants. Carbohydrates may be non-reducing sugars, preferably trehalose, sucrose, octasulfate, sorbitol or xylitol. In general, as used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; anti-oxidants, including ascorbic acid and methionine; chelating agents such as EDTA; metal complexes (e.g., Zn-protein complexes); biodegradable polymers, such as polyesters; salt-forming counter-ions, such as sodium, polyhydric sugar alcohols; amino acids, such as alanine, glycine, asparagine, 2-phenylalanine, and threonine; sugars or sugar alcohols, such as trehalose, sucrose, octasulfate, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Such formulations may be used for continuous administrations which may be intravenuous or subcutaneous with and/or without pump systems. Amino acids may be charged amino acids, preferably lysine, lysine acetate, arginine, glutamate and/or histidine. Surfactants may be detergents, preferably with a molecular weight of >1.2 KD and/or a polyether, preferably with a molecular weight of >3 KD. Non-limiting examples for preferred detergents are Tween 20, Tween 40, Tween 60, Tween 80 or Tween 85. Non-limiting examples for preferred polyethers are PEG 3000, PEG 3350, PEG 4000 or PEG 5000. Buffer systems used in the present invention can have a preferred pH of 5-9 and may comprise citrate, succinate, phosphate, histidine and acetate.

The compositions of the present invention comprising the CD33 targeting compound and at least one epigenetic factor in a single or separate formulations can be administered to the subject at a suitable dose which can be determined e.g. by dose escalating studies by administration of increasing doses of the polypeptide described herein exhibiting cross-species specificity described herein to non-chimpanzee primates, for instance macaques. As set forth above, the CD33 targeting composition described herein exhibiting cross-species specificity described herein can be advantageously used in identical form in preclinical testing in non-chimpanzee primates and as drug in humans. The composition or these compositions can also be administered in combination with additional other proteinaceous and non-proteinaceous drugs. These drugs may be administered simultaneously with the composition comprising the polypeptide described herein as defined herein or separately before or after administration of said polypeptide in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the composition of the invention might comprise, in addition to the polypeptide described herein defined herein, further biologically active agents, depending on the intended use of the composition. Such agents might be drugs acting on the gastro-intestinal system, drugs acting as cytostatica, drugs preventing hyperuricemia, drugs inhibiting immunoreactions (e.g. corticosteroids), drugs modulating the inflammatory response, drugs acting on the circulatory system and/or agents such as cytokines known in the art. It is also envisaged that the composition of the present invention comprising the CD33 targeting compound and at least one epigenetic factor in a single or separate formulations is applied in an additional co-therapy, i.e., in combination with another anti-cancer medicament.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4):1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc.

By "hepatic first-pass metabolism" is meant the propensity of a drug to be metabolized upon first contact with the liver, i.e. during its first pass through the liver.

"Volume of distribution" means the degree of retention of a drug throughout the various compartments of the body, like e.g. intracellular and extracellular spaces, tissues and organs, etc. and the distribution of the drug within these compartments.

"Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of comprising a CD33 targeting compound such as a bispecific single chain antibody exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the subject's own immune system. The term "patient" includes human and other mammalian subjects that receive either prophylactic or therapeutic treatment.

The term "effective and non-toxic dose" as used herein refers to a tolerable dose of a pharmaceutical composition (i.e. a pharmaceutical composition comprising the CD33 targeting compound and at least one epigenetic factor in a single or separate formulations) which is high enough to cause depletion of pathological cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

The appropriate dosage, or therapeutically effective amount, of t a pharmaceutical composition comprising the CD33 targeting compound and at least one epigenetic factor in a single or separate formulations will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies such as anti-cancer therapies as needed.

The pharmaceutical compositions of this invention are particularly useful for parenteral administration, i.e., subcutaneously, intramuscularly, intravenously, intra-articular and/or intra-synovial. Parenteral administration can be by bolus injection or continuous infusion.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

It has been surprisingly found in connection with the present invention that specific groups of epigenetic factors relate to an increase of the potency of a therapy approach making use of the engagement of T cells to CD33 positive target cells. 5-azacytidine (Vidaza™) and 5-aza-2'deoxycytidine (decitabine, Dacogen™) are nucleoside analogs that belong to a class of epigenetic therapeutics and are known to be capable of inducing tumor cell killing through the disruption of protein synthesis and inhibition of DNA methylation. Co-therapy approaches using the CD33 specific antibody lintuzumab and 5-azacytidine lead to an improved lintuzumab-mediated ADCC against AML target cells. However, in such study the incubation of AML cells or macrophages did not affect the CD33 expression on those cells (Sutherland et al. MAbs. 2010 July-August; 2(4): 440-448). Accordingly it has been concluded that since for the mode-of-action of lintuzumab requires a functional interaction between the $F_C$ domain of lintuzumab and the $F_C\gamma$ receptor of immune effector cells is required the pretreatment with epigenetic compounds increases the specific phagocytosis of target cells by the effector cells.

Thus the present finding are especially in the light of those known effect surprisingly, since the mode-of-action underlying the target cells lysis by T cells when engaged by the CD33 targeting compounds described herein is completely independent of any $F_C$-$F_C\gamma$ receptor interaction. In contrast to the previous studies, an increase of CD33 surface expression by treatment of target cells with epigenetic factors described herein was observed. Also, as apparent from the mode-of-action underlying the target cells lysis by T cells the observed synergistic effect is independent of any signal-transduction-effect which might be triggered by antibody binding to the CD33 surface molecule (e.g. a signaling pathway involving SHP-1, Syk, or both).

Moreover, as the speed and extent of myeloid leukemia cell blast lysis at a given time point was proportional to CD33 expression, this finding supports that the combination of an epigenetic therapy and a CD33 directed T cell engager would be synergistically more effective than either therapy administered separately. Accordingly, the described administration of one or more CD33 targeting compound in combination with epigenetic factors described herein may allow for lower doses of a bispecific T cell engager to be effective at a given time point.

As described above, examples for eipigentic factors suitable in the combination therapy approach according to the invention are selected from the group consisting of histone deacetylase (HDAC) inhibitors, DNA methyltransferase (DNMT) I inhibitors, hydroxyurea, Granulocyte-Colony Stimulating Factor (G-CSF), histone demethylase inhibitors and ATRA (All Trans-retinoic acid). The redirected lysis of target cells via the recruitment of T cells by a multispecific, at least bispecific, construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

The cytotoxic activity mediated by CD33/CD3 bispecific compounds described herein such as bispecific antibody constructs is preferably measured in a cell-based cytotoxicity assay. It is represented by the $EC_{50}$ value, which corresponds to the half maximal effective concentration (concentration of the compound which induces a cytotoxic response halfway between the baseline and maximum). Preferably, the $EC_{50}$ value of the CD33/CD3 bispecific antibody constructs is ≤20.000 pg/ml, more preferably ≤5000 pg/ml, even more preferably ≤1000 pg/ml, even more preferably ≤500 pg/ml, even more preferably ≤350 pg/ml, even more preferably ≤320 pg/ml, even more preferably ≤250 pg/ml, even more preferably ≤100 pg/ml, even more preferably ≤50 pg/ml, even more preferably ≤10 pg/ml, and most preferably ≤5 pg/ml.

Any of the above given $EC_{50}$ values can be combined with any one of the indicated scenarios of a cell-based cytotoxicity assay. For example, when (human) CD8 positive T cells or a macaque T cell line are used as effector cells, the $EC_{50}$ value of the CD33/CD3 bispecific antibody construct is preferably ≤1000 pg/ml, more preferably ≤500 pg/ml, even more preferably ≤250 pg/ml, even more preferably ≤100 pg/ml, even more preferably ≤50 pg/ml, even more preferably ≤10 pg/ml, and most preferably ≤5 pg/ml. If in this assay the target cells are (human or macaque) CD33 transfected cells such as CHO cells, the $EC_{50}$ value of the CD33/CD3 bispecific antibody construct is preferably ≤150 pg/ml, more preferably ≤100 pg/ml, even more preferably ≤50 pg/ml, even more preferably ≤30 pg/ml, even more preferably ≤10 pg/ml, and most preferably ≤5 pg/ml.

If the target cells are a CD33 positive natural expresser cell line, then the $EC_{50}$ value is preferably ≤350 pg/ml, more preferably ≤320 pg/ml, even more preferably ≤250 pg/ml, even more preferably ≤200 pg/ml, even more preferably ≤100 pg/ml, even more preferably ≤150 pg/ml, even more preferably ≤100 pg/ml, and most preferably ≤50 pg/ml, or lower.

When (human) PBMCs are used as effector cells, the $EC_{50}$ value of the CD33/CD3 bispecific antibody construct is preferably ≤1000 pg/ml, more preferably ≤750 pg/ml, more preferably ≤500 pg/ml, even more preferably ≤350 pg/ml, even more preferably ≤320 pg/ml, even more preferably ≤250 pg/ml, even more preferably ≤100 pg/ml, and most preferably ≤50 pg/ml, or lower.

The difference in cytotoxic activity between the monomeric and the dimeric isoform of individual CD33/CD3 bispecific antibody constructs is referred to as "potency gap". This potency gap can e.g. be calculated as ratio between $EC_{50}$ values of the molecule's monomeric and dimeric form. Potency gaps of the CD33/CD3 bispecific antibody constructs described herein are preferably ≤5, more preferably ≤4, even more preferably ≤3, even more preferably ≤2 and most preferably ≤1.

It is particularly preferred for the CD33 targeting compound described herein that the second binding domain capable of binding to the T cell CD3 receptor complex comprises a VL region comprising CDR-L1, CDR-L2 and CDR-L3 selected from:
(a) CDR-L1 as depicted in SEQ ID NO: 258, CDR-L2 as depicted in SEQ ID NO: 259 and CDR-L3 as depicted in SEQ ID NO: 260;
(b) CDR-L1 as depicted in SEQ ID NO: 261, CDR-L2 as depicted in SEQ ID NO: 262 and CDR-L3 as depicted in SEQ ID NO: 263; and
(c) CDR-L1 as depicted in SEQ ID NO: 264, CDR-L2 as depicted in SEQ ID NO: 265 and CDR-L3 as depicted in SEQ ID NO: 266.

In an alternatively preferred embodiment of the CD33 targeting compound described herein, the second binding domain capable of binding to the T cell CD3 receptor complex comprises a VH region comprising CDR-H 1, CDR-H2 and CDR-H3 selected from:

(a) CDR-H1 as depicted in SEQ ID NO: 228, CDR-H2 as depicted in SEQ ID NO: 229 and CDR-H3 as depicted in SEQ ID NO: 230;
(b) CDR-H1 as depicted in SEQ ID NO: 231, CDR-H2 as depicted in SEQ ID NO: 232 and CDR-H3 as depicted in SEQ ID NO: 233;
(c) CDR-H1 as depicted in SEQ ID NO: 234, CDR-H2 as depicted in SEQ ID NO: 235and CDR-H3 as depicted in SEQ ID NO: 236;
(d) CDR-H1 as depicted in SEQ ID NO: 237, CDR-H2 as depicted in SEQ ID NO: 238 and CDR-H3 as depicted in SEQ ID NO: 239;
(e) CDR-H1 as depicted in SEQ ID NO: 240, CDR-H2 as depicted in SEQ ID NO: 241 and CDR-H3 as depicted in SEQ ID NO: 242;
(f) CDR-H1 as depicted in SEQ ID NO: 243, CDR-H2 as depicted in SEQ ID NO: 244 and CDR-H3 as depicted in SEQ ID NO: 245;
(g) CDR-H1 as depicted in SEQ ID NO: 246, CDR-H2 as depicted in SEQ ID NO: 247and CDR-H3 as depicted in SEQ ID NO: 248;
(h) CDR-H1 as depicted in SEQ ID NO: 249, CDR-H2 as depicted in SEQ ID NO: 250 and CDR-H3 as depicted in SEQ ID NO: 251;
(i) CDR-H1 as depicted in SEQ ID NO: 252, CDR-H2 as depicted in SEQ ID NO: 253 and CDR-H3 as depicted in SEQ ID NO: 254; and
(j) CDR-H1 as depicted in SEQ ID NO: 255, CDR-H2 as depicted in SEQ ID NO: 256 and CDR-H3 as depicted in SEQ ID NO: 257.

It is further preferred for the CD33 targeting compound described herein that the second binding domain capable of binding to the T cell CD3 receptor complex comprises a VL region comprising an amino acid sequence selected from the group consisting of a VL region SEQ ID NOs: 160, 163, 190, 193, 202, and 205.

It is alternatively preferred that the second binding domain capable of binding to the T cell CD3 receptor complex comprises a VH region comprising an amino acid sequence selected from the group consisting of region SEQ ID NOs: 155, 158, 161, 164, 167, 170, 173, 176, 179, 182, 185, 188, 191, 194, 200, 203, 209, and 212.

More preferably, the CD33 targeting compound described herein is characterized by the second binding domain capable of binding to the T cell CD3 receptor complex comprising a VL region and a VH region selected from the group consisting of:
(a) a VL region as depicted in SEQ ID NO: 154 or 157and a VH region as depicted in SEQ ID NO: 155 or 158;
(b) a VL region as depicted in SEQ ID NO: 160 or 163 and a VH region as depicted in SEQ ID NO: 161 or 164;
(c) a VL region as depicted in SEQ ID NO: 166 or 169 and a VH region as depicted in SEQ ID NO: 167 or 170;
(d) a VL region as depicted in SEQ ID NO: 172 or 175 and a VH region as depicted in SEQ ID NO: 173 or 176;
(e) a VL region as depicted in SEQ ID NO: 178 or 181 and a VH region as depicted in SEQ ID NO: 179 or 182;
(f) a VL region as depicted in SEQ ID NO: 184 or 187 and a VH region as depicted in SEQ ID NO: 185 or 188;
(g) a VL region as depicted in SEQ ID NO: 190 or 193 and a VH region as depicted in SEQ ID NO: 191 or 194;
(h) a VL region as depicted in SEQ ID NO: 196 or 199 and a VH region as depicted in SEQ ID NO: 197 or 200;
(i) a VL region as depicted in SEQ ID NO: 202 or 205 and a VH region as depicted in SEQ ID NO: 203 or 206; and
(j) a VL region as depicted in SEQ ID NO: 208 or 211 and a VH region as depicted in SEQ ID NO: 209 or 212.

According to a preferred embodiment of the CD33 targeting compound described herein, in particular the second binding domain capable of binding to the T cell CD3 receptor complex, the pairs of VH-regions and VL-regions are in the format of a single chain antibody (scFv). The VH and VL regions are arranged in the order VH-VL or VL-VH. It is preferred that the VH-region is positioned N-terminally to a linker sequence. The VL-region is positioned C-terminally of the linker sequence.

A preferred embodiment of the CD33 targeting compound described herein is characterized by the second binding domain capable of binding to the T cell CD3 receptor complex comprising an amino acid sequence selected from the group consisting of SEQ ID NOs: 156, 159, 162, 165, 168, 171, 174, 177, 180, 183, 186, 189, 192, 195, 198, 201, 204, 207, 210, and 213.

The formulations described herein are useful as pharmaceutical compositions in the treatment, amelioration and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

Those "in need of treatment" include those already with the disorder, as well as those in which the disorder is to be prevented. The term "disease" is any condition that would benefit from treatment with the protein formulation described herein. This includes chronic and acute disorders or diseases including those pathological conditions that predispose the mammal to the disease in question. Non-limiting examples of diseases/disorders to be treated herein include the herein described myeloid leukemia.

In some embodiments, the invention provides a pharmaceutical composition comprising a therapeutically effective amount of one or a plurality of the antibody construct described herein together with a pharmaceutically effective diluents, carrier, solubilizer, emulsifier, preservative, and/or adjuvant. Pharmaceutical compositions described herein include, but are not limited to, liquid, frozen, and lyophilized compositions.

Preferably, formulation materials are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins);

proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins described herein. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefore. In certain embodiments of the invention, human antibody or antigen binding fragment thereof described herein or the antibody construct described herein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the human antibody or antigen binding fragment thereof described herein or the antibody construct described herein may be formulated as a lyophilizate using appropriate excipients such as sucrose.

The pharmaceutical compositions described herein can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired human antibody or antigen binding fragment thereof described herein or the antibody construct described herein in a pharmaceutically acceptable vehicle. A particularly suitable vehicle for parenteral injection is sterile distilled water in which the antibody construct described herein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Additional pharmaceutical compositions will be evident to those skilled in the art, including formulations involving the antibody construct described herein in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering antibody construct formulations, which can be used as pharmaceutical compositions, as described in international patent application WO 20061138181A2 (PCT/US2006/022599), which is incorporated by reference in its entirety herein.

As discussed above, certain embodiments involve antibody construct protein compositions, particularly pharmaceutical compositions of the invention, that comprise, in addition to the antibody construct described herein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the antibody construct formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the antibody construct formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the antibody construct formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

The antibody construct described herein generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, ophthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided. The therapeutically effective amount of an antibody construct protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the antibody construct described herein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of pharmaceutical composition of the invention comprising the CD33 targeting compound and at least one epigenetic factor in a single or separate formulations preferably results in a decrease in severity of disease symptoms, in increase in frequency or duration of disease symptom-free periods or a prevention of impairment or disability due to the disease affliction. For treating CD33-expressing tumors, a therapeutically effective amount of the CD33 targeting compound and at least one epigenetic factor in a single or separate formulations, e.g. an anti-CD33/CD3 antibody construct and the at least one epigenetic factor, preferably inhibits cell growth or tumor growth by at least about 20%, at least about 40%, at least about 50%, at least about 60%, at least about 70%, at least about 80%, or at least about 90% relative to untreated patients. The ability of a compounds to inhibit tumor growth may be evaluated in an animal model predictive of efficacy in human tumors.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

It should be understood that the inventions herein are not limited to particular methodology, protocols, or reagents, as such can vary. The discussion and examples provided herein are presented for the purpose of describing particular embodiments only and are not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

EXAMPLES

The following examples are provided for the purpose of illustrating specific embodiments or features of the present invention. These examples should not be construed as to limit the scope of this invention. The examples are included for purposes of illustration, and the present invention is limited only by the claims.

Example 1

Epigenetic Modifying Drugs as Sensitizing Agents for CD33 Targeting Compound-Induced Cytotoxicity The level of CD33 expression was identified as a critical variable for the extent of activity of a CD33 targeting compound described herein such as AMG330 against human AML cells. Accordingly, it was surprising to observe the potential of epigenetic modifying drugs such as histone deacetylase (HDAC) inhibitors or DNA methyltransferase (DNMT) I inhibitors as sensitizing agents for AMG 330-induced cytotoxicity.

For the experimental settings mononuclear cells were collected from healthy adult volunteers via leukapheresis, and T cells enriched through magnetic cell sorting (Pan T Cell Isolation Kit II; Miltenyi Biotec, Auburn, Calif.). Thawed cell aliquots were labeled with 3 µM CellVue Burgundy (eBioscience, San Diego, Calif.) according to the manufacturer's instructions.

Human myeloid OCI-AML3, KG-1a, ML-1, NB4, TF-1, and HL-60 cells were maintained as previously described (Walter et al. Blood. 2003; 102(4):1466-1473; Walter et al. Blood. 2004; 103(11):4276-4284, Walter et al. Blood. 2005; 105(3):1295-1302).

CD33 expression on parental AML cells and cell lines was quantified by flow cytometry using a phycoerythrin (PE)-conjugated anti-CD33 antibody (clone P67.6; BD Biosciences, San Jose, Calif., USA) (see Walter et al. Blood. 2005; 105(3):1295-1302).

For the quantification of compound induces cytotoxicity AML cells were taken during exponential growth and incubated at 37° C. (in 5% $CO_2$ and air) in 96-well round bottom plates (BD Falcon™) at $5-10 \times 10^3$ cells/well in 225 µL culture medium containing various concentrations of AMG 330 as well as T-cells at different effector:target (E:T) cell ratios. After 48 hours, cell numbers and drug-induced cytotoxicity, using 4′,6-diamidino-2-phenylindole (DAPI) to detect non-viable cells, were determined using a LSRII flow cytometer (BD Biosciences, San Jose, Calif.) and analyzed with FlowJo (Tree Star, Ashland, Oreg.). AML cells were identified by forward/side scatter properties and negativity for CellVue Burgundy dye.

To determine CD33 modulation, aliquots of AML cells were left untreated or incubated with either AMG 330 (250 pg/mL) or an unconjugated, unlabeled anti-CD33 antibody (clone P67.6; BD Biosciences, San Jose, Calif., USA; 2.5 pg/mL). After 48 hours, cells were washed in ice-cold Phosphate Buffered Saline (PBS, GIBCO Invitrogen) to remove unbound antibody and resuspended in PBS containing 2% fetal bovine serum. As AMG 330 does not compete for binding to CD33 with P67.6, aliquots of untreated and AMG 330-treated cells were incubated with P67.6 or no primary antibody followed by biotin-conjugated rat anti-mouse $IgG_1$ (used at 2.5 pg/mL in PBS/2% FBS) and streptavidin-phycoerythrin (PE) (used at 2.5 pg/mL in PBS/2% FBS: both from BD Biosciences). Likewise, aliquots of untreated and P67.6-treated cells were incubated with unconjugated P67.6 or without primary antibody; cells were then washed and incubated with biotin-conjugated rat anti-mouse $IgG_1$ monoclonal antibody followed by incubation with streptavidin-PE conjugate. To identify nonviable cells, all samples were stained with DAPI. At least 10,000 events were acquired, and DAPI⁻ cells were analyzed on a Canto flow cytometer (BD Biosciences) using FlowJo Software. Linear median fluorescence intensity (MFI) values were used to calculate the percentage of drug-bound CD33 internalization.

Figure 2:
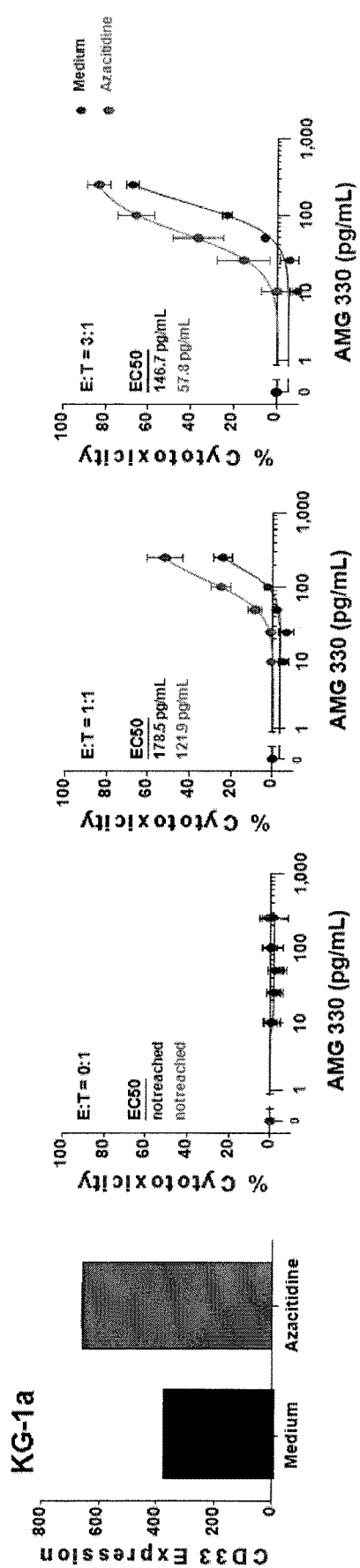
FIG. 2: Effect of azacitidine pretreatment on CD33 expression and AMG 330-induced cytotoxicity. Parental KG-1a cells were either left untreated or pretreated with azacitidine for 72 hours. Subsequently, CD33 expression was quantified, and cells treated with/without AMG 330 (0-250 pg/mL) and various effector:target (E:T) cell ratios using healthy donor T-cells. 48 hours later, cell counts were determined and cytotoxicity was assessed with DAPI staining to quantify drug-specific cytotoxicity. Results are shown as mean±SEM from 3 independent experiments performed in duplicate wells using a single healthy donor as source for exogenous T-cells.

As shown in FIG. 1, 3-day pretreatment with the HDAC inhibitor, panobinostat, resulted in significant increase in CD33 expression in OCI-AML3 and, markedly, KG-1a cells. More importantly, relative to untreated cells, cells pretreated with panobinostat for 3 days were modestly more sensitive to AMG 330-induced cytotoxicity (KG-1a>OCI-AML3). Pretreatment with the DNMT I inhibitor, azacitidine, for 3 days resulted in significant increase in CD33 expression on KG-1a. Consistently, after pretreatment with azacitidine, KG-1a cells became significantly more sensitive to AMG 330-induced cytotoxicity relative to untreated cells (FIG. 2).

Example 2

CD33 Up-Regulation on AML Cells to Increase AMG 330 Mediated Lysis Efficacy

Hydroxyurea
Up-Regulation of CD33 on AML Cell Lines:

AML cell lines HL-60, PL21, OCI-AML3, KG1a and MV4-11 were seeded in 24-well plates at $1 \times 10^{\wedge}6$ cells/ml on day 0. Cells were either left untreated (UT) or treated with 10 µM (H1) or 100 µM (H2) hydroxyurea (Sigma) for three consecutive days (day 0, day 1 and day 2). On day 3, cells were harvested, counted and analyzed for changes in CD33 surface expression level by flow cytometry.

Figure 3:
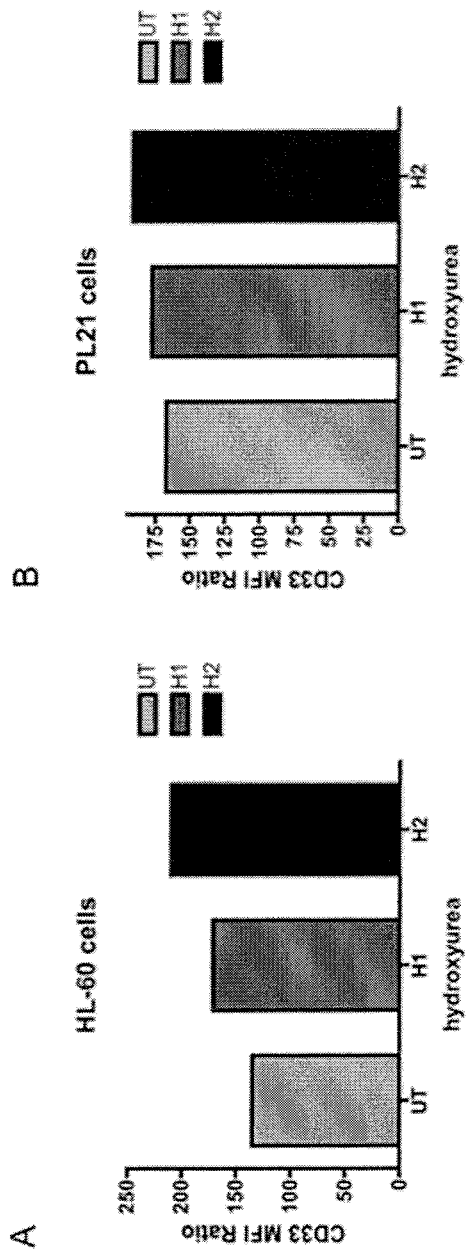
FIG. 3: Hydroxyurea-concentration dependant up-regulation of CD33 on A) HL-60 and B) PL21 AML cells.

FIG. 3 and Table 2 show an upregulation of CD33 on HL-60 and PL21 AML cells in a concentration dependant manner.

TABLE 2

CD33 MFI Ratios of HL-60 and PL21 AML cells after incubation with/without hydroxyurea determined by flow cytometry.

| CD33 MFI Ratio | UT | H1 | H2 |
| --- | --- | --- | --- |
| HL-60 | 134.9 | 171.3 | 210.0 |
| PL21 | 166.9 | 177.9 | 191.8 |

Up-Regulation of CD33 on Primary AML Cells:

Three primary AML samples were seeded in a 12-well plates at 1×10^6 cells/ml, as previously described (Krupka, Subklewe et. al, Blood 2014). Cells were either left untreated (UT) or treated with 10 μM (H1) or 100 μM (H2) hydroxyurea (Sigma) for three consecutive days (day 0, day 1 and day 2). On day 1-day 3, cells were harvested, counted and analyzed for changes in CD33 surface expression by flow cytometry.

Figure 4:
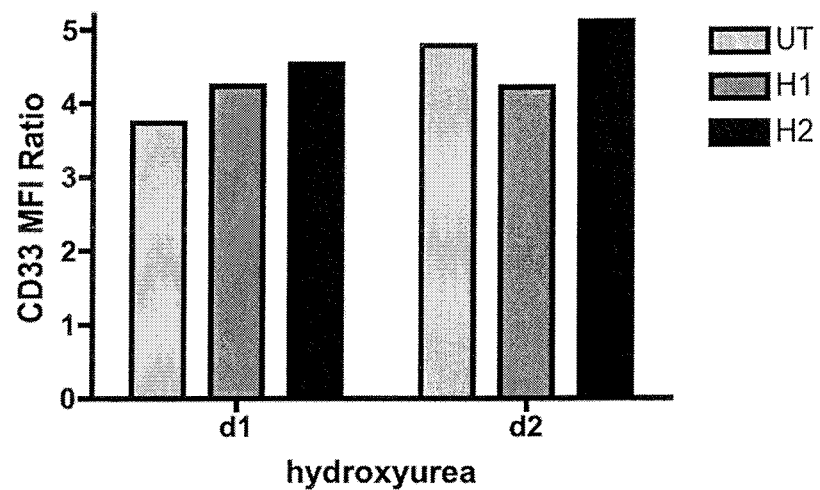
FIG. 4: Hydroxyurea dependant up-regulation of CD33 on primary AML cells from patient 2.

FIG. 4 and Table 3 show an up-regulation of CD33 in 1 of 3 patient samples on day 1 and day 2 of incubation with hydroxyurea.

Granulocyte-Colony Stimulating Factor (G-CSF) Up-Regulation of CD33 on AML Cell Lines:

AML cell lines OCI-AML3 and KG1α were seeded in 24-well plates at 5×10^5 cells/ml on day 0. Cells were either left untreated (UT) or treated with 200 ng/ml (C1) or 2000 ng/ml (C2) G-CSF (Peprotech) for 10 days. G-CSF was freshly added to the cultures biweekly. On day 10, cells were harvested and analyzed for changes in CD33 surface expression by flow cytometry.

Figure 5:
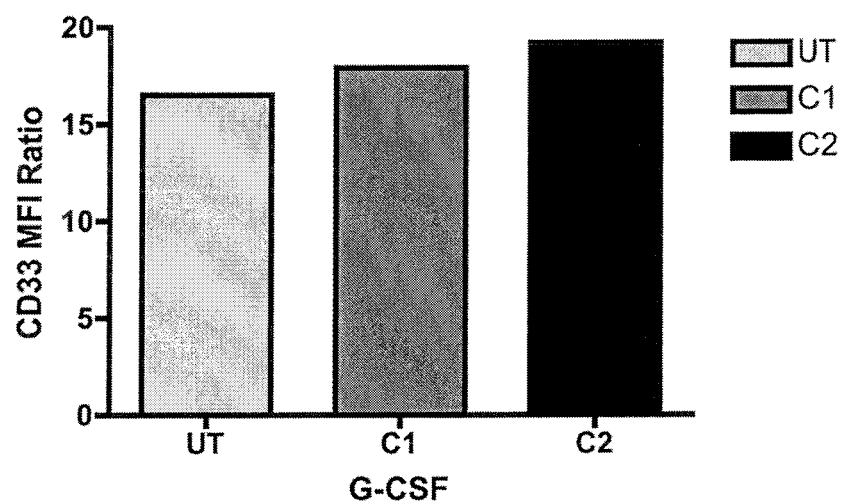
FIG. 5: G-CSF dependant up-regulation of CD33 on KG1α AML cells after 10 days of incubation.
Figure 6:
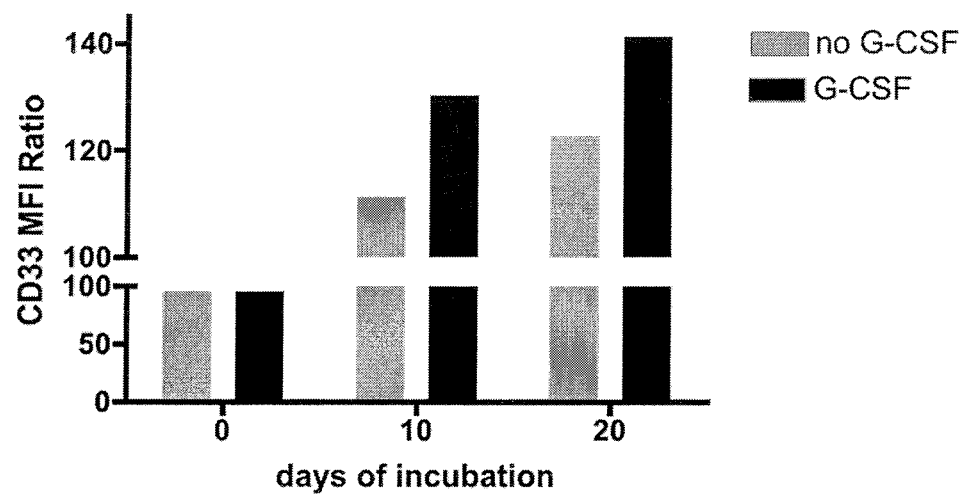
FIG. 6: G-CSF dependant up-regulation of CD33 on primary AML cells from patient 1 after 10 days of incubation.

FIG. 5 and Table 4 show a low upregulation of CD33 on KG1α AML cells in an concentration dependant manner.

TABLE 3

CD33 MFI Ratios of primary AML cells from patient 2 after 1 and 2 days of incubation with hydroxyurea determined by flow cytometry.

| CD33 MFI Ratio | UT | H1 | H2 |
|---|---|---|---|
| day 1 Patient 2 | 3.7 | 4.2 | 4.5 |
| day 2 Patient 2 | 4.8 | 4.2 | 5.1 |

TABLE 4

CD33 MFI Ratios of KG1α AML cells after 10 days of incubation with/without G-CSF determined by flow cytometry.

| CD33 MFI Ratio | UT | C1 | C2 |
|---|---|---|---|
| KG1α | 16.5 | 17.9 | 19.2 |

| SEQ ID NO. | DESIGNATION | SOURCE | TYPE | SEQUENCE |
|---|---|---|---|---|
| 1 | CD33 VH of AH3 | artificial | aa | QVQLVQSGAEVKKPGESVKVSCKASGYTFTNYGMNWVRQAPGQGLEWMGWINTYTGEPTYADDFKGRVTMSSDTSTSTAYLEINSLRSDDTAIYYCARWSWSDGYYVYFDYWGQGTTVTVSS |
| 2 | CD33 HCDR1 of AH3 | artificial | aa | NYGMN |
| 3 | CD33 HCDR2 of AH3 | artificial | aa | WINTYTGEPTYADDFKG |
| 4 | CD33 HCDR3 of AH3 | artificial | aa | WSWSDGYYVYFDY |
| 5 | CD33 VH of AH3 | artificial | nt | CAGGTGCAGCTGGTGCAGTCTGGAGCTGAGGTGAAAAAGCCTGGAGAGTCAGTCAAGGTCTCCTGCAAGGCTAGCGGGTATACCTTCACAAACTATGGAATGAACTGGGTGAGGCAGGCTCCAGGACAGGGTTTAGAGTGGATGGGCTGGATAAACACCTACACTGGAGAGCCAACATATGCTGATGACTTCAAGGGACGGGTTACCATGTCTTCGGATACCTCTACCAGCACTGCCTATTTGGAAATCAACAGCCTCAGAAGTGATGACACGGCTATATATTACTGTGCGCGCTGGAGTTGGAGTGATGGTTACTACGTTTACTTTGACTACTGGGGCCAAGGCACTACGGTCACCGTCTCCTCA |
| 6 | CD33 VL of AH3 | artificial | aa | DIVMTQSPDSLTVSLGERTTINCKSSQSVLDSSKNKNSLAWYQQKPGQPPKLLLSWASTRESGIPDRFSGSGSGTDFTLTIDSLQPEDSATYYCQQSAHFPITFGQGTRLEIK |
| 7 | CD33 LCDR1 of AH3 | artificial | aa | KSSQSVLDSSKNKNSLA |
| 8 | CD33 LCDR2 of AH3 | artificial | aa | WASTRES |
| 9 | CD33 LCDR3 of AH3 | artificial | aa | QQSAHFPIT |
| 10 | CD33 VL of AH3 | artificial | nt | GACATCGTGATGACACAGTCTCCAGACTCCCTGACTGTGTCTCTGGGCGAGAGGACCACCATCAACTGCAAGTCCAGCCAGAGTGTTTTAGACAGCTCCAAGAATAAGAACTCCTTAGCTTGGTACCAGCAGAAACCAGGACAGCCTCCTAAATTACTCCTTTCCTGGGCATCTACGCGGGAATCCGGGATCCCTGACCGATTCAGTGGCAGCGGGTCTGGGACAGATTTCACTCTCACTATTGACAGCCTGCAGCCTGAAGATTCTGCAACTTACTATTGTCAACAGTCTGCCCACTTCCCGATCACCTTTGGCCAAGGGACACGACTGGAGATTAAA |
| 11 | CD33 CD33 HL of AH3 | artificial | aa | QVQLVQSGAEVKKPGESVKVSCKASGYTFTNYGMNWVRQAPGQGLEWMGWINTYTGEPTYADDFKGRVTMSSDTSTSTAYLEINSLRSDDTAIYYCARWSWSDGYYVYFDYWGQGTTVTVSSGGGGSGGGGSGGGGSDIVMTQSPDSLTVSLGERTTINCKSSQSVLDSSKNKNSLAWYQQKPGQPPKLLLSWASTRESGIPDRFSGSGSGTDFTLTIDSLQPEDSATYYCQQSAHFPITFGQGTRLEIK |
| 12 | CD33 HL of AH3 | artificial | nt | CAGGTGCAGCTGGTGCAGTCTGGAGCTGAGGTGAAAAAGCCTGGAGAGTCAGTCAAGGTCTCCTGCAAGGCTAGCGGGTATACCTTCACAAACTATGGAATGAACTGGGTGAGGCAGGCTCCAGGACAGGGTTTAGAGTGGATGGGCTGGATAAACACCTACACTGGAGAGCCAACATATGCTGATGACTTCAAGGGACGGGTTACCATGTCTTCGGATACCTCTACCAGCACTGCCTATTTGGAAATCAACAGCCTCAGAAGTGATGACACGGCTATATATTACTGTGCGCGCTGGAGTTGGAGTGATGGTTACTACGTTTACTTTGACTACTGGGGCCAAGGCACTACGGTCACCGTCTCCTCAGGTGGTGGTGGTTCTGGCGGCGGCGGCTCCGGTGGTGGTGGTTCTGACATCGTGATGACACAGTCTCCAGACTCCCTGACTGTGTCTCTGGGCGAG |

| SEQ ID NO. | DESIGNATION | SOURCE | TYPE | SEQUENCE |
|---|---|---|---|---|
| | | | | AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAA |
| 13 | CD33 AH3 HL × H2C HL | artificial | aa | QVQLVQSGAEVKKPGESVKVSCKASGYTFTNYGMNWVRQAPGQGLEWMGWINTYTGEPTYADDFKG<br>RVTMSSDTSTSTAYLEINSLRSDDTAIYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 14 | CD33 AH3 HL × H2C HL | artificial | nt | CAGGTGCAGCTGGTGCAGTCTGGAGCTGAGGTGAAAAAGCCTGGAGAGTCAGTCAAGGTCTCCTGC<br>AAGGCTAGCGGGTATACCTTCACAAACTATGGAATGAACTGGGTGAGGCAGGCTCCAGGACAGGGT<br>TTAGAGTGGATGGGCTGGATAAACACCTACACTGGAGAGCCAACATATGCTGATGACTTCAAGGGA<br>CGGGTTACCATGTCTTCGGATACCTCTACCAGCACTGCCTATTTGGAAATCAACAGCCTCAGAAGT<br>GATGACACGGCTATATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCGGCTACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGCTCTATGGTACAGCAACCGCTGGGTGTTCGGTGGAGGAACCAAACTGACTGTCCTA |
| 15 | CD33 AH3 HL × F12Q HL | artificial | aa | QVQLVQSGAEVKKPGESVKVSCKASGYTFTNYGMNWVRQAPGQGLEWMGWINTYTGEPTYADDFKG<br>RVTMSSDTSTSTAYLEINSLRSDDTAIYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNSYAMNWVRQAPGKGLEWVARIRSKYNNYATYYADSVKGRFTISR<br>DDSKNTAYLQMNNLKTEDTAVYYCVRHGNFGNSYVSWWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 16 | CD33 AH3 HL × F12Q HL | artificial | nt | CAGGTGCAGCTGGTGCAGTCTGGAGCTGAGGTGAAAAAGCCTGGAGAGTCAGTCAAGGTCTCCTGC<br>AAGGCTAGCGGGTATACCTTCACAAACTATGGAATGAACTGGGTGAGGCAGGCTCCAGGACAGGGT<br>TTAGAGTGGATGGGCTGGATAAACACCTACACTGGAGAGCCAACATATGCTGATGACTTCAAGGGA<br>CGGGTTACCATGTCTTCGGATACCTCTACCAGCACTGCCTATTTGGAAATCAACAGCCTCAGAAGT<br>GATGACACGGCTATATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AGCTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGGCAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACGTTTCCTGGTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |

-continued

| SEQ ID NO. | DESIGNATION | SOURCE | TYPE | SEQUENCE |
|---|---|---|---|---|
| 17 | CD33 AH3 HL × I2C HL | artificial | aa | QVQLVQSGAEVKKPGESVKVSCKASGYTFTNYGMNWVRQAPGQGLEWMGWINTYTGEPTYADDFKG<br>RVTMSSDTSTSTAYLEINSLRSDDTAIYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 18 | CD33 AH3 HL × I2C HL | artificial | nt | CAGGTGCAGCTGGTGCAGTCTGGAGCTGAGGTGAAAAAGCCTGGAGAGTCAGTCAAGGTCTCCTGC<br>AAGGCTAGCGGGTATACCTTCACAAACTATGGAATGAACTGGGTGAGGCAGGCTCCAGGACAGGGT<br>TTAGAGTGGATGGGCTGGATAAACACCTACACTGGAGAGCCAACATATGCTGATGACTTCAAGGGA<br>CGGGTTACCATGTCTTCGGATACCTCTACCAGCACTGCCTATTTGGAAATCAACAGCCTCAGAAGT<br>GATGACACGGCTATATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGAACAGTCACACTCACTTGT<br>GGCTCCTCGACTGGGGCTGTTACATCTGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 19 | CD33 VH of AF5 | artificial | aa | QVQLVQSGAEVKKPGASVKVSCKASGYTFTNYGMNWVKQAPGQGLKWMGWINTYTGEPTYADDFKG<br>RVTMTSDTSTSTAYLELHNLRSDDTAVYYCARWSWSDGYYVYFDYWGQGTTVTVSS |
| 20 | CD33 HCDR1 of AF5 | artificial | aa | NYGMN |
| 21 | CD33 HCDR2 of AF5 | artificial | aa | WINTYTGEPTYADDFKG |
| 22 | CD33 HCDR3 of AF5 | artificial | aa | WSWSDGYYVYFDY |
| 23 | CD33 VH of AF5 | artificial | nt | CAGGTGCAGCTGGTGCAGTCTGGAGCTGAGGTGAAGAAGCCTGGAGCGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTTCGGATACCTCTACCAGCACTGCCTATTTGGAACTCCACAACCTCAGAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCA |
| 24 | CD33 VL of AF5 | artificial | aa | DIVMTQSPDSLTVSLGERTTINCKSSQSVLDSSKNKNSLAWYQQKPGQPPKLLLSWASTRESGIPD<br>RFSGSGSGTDFTLTIDSLQPEDSATYYCQQSAHFPITFGQGTRLEIK |
| 25 | CD33 LCDR1 of AF5 | artificial | aa | KSSQSVLDSSKNKNSLA |
| 26 | CD33 LCDR2 of AF5 | artificial | aa | WASTRES |
| 27 | CD33 LCDR3 of AF5 | artificial | aa | QQSAHFPIT |
| 28 | CD33 VL of AF5 | artificial | nt | GACATCGTGATGACACAGTCTCCAGACTCCCTGACTGTGTCTCTGGGCGAGAGGACCACCATCAAC<br>TGCAAGTCCAGCCAGAGTGTTTTAGACAGCTCCAAGAATAAGAACTCCTTAGCTTGGTACCAGCAG<br>AAACCAGGACAGCCTCCTAAATTACTCCTTTCCTGGGCATCTACGCGGGAATCCGGGATCCCTGAC<br>CGATTCAGTGGCAGCGGGTCTGGGACAGATTTCACTCTCACTATTGACAGCCTGCAGCCTGAAGAT<br>TCTGCAACTTACTATTGTCAACAGTCTGCCCACTTCCCGATCACCTTTGGCCAAGGGACACGACTG<br>GAGATTAAA |

| SEQ ID NO. | DESIGNATION | SOURCE | TYPE | SEQUENCE |
|---|---|---|---|---|
| 29 | CD33HL of AF5 | artificial | aa | QVQLVQSGAEVKKPGASVKVSCKASGYTFTNYGMNWVKQAPGQGLKWMGWINTYTGEPTYADDFKG<br>RVTMTSDTSTSTAYLELHNLRSDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIK |
| 30 | CD33 HL of AF5 | artificial | nt | CAGGTGCAGCTGGTGCAGTCTGGAGCTGAGGTGAAGAAGCCTGGAGCGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTTCGGATACCTCTACCAGCACTGCCTATTTGGAACTCCACAACCTCAGAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAA |
| 31 | CD33 AF5 HL × H2C HL | artificial | aa | QVQLVQSGAEVKKPGASVKVSCKASGYTFTNYGMNWVKQAPGQGLKWMGWINTYTGEPTYADDFKG<br>RVTMTSDTSTSTAYLELHNLRSDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 32 | CD33 AF5 HL × H2C HL | artificial | nt | CAGGTGCAGCTGGTGCAGTCTGGAGCTGAGGTGAAGAAGCCTGGAGCGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTTCGGATACCTCTACCAGCACTGCCTATTTGGAACTCCACAACCTCAGAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATTATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCTACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGCTCTATGGTACAGCAACCGCTGGGTGTTCGGTGGAGGAACCAAACTGACTGTCCTA |
| 33 | CD33 AF5 HL × F12Q HL | artificial | aa | QVQLVQSGAEVKKPGASVKVSCKASGYTFTNYGMNWVKQAPGQGLKWMGWINTYTGEPTYADDFKG<br>RVTMTSDTSTSTAYLELHNLRSDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNSYAMNWVRQAPGKGLEWVARIRSKYNNYATYYADSVKGRFTISR<br>DDSKNTAYLQMNNLKTEDTAVYYCVRHGNFGNSYVSWWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 34 | CD33 AF5 HL × F12Q HL | artificial | nt | CAGGTGCAGCTGGTGCAGTCTGGAGCTGAGGTGAAGAAGCCTGGAGCGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTTCGGATACCTCTACCAGCACTGCCTATTTGGAACTCCACAACCTCAGAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AGCTACGCCATGAACTGGGTCCGCCAGGCTCCAGGAAAGGGTTTGGAATGGGTTGCTCGCATAAGA |

| SEQ ID NO. | DESIGNATION | SOURCE | TYPE | SEQUENCE |
|---|---|---|---|---|
| | | | | AGTAAATATAATAATTATGCAACATATTATGCCGATTCAGTGAAAGGCAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACGTTTCCTGGTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 35 | CD33 AF5 HL × I2C HL | artificial | aa | QVQLVQSGAEVKKPGASVKVSCKASGYTFTNYGMNWVKQAPGQGLKWMGWINTYTGEPTYADDFKG RVTMTSDTSTSTAYLELHNLRSDDTAVYYCARWSWSDGYYVYFDYWGQGTTVTVSSGGGGSGGGGS GGGGSDIVMTQSPDSLTVSLGERTTINCKSSQSVLDSSKNKNSLAWYQQKPGQPPKLLLSWASTRE SGIPDRFSGSGSGTDFTLTIDSLQPEDSATYYCQQSAHFPITFGQGTRLEIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 36 | CD33 AF5 HL × I2C HL | artificial | nt | CAGGTGCAGCTGGTGCAGTCTGGAGCTGAGGTGAAGAAGCCTGGAGCGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTTCGGATACCTCTACCAGCACTGCCTATTTGGAACTCCACAACCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAAGAATAAGAACTCCTTA GCTTGGTACCAGCAGAAACAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGAGATTAAATCGGAGGTGGTGGCTCCGAGGTGCAGCTGGTGGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 37 | CD33 VH of AC8 | artificial | aa | QVQLVQSGAEVKKPGESVKVSCKASGYTFTNYGMNWVKQAPGQGLKWMGWINTYTGEPTYADDFKG RVTMTTDTSTSTAYMEIRNLRDDTAVYYCARWSWSDGYYVYFDYWGQGTTVTVSS |
| 38 | CD33 HCDR1 of AC8 | artificial | aa | NYGMN |
| 39 | CD33 HCDR2 of AC8 | artificial | aa | WINTYTGEPTYADDFKG |
| 40 | CD33 HCDR3 of AC8 | artificial | aa | WSWSDGYYVYFDY |
| 41 | CD33 VH of AC8 | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTACGGATACCTCTACCAGCACTGCCTATATGGAAATCCGCAACCTCAGAAAT GATGACACGGCTGTATATTACTGTGCGCGCTGGAGTTGGAGTGATGGTTACTACGTTTACTTTGAC TACTGGGGCCAAGGCACTACGGTCACCGTCTCCTCA |
| 42 | CD33 VL of AC8 | artificial | aa | DIVMTQSPDSLTVSLGERTTINCKSSQSVLDSSKNKNSLAWYQQKPGQPPKLLLSWASTRESGIPD RFSGSGSGTDFTLTIDSLQPEDSATYYCQQSAHFPITFGQGTRLEIK |
| 43 | CD33 LCDR1 of AC8 | artificial | aa | KSSQSVLDSSKNKNSLA |
| 44 | CD33 LCDR2 of AC8 | artificial | aa | WASTRES |
| 45 | CD33 LCDR3 of AC8 | artificial | aa | QQSAHFPIT |

| SEQ ID NO. | DESIGNATION | SOURCE | TYPE | SEQUENCE |
|---|---|---|---|---|
| 46 | CD33 VL of AC8 | artificial | nt | GACATCGTGATGACACAGTCTCCAGACTCCCTGACTGTGTCTCTGGGCGAGAGGACCACCATCAAC<br>TGCAAGTCCAGCCAGAGTGTTTTAGACAGCTCCAAGAATAAGAACTCCTTAGCTTGGTACCAGCAG<br>AAACCAGGACAGCCTCCTAAATTACTCCTTTCCTGGGCATCTACGCGGGAATCCGGGATCCCTGAC<br>CGATTCAGTGGCAGCGGGTCTGGGACAGATTTCACTCTCACTATTGACAGCCTGCAGCCTGAAGAT<br>TCTGCAACTTACTATTGTCAACAGTCTGCCCACTTCCCGATCACCTTTGGCCAAGGGACACGACTG<br>GAGATTAAA |
| 47 | CD33 HL of AC8 | artificial | aa | QVQLVQSGAEVKKPGESVKVSCKASGYTFTNYGMNWVKQAPGQGLKWMGWINTYTGEPTYADDFKG<br>RVTMTTDTSTSTAYMEIRNLRNDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIK |
| 48 | CD33 HL of AC8 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTACGGATACCTCTACCAGCACTGCCTATATGGAAATCCGCAACCTCAGAAAT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAA |
| 49 | CD33 AC8 HL × H2C HL | artificial | aa | QVQLVQSGAEVKKPGESVKVSCKASGYTFTNYGMNWVKQAPGQGLKWMGWINTYTGEPTYADDFKG<br>RVTMTTDTSTSTAYMEIRNLRNDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 50 | CD33 AC8 HL × H2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTACGGATACCTCTACCAGCACTGCCTATATGGAAATCCGCAACCTCAGAAAT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCTACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGCTCTATGGTACAGCAACCGCTGGGTGTTCGGTGGAGGAACCAAACTGACTGTCCTA |
| 51 | CD33 AC8 HL × F12Q HL | artificial | aa | QVQLVQSGAEVKKPGESVKVSCKASGYTFTNYGMNWVKQAPGQGLKWMGWINTYTGEPTYADDFKG<br>RVTMTTDTSTSTAYMEIRNLRNDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNSYAMNWVRQAPGKGLEWVARIRSKYNNYATYYADSVKGRFTISR<br>DDSKNTAYLQMNNLKTEDTAVYYCVRHGNFGNSYVSWWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 52 | CD33 AC8 HL × F12Q HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTACGGATACCTCTACCAGCACTGCCTATATGGAAATCCGCAACCTCAGAAAT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG |

| SEQ ID NO. | DESIGNATION | SOURCE | TYPE | SEQUENCE |
|---|---|---|---|---|
| | | | | AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AGCTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGGCAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACGTTTCCTGGTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 53 | CD33 AC8 HL × I2C HL | artificial | aa | QVQLVQSGAEVKKPGESVKVSCKASGYTFTNYGMNWVKQAPGQGLKWMGWINTYTGEPTYADDFKG<br>RVTMTTDTSTSTAYMEIRNLRNDDTAVYYCARWSWSDGYYVYFDYWGQGTTVTVSSGGGGSGGGGS<br>GGGGSDIVMTQSPDSLTVSLGERTTINCKSSQSVLDSSKNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 54 | CD33 AC8 HL × I2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTACGGATACCTCTACCAGCACTGCCTATATGGAAATCCGCAACCTCAGAAAT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCAAGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 55 | CD33 VH of AH11 | artificial | aa | QVQLVQSGAEVKKPGESVKVSCKASGYTFTNYGMNWVKQAPGQGLKWMGWINTYTGEPTYADDFKG<br>RVTMTSDTSTSTAYMEISSLRSDDTAVYYCARWSWSDGYYVYFDYWGQGTTVTVSS |
| 56 | CD33 HCDR1 of AH11 | artificial | aa | NYGMN |
| 57 | CD33 HCDR2 of AH11 | artificial | aa | WINTYTGEPTYADDFKG |
| 58 | HCDR3 | artificial | aa | WSWSDGYYVYFDY |
| 59 | CD33 VH of AH11 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGAATGAACTGGGTGAAGCAGGCTCCAGGACAGGGT<br>TTAAAGTGGATGGGCTGGATAAACACCTACACTGGAGAGCCAACATATGCTGATGACTTCAAGGGA<br>CGGGTTACCATGACTTCGGATACCTCTACCAGCACTGCCTATATGGAAATCAGCAGCCTCAGAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCA |
| 60 | CD33 VL of AH11 | artificial | aa | DIVMTQSPDSLTVSLGERTTINCKSSQSVLDSSKNKNSLAWYQQKPGQPPKLLLSWASTRESGIPD<br>RFSGSGSGTDFTLTIDSLQPEDSATYYCQQSAHFPITFGQGTRLEIK |
| 61 | CD33 LCDR1 of AH11 | artificial | aa | KSSQSVLDSSKNKNSLA |

| SEQ ID NO. | DESIGNATION | SOURCE | TYPE | SEQUENCE |
|---|---|---|---|---|
| 62 | CD33 LCDR2 of AH11 | artificial | aa | WASTRES |
| 63 | CD33 LCDR3 of AH11 | artificial | aa | QQSAHFPIT |
| 64 | CD33 VL of AH11 | artificial | nt | GACATCGTGATGACACAGTCTCCAGACTCCCTGACTGTGTCTCTGGGCGAGAGGACCACCATCAAC TGCAAGTCCAGCCAGAGTGTTTTAGACAGCTCCAAGAATAAGAACTCCTTAGCTTGGTACCAGCAG AAACCAGGACAGCCTCCTAAATTACTCCTTTCCTGGGCATCTACGCGGGAATCCGGGATCCCTGAC CGATTCAGTGGCAGCGGGTCTGGGACAGATTTCACTCTCACTATTGACAGCCTGCAGCCTGAAGAT TCTGCAACTTACTATTGTCAACAGTCTGCCCACTTCCCGATCACCTTTGGCCAAGGGACACGACTG GAGATTAAA |
| 65 | CD33 HL of AH11 | artificial | aa | QVQLVQSGAEVKKPGESVKVSCKASGYTFTNYGMNWVKQAPGQGLKWMGWINTYTGEPTYADDFKG RVTMTSDTSTSTAYMEISSLRSDDTAVYYCARWSWSDGYYVYFDYWGQGTTVTVSSGGGGSGGGGS GGGGSDIVMTQSPDSLTVSLGERTTINCKSSQSVLDSSKNKNSLAWYQQKPGQPPKLLLSWASTRE SGIPDRFSGSGSGTDFTLTIDSLQPEDSATYYCQQSAHFPITFGQGTRLEIK |
| 66 | CD33 HL of AH11 | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTTCGGATACCTCTACCAGCACTGCCTATATGGAAATCAGCAGCCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAAGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGAGATTAAA |
| 67 | CD33 AH11 HL × H2C HL | artificial | aa | QVQLVQSGAEVKKPGESVKVSCKASGYTFTNYGMNWVKQAPGQGLKWMGWINTYTGEPTYADDFKG RVTMTSDTSTSTAYMEISSLRSDDTAVYYCARWSWSDGYYVYFDYWGQGTTVTVSSGGGGSGGGGS GGGGSDIVMTQSPDSLTVSLGERTTINCKSSQSVLDSSKNKNSLAWYQQKPGQPPKLLLSWASTRE SGIPDRFSGSGSGTDFTLTIDSLQPEDSATYYCQQSAHFPITFGQGTRLEIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 68 | CD33 AH11 HL × H2C HL | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTTCGGATACCTCTACCAGCACTGCCTATATGGAAATCAGCAGCCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAAGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGAGATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCTACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGCTCTATGGTACAGCAACCGCTGGGTGTTCGGTGGAGGAACCAAACTGACTGTCCTA |
| 69 | CD33 AH11 HL × F12Q HL | artificial | aa | QVQLVQSGAEVKKPGESVKVSCKASGYTFTNYGMNWVKQAPGQGLKWMGWINTYTGEPTYADDFKG RVTMTSDTSTSTAYMEISSLRSDDTAVYYCARWSWSDGYYVYFDYWGQGTTVTVSSGGGGSGGGGS GGGGSDIVMTQSPDSLTVSLGERTTINCKSSQSVLDSSKNKNSLAWYQQKPGQPPKLLLSWASTRE SGIPDRFSGSGSGTDFTLTIDSLQPEDSATYYCQQSAHFPITFGQGTRLEIKSGGGGSEVQLVESG GGLVQPGGSLKLSCAASGFTFNSYAMNWVRQAPGKGLEWVARIRSKYNNYATYYADSVKGRFTISR DDSKNTAYLQMNNLKTEDTAVYYCVRHGNFGNSYVSWWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |

| SEQ ID NO. | DESIGNATION | SOURCE | TYPE | SEQUENCE |
|---|---|---|---|---|
| 70 | CD33 AH11 HL × F12Q HL | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTTCGGATACCTCTACCAGCACTGCCTATATGGAAATCAGCAGCCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAAGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGAGATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AGCTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGGCAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACGTTTCCTGGTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 71 | CD33 AH11 HL × I2C HL | artificial | aa | QVQLVQSGAEVKKPGESVKVSCKASGYTFTNYGMNWVKQAPGQGLKWMGWINTYTGEPTYADDFKG RVTMTSDTSTSTAYMEISSLRSDDTAVYYCARWSWSDGYYVYFDYWGQGTTVTVSSGGGGSGGGGS GGGGSDIVMTQSPDSLTVSLGERTTINCKSSQSVLDSSKNKNSLAWYQQKPGQPPKLLLSWASTRE SGIPDRFSGSGSGTDFTLTIDSLQPEDSATYYCQQSAHFPITFGQGTRLEIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 72 | CD33 AH11 HL × I2C HL | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAAAGTGGATGGGCTGGATAAACACCTACACTGGAGAGCCAACATATGCTGATGACTTCAAGGGA CGGGTTACCATGACTTCGGATACCTCTACCAGCACTGCCTATATGGAAATCAGCAGCCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAAGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGAGATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 73 | CD33 VH of B3 | artificial | aa | QVQLVQSGAEVKKPGESVKVSCKASGYTFTNYGMNWVKQAPGQGLEWMGWINTYTGETNYADKFQG RVTFTSDTSTSTAYMELRNLKSDDTAVYYCARWSWSDGYYVYFDYWGQGTTVTVSS |
| 74 | CD33 HCDR1 of B3 | artificial | aa | NYGMN |
| 75 | CD33 HCDR2 of B3 | artificial | aa | WINTYTGETNYADKFQG |
| 76 | CD33 HCDR3 of B3 | artificial | aa | WSWSDGYYVYFDY |
| 77 | CD33 VH of B3 | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGACAAATATGCTGATAAGTTCCAGGGA |

| SEQ ID NO. | DESIGNATION | SOURCE | TYPE | SEQUENCE |
|---|---|---|---|---|
| | | | | CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCA |
| 78 | CD33 VL of B3 | artificial | aa | DIVMTQSPDSMTVSLGERTTINCKSSQSVLDSSTNKNSLAWYQQKPGQPPKLLLSWASTRESGIPD<br>RFSGSGSGTDFTLTIDSLQPEDSATYYCQQSAHFPITFGQGTRLDIK |
| 79 | CD33 LCDR1 of B3 | artificial | aa | KSSQSVLDSSTNKNSLA |
| 80 | CD33 LCDR2 of B3 | artificial | aa | WASTRE |
| 81 | CD33 LCDR3 of B3 | artificial | aa | QQSAHFPIT |
| 82 | CD33 VL of B3 | artificial | nt | GACATCGTGATGACACAGTCTCCAGACTCCATGACTGTGTCTCTGGGCGAGAGGACCACCATCAAC<br>TGCAAGTCCAGCCAGAGTGTTTTAGACAGCTCCACGAATAAGAACTCCTTAGCTTGGTACCAGCAG<br>AAACCAGGACAGCCTCCTAAATTACTCCTTTCCTGGGCATCTACGCGGGAATCCGGGATCCCTGAC<br>CGATTCAGTGGCAGCGGGTCTGGGACAGATTTCACTCTCACTATTGACAGCCTGCAGCCTGAAGAT<br>TCTGCAACTTACTATTGTCAACAGTCTGCCCACTTCCCGATCACCTTTGGCCAAGGGACACGACTG<br>GACATTAAA |
| 83 | CD33 HL of B3 | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYVYFDYWGQGTTVTVSSGGGGSGGGGS<br>GGGGSDIVMTQSPDSMTVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLDIK |
| 84 | CD33 HL of B3 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCATGACTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGACATTAAA |
| 85 | CD33 B3 HL × H2C HL | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYVYFDYWGQGTTVTVSSGGGGSGGGGS<br>GGGGSDIVMTQSPDSMTVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLDIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 86 | CD33 B3 HL × H2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCATGACTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGACATTAAATCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCTACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGCTCTATGGTACAGCAACCGCTGGGTGTTCGGTGGAGGAACCAAACTGACTGTCCTA |

-continued

| SEQ ID NO. | DESIGNATION | SOURCE | TYPE | SEQUENCE |
|---|---|---|---|---|
| 87 | CD33 B3 HL × F12Q HL | artificial | aa | QVQLVQSGAEVKKPGESVKVSCKASGYTFTNYGMNWVKQAPGQGLEWMGWINTYTGETNYADKFQG RVTFTSDTSTSTAYMELRNLKSDDTAVYYCARWSWSDGYYVFDYWGQGTTVTVSSGGGGSGGGGS GGGGSDIVMTQSPDSMTVSLGERTTINCKSSQSVLDSSTNKNSLAWYQQKPGQPPKLLLSWASTRE SGIPDRFSGSGSGTDFTLTIDSLQPEDSATYYCQQSAHFPITFGQGTRLDIKSGGGGSEVQLVESG GGLVQPGGSLKLSCAASGFTFNSYAMNWVRQAPGKGLEWVARIRSKYNNYATYYADSVKGRFTISR DDSKNTAYLQMNNLKTEDTAVYYCVRHGNFGNSYVSWWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 88 | CD33 B3 HL × F12Q HL | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGACAAACTATGCTGATAAGTTCCAGGGA CGCGTTACCTTCACTTCGGATACCTCTACCAGCACTGCCTATATGGAACTCCGCAACCTCAAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCATGACTGTGTCTCTGGGCGAG AGGACCACCATCAACTGCAAGTCCAGCCAGAGTGTTTTAGACAGCTCCACGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGACATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AGCTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGGCAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACGTTTCCTGGTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 89 | CD33 B3 HL × I2C HL | artificial | aa | QVQLVQSGAEVKKPGESVKVSCKASGYTFTNYGMNWVKQAPGQGLEWMGWINTYTGETNYADKFQG RVTFTSDTSTSTAYMELRNLKSDDTAVYYCARWSWSDGYYVFDYWGQGTTVTVSSGGGGSGGGGS GGGGSDIVMTQSPDSMTVSLGERTTINCKSSQSVLDSSTNKNSLAWYQQKPGQPPKLLLSWASTRE SGIPDRFSGSGSGTDFTLTIDSLQPEDSATYYCQQSAHFPITFGQGTRLDIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 90 | CD33 B3 HL × I2C HL | artificial | nt | CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGACAAACTATGCTGATAAGTTCCAGGGA CGCGTTACCTTCACTTCGGATACCTCTACCAGCACTGCCTATATGGAACTCCGCAACCTCAAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCATGACTGTGTCTCTGGGCGAG AGGACCACCATCAACTGCAAGTCCAGCCAGAGTGTTTTAGACAGCTCCACGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CTGCAGCCTGAAGATTCTGCAACTTACTATTGTCAACAGTCTGCCCACTTCCCGATCACCTTTGGC CAAGGGACACGACTGGACATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 91 | CD33 VH of F2 | artificial | aa | QVQLVQSGAEVKKPGESVKVSCKASGYTFTNYGMNWVKQAPGQGLEWMGWINTYTGETNYADKFQG RVTFTSDTSTSTAYMELRNLKSDDTAVYYCARWSWSDGYYVFDYWGQGTTVTVSS |
| 92 | CD33 HCDR1 of F2 | artificial | aa | NYGMN |
| 93 | CD33 HCDR2 of F2 | artificial | aa | WINTYTGETNYADKFQG |

| SEQ ID NO. | DESIGNATION | SOURCE | TYPE | SEQUENCE |
|---|---|---|---|---|
| 94 | CD33 HCDR3 of F2 | artificial | aa | WSWSDGYYVYFDY |
| 95 | CD33 VH of F2 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCA |
| 96 | CD33 VL of F2 | artificial | aa | DIVMTQSPDSLSVSLGERTTINCKSSQSVLDSSTNKNSLAWYQQKPGQPPKLLLSWASTRESGIPD<br>RFSGSGSGTDFTLTIDSLQPEDSATYYCQQSAHFPITFGQGTRLEIK |
| 97 | CD33 LCDR1 of F2 | artficial | aa | KSSQSVLDSSTNKNSLA |
| 98 | CD33 LCDR2 of F2 | artificial | aa | WASTRES |
| 99 | CD33 LCDR3 of F2 | artificial | aa | QQSAHFPIT |
| 100 | CD33 VL of F2 | artificial | nt | GACATCGTGATGACACAGTCTCCAGACTCCCTGTCTGTGTCTCTGGGCGAGAGGACCACCATCAAC<br>TGCAAGTCCAGCCAGAGTGTTTTAGACAGCTCCACGAATAAGAACTCCTTAGCTTGGTACCAGCAG<br>AAACCAGGACAGCCTCCTAAATTACTCCTTTCCTGGGCATCTACGCGGGAATCCGGGATCCCTGAC<br>CGATTCAGTGGCAGCGGGTCTGGGACAGATTTCACTCTCACTATTGACAGCCTGCAGCCTGAAGAT<br>CTGCAACTTACTATTGTCAACAGTCTGCCCACTTCCCGATCACCTTTGGCCAAGGGACACGACTG<br>GAGATTAAA |
| 101 | CD33 HL of F2 | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYYVYFDYWGQGTTVTVSSGGGGSGGGGS<br>GGGGSDIVMTQSPDSLSVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLEIK |
| 102 | CD33 HL of F2 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGTCTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATCTGCAACTTACTATTGTCAACAGTCTGCCCACTTCCCGATCACCTTTGGC<br>CAAGGGACACGACTGGAGATTAAA |
| 103 | CD33 F2 HL × H2C HL | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYYVYFDYWGQGTTVTVSSGGGGSGGGGS<br>GGGGSDIVMTQSPDSLSVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 104 | CD33 F2 HL × H2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGTCTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATCTGCAACTTACTATTGTCAACAGTCTGCCCACTTCCCGATCACCTTTGGC<br>CAAGGGACACGACTGGAGATTAAATCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT |

| SEQ ID NO. | DESIGNATION | SOURCE | TYPE | SEQUENCE |
|---|---|---|---|---|
| | | | | CAGACTGTTGTGACTCAGGAACCTTCACTCACCGTATCACCTGGTGGAACAGTCACACTCACTTGT<br>GGCTCCTCGACTGGGGCTGTTACATCTGGCTACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGCTCTATGGTACAGCAACCGCTGGGTGTTCGGTGGAGGAACCAAACTGACTGTCCTA |
| 105 | CD33 F2 HL × F12Q HL | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYYVYFDYWGQGTTVTVSSGGGGSGGGGS<br>GGGGSDIVMTQSPDSLSVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNSYAMNWVRQAPGKGLEWVARIRSKYNNYATYYADSVKGRFTISR<br>DDSKNTAYLQMNNLKTEDTAVYYCVRHGNFGNSYVSWWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 106 | CD33 F2 HL × F12Q HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGATCCCTGTCTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AGCTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGGCAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACGTTTCCTGGTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 107 | CD33 F2 HL × I2C HL | artificial | aa | QVQLVQSGAEVKKPGESVKVSCKASGYTFTNYGMNWVKQAPGQGLEWMGWINTYTGETNYADKFQG<br>RVTFTSDTSTSTAYMELRNLKSDDTAVYYCARWSWSDGYYVYFDYWGQGTTVTVSSGGGGSGGGGS<br>GGGGSDIVMTQSPDSLSVSLGERTTINCKSSQSVLDSSTNKNSLAWYQQKPGQPPKLLLSWASTRE<br>SGIPDRFSGSGSGTDFTLTIDSLQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQGTLVTVSSGGGGSGGGGSGGGGS<br>QTVVTQEPSLTVSPGGTVTLTCGSSTGAVTSGNYPNWVQQKPGQAPRGLIGGTKFLAPGTPARFSG<br>SLLGGKAALTLSGVQPEDEAEYYCVLWYSNRWVFGGGTKLTVL |
| 108 | CD33 F2 HL × I2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGACAAACTATGCTGATAAGTTCCAGGGA<br>CGCGTTACCTTCACTTCGGATACCTCTACCAGCACTGCCTATATGGAACTCCGCAACCTCAAAAGT<br>GATGACACGGCTGTATATTACTGTGCGCGCTGGAGTTGGAGTGATGGTTACTACGTTTACTTTGAC<br>TACTGGGGCCAAGGCACTACGGTCACCGTCTCCTCAGGTGGTGGTGGTTCTGGCGGCGGCGGCTCC<br>GGTGGTGGTGGTTCTGACATCGTGATGACACAGTCTCCAGATCCCTGTCTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CTGCAGCCTGAAGATTCTGCAACTTACTATTGTCAACAGTCTGCCCACTTCCCGATCACCTTTGGC<br>CAAGGGACACGACTGGAGATTAAATCCGGAGGTGGTGGCTCCGAGGTGCAGCTGGTCGAGTCTGGA<br>GGAGGATTGGTGCAGCCTGGAGGGTCATTGAAACTCTCATGTGCAGCCTCTGGATTCACCTTCAAT<br>AAGTACGCCATGAACTGGGTCCGCCAGGCTCCAGGAAAGGGTTTGGAATGGGTTGCTCGCATAAGA<br>AGTAAATATAATAATTATGCAACATATTATGCCGATTCAGTGAAAGACAGGTTCACCATCTCCAGA<br>GATGATTCAAAAAACACTGCCTATCTACAAATGAACAACTTGAAAACTGAGGACACTGCCGTGTAC<br>TACTGTGTGAGACATGGGAACTTCGGTAATAGCTACATATCCTACTGGGCTTACTGGGGCCAAGGG<br>ACTCTGGTCACCGTCTCCTCAGGTGGTGGTGGTTCTGGCGGCGGCGGCTCCGGTGGTGGTGGTTCT<br>CAGACTGTTGTGACTCAGGAACCTTCACTCACCGTATCACCTGGTGGAACAGTCACACTCACTTGT<br>GGCTCCTCGACTGGGGCTGTTACATCTGGCAACTACCCAAACTGGGTCCAACAAAAACCAGGTCAG<br>GCACCCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 109 | CD33 VH of B10 | artificial | aa | QVQLVQSGAEVKKPGESVKVSCKASGYTFTNYGMNWVKQAPGQGLEWMGWINTYTGEPTYADKFQG<br>RVTMTTDTSTSTAYMEIRNLRSDDTAVYYCARWSWSDGYYVYFDYWGQGTTVTVSS |

| SEQ ID NO. | DESIGNATION | SOURCE | TYPE | SEQUENCE |
|---|---|---|---|---|
| 110 | CD33 HCDR1 of B10 | Artificial | aa | NYGMN |
| 111 | CD33 HCDR2 of B10 | artificial | aa | WINTYTGEPTYADKFQG |
| 112 | CD33 HCDR3 of B10 | artificial | aa | WSWSDGYYVYFDY |
| 113 | CD33 VH of B10 | artificial | nt | CAGGTGCAGCTGGTGCAGTCTGGAGCTGAGGTGAAGAAGCCTGGTGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGCCAACCTATGCTGATAAGTTCCAGGGA CGCGTTACCATGACTACGGATACCTCTACCAGCACTGCCTATATGGAAATCCGCAACCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCA |
| 114 | CD33 VL of B10 | artificial | aa | DIVMTQSPDSLTVSLGERTTINCKSSQSVLDSSNNKNSLAWYQQKPGQPPKLLLSWASTRESGIPD RFSGSGSGTDFTLTIDGLQPEDSATYYCQQSAHFPITFGQGTRLEIK |
| 115 | CD33 LCDR1 of B10 | artificial | aa | KSSQSVLDSSNNKNSLA |
| 116 | CD33 LCDR2 of B10 | artificial | aa | WASTRES |
| 117 | CD33 LCDR3 of B10 | artificial | aa | QQSAHFPIT |
| 118 | CD33 VL of B10 | artificial | nt | GACATCGTGATGACACAGTCTCCAGACTCCCTGACTGTGTCTCTGGGCGAGAGGACCACCATCAAC TGCAAGTCCAGCCAGAGTGTTTTAGACAGCTCCAACAATAAGAACTCCTTAGCTTGGTACCAGCAG AAACCAGGACAGCCTCCTAAATTACTCCTTTCCTGGGCATCTACGCGGGAATCCGGGATCCCTGAC CGATTCAGTGGCAGCGGTTCTGGGACAGATTTCACTCTCACTATTGACGGCCTGCAGCCTGAAGAT CTGCAACTTACTATTGTCAACAGTCTGCCCACTTCCCGATCACCTTTGGCCAAGGGACACGACTG GAGATTAAA |
| 119 | CD33 HL of B10 | artificial | aa | QVQLVQSGAEVKKPGESVKVSCKASGYTFTNYGMNWVKQAPGQGLEWMGWINTYTGEPTYADKFQG RVTMTTDTSTSTAYMEIRNLRSDDTAVYYCARWSWSDGYYVYFDYWGQGTTVTVSSGGGGSGGGGS GGGGSDIVMTQSPDSLTVSLGERTTINCKSSQSVLDSSNNKNSLAWYQQKPGQPPKLLLSWASTRE SGIPDRFSGSGSGTDFTLTIDGLQPEDSATYYCQQSAHFPITFGQGTRLEIK |
| 120 | CD33 HL of B10 | artificial | nt | CAGGTGCAGCTGGTGCAGTCTGGAGCTGAGGTGAAGAAGCCTGGTGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGCCAACCTATGCTGATAAGTTCCAGGGA CGCGTTACCATGACTACGGATACCTCTACCAGCACTGCCTATATGGAAATCCGCAACCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAACAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGTTCTGGGACAGATTTCACTCTCACTATTGACGGC CTGCAGCCTGAAGATTCTGCAACTTACTATTGTCAACAGTCTGCCCACTTCCCGATCACCTTTGGC CAAGGGACACGACTGGAGATTAAA |
| 121 | CD33 B10 HL × H2C HL | artificial | aa | QVQLVQSGAEVKKPGESVKVSCKASGYTFTNYGMNWVKQAPGQGLEWMGWINTYTGEPTYADKFQG RVTMTTDTSTSTAYMEIRNLRSDDTAVYYCARWSWSDGYYVYFDYWGQGTTVTVSSGGGGSGGGGS GGGGSDIVMTQSPDSLTVSLGERTTINCKSSQSVLDSSNNKNSLAWYQQKPGQPPKLLLSWASTRE SGIPDRFSGSGSGTDFTLTIDGLQPEDSATYYCQQSAHFPITFGQGTRLEIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 122 | CD33 B10 HL × H2C HL | artificial | nt | CAGGTGCAGCTGGTGCAGTCTGGAGCTGAGGTGAAGAAGCCTGGTGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGCCAACCTATGCTGATAAGTTCCAGGGA CGCGTTACCATGACTACGGATACCTCTACCAGCACTGCCTATATGGAAATCCGCAACCTCAGAAGT GATGACACGGCTGTATATTACTGTGCGCGCTGGAGTTGGAGTGATGGTTACTACGTTTACTTTGAC TACTGGGGCCAAGGCACTACGGTCACCGTCTCCTCAGGTGGTGGTGGTTCTGGCGGCGGCGGCTCC GGTGGTGGTGGTTCTGACATCGTGATGACACAGTCTCCAGACTCCCTGACTGTGTCTCTGGGCGAG AGGACCACCATCAACTGCAAGTCCAGCCAGAGTGTTTTAGACAGCTCCAACAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGTTCTGGGACAGATTTCACTCTCACTATTGACGGC CTGCAGCCTGAAGATTCTGCAACTTACTATTGTCAACAGTCTGCCCACTTCCCGATCACCTTTGGC CAAGGGACACGACTGGAGATTAAATCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT |

| SEQ ID NO. | DESIGNATION | SOURCE | TYPE | SEQUENCE |
|---|---|---|---|---|
| | | | | AAGTACGCCATGAACTGGGTCCGCCAGGCTCCAGGAAAGGGTTTGGAATGGGTTGCTCGCATAAGA |
| | | | | AGTAAATATAATAATTATGCAACATATTATGCCGATTCAGTGAAAGACAGGTTCACCATCTCCAGA |
| | | | | GATGATTCAAAAAACACTGCCTATCTACAAATGAACAACTTGAAAACTGAGGACACTGCCGTGTAC |
| | | | | TACTGTGTGAGACATGGGAACTTCGGTAATAGCTACATATCCTACTGGGCTTACTGGGGCCAAGGG |
| | | | | ACTCTGGTCACCGTCTCCTCAGGTGGTGGTGGTTCTGGCGGCGGCGGCTCCGGTGGTGGTGGTTCT |
| | | | | CAGACTGTTGTGACTCAGGAACCTTCACTCACCGTATCACCTGGTGGAACAGTCACACTCACTTGT |
| | | | | GGCTCCTCGACTGGGGCTGTTACATCTGGCTACTACCCAAACTGGGTCCAACAAAAACCAGGTCAG |
| | | | | GCACCCCGTGGTCTAATAGGTGGGACTAAGTTCCTCGCCCCCGGTACTCCTGCCAGATTCTCAGGC |
| | | | | TCCCTGCTTGGAGGCAAGGCTGCCCTCACCCTCTCAGGGGTACAGCCAGAGGATGAGGCAGAATAT |
| | | | | TACTGTGCTCTATGGTACAGCAACCGCTGGGTGTTCGGTGGAGGAACCAAACTGACTGTCCTA |
| 123 | CD33 B10 HL × F12Q HL | artificial | aa | QVQLVQSGAEVKKPGESVKVSCKASGYTFTNYGMNWVKQAPGQGLEWMGWINTYTGEPTYADKFQG
RVTMTTDTSTSTAYMEIRNLRSDDTAVYYCARWSWSDGYYVYFDYWGQGTTVTVSSGGGGSGGGGS
GGGGSDIVMTQSPDSLTVSLGERTTINCKSSQSVLDSSNNKNSLAWYQQKPGQPPKLLLSWASTRE
SGIPDRFSGSGSGTDFTLTIDGLQPEDSATYYCQQSAHFPITFGQGTRLEIKSGGGGSEVQLVESG
GGLVQPGGSLKLSCAASGFTFNSYAMNWVRQAPGKGLEWVARIRSKYNNYATYYADSVKGRFTISR
DDSKNTAYLQMNNLKTEDTAVYYCVRHGNFGNSYVSWWAYWGQGTLVTVSSGGGGSGGGGSGGGGS
QTVVTQEPSLTVSPGGTVTLTCGSSTGAVTSGNYPNWVQQKPGQAPRGLIGGTKFLAPGTPARFSG
SLLGGKAALTLSGVQPEDEAEYYCVLWYSNRWVFGGGTKLTVL |
| 124 | CD33 B10 HL × F12Q HL | artificial | nt | CAGGTGCAGCTGGTGCAGTCTGGAGCTGAGGTGAAGAAGCCTGGTGAGTCAGTCAAGGTCTCCTGC
AAGGCTAGCGGGTATACCTTCACAAACTATGGAATGAACTGGGTGAAGCAGGCTCCAGGACAGGGT
TTAGAGTGGATGGGCTGGATAAACACCTACACTGGAGAGCCAACCTATGCTGATAAGTTCCAGGGA
CGCGTTACCATGACTACGGATACCTCTACCAGCACTGCCTATATGGAAATCCGCAACCTCAGAAGT
GATGACACGGCTGTATATTACTGTGCGCGCTGGAGTTGGAGTGATGGTTACTACGTTTACTTTGAC
TACTGGGGCCAAGGCACTACGGTCACCGTCTCCTCAGGTGGTGGTGGTTCTGGCGGCGGCGGCTCC
GGTGGTGGTGGTTCTGACATCGTGATGACACAGTCTCCAGACTCCCTGACTGTGTCTCTGGGCGAG
AGGACCACCATCAACTGCAAGTCCAGCCAGAGTGTTTTAGACAGCTCCAACAATAAGAACTCCTTA
GCTTGGTACCAGCAGAAACCAGGACAGCCTCCTAAATTACTCCTTTCCTGGGCATCTACGCGGGAA
TCCGGGATCCCTGACCGATTCAGTGGCAGCGGTTCTGGGACAGATTTCACTCTCACTATTGACGGC
CTGCAGCCTGAAGATTCTGCAACTTACTATTGTCAACAGTCTGCCCACTTCCCGATCACCTTTGGC
CAAGGGACACGACTGGAGATTAAATCCGGAGGTGGTGGCTCCGAGGTGCAGCTGGTCGAGTCTGGA
GGAGGATTGGTGCAGCCTGGAGGGTCATTGAAACTCTCATGTGCAGCCTCTGGATTCACCTTCAAT
AGCTACGCCATGAACTGGGTCCGCCAGGCTCCAGGAAAGGGTTTGGAATGGGTTGCTCGCATAAGA
AGTAAATATAATAATTATGCAACATATTATGCCGATTCAGTGAAAGGCAGGTTCACCATCTCCAGA
GATGATTCAAAAAACACTGCCTATCTACAAATGAACAACTTGAAAACTGAGGACACTGCCGTGTAC
TACTGTGTGAGACATGGGAACTTCGGTAATAGCTACGTTTCCTGGTGGGCTTACTGGGGCCAAGGG
ACTCTGGTCACCGTCTCCTCAGGTGGTGGTGGTTCTGGCGGCGGCGGCTCCGGTGGTGGTGGTTCT
CAGACTGTTGTGACTCAGGAACCTTCACTCACCGTATCACCTGGTGGAACAGTCACACTCACTTGT
GGCTCCTCGACTGGGGCTGTTACATCTGGCAACTACCCAAACTGGGTCCAACAAAAACCAGGTCAG
GCACCCCGTGGTCTAATAGGTGGGACTAAGTTCCTCGCCCCCGGTACTCCTGCCAGATTCTCAGGC
TCCCTGCTTGGAGGCAAGGCTGCCCTCACCCTCTCAGGGGTACAGCCAGAGGATGAGGCAGAATAT
TACTGTGTTCTATGGTACAGCAACCGCTGGGTGTTCGGTGGAGGAACCAAACTGACTGTCCTA |
| 125 | CD33 B10 HL × I2C HL | artificial | aa | QVQLVQSGAEVKKPGESVKVSCKASGYTFTNYGMNWVKQAPGQGLEWMGWINTYTGEPTYADKFQG
RVTMTTDTSTSTAYMEIRNLRSDDTAVYYCARWSWSDGYYVYFDYWGQGTTVTVSSGGGGSGGGGS
GGGGSDIVMTQSPDSLTVSLGERTTINCKSSQSVLDSSNNKNSLAWYQQKPGQPPKLLLSWASTRE
SGIPDRFSGSGSGTDFTLTIDGLQPEDSATYYCQQSAHFPITFGQGTRLEIKSGGGGSEVQLVESG
GGLVQPGGSLKLSCAASGFTFNKYAMNWVRQAPGKGLEWVARIRSKYNNYATYYADSVKDRFTISR
DDSKNTAYLQMNNLKTEDTAVYYCVRHGNFGNSYISYWAYWGQGTLVTVSSGGGGSGGGGSGGGGS
QTVVTQEPSLTVSPGGTVTLTCGSSTGAVTSGNYPNWVQQKPGQAPRGLIGGTKFLAPGTPARFSG
SLLGGKAALTLSGVQPEDEAEYYCVLWYSNRWVFGGGTKLTVL |
| 126 | CD33 B10 HL × I2C HL | artificial | nt | CAGGTGCAGCTGGTGCAGTCTGGAGCTGAGGTGAAGAAGCCTGGTGAGTCAGTCAAGGTCTCCTGC
AAGGCTAGCGGGTATACCTTCACAAACTATGGAATGAACTGGGTGAAGCAGGCTCCAGGACAGGGT
TTAGAGTGGATGGGCTGGATAAACACCTACACTGGAGAGCCAACCTATGCTGATAAGTTCCAGGGA
CGCGTTACCATGACTACGGATACCTCTACCAGCACTGCCTATATGGAAATCCGCAACCTCAGAAGT
GATGACACGGCTGTATATTACTGTGCGCGCTGGAGTTGGAGTGATGGTTACTACGTTTACTTTGAC
TACTGGGGCCAAGGCACTACGGTCACCGTCTCCTCAGGTGGTGGTGGTTCTGGCGGCGGCGGCTCC
GGTGGTGGTGGTTCTGACATCGTGATGACACAGTCTCCAGACTCCCTGACTGTGTCTCTGGGCGAG
AGGACCACCATCAACTGCAAGTCCAGCCAGAGTGTTTTAGACAGCTCCAACAATAAGAACTCCTTA
GCTTGGTACCAGCAGAAACCAGGACAGCCTCCTAAATTACTCCTTTCCTGGGCATCTACGCGGGAA
TCCGGGATCCCTGACCGATTCAGTGGCAGCGGTTCTGGGACAGATTTCACTCTCACTATTGACGGC
CTGCAGCCTGAAGATTCTGCAACTTACTATTGTCAACAGTCTGCCCACTTCCCGATCACCTTTGGC
CAAGGGACACGACTGGAGATTAAATCCGGAGGTGGTGGCTCCGAGGTGCAGCTGGTCGAGTCTGGA
GGAGGATTGGTGCAGCCTGGAGGGTCATTGAAACTCTCATGTGCAGCCTCTGGATTCACCTTCAAT
AAGTACGCCATGAACTGGGTCCGCCAGGCTCCAGGAAAGGGTTTGGAATGGGTTGCTCGCATAAGA
AGTAAATATAATAATTATGCAACATATTATGCCGATTCAGTGAAAGACAGGTTCACCATCTCCAGA
GATGATTCAAAAAACACTGCCTATCTACAAATGAACAACTTGAAAACTGAGGACACTGCCGTGTAC
TACTGTGTGAGACATGGGAACTTCGGTAATAGCTACATATCCTACTGGGCTTACTGGGGCCAAGGG
ACTCTGGTCACCGTCTCCTCAGGTGGTGGTGGTTCTGGCGGCGGCGGCTCCGGTGGTGGTGGTTCT
CAGACTGTTGTGACTCAGGAACCTTCACTCACCGTATCACCTGGTGGAACAGTCACACTCACTTGT
GGCTCCTCGACTGGGGCTGTTACATCTGGCAACTACCCAAACTGGGTCCAACAAAAACCAGGTCAG |

-continued

| SEQ ID NO. | DESIGNATION | SOURCE | TYPE | SEQUENCE |
|---|---|---|---|---|
| | | | | GCACCCGTGGTCTAATAGGTGGGACTAAGTTCCTCGCCCCCGGTACTCCTGCCAGATTCTCAGGC<br>TCCCTGCTTGGAGGCAAGGCTGCCCTCACCCTCTCAGGGGTACAGCCAGAGGATGAGGCAGAATAT<br>TACTGTGTTCTATGGTACAGCAACCGCTGGGTGTTCGGTGGAGGAACCAAACTGACTGTCCTA |
| 127 | CD33 VH of E11 | artificial | aa | QVQLVQSGAEVKKPGESVKVSCKASGYTFTNYGMNWVKQAPGQGLEWMGWINTYTGEPTYADKFQG<br>RVTMTTDTSTSTAYMEIRNLGGDDTAVYYCARWSWSDGYYVYFDYWGQGTSVTVSS |
| 128 | CD33 HCDR1 of E11 | artificial | aa | NYGMN |
| 129 | CD33 HCDR2 of E11 | artificial | aa | WINTYTGEPTYADKFQG |
| 130 | CD33 HCDR3 of E11 | artificial | aa | WSWSDGYYVYFDY |
| 131 | CD33 VH of E11 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGCCAACCTATGCTGATAAGTTCCAGGGA<br>CGCGTTACCATGACTACGGATACCTCTACCAGCACTGCCTATATGGAAATCCGCAACCTCGGAGGT<br>GATGACACGGCTGTATATTACTGTGCGCGCTGGAGTTGGAGTGATGGTTACTACGTTTACTTTGAC<br>TACTGGGGCCAAGGCACTTCGGTCACCGTCTCCTCA |
| 132 | CD33 VL of E11 | artificial | aa | DIVMTQSPDSLTVSLGERTTINCKSSQSVLDSSTNKNSLAWYQQKPGQPPKLLLSWASTRESGIPD<br>RFSGSGSGTDFTLTIDSPQPEDSATYYCQQSAHFPITFGQGTRLEIK |
| 133 | CD33 LCDR1 of E11 | artificial | aa | KSSQSVLDSSTNKNSLA |
| 134 | CD33 LCDR2 of E11 | artificial | aa | WASTRES |
| 135 | CD33 LCDR3 of E11 | artificial | aa | QQSAHFPIT |
| 136 | CD33 VL of E11 | artificial | nt | GACATCGTGATGACACAGTCTCCAGACTCCCTGACTGTGTCTCTGGGCGAGAGGACCACCATCAAC<br>TGCAAGTCCAGCCAGAGTGTTTTAGACAGCTCCACGAATAAGAACTCCTTAGCTTGGTACCAGCAG<br>AAACCAGGACAGCCTCCTAAATTACTCCTTTCCTGGGCATCTACGCGGGAATCCGGGATCCCTGAC<br>CGATTCAGTGGCAGCGGGTCTGGGACAGATTTCACTCTCACTATTGACAGCCCGCAGCCTGAAGAT<br>TCTGCAACTTACTATTGTCAACAGTCTGCCCACTTCCCGATCACCTTTGGCCAAGGGACACGACTG<br>GAGATTAAA |
| 137 | CD33 HL of E11 | artificial | aa | QVQLVQSGAEVKKPGESVKVSCKASGYTFTNYGMNWVKQAPGQGLEWMGWINTYTGEPTYADKFQG<br>RVTMTTDTSTSTAYMEIRNLGGDDTAVYYCARWSWSDGYYVYFDYWGQGTSVTVSSGGGGSGGGGS<br>GGGGSDIVMTQSPDSLTVSLGERTTINCKSSQSVLDSSTNKNSLAWYQQKPGQPPKLLLSWASTRE<br>SGIPDRFSGSGSGTDFTLTIDSPQPEDSATYYCQQSAHFPITFGQGTRLEIK |
| 138 | CD33 HL of E11 | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGCCAACCTATGCTGATAAGTTCCAGGGA<br>CGCGTTACCATGACTACGGATACCTCTACCAGCACTGCCTATATGGAAATCCGCAACCTCGGAGGT<br>GATGACACGGCTGTATATTACTGTGCGCGCTGGAGTTGGAGTGATGGTTACTACGTTTACTTTGAC<br>TACTGGGGCCAAGGCACTTCGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CCGCAGCCTGAAGATTCTGCAACTTACTATTGTCAACAGTCTGCCCACTTCCCGATCACCTTTGGC<br>CAAGGGACACGACTGGAGATTAAA |
| 139 | CD33 E11 HL x H2C HL | artificial | aa | QVQLVQSGAEVKKPGESVKVSCKASGYTFTNYGMNWVKQAPGQGLEWMGWINTYTGEPTYADKFQG<br>RVTMTTDTSTSTAYMEIRNLGGDDTAVYYCARWSWSDGYYVYFDYWGQGTSVTVSSGGGGSGGGGS<br>GGGGSDIVMTQSPDSLTVSLGERTTINCKSSQSVLDSSTNKNSLAWYQQKPGQPPKLLLSWASTRE<br>SGIPDRFSGSGSGTDFTLTIDSPQPEDSATYYCQQSAHFPITFGQGTRLEIKSGGGGSEVQLVESG<br>GGLVQPGGSLKLSCAASGFTFNKYAMNWVRQAPGKGLEWVARIRSKYNNYATYYADSVKDRFTISR<br>DDSKNTAYLQMNNLKTEDTAVYYCVRHGNFGNSYISYWAYWGQTLVTVSSGGGGSGGGGSGGGGS<br>QTVVTQEPSLTVSPGGTVTLTCGSSTGAVTSGYYPNWVQQKPGQAPRGLIGGTKFLAPGTPARFSG<br>SLLGGKAALTLSGVQPEDEAEYYCALWYSNRWVFGGGTKLTVL |
| 140 | CD33 E11 HL x H2C HL | artificial | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGCCAACCTATGCTGATAAGTTCCAGGGA<br>CGCGTTACCATGACTACGGATACCTCTACCAGCACTGCCTATATGGAAATCCGCAACCTCGGAGGT<br>GATGACACGGCTGTATATTACTGTGCGCGCTGGAGTTGGAGTGATGGTTACTACGTTTACTTTGAC<br>TACTGGGGCCAAGGCACTTCGGTCACCGTCTCCTCAGGTGGTGGTGGTTCTGGCGGCGGCGGCTCC |

| SEQ ID NO. | DESIGNATION | SOURCE | TYPE | SEQUENCE |
|---|---|---|---|---|
| | | | | GGTGGTGGTGGTTCTGACATCGTGATGACACAGTCTCCAGACTCCCTGACTGTGTCTCTGGGCGAG
AGGACCACCATCAACTGCAAGTCCAGCCAGAGTGTTTTAGACAGCTCCACGAATAAGAACTCCTTA
GCTTGGTACCAGCAGAAACCAGGACAGCCTCCTAAATTACTCCTTTCCTGGGCATCTACGCGGGAA
TCCGGGATCCCTGACCGATTCAGTGGCAGCGGGTCTGGGACAGATTTCACTCTCACTATTGACAGC
CCGCAGCCTGAAGATTCTGCAACTTACTATTGTCAACAGTCTGCCCACTTCCCGATCACCTTTGGC
CAAGGGACACGACTGGAGATTAAATCCGGAGGTGGTGGCTCCGAGGTGCAGCTGGTCGAGTCTGGA
GGAGGATTGGTGCAGCCTGGAGGGTCATTGAAACTCTCATGTGCAGCCTCTGGATTCACCTTCAAT
AAGTACGCCATGAACTGGGTCCGCCAGGCTCCAGGAAAGGGTTTGGAATGGGTTGCTCGCATAAGA
AGTAAATATAATAATTATGCAACATATTATGCCGATTCAGTGAAAGACAGGTTCACCATCTCCAGA
GATGATTCAAAAAACACTGCCTATCTACAAATGAACAACTTGAAAACTGAGGACACTGCCGTGTAC
TACTGTGTGAGACATGGGAACTTCGGTAATAGCTACATATCCTACTGGGCTTACTGGGGCCAAGGG
ACTCTGGTCACCGTCTCCTCAGGTGGTGGTGGTTCTGGCGGCGGCGGCTCCGGTGGTGGTGGTTCT
CAGACTGTTGTGACTCAGGAACCTTCACTCACCGTATCACCTGGTGGAACAGTCACACTCACTTGT
GGCTCCTCGACTGGGGCTGTTACATCTGGCTACTACCCAAACTGGGTCCAACAAAAACCAGGTCAG
GCACCCCGTGGTCTAATAGGTGGGACTAAGTTCCTCGCCCCGGTACTCCTGCCAGATTCTCAGGC
TCCCTGCTTGGAGGCAAGGCTGCCCTCACCCTCTCAGGGGTACAGCCAGAGGATGAGGCAGAATAT
TACTGTGCTCTATGGTACAGCAACCGCTGGGTGTTCGGTGGAGGAACCAAACTGACTGTCCTA |
| 141 | CD33 E11 HL × F12Q HL | artificial | aa | QVQLVQSGAEVKKPGESVKVSCKASGYTFTNYGMNWVKQAPGQGLEWMGWINTYTGEPTYADKFQG
RVTMTTDTSTSTAYMEIRNLGDDTAVYYCARWSWSDGYYVYFDYWGQGTSVTVSSGGGGSGGGGS
GGGGSDIVMTQSPDSLTVSLGERTTINCKSSQSVLDSSTNKNSLAWYQQKPGQPPKLLLSWASTRE
SGIPDRFSGSGSGTDFTLTIDSPQPEDSATYYCQQSAHFPITFGQGTRLEIKSGGGGSEVQLVESG
GGLVQPGGSLKLSCAASGFTFNSYAMNWVRQAPGKGLEWVARIRSKYNNYATYYADSVKGRFTISR
DDSKNTAYLQMNNLKTEDTAVYYCVRHGNFGNSYVSWWAYWGQGTLVTVSSGGGGSGGGGSGGGGS
QTVVTQEPSLTVSPGGTVTLTCGSSTGAVTSGNYPNWVQQKPGQAPRGLIGGTKFLAPGTPARFSG
SLLGGKAALTLSGVQPEDEAEYYCVLWYSNRWVFGGGTKLTVL |
| 142 | CD33 E11 HL × F12Q HL | artificial | nt | CAGGTGCAGCTGGTGCAGTCTGGAGCTGAGGTGAAGAAGCCTGGAGAGTCAGTCAAGGTCTCCTGC
AAGGCTAGCGGGTATACCTTCACAAACTATGGAATGAACTGGGTGAAGCAGGCTCCAGGACAGGGT
TTAGAGTGGATGGGCTGGATAAACACCTACACTGGAGAGCCAACCTATGCTGATAAGTTCCAGGGA
CGCGTTACCATGACTACGGATACCTCTACCAGCACTGCCTATATGGAAATCCGCAACCTCGGAGGT
GATGACACGGCTGTATATTACTGTGCGCGCTGGAGTTGGAGTGATGGTTACTACGTTTACTTTGAC
TACTGGGGCCAAGGCACTTCGGTCACCGTCTCCTCAGGTGGTGGTGGTTCTGGCGGCGGCGGCTCC
GGTGGTGGTGGTTCTGACATCGTGATGACACAGTCTCCAGACTCCCTGACTGTGTCTCTGGGCGAG
AGGACCACCATCAACTGCAAGTCCAGCCAGAGTGTTTTAGACAGCTCCACGAATAAGAACTCCTTA
GCTTGGTACCAGCAGAAACCAGGACAGCCTCCTAAATTACTCCTTTCCTGGGCATCTACGCGGGAA
TCCGGGATCCCTGACCGATTCAGTGGCAGCGGGTCTGGGACAGATTTCACTCTCACTATTGACAGC
CCGCAGCCTGAAGATTCTGCAACTTACTATTGTCAACAGTCTGCCCACTTCCCGATCACCTTTGGC
CAAGGGACACGACTGGAGATTAAATCCGGAGGTGGTGGCTCCGAGGTGCAGCTGGTCGAGTCTGGA
GGAGGATTGGTGCAGCCTGGAGGGTCATTGAAACTCTCATGTGCAGCCTCTGGATTCACCTTCAAT
AGCTACGCCATGAACTGGGTCCGCCAGGCTCCAGGAAAGGGTTTGGAATGGGTTGCTCGCATAAGA
AGTAAATATAATAATTATGCAACATATTATGCCGATTCAGTGAAAGGCAGGTTCACCATCTCCAGA
GATGATTCAAAAAACACTGCCTATCTACAAATGAACAACTTGAAAACTGAGGACACTGCCGTGTAC
TACTGTGTGAGACATGGGAACTTCGGTAATAGCTACGTTTCCTGGTGGGCTTACTGGGGCCAAGGG
ACTCTGGTCACCGTCTCCTCAGGTGGTGGTGGTTCTGGCGGCGGCGGCTCCGGTGGTGGTGGTTCT
CAGACTGTTGTGACTCAGGAACCTTCACTCACCGTATCACCTGGTGGAACAGTCACACTCACTTGT
GGCTCCTCGACTGGGGCTGTTACATCTGGCTACTACCCAAACTGGGTCCAACAAAAACCAGGTCAG
GCACCCCGTGGTCTAATAGGTGGGACTAAGTTCCTCGCCCCGGTACTCCTGCCAGATTCTCAGGC
TCCCTGCTTGGAGGCAAGGCTGCCCTCACCCTCTCAGGGGTACAGCCAGAGGATGAGGCAGAATAT
TACTGTGTTCTATGGTACAGCAACCGCTGGGTGTTCGGTGGAGGAACCAAACTGACTGTCCTA |
| 143 | CD33 E11 HL × I2C HL | artificial | aa | QVQLVQSGAEVKKPGESVKVSCKASGYTFTNYGMNWVKQAPGQGLEWMGWINTYTGEPTYADKFQG
RVTMTTDTSTSTAYMEIRNLGDDTAVYYCARWSWSDGYYVYFDYWGQGTSVTVSSGGGGSGGGGS
GGGGSDIVMTQSPDSLTVSLGERTTINCKSSQSVLDSSTNKNSLAWYQQKPGQPPKLLLSWASTRE
SGIPDRFSGSGSGTDFTLTIDSPQPEDSATYYCQQSAHFPITFGQGTRLEIKSGGGGSEVQLVESG
GGLVQPGGSLKLSCAASGFTFNKYAMNWVRQAPGKGLEWVARIRSKYNNYATYYADSVKDRFTISR
DDSKNTAYLQMNNLKTEDTAVYYCVRHGNFGNSYISYWAYWGQGTLVTVSSGGGGSGGGGSGGGGS
QTVVTQEPSLTVSPGGTVTLTCGSSTGAVTSGNYPNWVQQKPGQAPRGLIGGTKFLAPGTPARFSG
SLLGGKAALTLSGVQPEDEAEYYCVLWYSNRWVFGGGTKLTVL |
| 144 | CD33 E11 HL × I2C HL | artificial | nt | CAGGTGCAGCTGGTGCAGTCTGGAGCTGAGGTGAAGAAGCCTGGAGAGTCAGTCAAGGTCTCCTGC
AAGGCTAGCGGGTATACCTTCACAAACTATGGAATGAACTGGGTGAAGCAGGCTCCAGGACAGGGT
TTAGAGTGGATGGGCTGGATAAACACCTACACTGGAGAGCCAACCTATGCTGATAAGTTCCAGGGA
CGCGTTACCATGACTACGGATACCTCTACCAGCACTGCCTATATGGAAATCCGCAACCTCGGAGGT
GATGACACGGCTGTATATTACTGTGCGCGCTGGAGTTGGAGTGATGGTTACTACGTTTACTTTGAC
TACTGGGGCCAAGGCACTTCGGTCACCGTCTCCTCAGGTGGTGGTGGTTCTGGCGGCGGCGGCTCC
GGTGGTGGTGGTTCTGACATCGTGATGACACAGTCTCCAGACTCCCTGACTGTGTCTCTGGGCGAG
AGGACCACCATCAACTGCAAGTCCAGCCAGAGTGTTTTAGACAGCTCCACGAATAAGAACTCCTTA
GCTTGGTACCAGCAGAAACCAGGACAGCCTCCTAAATTACTCCTTTCCTGGGCATCTACGCGGGAA
TCCGGGATCCCTGACCGATTCAGTGGCAGCGGGTCTGGGACAGATTTCACTCTCACTATTGACAGC
CCGCAGCCTGAAGATTCTGCAACTTACTATTGTCAACAGTCTGCCCACTTCCCGATCACCTTTGGC
CAAGGGACACGACTGGAGATTAAATCCGGAGGTGGTGGCTCCGAGGTGCAGCTGGTCGAGTCTGGA
GGAGGATTGGTGCAGCCTGGAGGGTCATTGAAACTCTCATGTGCAGCCTCTGGATTCACCTTCAAT
AAGTACGCCATGAACTGGGTCCGCCAGGCTCCAGGAAAGGGTTTGGAATGGGTTGCTCGCATAAGA
AGTAAATATAATAATTATGCAACATATTATGCCGATTCAGTGAAAGACAGGTTCACCATCTCCAGA |

| SEQ ID NO. | DESIGNATION | SOURCE | TYPE | SEQUENCE |
|---|---|---|---|---|
| | | | | GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA |
| 145 | CD33 | human | nt | ATGGGATGGAGCTGTATCATCCTCTTCTTGGTAGCAACAGCTACAGGTGTACACTCCGATCCAAAT TTCTGGCTGCAAGTGCAGGAGTCAGTGACGGTACAGGAGGGTTTGTGCGTCCTCGTGCCCTGCACT TTCTTCCATCCCATACCCTACTACGACAAGAACTCCCCAGTTCATGGTTACTGGTTCCGGGAAGGA GCCATTATATCCGGGGACTCTCCAGTGGCCACAAACAAGCTAGATCAAGAAGTACAGGAGGAGACT CAGGGCAGATTCCGCCTCCTTGGGGATCCCAGTAGGAACAACTGCTCCCTGAGCATCGTAGACGCC AGGAGGAGGGATAATGGTTCATACTTCTTTCGGATGGAGAGAGGAAGTACCAAATACAGTTACAAA TCTCCCCAGCTCTCTGTGCATGTGACAGACTTGACCCACAGGCCCAAAATCCTCATCCCTGGCACT CTAGAACCCGGCCACTCCAAAAACCTGACCTGCTCTGTGTCCTGGGCCTGTGAGCAGGGAACACCC CCGATCTTCTCCTGGTTGTCAGCTGCCCCCACTTCCCTGGGCCGGACTACTCACTCCTCGGTG CTCATAATCACCCCACGGCCCCAGGACCACGGCACCAACCTGACCTGTCAGGTGAAGTTCGCTGGA GCTGGTGTGACTACGGAGAGAACCATCCAGCTCAACGTCACCTATGTTCCACAGAACCCAACAACT GGTATCTTTCCAGGAGATGGCTCAGGGAAACAAGAGACCAGAGCAGGAGTGGTTCATGGGGCCATT GGAGGAGCTGGTGTTACAGCCCTGCTCGCTCTTTGTCTCTGCCTCATCTTCTTCATAGTGAAGACC CACAGGAGGAAAGCAGCCAGGACAGCAGTGGGCAGGAATGACACCCACCCTACCACAGGGTCAGCC TCCCCGAAACACCAGAAGAAGTCCAAGTTACATGGCCCCACTGAAACCTCAAGCTGTTCAGGTGCC GCCCCTACTGTGGAGATGGATGAGGAGCTGCATTATGCTTCCCTCAACTTTCATGGGATGAATCCT TCCAAGGACACCTCCACCGAATACTCAGAGGTCAGGACCCAGTCCGGGCATCATCACCATCATCAT TGA |
| 146 | CD33 | human | aa | MGWSCIILFLVATATGVHSDPNFWLQVQESVTVQEGLCVLVPCTFFHPIPYYDKNSPVHGYWFREG AIISGDSPVATNKLDQEVQEETQGRFRLLGDPSRNNCSLSIVDARRRDNGSYFFRMERGSTKYSYK SPQLSVHVTDLTHRPKILIPGTLEPGHSKNLTCSVSWACEQGTPPIFSWLSAAPTSLGPRTTHSSV LIITPRPQDHGTNLTCQVKFAGAVTTERTIQLNVTYVPQNPTTGIFPGDGSGKQETRAGVVHGAI GGAGVTALLALCLLIFFIVKTHRRKAARTAVGRNDTHPTTGSASPKHQKKSKLHGPTETSSCSGA APTVEMDEELHYASLNFHGMNPSKDTSTEYSEVRTQSGHHHHHH |
| 147 | CD33 | macaque | nt | ATGCCGCTGCTGCTACTGCTGCCCCTGCTGTGGGCAGGGGCCCTGGCTATGGATCCAAGAGTCAGG CTGGAAGTGCAGGAGTCAGTGACAGTACAGGAGGGTTTGTGCGTCCTTGTGCCCTGCACTTTCTTC CATCCCGTACCCTACCACACCAGGAATTCCCCAGTTCATGGTTACTGGTTCCGGGAAGGAGCCATT GTATCCTTGGACTCTCCAGTGGCCACAAACAAGCTAGATCAAGAAGTACAGGAGGAGACCCAGGGC CGATTCCGCCTCCTTGGGGATCCCAGTAGGAACAACTGCTCCCTGAGCATCGTAGATGCCAGGAGG AGGGATAACGGTTCATACTTCTTTCGGATGGAGAAAGGAAGTACCAAATACAGTTACAAATCTACC CAGCTCTCTGTGCATGTGACAGACTTGACCCACAGGCCCAAAATCCTCATCCCTGGAGCCCTAGAC CCTGACCACTCCAAAAACCTGACCTGCTCTGTGCCCTGGGCCTGTGAGCAGGGAACACCTCCAATC TTCTCCTGGATGTCAGCTGCCCCACCTCCCTGGGCCTCAGGACCACTCACTCCTCGGTGCTCATA ATCACCCCACGGCCCCAGGACCACGGCACCAACCTCACCTGTCAGGTGAAGTTCCCTGGAGCTGGC GTGACCACGGAGAGAACCATCCAGCTCAATGTCTCCTATGCTTCACAGAACCCAAGAACTGATATC TTTCTAGGAGACGGCTCAGGGAAACAAGGAGTGGTTCAGGGAGCCATCGGGGAGCTGGTGTCACA GTCCTGCTCGCTCTTTGTCTCTGCCTCATCTTCTTCACAGTGAAGACTCACAGGAGGAAAGCAGCC AGGACAGCAGTGGGCAGGATCGACACCCACCCCGCCACAGGGCCAACATCCTCGAAACACCAGAAG AAGTCCAAGTTACATGGCGCCACTGAAACCTCAGGCTGTTCAGGTACCACCCTTACTGTGGAGATG GATGAGGAGCTGCACTACGCTTCCCTCAACTTTCATGGGATGAATCCTTCTGAGGACACCTCCACC GAATACTCAGAGGTCAGGACCCAGTGA |
| 148 | CD33 UD H2C HL x AF5 HL | artificial | aa | EVQLVESGGGLVQPGGSLKLSCAASGFTFNKYAMNWVRQAPGKGLEWVARIRSKYNNYATYYADSV KDRFTISRDDSKNTAYLQMNNLKTEDTAVYYCVRHGNFGNSYISYWAYWGQGTLVTVSSGGGGSGG GGSGGGGSQTVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVLSGGGGSGVQLVQSGA EVKKPGASVKVSCKASGYTFTNYGMNWVKQAPGQGLKWMGWINTYTGEPTYADDFKGRVTMTSDTS TSTAYLELHNLRSDDTAVYYCARWSWSDGYYVFDYWGQGTTVTVSSggggsggggsggggsDIVM TQSPDSLTVSLGERTTINCKSSQSVLDSSKNKNSLAWYQQKPGQPPKLLLSWASTRESGIPDRFSG SGSGTDFTLTIDSLQPEDSATYYCQQSAHFPITFGQGTRLEIK |
| 149 | CD33 UD H2C HL x AF5 HL | artificial | nt | GAGGTGCAGCTGGTCGAGTCTGGAGGAGGATTGGTGCAGCCTGGAGGGTCATTGAAACTCTCATGT GCAGCCTCTGGATTCACCTTCAATAAGTACGCCATGAACTGGGTCCGCCAGGCTCCAGGAAAGGGT TTGGAATGGGTTGCTCGCATAAGAAGTAAATATAATAATTATGCAACATATTATGCCGATTCAGTG AAAGACAGGTTCACCATCTCCAGAGATGATTCAAAAAACACTGCCTATCTACAAATGAACAACTTG AAAACTGAGGACACTGCCGTGTACTACTGTGTGAGACATGGGAACTTCGGTAATAGCTACATATCC TACTGGGCTTACTGGGGCCAAGGGACTCTGGTCACCGTCTCCTCAGGTGGTGGTGGTTCTGGCGGC GGCGGCTCCGGTGGTGGTGGTTCTCAGACTGTTGTGACTCAGGAACCTTCACTCACCGTATCACCT GGTGGAACAGTCACACTCACTTGTGGCTCCTCGACTGGGGCTGTTACATCTGGCTACTACCCAAAC TGGGTCCAACAAAAACCAGGTCAGGCACCCCGTGGTCTAATAGGTGGGACTAAGTTCCTCGCCCCC GGTACTCCTGCCAGATTCTCAGGCTCCCTGCTTGGAGGCAAGGCTGCCCTCACCCTCTCAGGGGTA CAGCCAGAGGATGAGGCAGAATATTACTGTGCTCTATGGTACAGCAACCGCTGGGTGTTCGGTGGA GGAACCAAACTGACTGTCCTATCCGGAGGTGGTGGCTCCAGGTGCAGCTGGTCCAGTCTGGAGCT GAGGTGAAGAAGCCTGGAGCGTCAGTCAAGGTCTCCTGCAAGGCTAGCGGGTATACCTTCACAAAC |

| SEQ ID NO. | DESIGNATION | SOURCE | TYPE | SEQUENCE |
|---|---|---|---|---|
| | | | | TATGGAATGAACTGGGTGAAGCAGGCTCCAGGACAGGGTTTAAAGTGGATGGGCTGGATAAACACC<br>TACACTGGAGAGCCAACATATGCTGATGACTTCAAGGGACGGGTTACCATGACTTCGGATACCTCT<br>ACCAGCACTGCCTATTTGGAACTCCACAACCTCAGAAGTGATGACACGGCTGTATATTACTGTGCG<br>CGCTGGAGTTGGAGTGATGGTTACTACGTTTACTTTGACTACTGGGGCCAAGGCACTACGGTCACC<br>GTCTCCTCAGGTGGTGGTGGTTCTGGCGGCGGCGGCTCCGGTGGTGGTGGTTCTGACATCGTGATG<br>ACACAGTCTCCAGACTCCCTGACTGTGTCTCTGGGCGAGAGGACCACCATCAACTGCAAGTCCAGC<br>CAGAGTGTTTTAGACAGCTCCAAGAATAAGAACTCCTTAGCTTGGTACCAGCAGAAACCAGGACAG<br>CCTCCTAAATTACTCCTTTCCTGGGCATCTACGCGGGAATCCGGGATCCCTGACCGATTCAGTGGC<br>AGCGGGTCTGGGACAGATTTCACTCTCACTATTGACAGCCTGCAGCCTGAAGATTCTGCAACTTAC<br>TATTGTCAACAGTCTGCCCACTTCCCGATCACCTTTGGCCAAGGGACACGACTGGAGATTAAA |
| 150 | CD33 UD F12Q HL x AF5 HL | artificial | aa | EVQLVESGGGLVQPGGSLKLSCAASGFTFNSYAMNWVRQAPGKGLEWVARIRSKYNNYATYYADSV<br>KGRFTISRDDSKNTAYLQMNNLKTEDTAVYYCVRHGNFGNSYVSWWAYWGQGTLVTVSSGGGGSGG<br>GGGSGGGGSQTVVTQEPSLTVSPGGTVTLTCGSSTGAVTSGNYPNWVQQKPGQAPRGLIGGTKFLAP<br>GTPARFSGSLLGGKAALTLSGVQPEDEAEYYCVLWYSNRWVFGGGTKLTVLSGGGGSQVQLVQSGA<br>EVKKPGASVKVSCKASGYTFTNYGMNWVKQAPGQGLKWMGWINTYTGEPTYADDFKGRVTMTSDTS<br>TSTAYLELHNLRSDDTAVYYCARWSWSDGYYVYFDYWGQGTTVTVSSggggsggggsggggsDIVM<br>TQSPDSLTVSLGERTTINCKSSQSVLDSSKNKNSLAWYQQKPGQPPKLLLSWASTRESGIPDRFSG<br>SGSGTDFTLTIDSLQPEDSATYYCQQSAHFPITFGQGTRLEIK |
| 151 | CD33 UD F12Q HL x AF5 HL | artificial | nt | GAGGTGCAGCTGGTCGAGTCTGGAGGAGGATTGGTGCAGCCTGGAGGGTCATTGAAACTCTCATGT<br>GCAGCCTCTGGATTCACCTTCAATAGCTACGCCATGAACTGGGTCCGCCAGGCTCCAGGAAAGGGT<br>TTGGAATGGGTTGCTCGCATAAGAAGTAAATATAATAATTATGCAACATATTATGCCGATTCAGTG<br>AAAGGCAGGTTCACCATCTCCAGAGATGATTCAAAAAACACTGCCTATCTACAAATGAACAACTTG<br>AAAACTGAGGACACTGCCGTGTACTACTGTGTGAGACATGGGAACTTCGGTAATAGCTACGTTTCC<br>TGGTGGGCTTACTGGGGCCAAGGGACTCTGGTCACCGTCTCCTCAGGTGGTGGTGGTTCTGGCGGC<br>GGCGGCTCCGGTGGTGGTGGTTCTCAGACTGTTGTGACTCAGGAACCTTCACTCACCGTATCACCT<br>GGTGGAACAGTCACACTCACTTGTGGCTCCTCGACTGGGGCTGTTACATCTGGCAACTACCCAAAC<br>TGGGTCCAACAAAAACCAGGTCAGGCACCCCGTGGTCTAATAGGTGGGACTAAGTTCCTCGCCCCC<br>GGTACTCCTGCCAGATTCTCAGGCTCCCTGCTTGGAGGCAAGGCTGCCCTCACCCTCTCAGGGGTA<br>CAGCCAGAGGATGAGGCAGAATATTACTGTGTTCTATGGTACAGCAACCGCTGGGTGTTCGGTGGA<br>GGAACCAAACTGACTGTCCTATCCGGAGGTGGTGGCTCCCAGGTGCAGCTGGTCCAGTCTGGAGCT<br>GAGGTGAAGAAGCCTGGAGCGTCAGTCAAGGTCTCCTGCAAGGCTAGCGGGTATACCTTCACAAAC<br>TATGGAATGAACTGGGTGAAGCAGGCTCCAGGACAGGGTTTAAAGTGGATGGGCTGGATAAACACC<br>TACACTGGAGAGCCAACATATGCTGATGACTTCAAGGGACGGGTTACCATGACTTCGGATACCTCT<br>ACCAGCACTGCCTATTTGGAACTCCACAACCTCAGAAGTGATGACACGGCTGTATATTACTGTGCG<br>CGCTGGAGTTGGAGTGATGGTTACTACGTTTACTTTGACTACTGGGGCCAAGGCACTACGGTCACC<br>GTCTCCTCAGGTGGTGGTGGTTCTGGCGGCGGCGGCTCCGGTGGTGGTGGTTCTGACATCGTGATG<br>ACACAGTCTCCAGACTCCCTGACTGTGTCTCTGGGCGAGAGGACCACCATCAACTGCAAGTCCAGC<br>CAGAGTGTTTTAGACAGCTCCAAGAATAAGAACTCCTTAGCTTGGTACCAGCAGAAACCAGGACAG<br>CCTCCTAAATTACTCCTTTCCTGGGCATCTACGCGGGAATCCGGGATCCCTGACCGATTCAGTGGC<br>AGCGGGTCTGGGACAGATTTCACTCTCACTATTGACAGCCTGCAGCCTGAAGATTCTGCAACTTAC<br>TATTGTCAACAGTCTGCCCACTTCCCGATCACCTTTGGCCAAGGGACACGACTGGAGATTAAA |
| 152 | CD33 UD I2C HL x AF5 HL | artificial | aa | EVQLVESGGGLVQPGGSLKLSCAASGFTFNKYAMNWVRQAPGKGLEWVARIRSKYNNYATYYADSV<br>KDRFTISRDDSKNTAYLQMNNLKTEDTAVYYCVRHGNFGNSYISYWAYWGQGTLVTVSSGGGGSGG<br>GGGSGGGGSQTVVTQEPSLTVSPGGTVTLTCGSSTGAVTSGNYPNWVQQKPGQAPRGLIGGTKFLAP<br>GTPARFSGSLLGGKAALTLSGVQPEDEAEYYCVLWYSNRWVFGGGTKLTVLSGGGGSQVQLVQSGA<br>EVKKPGASVKVSCKASGYTFTNYGMNWVKQAPGQGLKWMGWINTYTGEPTYADDFKGRVTMTSDTS<br>TSTAYLELHNLRSDDTAVYYCARWSWSDGYYVYFDYWGQGTTVTVSSggggsggggsggggsDIVM<br>TQSPDSLTVSLGERTTINCKSSQSVLDSSKNKNSLAWYQQKPGQPPKLLLSWASTRESGIPDRFSG<br>SGSGTDFTLTIDSLQPEDSATYYCQQSAHFPITFGQGTRLEIK |
| 153 | CD33 UD I2C HL x AF5 HL | artificial | nt | GAGGTGCAGCTGGTCGAGTCTGGAGGAGGATTGGTGCAGCCTGGAGGGTCATTGAAACTCTCATGT<br>GCAGCCTCTGGATTCACCTTCAATAAGTACGCCATGAACTGGGTCCGCCAGGCTCCAGGAAAGGGT<br>TTGGAATGGGTTGCTCGCATAAGAAGTAAATATAATAATTATGCAACATATTATGCCGATTCAGTG<br>AAAGACAGGTTCACCATCTCCAGAGATGATTCAAAAAACACTGCCTATCTACAAATGAACAACTTG<br>AAAACTGAGGACACTGCCGTGTACTACTGTGTGAGACATGGGAACTTCGGTAATAGCTACATATCC<br>TACTGGGCTTACTGGGGCCAAGGGACTCTGGTCACCGTCTCCTCAGGTGGTGGTGGTTCTGGCGGC<br>GGCGGCTCCGGTGGTGGTGGTTCTCAGACTGTTGTGACTCAGGAACCTTCACTCACCGTATCACCT<br>GGTGGAACAGTCACACTCACTTGTGGCTCCTCGACTGGGGCTGTTACATCTGGCAACTACCCAAAC<br>TGGGTCCAACAAAAACCAGGTCAGGCACCCCGTGGTCTAATAGGTGGGACTAAGTTCCTCGCCCCC<br>GGTACTCCTGCCAGATTCTCAGGCTCCCTGCTTGGAGGCAAGGCTGCCCTCACCCTCTCAGGGGTA<br>CAGCCAGAGGATGAGGCAGAATATTACTGTGTTCTATGGTACAGCAACCGCTGGGTGTTCGGTGGA<br>GGAACCAAACTGACTGTCCTATCCGGAGGTGGTGGCTCCCAGGTGCAGCTGGTCCAGTCTGGAGCT<br>GAGGTGAAGAAGCCTGGAGCGTCAGTCAAGGTCTCCTGCAAGGCTAGCGGGTATACCTTCACAAAC<br>TATGGAATGAACTGGGTGAAGCAGGCTCCAGGACAGGGTTTAAAGTGGATGGGCTGGATAAACACC<br>TACACTGGAGAGCCAACATATGCTGATGACTTCAAGGGACGGGTTACCATGACTTCGGATACCTCT<br>ACCAGCACTGCCTATTTGGAACTCCACAACCTCAGAAGTGATGACACGGCTGTATATTACTGTGCG<br>CGCTGGAGTTGGAGTGATGGTTACTACGTTTACTTTGACTACTGGGGCCAAGGCACTACGGTCACC<br>GTCTCCTCAGGTGGTGGTGGTTCTGGCGGCGGCGGCTCCGGTGGTGGTGGTTCTGACATCGTGATG<br>ACACAGTCTCCAGACTCCCTGACTGTGTCTCTGGGCGAGAGGACCACCATCAACTGCAAGTCCAGC<br>CAGAGTGTTTTAGACAGCTCCAAGAATAAGAACTCCTTAGCTTGGTACCAGCAGAAACCAGGACAG |

-continued

| SEQ ID NO. | DESIGNATION | SOURCE | TYPE | SEQUENCE |
|---|---|---|---|---|
| | | | | CCTCCTAAATTACTCCTTTCCTGGGCATCTACGCGGGAATCCGGGATCCCTGACCGATTCAGTGGC |
| | | | | AGCGGGTCTGGGACAGATTTCACTCTCACTATTGACAGCCTGCAGCCTGAAGATTCTGCAACTTAC |
| | | | | TATTGTCAACAGTCTGCCCACTTCCCGATCACCTTTGGCCAAGGGACACGACTGGAGATTAAA |
| 154 | VL of F6A | artificial | aa | QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 155 | VH of F6A | artificial | aa | EVQLVESGGGLVQPGGSLKLSCAASGFTFNIYAMNWVRQAPGKGLEWVARIRSKYNNYATYYADSV KSRFTISRDDSKNTAYLQMNNLKTEDTAVYYCVRHGNFGNSYVSFFAYWGQGTLVTVSS |
| 156 | VH-VL of F6A | artificial | aa | EVQLVESGGGLVQPGGSLKLSCAASGFTFNIYAMNWVRQAPGKGLEWVARIRSKYNNYATYYADSV KSRFTISRDDSKNTAYLQMNNLKTEDTAVYYCVRHGNFGNSYVSFFAYWGQGTLVTVSSGGGGSGG GGSGGGGSQTVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 157 | VL-P of F6A | artificial | aa | ELVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 158 | VH-P of F6A | artificial | aa | EVQLLESGGGLVQPGGSLKLSCAASGFTFNIYAMNWVRQAPGKGLEWVARIRSKYNNYATYYADSV KSRFTISRDDSKNTAYLQMNNLKTEDTAVYYCVRHGNFGNSYVSFFAYWGQGTLVTVSS |
| 159 | VH-VL-P of F6A | artificial | aa | EVQLLESGGGLVQPGGSLKLSCAASGFTFNIYAMNWVRQAPGKGLEWVARIRSKYNNYATYYADSV KSRFTISRDDSKNTAYLQMNNLKTEDTAVYYCVRHGNFGNSYVSFFAYWGQGTLVTVSSGGGGSGG GGSGGGGSELVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 160 | VL of H2C | artificial | aa | QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 161 | VH of H2C | artificial | aa | EVQLVESGGGLVQPGGSLKLSCAASGFTFNKYAMNWVRQAPGKGLEWVARIRSKYNNYATYYADSV KDRFTISRDDSKNTAYLQMNNLKTEDTAVYYCVRHGNFGNSYISYWAYWGQGTLVTVSS |
| 162 | VH-VL of H2C | artificial | aa | EVQLVESGGGLVQPGGSLKLSCAASGFTFNKYAMNWVRQAPGKGLEWVARIRSKYNNYATYYADSV KDRFTISRDDSKNTAYLQMNNLKTEDTAVYYCVRHGNFGNSYISYWAYWGQGTLVTVSSGGGGSGG GGSGGGGSQTVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 163 | VL-P of H2C | artificial | aa | ELVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 164 | VH-P of H2C | artificial | aa | EVQLLESGGGLVQPGGSLKLSCAASGFTFNKYAMNWVRQAPGKGLEWVARIRSKYNNYATYYADSV KDRFTISRDDSKNTAYLQMNNLKTEDTAVYYCVRHGNFGNSYISYWAYWGQGTLVTVSS |
| 165 | VH-VL-P of H2C | artificial | aa | EVQLLESGGGLVQPGGSLKLSCAASGFTFNKYAMNWVRQAPGKGLEWVARIRSKYNNYATYYADSV KDRFTISRDDSKNTAYLQMNNLKTEDTAVYYCVRHGNFGNSYISYWAYWGQGTLVTVSSGGGGSGG GGSGGGGSELVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 166 | VL of H1E | artificial | aa | QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 167 | VH of H1E | artificial | aa | EVQLVESGGGLEQPGGSLKLSCAASGFTFNSYAMNWVRQAPGKGLEWVARIRSKYNNYATYYADSV KGRFTISRDDSKNTAYLQMNNLKTEDTAVYYCVRHGNFGNSYLSFWAYWGQGTLVTVSS |
| 168 | VH-VL of H1E | artificial | aa | EVQLVESGGGLEQPGGSLKLSCAASGFTFNSYAMNWVRQAPGKGLEWVARIRSKYNNYATYYADSV KGRFTISRDDSKNTAYLQMNNLKTEDTAVYYCVRHGNFGNSYLSFWAYWGQGTLVTVSSGGGGSGG GGSGGGGSQTVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 169 | VL-P of H1E | artificial | aa | ELVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 170 | VH-P of H1E | artificial | aa | EVQLLESGGGLEQPGGSLKLSCAASGFTFNSYAMNWVRQAPGKGLEWVARIRSKYNNYATYYADSV KGRFTISRDDSKNTAYLQMNNLKTEDTAVYYCVRHGNFGNSYLSFWAYWGQGTLVTVSS |
| 171 | VH-VL-P of H1E | artificial | aa | EVQLLESGGGLEQPGGSLKLSCAASGFTFNSYAMNWVRQAPGKGLEWVARIRSKYNNYATYYADSV KGRFTISRDDSKNTAYLQMNNLKTEDTAVYYCVRHGNFGNSYLSFWAYWGQGTLVTVSSGGGGSGG GGSGGGGSELVVTQEPSLTVSPGGTVTLTCGSSTGAVTSGYYPNWVQQKPGQAPRGLIGGTKFLAP GTPARFSGSLLGGKAALTLSGVQPEDEAEYYCALWYSNRWVFGGGTKLTVL |
| 172 | VL of G4H | artificial | aa | QTVVTQEPSLTVSPGGTVTLTCGSSTGAVTSGYYPNWVQQKPGQAPRGLIGGTKFLAPGTPARFSG SLLGGKAALTLSGVQPEDEAEYYCALWYSNRWVFGGGTKLTVL |
| 173 | VH of G4H | artificial | aa | EVQLVESGGGLVQPGGSLKLSCAASGFTFNRYAMNWVRQAPGKGLEWVARIRSKYNNYATYYADSV KGRFTISRDDSKNTAYLQMNNLKTEDTAVYYCVRHGNFGNSYLSYFAYWGQGTLVTVSS |

| SEQ ID NO. | DESIGNATION | SOURCE | TYPE | SEQUENCE |
|---|---|---|---|---|
| 174 | VH-VL of G4H | artificial | aa | EVQLVESGGGLVQPGGSLKLSCAASGFTFNRYAMNWVRQAPGKGLEWVARIRSKYNNYATYYADSVKGRFTISRDDSKNTAYLQMNNLKTEDTAVYYCVRHGNFGNSYLSYFAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 175 | VL-P of G4H | artificial | aa | ELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 176 | VH-P of G4H | artificial | aa | EVQLLESGGGLVQPGGSLKLSCAASGFTFNRYAMNWVRQAPGKGLEWVARIRSKYNNYATYYADSVKGRFTISRDDSKNTAYLQMNNLKTEDTAVYYCVRHGNFGNSYLSYFAYWGQGTLVTVSS |
| 177 | VH-VL-P of G4H | artificial | aa | EVQLLESGGGLVQPGGSLKLSCAASGFTFNRYAMNWVRQAPGKGLEWVARIRSKYNNYATYYADSVKGRFTISRDDSKNTAYLQMNNLKTEDTAVYYCVRHGNFGNSYLSYFAYWGQGTLVTVSSGGGGSGGGGSGGGGSELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 178 | VL of A2J | artificial | aa | QTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 179 | VH of A2J | artificial | aa | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSS |
| 180 | VH-VL of A2J | artificial | aa | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSSGGGGSGGGGSGGGGSQTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 181 | VL-P of A2J | artificial | aa | ELVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 182 | VH-P of A2J | artificial | aa | EVQLLESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSS |
| 183 | VH-VL-P of A2J | artificial | aa | EVQLLESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYLSWWAYWGQGTLVTVSSGGGGSGGGGSGGGGSELVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 184 | VL of E1L | artificial | aa | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 185 | VH of E1L | artificial | aa | EVQLVESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSS |
| 186 | VH-VL of E1L | artificial | aa | EVQLVESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 187 | VL-P of E1L | artificial | aa | ELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 188 | VH-P of E1L | artificial | aa | EVQLLESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSS |
| 189 | VH-VL-P of E1L | artificial | aa | EVQLLESGGGLVQPGGSLKLSCAASGFTFNKYAMNWVRQAPGKGLEWVARIRSKYNNYATYYADSVKSRFTISRDDSKNTAYLQMNNLKTEDTAVYYCVRHGNFGNSYTSYYAYWGQGTLVTVSSGGGGSGGGGSGGGGSELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 190 | VL of E2M | artificial | aa | QTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 191 | VH of E2M | artificial | aa | EVQLVESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSS |
| 192 | VH-VL of E2M | artificial | aa | EVQLVESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSSGGGGSGGGGSGGGGSQTVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 193 | VL-P of E2M | artificial | aa | ELVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |

| SEQ ID NO. | DESIGNATION | SOURCE | TYPE | SEQUENCE |
|---|---|---|---|---|
| 194 | VH-P of E2M | artificial | aa | EVQLLESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSS |
| 195 | VH-VL-P of E2M | artificial | aa | EVQLLESGGGLVQPGGSLKLSCAASGFTFNGYAMNWVRQAPGKGLEWVARIRSKYNNYATYYADSVKERFTISRDDSKNTAYLQMNNLKTEDTAVYYCVRHRNFGNSYLSWFAYWGQGTLVTVSSGGGGSGGGGSGGGGSELVVTQEPSLTVSPGGTVTLTCRSSTGAVTSGYYPNWVQQKPGQAPRGLIGATDMRPSGTPARFSGSLLGGKAALTLSGVQPEDEAEYYCALWYSNRWVFGGGTKLTVL |
| 196 | VL of F7O | artificial | aa | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 197 | VH of F7O | artificial | aa | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSS |
| 198 | VH-VL of F7O | artificial | aa | EVQLVESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSSGGGGSGGGGSGGGGSQTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 199 | VL-P of F7O | artificial | aa | ELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 200 | VH-P of F7O | artificial | aa | EVQLLESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSS |
| 201 | VH-VL-P of F7O | artificial | aa | EVQLLESGGGLVQPGGSLKLSCAASGFTFNVYAMNWVRQAPGKGLEWVARIRSKYNNYATYYADSVKKRFTISRDDSKNTAYLQMNNLKTEDTAVYYCVRHGNFGNSYISWWAYWGQGTLVTVSSGGGGSGGGGSGGGGSELVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVFGGGTKLTVL |
| 202 | VL of F12Q | artificial | aa | QTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 203 | VH of F12Q | artificial | aa | EVQLVESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSS |
| 204 | VH-VL of F12Q | artificial | aa | EVQLVESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 205 | VL-P of F12Q | artificial | aa | ELVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 206 | VH-P of F12Q | artificial | aa | EVQLLESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSS |
| 207 | VH-VL-P of F12Q | artificial | aa | EVQLLESGGGLVQPGGSLKLSCAASGFTFNSYAMNWVRQAPGKGLEWVARIRSKYNNYATYYADSVKGRFTISRDDSKNTAYLQMNNLKTEDTAVYYCVRHGNFGNSYVSWWAYWGQGTLVTVSSGGGGSGGGGSGGGGSELVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 208 | VL of I2C | artificial | aa | QTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 209 | VH of I2C | artificial | aa | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS |
| 210 | VH-VL of I2C | artificial | aa | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 211 | VL-P of I2C | artificial | aa | ELVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |
| 212 | VH-P of I2C | artificial | aa | EVQLLESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS |
| 213 | VH-VL-P of I2C | artificial | aa | EVQLLESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSELVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVL |

| SEQ ID NO. | DESIGNATION | SOURCE | TYPE | SEQUENCE |
|---|---|---|---|---|
| 214 | SA21-CD33 E11 HL × I2C HL (His Tag) | | nt | CGCCTGATTGAAGATATTTGCCTGCCGCGCTGGGGCTGCCTGTGGGAAGATGAT CAGGTGCAGCTGGTGCAGTCTGGAGCTGAGGTGAAGAAGCCTGGAGAGTCAGTCAAGGTCTCCTGC AAGGCTAGCGGGTATACCTTCACAAACTATGGAATGAACTGGGTGAAGCAGGCTCCAGGACAGGGT TTAGAGTGGATGGGCTGGATAAACACCTACACTGGAGAGCCAACCTATGCTGATAAGTTCCAGGGA CGCGTTACCATGACTACGGATACCTCTACCAGCACTGCCTATATGGAAATCCGCAACCTCGGAGGT GATGACACGGCTGTATATTACTGTGCGCGCTGGAGTTGGAGTGATGGTTACTACGTTTACTTTGAC TACTGGGGCCAAGGCACTTCGGTCACCGTCTCCTCAGGTGGTGGTGGTTCTGGCGGCGGCGGCTCC GGTGGTGGTGGTTCTGACATCGTGATGACACAGTCTCCAGATCCCTGACTGTGTCTCTGGGCGAG AGGACCACCATCAACTGCAAGTCCAGCCAGAGTGTTTTAGACAGCTCCACGAATAAGAACTCCTTA GCTTGGTACCAGCAGAAACCAGGACAGCCTCCTAAATTACTCCTTTCCTGGGCATCTACGCGGGAA TCCGGGATCCCTGACCGATTCAGTGGCAGCGGGTCTGGGACAGATTTCACTCTCACTATTGACAGC CCGCAGCCTGAAGATTCTGCAACTTACTATTGTCAACAGTCTGCCCACTTCCCGATCACCTTTGGC CAAGGGACACGACTGGAGATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA CATCACCATCACCATCAC |
| 215 | SA21-CD33 E11 HL × I2C HL H6 | | aa | RLIEDICLPRWGCLWEDDQVQLVQSGAEVKKPGESVKVSCKASGYTFTNYGMNWVKQAPGQGLEWM GWINTYTGEPTYADKFQGRVTMTTDTSTSTAYMEIRNLGGDDTAVYYCARWSWSDGYYVYFDYWGQ GTSVTVSSGGGGSGGGGSGGGGSDIVMTQSPDSLTVSLGERTTINCKSSQSVLDSSTNKNSLAWYQ QKPGQPPKLLLSWASTRESGIPDRFSGSGSGTDFTLTIDSPQPEDSATYYCQQSAHFPITFGQGTR LEIKSGGGGSEVQLVESGGGLVQPGGSLKLSCAASGFTFNKYAMNWVRQAPGKGLEWVARIRSKYN NYATYYADSVKDRFTISRDDSKNTAYLQMNNLKTEDTAVYYCVRHGNFGNSYISYWAYWGQGTLVT VSSGGGGSGGGGSGGGGSQTVVTQEPSLTVSPGGTVTLTCGSSTGAVTSGNYPNWVQQKPGQAPRG LIGGTKFLAPGTPARFSGSLLGGKAALTLSGVQPEDEAEYYCVLWYSNRWVFGGGTKLTVLHHHHH H |
| 216 | SA25-CD33 E11 HL × I2C HL with His tag | | nt | GAGGACATCTGCCTGCCCAGATGGGGCTGCCTGTGGGAGGACCAGGTGCAGCTGGTGCAGTCTGGA GCTGAGGTGAAGAAGCCTGGAGAGTCAGTCAAGGTCTCCTGCAAGGCTAGCGGGTATACCTTCACA AACTATGGAATGAACTGGGTGAAGCAGGCTCCAGGACAGGGTTTAGAGTGGATGGGCTGGATAAAC ACCTACACTGGAGAGCCAACCTATGCTGATAAGTTCCAGGGACGCGTTACCATGACTACGGATACC TCTACCAGCACTGCCTATATGGAAATCCGCAACCTCGGAGGTGATGACACGGCTGTATATTACTGT GCGCGCTGGAGTTGGAGTGATGGTTACTACGTTTACTTTGACTACTGGGGCCAAGGCACTTCGGTC ACCGTCTCCTCAGGTGGTGGTGGTTCTGGCGGCGGCGGCTCCGGTGGTGGTGGTTCTGACATCGTG ATGACACAGTCTCCAGACTCCCTGACTGTGTCTCTGGGCGAGAGGACCACCATCAACTGCAAGTCC AGCCAGAGTGTTTTAGACAGCTCCACGAATAAGAACTCCTTAGCTTGGTACCAGCAGAAACCAGGA CAGCCTCCTAAATTACTCCTTTCCTGGGCATCTACGCGGGAATCCGGGATCCCTGACCGATTCAGT GGCAGCGGGTCTGGGACAGATTTCACTCTCACTATTGACAGCCCGCAGCCTGAAGATTCTGCAACT TACTATTGTCAACAGTCTGCCCACTTCCCGATCACCTTTGGCCAAGGGACACGACTGGAGATTAAA TCCGGAGGTGGTGGCTCCGAGGTGCAGCTGGTCGAGTCTGGAGGAGGATTGGTGCAGCCTGGAGGG TCATTGAAACTCTCATGTGCAGCCTCTGGATTCACCTTCAATAAGTACGCCATGAACTGGGTCCGC CAGGCTCCAGGAAAGGGTTTGGAATGGGTTGCTCGCATAAGAAGTAAATATAATAATTATGCAACA TATTATGCCGATTCAGTGAAAGACAGGTTCACCATCTCCAGAGATGATTCAAAAAACACTGCCTAT CTACAAATGAACAACTTGAAAACTGAGGACACTGCCGTGTACTACTGTGTGAGACATGGGAACTTC GGTAATAGCTACATATCCTACTGGGCTTACTGGGGCCAAGGGACTCTGGTCACCGTCTCCTCAGGT GGTGGTGGTTCTGGCGGCGGCGGCTCCGGTGGTGGTGGTTCTCAGACTGTTGTGACTCAGGAACCT TCACTCACCGTATCACCTGGTGGAACAGTCACACTCACTTGTGGCTCCTCGACTGGGGCTGTTACA TCTGGCAACTACCCAAACTGGGTCCAACAAAAACCAGGTCAGGCACCCCGTGGTCTAATAGGTGGG ACTAAGTTCCTCGCCCCCGGTACTCCTGCCAGATTCTCAGGCTCCCTGCTTGGAGGCAAGGCTGCC CTCACCCTCTCAGGGGTACAGCCAGAGGATGAGGCAGAATATTACTGTGTTCTATGGTACAGCAAC CGCTGGGTGTTCGGTGGAGGAACCAAACTGACTGTCCTACATCACCATCACCATCAC |
| 217 | SA25-CD33 E11 HL × I2C HL H6 | | aa | EDICLPRWGCLWEDQVQLVQSGAEVKKPGESVKVSCKASGYTFTNYGMNWVKQAPGQGLEWMGWIN TYTGEPTYADKFQGRVTMTTDTSTSTAYMEIRNLGGDDTAVYYCARWSWSDGYYVYFDYWGQGTSV TVSSGGGGSGGGGSGGGGSDIVMTQSPDSLTVSLGERTTINCKSSQSVLDSSTNKNSLAWYQQKPG QPPKLLLSWASTRESGIPDRFSGSGSGTDFTLTIDSPQPEDSATYYCQQSAHFPITFGQGTRLEIK SGGGGSEVQLVESGGGLVQPGGSLKLSCAASGFTFNKYAMNWVRQAPGKGLEWVARIRSKYNNYAT YYADSVKDRFTISRDDSKNTAYLQMNNLKTEDTAVYYCVRHGNFGNSYISYWAYWGQGTLVTVSSG GGGSGGGGSGGGGSQTVVTQEPSLTVSPGGTVTLTCGSSTGAVTSGNYPNWVQQKPGQAPRGLIGG TKFLAPGTPARFSGSLLGGKAALTLSGVQPEDEAEYYCVLWYSNRWVFGGGTKLTVLHHHHHH |

| SEQ ID NO. | DESIGNATION | SOURCE | TYPE | SEQUENCE |
|---|---|---|---|---|
| 218 | SA08-CD33 E11 HL × I2C HL with His tag | | nt | CAGGGCCTGATCGGCGACATCTGCCTGCCCAGATGGGGCTGCCTGTGGGGCGACTCCGTGAAACAG GTGCAGCTGGTGCAGTCTGGAGCTGAGGTGAAGAAGCCTGGAGAGTCAGTCAAGGTCTCCTGCAAG GCTAGCGGGTATACCTTCACAAACTATGGAATGAACTGGGTGAAGCAGGCTCCAGGACAGGGTTTA GAGTGGATGGGCTGGATAAACACCTACACTGGAGAGCCAACCTATGCTGATAAGTTCCAGGGACGC GTTACCATGACTACGGATACCTCTACCAGCACTGCCTATATGGAAATCCGCAACCTCGGAGGTGAT GACACGGCTGTATATTACTGTGCGCGCTGGAGTTGGAGTGATGGTTACTACGTTTACTTTGACTAC TGGGGCCAAGGCACTTCGGTCACCGTCTCCTCAGGTGGTGGTGGTTCTGGCGGCGGCGGCTCCGGT GGTGGTGGTTCTGACATCGTGATGACACAGTCTCCAGACTCCCTGACTGTGTCTCTGGGCGAGAGG ACCACCATCAACTGCAAGTCCAGCCAGAGTGTTTTAGACAGCTCCACGAATAAGAACTTCTTAGCT TGGTACCAGCAGAAACCAGGACAGCCTCCTAAATTACTCCTTTCCTGGGCATCTACGCGGGAATCC GGGATCCCTGACCGATTCAGTGGCAGCGGGTCTGGGACAGATTTCACTCTCACTATTGACAGCCCG CAGCCTGAAGATTCTGCAACTTACTATTGTCAACAGTCTGCCCACTTCCCGATCACCTTTGGCCAA GGGACACGACTGGAGATTAAATCCGGAGGTGGTGGCTCCGAGGTGCAGCTGGTCGAGTCTGGAGGA GGATTGGTGCAGCCTGGAGGGTCATTGAAACTCTCATGTGCAGCCTCTGGATTCACCTTCAATAAG TACGCCATGAACTGGGTCCGCCAGGCTCCAGGAAAGGGTTTGGAATGGGTTGCTCGCATAAGAAGT AAATATAATAATTATGCAACATATTATGCCGATTCAGTGAAAGACAGGTTCACCATCTCCAGAGAT GATTCAAAAAACACTGCCTATCTACAAATGAACAACTTGAAAACTGAGGACACTGCCGTGTACTAC TGTGTGAGACATGGAACTTCGGTAATAGCTACATATCCTACTGGGCTTACTGGGGCCAAGGGACT CTGGTCACCGTCTCCTCAGGTGGTGGTGGTTCTGGCGGCGGCGGCTCCGGTGGTGGTGGTTCTCAG ACTGTTGTGACTCAGGAACCTTCACTCACCGTATCACCTGGTGGAACAGTCACACTCACTTGTGGC TCCTCGACTGGGGCTGTTACATCTGGCAACTACCCAAACTGGGTCCAACAAAAACCAGGTCAGGCA CCCCGTGGTCTAATAGGTGGGACTAAGTTCCTCGCCCCCGGTACTCCTGCCAGATTCTCAGGCTCC CTGCTTGGAGGCAAGGCTGCCCTCACCCTCTCAGGGTACAGCCAGAGGATGAGGCAGAATATTAC TGTGTTCTATGGTACAGCAACCGCTGGGTGTTCGGTGGAGGAACCAAACTGACTGTCCTA CATCACCATCACCATCAC |
| 219 | SA08-CD33 E11 HL × I2C HL H6 | | aa | QGLIGDICLPRWGCLWGDSVKQVQLVQSGAEVKKPGESVKVSCKASGYTFTNYGMNWVKQAPGQGL EWMGWINTYTGEPTYADKFQGRVTMTTDTSTSTAYMEIRNLGGDDTAVYYCARWSWSDGYYVYFDY WGQGTSVTVSSGGGGSGGGGSGGGGSDIVMTQSPDSLTVSLGERTTINCKSSQSVLDSSTNKNSLA WYQQKPGQPPKLLLSWASTRESGIPDRFSGSGSGTDFTLTIDSPQPEDSATYYCQQSAHFPITFGQ GTRLEIKSGGGGSEVQLVESGGGLVQPGGSLKLSCAASGFTFNKYAMNWVRQAPGKGLEWVARIRS KYNNYATYYADSVKDRFTISRDDSKNTAYLQMNNLKTEDTAVYYCVRHGNFGNSYISYWAYWGQGT LVTVSSGGGGSGGGGSGGGGSQTVVTQEPSLTVSPGGTVTLTCGSSTGAVTSGNYPNWVQQKPGQA PRGLIGGTKFLAPGTPARFSGSLLGGKAALTLSGVQPEDEAEYYCVLWYSNRWVFGGGTKLTVLHH HHHH |
| 220 | SA21-CD33 E11 HL × I2C HL | | nt | CGCCTGATTGAAGATATTTGCCTGCCCGCGCTGGGGCTGCCTGTGGGAAGATGATCAGGTGCAGCTG GTGCAGTCTGGAGCTGAGGTGAAGAAGCCTGGAGAGTCAGTCAAGGTCTCCTGCAAGGCTAGCGGG TATACCTTCACAAACTATGGAATGAACTGGGTGAAGCAGGCTCCAGGACAGGGTTTAGAGTGGATG GGCTGGATAAACACCTACACTGGAGAGCCAACCTATGCTGATAAGTTCCAGGGACGCGTTACCATG ACTACGGATACCTCTACCAGCACTGCCTATATGGAAATCCGCAACCTCGGAGGTGATGACACGGCT GTATATTACTGTGCGCGCTGGAGTTGGAGTGATGGTTACTACGTTTACTTTGACTACTGGGGCCAA GGCACTTCGGTCACCGTCTCCTCAGGTGGTGGTGGTTCTGGCGGCGGCGGCTCCGGTGGTGGTGGT TCTGACATCGTGATGACACAGTCTCCAGACTCCCTGACTGTGTCTCTGGGCGAGAGGACCACCATC AACTGCAAGTCCAGCCAGAGTGTTTTAGACAGCTCCACGAATAAGAACTTCTTAGCTTGGTACCAG CAGAAACCAGGACAGCCTCCTAAATTACTCCTTTCCTGGGCATCTACGCGGGAATCCGGGATCCCT GACCGATTCAGTGGCAGCGGGTCTGGGACAGATTTCACTCTCACTATTGACAGCCCGCAGCCTGAA GATTCTGCAACTTACTATTGTCAACAGTCTGCCCACTTCCCGATCACCTTTGGCCAAGGGACACGA CTGGAGATTAAATCCGGAGGTGGTGGCTCCGAGGTGCAGCTGGTCGAGTCTGGAGGAGGATTGGTG CAGCCTGGAGGGTCATTGAAACTCTCATGTGCAGCCTCTGGATTCACCTTCAATAAGTACGCCATG AACTGGGTCCGCCAGGCTCCAGGAAAGGGTTTGGAATGGGTTGCTCGCATAAGAAGTAAATATAAT AATTATGCAACATATTATGCCGATTCAGTGAAAGACAGGTTCACCATCTCCAGAGATGATTCAAAA AACACTGCCTATCTACAAATGAACAACTTGAAAACTGAGGACACTGCCGTGTACTACTGTGTGAGA CATGGGAACTTCGGTAATAGCTACATATCCTACTGGGCTTACTGGGGCCAAGGGACTCTGGTCACC GTCTCCTCAGGTGGTGGTGGTTCTGGCGGCGGCGGCTCCGGTGGTGGTGGTTCTCAGACTGTTGTG ACTCAGGAACCTTCACTCACCGTATCACCTGGTGGAACAGTCACACTCACTTGTGGCTCCTCGACT GGGGCTGTTACATCTGGCAACTACCCAAACTGGGTCCAACAAAAACCAGGTCAGGCACCCCGTGGT CTAATAGGTGGGACTAAGTTCCTCGCCCCCGGTACTCCTGCCAGATTCTCAGGCTCCCTGCTTGGA GGCAAGGCTGCCCTCACCCTCTCAGGGTACAGCCAGAGGATGAGGCAGAATATTACTGTGTTCTA TGGTACAGCAACCGCTGGGTGTTCGGTGGAGGAACCAAACTGACTGTCCTA |
| 221 | SA21-CD33 E11 HL × I2C HL | | aa | RLIEDICLPRWGCLWEDDQVQLVQSGAEVKKPGESVKVSCKASGYTFTNYGMNWVKQAPGQGLEWM GWINTYTGEPTYADKFQGRVTMTTDTSTSTAYMEIRNLGGDDTAVYYCARWSWSDGYYVYFDYWGQ GTSVTVSSGGGGSGGGGSGGGGSDIVMTQSPDSLTVSLGERTTINCKSSQSVLDSSTNKNSLAWYQ QKPGQPPKLLLSWASTRESGIPDRFSGSGSGTDFTLTIDSPQPEDSATYYCQQSAHFPITFGQGTR LEIKSGGGGSEVQLVESGGGLVQPGGSLKLSCAASGFTFNKYAMNWVRQAPGKGLEWVARIRSKYN NYATYYADSVKDRFTISRDDSKNTAYLQMNNLKTEDTAVYYCVRHGNFGNSYISYWAYWGQGTLVT VSSGGGGSGGGGSGGGGSQTVVTQEPSLTVSPGGTVTLTCGSSTGAVTSGNYPNWVQQKPGQAPRG LIGGTKFLAPGTPARFSGSLLGGKAALTLSGVQPEDEAEYYCVLWYSNRWVFGGGTKLTVL |
| 222 | SA25-CD33 E11 HL × I2C HL | | nt | GAGGACATCTGCCTGCCCAGATGGGGCTGCCTGTGGGAGGACCAGGTGCAGCTGGTGCAGTCTGGA GCTGAGGTGAAGAAGCCTGGAGAGTCAGTCAAGGTCTCCTGCAAGGCTAGCGGGTATACCTTCACA AACTATGGAATGAACTGGGTGAAGCAGGCTCCAGGACAGGGTTTAGAGTGGATGGGCTGGATAAAC ACCTACACTGGAGAGCCAACCTATGCTGATAAGTTCCAGGGACGCGTTACCATGACTACGGATACC |

| SEQ ID NO. | DESIGNATION | SOURCE | TYPE | SEQUENCE |
|---|---|---|---|---|
| | | | | TCTACCAGCACTGCCTATATGGAAATCCGCAACCTCGGAGGTGATGACACGGCTGTATATTACTGT<br>GCGCGCTGGAGTTGGAGTGATGGTTACTACGTTTACTTTGACTACTGGGGCCAAGGCACTTCGGTC<br>ACCGTCTCCTCAGGTGGTGGTGGTTCTGGCGGCGGCGGCTCCGGTGGTGGTGGTTCTGACATCGTG<br>ATGACACAGTCTCCAGACTCCCTGACTGTGTCTCTGGGCGAGAGGACCACCATCAACTGCAAGTCC<br>AGCCAGAGTGTTTTAGACAGCTCCACGAATAAGAACTCCTTAGCTTGGTACCAGCAGAAACCAGGA<br>CAGCCTCCTAAATTACTCCTTTCCTGGGCATCTACGCGGGAATCCGGGATCCCTGACCGATTCAGT<br>GGCAGCGGGTCTGGGACAGATTTCACTCTCACTATTGACAGCCCGCAGCCTGAAGATTCTGCAACT<br>TACTATTGTCAACAGTCTGCCCACTTCCCGATCACCTTTGGCCAAGGGACACGACTGGAGATTAAA<br>TCCGGAGGTGGTGGCTCCGAGGTGCAGCTGGTCGAGTCTGGAGGAGGATTGGTGCAGCCTGGAGGG<br>TCATTGAAACTCTCATGTGCAGCCTCTGGATTCACCTTCAATAAGTACGCCATGAACTGGGTCCGC<br>CAGGCTCCAGGAAAGGGTTTGGAATGGGTTGCTCGCATAAGAAGTAAATATAATAATTATGCAACA<br>TATTATGCCGATTCAGTGAAAGACAGGTTCACCATCTCCAGAGATGATTCAAAAAACACTGCCTAT<br>CTACAAATGAACAACTTGAAAACTGAGGACACTGCCGTGTACTACTGTGTGAGACATGGGAACTTC<br>GGTAATAGCTACATATCCTACTGGGCTTACTGGGGCCAAGGGACTCTGGTCACCGTCTCCTCAGGT<br>GGTGGTGGTTCTGGCGGCGGCGGCTCCGGTGGTGGTGGTTCTCAGACTGTTGTGACTCAGGAACCT<br>TCACTCACCGTATCACCTGGTGGAACAGTCACACTCACTTGTGGCCTCCGACTGGGGCTGTTACA<br>TCTGGCAACTACCCAAACTGGGTCCAACAAAAACCAGGTCAGGCACCCCGTGGTCTAATAGGTGGG<br>ACTAAGTTCCTCGCCCCCGGTACTCCTGCCAGATTCTCAGGCTCCCTGCTTGGAGGCAAGGCTGCC<br>CTCACCCTCTCAGGGGTACAGCCAGAGGATGAGGCAGAATATTACTGTGTTCTATGGTACAGCAAC<br>CGCTGGGTGTTCGGTGGAGGAACCAAACTGACTGTCCTA |
| 223 | SA25-CD33<br>E11 HL ×<br>I2C HL | | aa | EDICLPRWGCLWEDQVQLVQSGAEVKKPGESVKVSCKASGYTFTNYGMNWVKQAPGQGLEWMGWIN<br>TYTGEPTYADKFQGRVTMTTDTSTSTAYMEIRNLGGDDTAVYYCARWSWSDGYYVYFDYWGQGTSV<br>TVSSGGGGSGGGGSGGGGSDIVMTQSPDSLTVSLGERTTINCKSSQSVLDSSTNKNSLAWYQQKPG<br>QPPKLLLSWASTRESGIPDRFSGSGSGTDFTLTIDSPQPEDSATYYCQQSAHFPITFGQGTRLEIK<br>SGGGGSEVQLVESGGGLVQPGGSLKLSCAASGFTFNKYAMNWVRQAPGKGLEWVARIRSKYNNYAT<br>YYADSVKDRFTISRDDSKNTAYLQMNNLKTEDTAVYYCVRHGNFGNSYISYWAYWGQGTLVTVSSG<br>GGGSGGGGSGGGGSQTVVTQEPSLTVSPGGTVTLTCGSSTGAVTSGNYPNWVQQKPGQAPRGLIGG<br>TKFLAPGTPARFSGSLLGGKAALTLSGVQPEDEAEYYCVLWYSNRWVFGGGTKLTVL |
| 224 | SA08-CD33<br>E11 HL ×<br>I2C HL | | nt | CAGGGCCTGATCGGCGACATCTGCCTGCCCAGATGGGGCTGCCTGTGGGGCGACTCCGTGAAACAG<br>GTGCAGCTGGTGCAGTCTGGAGCTGAGGTGAAGAAGCCTGGAGAGTCAGTCAAGGTCTCCTGCAAG<br>GCTAGCGGGTATACCTTCACAAACTATGGAATGAACTGGGTGAAGCAGGCTCCAGGACAGGGTTTA<br>GAGTGGATGGGCTGGATAAACACCTACACTGGAGAGCCAACCTATGCTGATAAGTTCCAGGGACGC<br>GTTACCATGACTACGGATACCTCTACCAGCACTGCCTATATGGAAATCCGCAACCTCGGAGGTGAT<br>GACACGGCTGTATATTACTGTGCGCGCTGGAGTTGGAGTGATGGTTACTACGTTTACTTTGACTAC<br>TGGGGCCAAGGCACTTCGGTCACCGTCTCCTCAGGTGGTGGTGGTTCTGGCGGCGGCGGCTCCGGT<br>GGTGGTGGTTCTGACATCGTGATGACACAGTCTCCAGACTCCCTGACTGTGTCTCTGGGCGAGAGG<br>ACCACCATCAACTGCAAGTCCAGCCAGAGTGTTTTAGACAGCTCCACGAATAAGAACTCCTTAGCT<br>TGGTACCAGCAGAAACCAGGACAGCCTCCTAAATTACTCCTTTCCTGGGCATCTACGCGGGAATCC<br>GGGATCCCTGACCGATTCAGTGGCAGCGGGTCTGGGACAGATTTCACTCTCACTATTGACAGCCCG<br>CAGCCTGAAGATTCTGCAACTTACTATTGTCAACAGTCTGCCCACTTCCCGATCACCTTTGGCCAA<br>GGGACACGACTGGAGATTAAATCCGGAGGTGGTGGCTCCGAGGTGCAGCTGGTCGAGTCTGGAGGA<br>GGATTGGTGCAGCCTGGAGGGTCATTGAAACTCTCATGTGCAGCCTCTGGATTCACCTTCAATAAG<br>TACGCCATGAACTGGGTCCGCCAGGCTCCAGGAAAGGGTTTGGAATGGGTTGCTCGCATAAGAAGT<br>AAATATAATAATTATGCAACATATTATGCCGATTCAGTGAAAGACAGGTTCACCATCTCCAGAGAT<br>GATTCAAAAAACACTGCCTATCTACAAATGAACAACTTGAAAACTGAGGACACTGCCGTGTACTAC<br>TGTGTGAGACATGGGAACTTCGGTAATAGCTACATATCCTACTGGGCTTACTGGGGCCAAGGGACT<br>CTGGTCACCGTCTCCTCAGGTGGTGGTGGTTCTGGCGGCGGCGGCTCCGGTGGTGGTGGTTCTCAG<br>ACTGTTGTGACTCAGGAACCTTCACTCACCGTATCACCTGGTGGAACAGTCACACTCACTTGTGGC<br>CTCCGACTGGGGCTGTTACATCTGGCAACTACCCAAACTGGGTCCAACAAAAACCAGGTCAGGCA<br>CCCCGTGGTCTAATAGGTGGGACTAAGTTCCTCGCCCCCGGTACTCCTGCCAGATTCTCAGGCTCC<br>CTGCTTGGAGGCAAGGCTGCCCTCACCCTCTCAGGGGTACAGCCAGAGGATGAGGCAGAATATTAC<br>TGTGTTCTATGGTACAGCAACCGCTGGGTGTTCGGTGGAGGAACCAAACTGACTGTCCTA |
| 225 | SA08-CD33<br>E11 HL ×<br>I2C HL | | aa | QGLIGDICLPRWGCLWGDSVKQVQLVQSGAEVKKPGESVKVSCKASGYTFTNYGMNWVKQAPGQGL<br>EWMGWINTYTGEPTYADKFQGRVTMTTDTSTSTAYMEIRNLGGDDTAVYYCARWSWSDGYYVYFDY<br>WGQGTSVTVSSGGGGSGGGGSGGGGSDIVMTQSPDSLTVSLGERTTINCKSSQSVLDSSTNKNSLA<br>WYQQKPGQPPKLLLSWASTRESGIPDRFSGSGSGTDFTLTIDSPQPEDSATYYCQQSAHFPITFGQ<br>GTRLEIKSGGGGSEVQLVESGGGLVQPGGSLKLSCAASGFTFNKYAMNWVRQAPGKGLEWVARIRS<br>KYNNYATYYADSVKDRFTISRDDSKNTAYLQMNNLKTEDTAVYYCVRHGNFGNSYISYWAYWGQGT<br>LVTVSSGGGGSGGGGSGGGGSQTVVTQEPSLTVSPGGTVTLTCGSSTGAVTSGNYPNWVQQKPGQA<br>PRGLIGGTKFLAPGTPARFSGSLLGGKAALTLSGVQPEDEAEYYCVLWYSNRWVFGGGTKLTVL |
| 226 | CD33 E11<br>HL × I2C<br>HL<br>(His Tag) | | nt | CAGGTGCAGCTGGTGCAGTCTGGAGCTGAGGTGAAGAAGCCTGGAGAGTCAGTCAAGGTCTCCTGC<br>AAGGCTAGCGGGTATACCTTCACAAACTATGGAATGAACTGGGTGAAGCAGGCTCCAGGACAGGGT<br>TTAGAGTGGATGGGCTGGATAAACACCTACACTGGAGAGCCAACCTATGCTGATAAGTTCCAGGGA<br>CGCGTTACCATGACTACGGATACCTCTACCAGCACTGCCTATATGGAAATCCGCAACCTCGGAGGT<br>GATGACACGGCTGTATATTACTGTGCGCGCTGGAGTTGGAGTGATGGTTACTACGTTTACTTTGAC<br>TACTGGGGCCAAGGCACTTCGGTCACCGTCTCCTCAGGTGGTGGTGGTTCTGGCGGCGGCGGCTCC<br>GGTGGTGGTGGTTCTGACATCGTGATGACACAGTCTCCAGACTCCCTGACTGTGTCTCTGGGCGAG<br>AGGACCACCATCAACTGCAAGTCCAGCCAGAGTGTTTTAGACAGCTCCACGAATAAGAACTCCTTA<br>GCTTGGTACCAGCAGAAACCAGGACAGCCTCCTAAATTACTCCTTTCCTGGGCATCTACGCGGGAA<br>TCCGGGATCCCTGACCGATTCAGTGGCAGCGGGTCTGGGACAGATTTCACTCTCACTATTGACAGC<br>CCGCAGCCTGAAGATTCTGCAACTTACTATTGTCAACAGTCTGCCCACTTCCCGATCACCTTTGGC |

| SEQ ID NO. | DESIGNATION | SOURCE | TYPE | SEQUENCE |
|---|---|---|---|---|
| | | | | CAAGGGACACGACTGGAGATTAAATCCGGAGGTGGTGGCTCCGAGGTGCAGCTGGTCGAGTCTGGA GGAGGATTGGTGCAGCCTGGAGGGTCATTGAAACTCTCATGTGCAGCCTCTGGATTCACCTTCAAT AAGTACGCCATGAACTGGGTCCGCCAGGCTCCAGGAAAGGGTTTGGAATGGGTTGCTCGCATAAGA AGTAAATATAATAATTATGCAACATATTATGCCGATTCAGTGAAAGACAGGTTCACCATCTCCAGA GATGATTCAAAAAACACTGCCTATCTACAAATGAACAACTTGAAAACTGAGGACACTGCCGTGTAC TACTGTGTGAGACATGGGAACTTCGGTAATAGCTACATATCCTACTGGGCTTACTGGGGCCAAGGG ACTCTGGTCACCGTCTCCTCAGGTGGTGGTGGTTCTGGCGGCGGCGGCTCCGGTGGTGGTGGTTCT CAGACTGTTGTGACTCAGGAACCTTCACTCACCGTATCACCTGGTGGAACAGTCACACTCACTTGT GGCTCCTCGACTGGGGCTGTTACATCTGGCAACTACCCAAACTGGGTCCAACAAAAACCAGGTCAG GCACCCCGTGGTCTAATAGGTGGGACTAAGTTCCTCGCCCCCGGTACTCCTGCCAGATTCTCAGGC TCCCTGCTTGGAGGCAAGGCTGCCCTCACCCTCTCAGGGGTACAGCCAGAGGATGAGGCAGAATAT TACTGTGTTCTATGGTACAGCAACCGCTGGGTGTTCGGTGGAGGAACCAAACTGACTGTCCTA CATCACCATCACCATCAC |
| 227 | CD33 E11 HL × I2C HL H6 | | aa | QVQLVQSGAEVKKPGESVKVSCKASGYTFTNYGMNWVKQAPGQGLEWMGWINTYTGEPTYADKFQG RVTMTTDTSTSTAYMEIRNLGGDDTAVYYCARWSWSDGYYVYFDYWGQGTSVTVSSGGGGSGGGGS GGGGSDIVMTQSPDSLTVSLGERTTINCKSSQSVLDSSTNKNSLAWYQQKPGQPPKLLLSWASTRE SGIPDRFSGSGSGTDFTLTIDSPQPEDSATYYCQQSAHFPITFGQGTRLEIKSGGGGSEVQLVESG GGLVQPGGSLKLSCAASGFTFNKYAMNWVRQAPGKGLEWVARIRSKYNNYATYYADSVKDRFTISR DDSKNTAYLQMNNLKTEDTAVYYCVRHGNFGNSYISYWAYWGQTLVTVSSGGGGSGGGGSGGGGS QTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVLHHHHHH |

The invention claimed is:

1. A pharmaceutical composition comprising a CD33 targeting compound and at least one epigenetic factor, wherein
   (a) the CD33 targeting compound is a bispecific construct comprising a first binding domain specifically binding to CD33 comprising
      a VL chain comprising the amino acid sequences of CDR1, CDR2, and CDR3 set forth in
         (i) SEQ ID NOs: 7, 8, and 9, respectively;
         (ii) SEQ ID NOs: 25, 26, and 27, respectively;
         (iii) SEQ ID NOs: 43, 44, and 45, respectively;
         (iv) SEQ ID NOs: 61, 62, and 63, respectively;
         (v) SEQ ID NOs: 79, 80, and 81, respectively;
         (vi) SEQ ID NOs: 97, 98, and 99, respectively;
         (vii) SEQ ID NOs: 115, 116, and 117, respectively;
         (viii) SEQ ID NOs: 133, 134, and 135, respectively; and
      a VH chain comprising the amino acid sequences of CDR1, CDR2, and CDR3 set forth in
         (i) SEQ ID NOs: 2, 3, and 4, respectively;
         (ii) SEQ ID NOs: 20, 21, and 22, respectively;
         (iii) SEQ ID NOs: 38, 39, and 40, respectively;
         (iv) SEQ ID NOs: 56, 57, and 58, respectively;
         (v) SEQ ID NOs: 74, 75, and 76, respectively;
         (vi) SEQ ID NOs: 92, 93, and 94, respectively;
         (vii) SEQ ID NOs: 110, 111, and 112, respectively;
         (viii) SEQ ID NOs: 128, 129, and 130, respectively; and a second binding domain specifically binding to CD3 comprising
  a VL chain comprising the amino acid sequences of CDR1, CDR2, and CDR3 set forth in
    (i) SEQ ID NOs: 258, 259, and 260, respectively;
    (ii) SEQ ID NOs: 261, 263, and 264, respectively; and
    (iii) SEQ ID NOs: 264, 265, and 266, respectively; and
  a VH chain comprising the amino acid sequence of CDR1, CDR2, and CDR3 set forth in
    (i) SEQ ID NOs: 228, 229, and 230, respectively;
    (ii) SEQ ID NOs: 231, 232, and 233, respectively;
    (iii) SEQ ID NOs: 234, 235, and 236, respectively;
    (iv) SEQ ID NOs: 237, 238, and 239, respectively;
    (v) SEQ ID NOs: 240, 241, and 242, respectively;
    (vi) SEQ ID NOs: 243, 244, and 245, respectively;
    (vii) SEQ ID NOs: 246, 247, and 248, respectively;
    (viii) SEQ ID NOs: 249, 250, and 251, respectively;
    (ix) SEQ ID NOs: 252, 253, and 254, respectively; and
    (x) SEQ ID NOs: 255, 256, and 257, respectively; and
  (b) the at least one epigenetic factor is selected from the group consisting of a histone deacetylase (HDAC) inhibitor, a DNA methyltransferase (DNMT) I inhibitor, hydroxyurea, Granulocyte-Colony Stimulating Factor (G-CSF), a histone methyltransferase (HMT) inhibitor, and all trans-retinoic acid (ATRA).

2. The pharmaceutical composition of claim 1, wherein the bispecific construct is a bispecific antibody construct.

3. The pharmaceutical composition of claim 2, wherein the bispecific antibody construct is a bispecific single chain antibody construct.

4. The pharmaceutical composition of claim 2, wherein the bispecific antibody construct binds to human and cynomolgous CD3 and human and cynomolgous CD33.

5. The pharmaceutical composition of claim 1, wherein the first binding domain specifically binding to CD33 comprises a VL chain comprising the amino acid sequence set forth in any one of SEQ ID NO: 6, 24, 42, 60, 78, 96, 114 or 132 and a VH chain comprising the amino acid sequence set forth in any one of SEQ ID NO:1, 19, 37, 55, 73, 91, 109 or 127.

6. The pharmaceutical composition of claim 5, wherein the bispecific antibody construct comprises the amino acid sequence set forth in SEQ ID NO:13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 or 227.

7. A method for treating a patient with a CD33 associated myeloid leukemia, the method comprising administering an effective amount of a pharmaceutical composition comprising a CD33 targeting compound and at least one epigenetic factor, wherein
  (a) the CD33 targeting compound is a bispecific construct comprising a first binding domain specifically binding to CD33 comprising
    a VL chain comprising the amino acid sequences of CDR1, CDR2, and CDR3 set forth in
      (i) SEQ ID NOs: 7, 8, and 9, respectively;
      (ii) SEQ ID NOs: 25, 26, and 27, respectively;
      (iii) SEQ ID NOs: 43, 44, and 45, respectively;
      (iv) SEQ ID NOs: 61, 62, and 63, respectively;
      (v) SEQ ID NOs: 79, 80, and 81, respectively;
      (vi) SEQ ID NOs: 97, 98, and 99, respectively;
      (vii) SEQ ID NOs: 115, 116, and 117, respectively;
      (viii) SEQ ID NOs: 133, 134, and 135, respectively; and
    a VH chain comprising the amino acid sequences of CDR1, CDR2, and CDR3 set forth in
      (i) SEQ ID NOs: 2, 3, and 4, respectively;
      (ii) SEQ ID NOs: 20, 21, and 22, respectively;
      (iii) SEQ ID NOs: 38, 39, and 40, respectively;
      (iv) SEQ ID NOs: 56, 57, and 58, respectively;
      (v) SEQ ID NOs: 74, 75, and 76, respectively;
      (vi) SEQ ID NOs: 92, 93, and 94, respectively;
      (vii) SEQ ID NOs: 110, 111, and 112, respectively;
      (viii) SEQ ID NOs: 128, 129, and 130, respectively; and
    a second binding domain specifically binding to CD3 comprising
      a VL chain comprising the amino acid sequence of CDR1, CDR2, and CDR3 set forth in
        (i) SEQ ID NOs: 258, 259, and 260, respectively;
        (ii) SEQ ID NOs: 261, 263, and 264, respectively;
        (iii) SEQ ID NOs: 264, 265, and 266, respectively; and
      a VH chain comprising the amino acid sequence of CDR1, CDR2, and CDR3 set forth in
        (i) SEQ ID NOs: 228, 229, and 230, respectively;
        (ii) SEQ ID NOs: 231, 232, and 233, respectively;
        (iii) SEQ ID NOs: 234, 235, and 236, respectively;
        (iv) SEQ ID NOs: 237, 238, and 239, respectively;
        (v) SEQ ID NOs: 240, 241, and 242, respectively;
        (vi) SEQ ID NOs: 243, 244, and 245, respectively;
        (vii) SEQ ID NOs: 246, 247, and 248, respectively;
        (viii) SEQ ID NOs: 249, 250, and 251, respectively;
        (ix) SEQ ID NOs: 252, 253, and 254, respectively; and
        (x) SEQ ID NOs: 255, 256, and 257, respectively and
  (b) the at least one epigenetic factor is selected from the group consisting of a histone deacetylase (HDAC) inhibitor, a DNA methyltransferase (DNMT) I inhibitor, hydroxyurea, Granulocyte-Colony Stimulating Factor (G-CSF), a histone methyltransferase (HMT) inhibitor, and all trans-retinoic acid (ATRA).

8. The method of claim 7, wherein
  (a) the HDAC inhibitor is selected from the group consisting of panobinostat, vorinostat, romidepsin, N-acetyldinaline, belinostat, givinostat, entinostat, mocetinostat, EVP-0334, SRT501, CUDC-101, Quisinostat, abexinostat, LAQ824, and valproic acid;
  (b) the DNMT I inhibitor is selected from the group consisting of 5-azacitidine, decitabine, hydralazine, zebularine, procainamide, (-)-epigallocatechin-3-gallate, MG98, RG108, and SGI-110; and/or
  (c) the HMT inhibitor is selected from the group consisting of LSD1 (KDM1A) demethylase inhibitor, and chaetocin.

9. The method of claim 7, wherein the epigenetic factor is administered prior to administering the CD33 targeting compound.

10. The method of claim 7, wherein a first dose of the epigenetic factor is administered according to a treatment regimen selected from the group consisting of:
  (a) prior to administering the CD33 targeting compound;
  (b) prior to administering the CD33 targeting compound and then continuously during administering the CD33 targeting compound;
  (c) subsequent to administering the CD33 targeting compound; and
  (d) simultaneously with administering the CD33 targeting compound.

11. The method of claim 7, wherein the bispecific construct is a bispecific antibody construct.

12. The method of claim 11, wherein the bispecific antibody construct is a bispecific single chain antibody construct.

13. The method of claim 11, wherein the bispecific antibody construct binds to human and cynomolgous CD3 and human and cynomolgous CD33.

14. The method of claim 11, wherein the bispecific antibody construct comprises
   a first binding domain specifically binding to CD33 and comprising a VL chain comprising the amino acid sequence set forth in SEQ ID NO: 6, 24, 42, 60, 78, 96, 114 or 132 and a VH chain comprising the amino acid sequence set forth in SEQ ID NO:1, 19, 37, 55, 73, 91, 109 or 127; and
   a second binding domain specifically binding to CD3 and comprising a VL chain comprising the amino acid sequence set forth in SEQ ID NO: 154, 157, 160, 163, 166, 169 or 172 and a VH chain comprising the amino acid sequence set forth in SEQ ID NO:155, 158, 161, 164, 167, 170 or 173.

15. The method of claim 14, wherein the bispecific antibody construct comprises the amino acid sequence set forth in any of SEQ ID NO: 13, 15, 17, 31, 33, 35, 49, 51, 53, 67, 69, 71, 85, 87, 89, 103, 105, 107, 121, 123, 125, 139, 141, 143, 148, 150, 152, 215, 217, 219, 221, 223, 225 or 227.

16. The method of claim 7, wherein the myeloid leukemia is selected from the group consisting of acute myeloblastic leukemia, chronic neutrophilic leukemia, myeloid dendritic cell leukemia, accelerated phase chronic myelogenous leukemia, acute myelomonocytic leukemia, juvenile myelomonocytic leukemia, chronic myelomonocytic leukemia, acute basophilic leukemia, acute eosinophilic leukemia, chronic eosinophilic leukemia, Acute megakaryoblastic leukemia, essential thrombocytosis, acute erythroid leukemia, polycythemia vera, myelodysplastic syndrome, acute panmyelosis, myeloid sarcoma, and acute biphenotypic leukaemia.

17. A kit comprising a pharmaceutical composition comprising a CD33 targeting compound and at least one epigenetic factor, wherein
   (a) the CD33 targeting compound is a bispecific construct comprising a first binding domain specifically binding to CD33 comprising
   a VL chain comprising the amino acid sequences of CDR1, CDR2, and CDR3 set forth in
      (i) SEQ ID NOs: 7, 8, and 9, respectively;
      (ii) SEQ ID NOs: 25, 26, and 27, respectively;
      (iii) SEQ ID NOs: 43, 44, and 45, respectively;
      (iv) SEQ ID NOs: 61, 62, and 63, respectively;
      (v) SEQ ID NOs: 79, 80, and 81, respectively;
      (vi) SEQ ID NOs: 97, 98, and 99, respectively;
      (vii) SEQ ID NOs: 115, 116, and 117, respectively;
      (viii) SEQ ID NOs: 133, 134, and 135, respectively; and
   a VH chain comprising the amino acid sequences of CDR1, CDR2, and CDR3 set forth in
      (i) SEQ ID NOs: 2, 3, and 4, respectively;
      (ii) SEQ ID NOs: 20, 21, and 22, respectively;
      (iii) SEQ ID NOs: 38, 39, and 40, respectively;
      (iv) SEQ ID NOs: 56, 57, and 58, respectively;
      (v) SEQ ID NOs: 74, 75, and 76, respectively;
      (vi) SEQ ID NOs: 92, 93, and 94, respectively;
      (vii) SEQ ID NOs: 110, 111, and 112, respectively;
      (viii) SEQ ID NOs: 128, 129, and 130, respectively; and
   a second binding domain specifically binding to CD3 comprising
   a VL chain comprising the amino acid sequence of CDR1, CDR2, and CDR3 set forth in
      (i) SEQ ID NOs: 258, 259, and 260, respectively;
      (ii) SEQ ID NOs: 261, 263, and 264, respectively;
      (iii) SEQ ID NOs: 264, 265, and 266, respectively; and
   a VH chain comprising the amino acid sequence of CDR1, CDR2, and CDR3 set forth in
      (i) SEQ ID NOs: 228, 229, and 230, respectively;
      (ii) SEQ ID NOs: 231, 232, and 233, respectively;
      (iii) SEQ ID NOs: 234, 235, and 236, respectively;
      (iv) SEQ ID NOs: 237, 238, and 239, respectively;
      (v) SEQ ID NOs: 240, 241, and 242, respectively;
      (vi) SEQ ID NOs: 243, 244, and 245, respectively;
      (vii) SEQ ID NOs: 246, 247, and 248, respectively;
      (viii) SEQ ID NOs: 249, 250, and 251, respectively;
      (ix) SEQ ID NOs: 252, 253, and 254, respectively; and
      (x) SEQ ID NOs: 255, 256, and 257, respectively and
   (b) the at least one epigenetic factor is selected from the group consisting of a histone deacetylase (HDAC) inhibitor, a DNA methyltransferase (DNMT) I inhibitor, hydroxyurea, Granulocyte-Colony Stimulating Factor (G-CSF), a histone methyltransferase (HMT) inhibitor, and all trans-retinoic acid (ATRA).

18. The kit of claim 17 further comprising a protocol for use, wherein the protocol teaches administering the epigenetic factor prior to administering the CD33 targeting compound in treating a patient with myeloid leukemia.

19. The pharmaceutical composition of claim 1, wherein the second binding domain specifically binding to CD3 comprises a VL chain comprising the amino acid sequence set forth in any one of SEQ ID NO: 160, 163, 190, 193, 202, or 205 and a VH chain comprising the amino acid sequence set forth in any one of SEQ ID NO: 155, 158, 161, 164, 167, 170, 173, 176, 179, 182, 185, 188, 191, 194, 197, 200, 203, 206, 209, and 212.

20. The pharmaceutical composition of claim 1, wherein the second binding domain specifically binding to CD3 comprises a VL region and a VH region selected from the group consisting of:
   (a) a VL region as depicted in SEQ ID NO: 154 or 157 and a VH region as depicted in SEQ ID NO: 155 or 158;
   (b) a VL region as depicted in SEQ ID NO: 160 or 163 and a VH region as depicted in SEQ ID NO: 161 or 164;
   (c) a VL region as depicted in SEQ ID NO: 166 or 169 and a VH region as depicted in SEQ ID NO: 167 or 170;
   (d) a VL region as depicted in SEQ ID NO: 172 or 175 and a VH region as depicted in SEQ ID NO: 173 or 176;
   (e) a VL region as depicted in SEQ ID NO: -178 or 181 and a VH region as depicted in SEQ ID NO: 179 or 182;
   (f) a VL region as depicted in SEQ ID NO: 184 or 187 and a VH region as depicted in SEQ ID NO: 185 or 188;
   (g) a VL region as depicted in SEQ ID NO: 190 or 193 and a VH region as depicted in SEQ ID NO: 191 or 194;
   (h) a VL region as depicted in SEQ ID NO: 196 or 199 and a VH region as depicted in SEQ ID NO: 197 or 200;
   (i) a VL region as depicted in SEQ ID NO: 202 or 205 and a VH region as depicted in SEQ ID NO: 203 or 206; and
   (j) a VL region as depicted in SEQ ID NO: 208 or 211 and a VH region as depicted in SEQ ID NO: 209 or 212.

21. The pharmaceutical composition of claim 1, wherein the second binding domain specifically binding to CD3 comprises the amino acid sequence set forth in any one of SEQ ID NO: 156, 159, 162, 165, 168, 171, 174, 177, 180, 183, 186, 189, 192, 195, 198, 201, 204, 207, 210, or 213.

* * * * *